US011883432B2

(12) United States Patent
Carton et al.

(10) Patent No.: US 11,883,432 B2
(45) Date of Patent: Jan. 30, 2024

(54) CHIMERIC ANTIGEN RECEPTOR SYSTEM WITH ADAPTABLE RECEPTOR SPECIFICITY

(71) Applicant: CENTURY THERAPEUTICS, INC., Philadelphia, PA (US)

(72) Inventors: Jill Marinari Carton, Philadelphia, PA (US); Michael Francis Naso, Philadelphia, PA (US); Luis Ghira Borges, Philadelphia, PA (US); John Wheeler, Philadelphia, PA (US); Andrew Devaney, Philadelphia, PA (US)

(73) Assignee: CENTURY THERAPEUTICS, INC., Philadelphia, PA (US)

( * ) Notice: Subject to any disclaimer, the term of this patent is extended or adjusted under 35 U.S.C. 154(b) by 0 days.

(21) Appl. No.: 17/554,062

(22) Filed: Dec. 17, 2021

(65) Prior Publication Data

US 2022/0193133 A1    Jun. 23, 2022

Related U.S. Application Data

(60) Provisional application No. 63/127,587, filed on Dec. 18, 2020.

(51) Int. Cl.
*A61K 39/00* (2006.01)
*A61K 35/17* (2015.01)
*C12N 5/0783* (2010.01)

(52) U.S. Cl.
CPC ............ *A61K 35/17* (2013.01); *C12N 5/0636* (2013.01)

(58) Field of Classification Search
None
See application file for complete search history.

(56) References Cited

U.S. PATENT DOCUMENTS

| | | |
|---|---|---|
| 4,650,764 A | 3/1987 | Temin et al. |
| 4,980,289 A | 12/1990 | Temin et al. |
| 5,071,743 A | 12/1991 | Slilaty et al. |
| 5,122,458 A | 6/1992 | Post et al. |
| 5,124,263 A | 6/1992 | Temin et al. |
| 5,168,062 A | 12/1992 | Stinski |
| 5,384,253 A | 1/1995 | Krzyzek et al. |
| 5,385,839 A | 1/1995 | Stinski |
| 5,399,346 A | 3/1995 | Anderson et al. |
| 5,538,880 A | 7/1996 | Lundquist et al. |
| 5,550,318 A | 8/1996 | Adams et al. |
| 5,610,042 A | 3/1997 | Chang et al. |
| 5,702,931 A | 12/1997 | Andrews et al. |
| 5,780,270 A | 7/1998 | Lesley |
| 5,789,166 A | 8/1998 | Bauer et al. |
| 5,858,358 A | 1/1999 | June et al. |
| 5,883,223 A | 3/1999 | Gray |
| 5,932,419 A | 8/1999 | Bauer et al. |
| 6,242,222 B1 | 6/2001 | Gifford |
| 6,352,694 B1 | 3/2002 | June et al. |
| 6,534,055 B1 | 3/2003 | June et al. |
| 6,692,964 B1 | 2/2004 | June et al. |
| 6,693,086 B1 | 2/2004 | Dow et al. |
| 6,797,514 B2 | 9/2004 | Berenson et al. |
| 6,867,041 B2 | 3/2005 | Berenson et al. |
| 6,887,466 B2 | 5/2005 | June et al. |
| 6,905,680 B2 | 6/2005 | June et al. |
| 6,905,681 B1 | 6/2005 | June et al. |
| 6,905,874 B2 | 6/2005 | Berenson et al. |
| 6,949,520 B1 | 9/2005 | Hartmann et al. |
| 7,067,318 B2 | 6/2006 | June et al. |
| 7,144,575 B2 | 12/2006 | June et al. |
| 7,172,869 B2 | 2/2007 | June et al. |
| 7,175,843 B2 | 2/2007 | June et al. |
| 7,232,566 B2 | 6/2007 | June et al. |
| 7,244,826 B1 | 7/2007 | Marks et al. |
| 7,435,596 B2 | 10/2008 | Campana et al. |
| 7,446,190 B2 | 11/2008 | Sadelain et al. |
| 7,803,376 B2 | 9/2010 | Velardi et al. |
| 3,026,097 A1 | 9/2011 | Campana et al. |
| 8,283,450 B2 | 12/2012 | Kato et al. |
| 8,287,865 B2 | 12/2012 | Hansen et al. |
| 8,338,172 B2 | 12/2012 | Funaro et al. |
| 8,530,636 B2 | 9/2013 | Wandless et al. |
| 8,697,845 B2 | 4/2014 | Ward et al. |
| 8,748,585 B2 | 6/2014 | Attinger et al. |

(Continued)

FOREIGN PATENT DOCUMENTS

| | | |
|---|---|---|
| CA | 3048979 A1 | 7/2018 |
| EP | 0273085 | 7/1988 |

(Continued)

OTHER PUBLICATIONS

Janeway et al. Immunobiology 5, 2001, p. 106-108.*
Themeli et al., 2013 Nature Biotechnology, pp. 928-933 Generation of tumor-targeted human T lymphocytes from induced pluripotent stem cells for cancer therapy.*
Ngo, in the Protein Folding Problem and Tertiary Structure Prediction, Merz et al. (eds.), Birkhauser Boston: Boston, MA, pp. 433 and 492-495, 1994.*
Rudinger (in Peptide Hormones, Parsons (ed.), University Park Press: Baltimore, MD, pp. 1-7, 1976.*
Kimchi-Sarfaty C et al., A "silent" polymorphism in the MDR1 gene changes substrate specificity.Science. Jan. 26, 2007;315(5811): 525-8.*
Sardesai et al.; Electroporation delivery of DNA vaccines: prospects for success; Curr. Opin. Immunol.; Jun. 2011; 23(3); 421-9. (Author Manuscript).

(Continued)

*Primary Examiner* — Maria G Leavitt
(74) *Attorney, Agent, or Firm* — Troutman Pepper Hamilton Sanders LLP

(57) ABSTRACT

The present disclosure provides chimeric antigen receptors (CARs), particularly CARs that have adaptable receptor specificity (arCARs). Also provided are polypeptides of the CARs and other related molecules, polynucleotides, vectors, and cell compositions comprising the same. Pharmaceutical compositions comprising the polypeptides, polynucleotides, vectors, or cells of the present disclosure, and their uses in treating a disease in a subject are also provided.

13 Claims, 57 Drawing Sheets

Specification includes a Sequence Listing.

(56) References Cited

U.S. PATENT DOCUMENTS

| | | |
|---|---|---|
| 8,834,900 B2 | 9/2014 | Krieg et al. |
| 8,877,182 B2 | 11/2014 | Alici |
| 8,946,385 B2 | 2/2015 | Kawai |
| 9,034,650 B2 | 5/2015 | Padidam |
| 9,181,322 B2 | 11/2015 | Campbell |
| 9,371,386 B2 | 6/2016 | Vallera et al. |
| 9,394,368 B2 | 7/2016 | Brogdon et al. |
| 9,402,865 B2 | 8/2016 | Powell et al. |
| 9,404,083 B2 | 8/2016 | Yonemitsu et al. |
| 9,409,994 B2 | 8/2016 | Ho et al. |
| 9,416,190 B2 | 8/2016 | Ho et al. |
| 9,422,351 B2 | 8/2016 | Scholler et al. |
| 9,428,570 B2 | 8/2016 | Lawson et al. |
| 9,428,573 B2 | 8/2016 | Wong et al. |
| 9,446,105 B2 | 9/2016 | Powell |
| 9,447,194 B2 | 9/2016 | Jensen |
| 9,464,274 B2 | 10/2016 | Hariri et al. |
| 9,475,883 B2 | 10/2016 | Chang et al. |
| 9,493,569 B2 | 11/2016 | Igawa et al. |
| 9,499,623 B2 | 11/2016 | Ashkenazi et al. |
| 9,499,629 B2 | 11/2016 | June et al. |
| 9,511,092 B2 | 12/2016 | Campana et al. |
| 9,518,118 B2 | 12/2016 | Chen et al. |
| 9,534,058 B2 | 1/2017 | Stull et al. |
| 9,629,877 B2 | 4/2017 | Cooper et al. |
| 9,757,458 B2 | 9/2017 | Chang et al. |
| 9,765,330 B1 | 9/2017 | Niazi et al. |
| 9,782,462 B2 | 10/2017 | Bancel et al. |
| 9,833,476 B2 | 12/2017 | Zhang et al. |
| 9,855,297 B2 | 1/2018 | Duchateau et al. |
| 9,868,774 B2 | 1/2018 | Orentas et al. |
| 9,932,607 B2 | 4/2018 | Calos et al. |
| 10,077,312 B2 | 9/2018 | Urech et al. |
| 10,081,817 B2 | 9/2018 | Padidam |
| 10,093,738 B2 | 10/2018 | Johnson et al. |
| 10,098,926 B2 | 10/2018 | Pule et al. |
| 10,144,770 B2 | 12/2018 | Campana et al. |
| 10,166,255 B2 | 1/2019 | Moriarity et al. |
| 10,189,903 B2 | 1/2019 | Jensen |
| 10,253,086 B2 | 4/2019 | Bitter et al. |
| 10,287,606 B2 | 5/2019 | Valamehr et al. |
| 10,344,280 B1 | 7/2019 | Niazi et al. |
| 10,370,452 B2 | 8/2019 | Themeli et al. |
| 10,391,155 B2 | 8/2019 | Young et al. |
| 10,406,177 B2 | 9/2019 | Moriarity et al. |
| 10,428,305 B2 | 10/2019 | Campana et al. |
| 10,464,989 B2 | 11/2019 | Walcheck et al. |
| 10,494,645 B2 | 12/2019 | Auricchio et al. |
| 10,519,248 B2 | 12/2019 | Cheung et al. |
| 10,525,110 B2 | 1/2020 | Slawin et al. |
| 10,538,739 B2 | 1/2020 | Campana et al. |
| 10,603,378 B2 | 3/2020 | June et al. |
| 10,603,380 B2 | 3/2020 | Wiltzius |
| 10,633,450 B2 | 4/2020 | Kohrt et al. |
| 10,654,928 B2 | 5/2020 | Kloss et al. |
| 10,682,378 B2 | 6/2020 | Zhang et al. |
| 10,696,723 B2 | 6/2020 | Winston et al. |
| 10,703,816 B2 | 7/2020 | Orentas et al. |
| 10,709,775 B2 | 7/2020 | Dusseaux |
| 10,738,116 B2 | 8/2020 | Fry et al. |
| 10,774,309 B2 | 9/2020 | Campana et al. |
| 10,800,828 B2 | 10/2020 | Young et al. |
| 10,801,012 B2 | 10/2020 | Campana et al. |
| 10,813,952 B2 | 10/2020 | Childs et al. |
| 10,827,606 B2 | 11/2020 | Chen et al. |
| 10,829,556 B2 | 11/2020 | Jensen |
| 10,829,737 B2 | 11/2020 | Campana et al. |
| 10,836,998 B2 | 11/2020 | Duchateau et al. |
| 10,836,999 B2 | 11/2020 | Campana et al. |
| 10,912,797 B2 | 2/2021 | Moriarity et al. |
| 10,912,799 B2 | 2/2021 | Mukherjee et al. |
| 10,927,346 B2 | 2/2021 | Valamehr et al. |
| 10,934,336 B2 | 3/2021 | Zhao et al. |
| 10,941,381 B2 | 3/2021 | Cui |
| 10,960,024 B2 | 3/2021 | Klingemann et al. |
| 10,975,149 B2 | 4/2021 | Huntington et al. |
| 10,975,392 B2 | 4/2021 | Tsai et al. |
| 10,981,970 B2 | 4/2021 | Puléet al. |
| 11,028,143 B2 | 6/2021 | Zhao et al. |
| 11,041,021 B2 | 6/2021 | Chang et al. |
| 11,058,723 B2 | 7/2021 | Klingemann et al. |
| 11,072,781 B2 | 7/2021 | Valamehr et al. |
| 11,077,143 B2 | 8/2021 | Klingemann et al. |
| 11,090,335 B2 | 8/2021 | Dai et al. |
| 11,104,735 B2 | 8/2021 | Huntington et al. |
| 11,129,850 B2 | 9/2021 | Klingemann et al. |
| 11,154,574 B2 | 10/2021 | Moriarity et al. |
| 11,207,350 B2 | 12/2021 | Lee et al. |
| 11,214,619 B2 | 1/2022 | Prinz et al. |
| 11,220,551 B2 | 1/2022 | Moffat et al. |
| 11,229,669 B2 | 1/2022 | Sadelain et al. |
| 11,230,699 B2 | 1/2022 | Lee et al. |
| 11,242,375 B2 | 2/2022 | Adusumilli et al. |
| 11,254,912 B2 | 2/2022 | Terrett et al. |
| 11,266,692 B2 | 3/2022 | Moriarity et al. |
| 11,267,901 B2 | 3/2022 | Fedorov et al. |
| 11,344,577 B2 | 5/2022 | Cooper et al. |
| 11,365,394 B2 | 6/2022 | Valamehr et al. |
| 2002/0127227 A1 | 9/2002 | Holmes et al. |
| 2003/0175276 A1 | 9/2003 | Thorpe et al. |
| 2004/0058445 A1 | 3/2004 | Ledbetter et al. |
| 2004/0115193 A1 | 6/2004 | Hansen et al. |
| 2004/0166544 A1 | 8/2004 | Morton et al. |
| 2004/0229301 A1 | 11/2004 | Wang |
| 2005/0048549 A1 | 3/2005 | Cao et al. |
| 2005/0059113 A1 | 3/2005 | Bedian et al. |
| 2006/0046294 A1 | 3/2006 | Ow et al. |
| 2006/0057138 A1 | 3/2006 | Wood et al. |
| 2006/0057147 A1 | 3/2006 | Youko et al. |
| 2007/0160578 A1 | 7/2007 | Waldmann et al. |
| 2007/0202103 A1 | 8/2007 | Gillies et al. |
| 2009/0028877 A1 | 1/2009 | Iida et al. |
| 2009/0117096 A1 | 5/2009 | Felding-Habermann et al. |
| 2010/0008978 A1 | 1/2010 | Drummond et al. |
| 2010/0068815 A1 | 3/2010 | Ow et al. |
| 2010/0284906 A1 | 11/2010 | Hansen et al. |
| 2011/0020218 A1 | 1/2011 | Klinguer-Hamour et al. |
| 2011/0059076 A1 | 3/2011 | McDonagh et al. |
| 2011/0129458 A1 | 6/2011 | Dolk et al. |
| 2011/0129464 A1 | 6/2011 | Adams et al. |
| 2011/0136237 A1 | 6/2011 | Ow et al. |
| 2011/0177074 A1 | 7/2011 | Sivakumar et al. |
| 2012/0213783 A1 | 8/2012 | Rosenberg et al. |
| 2013/0011376 A1 | 1/2013 | Peled et al. |
| 2013/0034559 A1 | 2/2013 | Queva et al. |
| 2013/0089544 A1 | 4/2013 | Cartilage et al. |
| 2013/0171064 A1 | 7/2013 | Hansen et al. |
| 2013/0171152 A1 | 7/2013 | Spriggs et al. |
| 2013/0216528 A1 | 8/2013 | Cheung et al. |
| 2013/0266564 A1 | 10/2013 | Jaramillo et al. |
| 2013/0291136 A1 | 10/2013 | Freeman et al. |
| 2013/0315884 A1 | 11/2013 | Galetto et al. |
| 2014/0037628 A1 | 2/2014 | Morgan et al. |
| 2014/0105914 A1 | 4/2014 | David et al. |
| 2014/0134142 A1 | 5/2014 | Smith et al. |
| 2014/0134195 A1 | 5/2014 | Russell |
| 2014/0161794 A1 | 6/2014 | Lugovskoy et al. |
| 2014/0242701 A1 | 8/2014 | Shiku et al. |
| 2014/0271582 A1 | 9/2014 | Forman et al. |
| 2015/0017136 A1 | 1/2015 | Galetto et al. |
| 2015/0037887 A1 | 2/2015 | Deng et al. |
| 2015/0086574 A1 | 3/2015 | Karsunky et al. |
| 2015/0104443 A1 | 4/2015 | Moon et al. |
| 2015/0118207 A1 | 4/2015 | Min et al. |
| 2015/0125472 A1 | 5/2015 | Damelin et al. |
| 2015/0140023 A1 | 5/2015 | Birkle et al. |
| 2015/0190506 A1 | 7/2015 | Cheung et al. |
| 2015/0203817 A1 | 7/2015 | Galetto et al. |
| 2015/0239974 A1 | 8/2015 | Chang et al. |
| 2015/0239980 A1 | 8/2015 | Flanagan et al. |
| 2015/0259419 A1 | 9/2015 | Liu et al. |
| 2015/0259420 A1 | 9/2015 | Triebel et al. |
| 2015/0274824 A1 | 10/2015 | Blanc et al. |
| 2015/0283234 A1 | 10/2015 | Graziano et al. |

(56) References Cited

U.S. PATENT DOCUMENTS

| | | |
|---|---|---|
| 2015/0290316 A1 | 10/2015 | Graziano et al. |
| 2015/0299317 A1 | 10/2015 | Orentas et al. |
| 2015/0299326 A1 | 10/2015 | Wu et al. |
| 2015/0315293 A1 | 11/2015 | Damelin et al. |
| 2016/0009811 A1 | 1/2016 | Theuer et al. |
| 2016/0017052 A1 | 1/2016 | Kelley et al. |
| 2016/0030595 A1 | 2/2016 | Waldman et al. |
| 2016/0036472 A1 | 2/2016 | Chang |
| 2016/0039942 A1 | 2/2016 | Cobbold et al. |
| 2016/0046723 A1 | 2/2016 | Reyes et al. |
| 2016/0053017 A1 | 2/2016 | Orentas et al. |
| 2016/0075784 A1 | 3/2016 | Yu et al. |
| 2016/0075787 A1 | 3/2016 | Zheng et al. |
| 2016/0090427 A1 | 3/2016 | Lee et al. |
| 2016/0102146 A1 | 4/2016 | Hongo et al. |
| 2016/0108123 A1 | 4/2016 | Freeman et al. |
| 2016/0115240 A1 | 4/2016 | Evans et al. |
| 2016/0120905 A1 | 5/2016 | Galetto et al. |
| 2016/0120906 A1 | 5/2016 | Galetto et al. |
| 2016/0130357 A1 | 5/2016 | Mukherjee |
| 2016/0137740 A1 | 5/2016 | Hammond et al. |
| 2016/0145332 A1 | 5/2016 | Mackay et al. |
| 2016/0145337 A1 | 5/2016 | Galetto et al. |
| 2016/0145350 A1 | 5/2016 | Lonberg et al. |
| 2016/0152723 A1 | 6/2016 | Chen et al. |
| 2016/0159905 A1 | 6/2016 | Abdiche et al. |
| 2016/0159906 A1 | 6/2016 | Sun et al. |
| 2016/0159910 A1 | 6/2016 | Leong et al. |
| 2016/0168242 A1 | 6/2016 | Hass et al. |
| 2016/0194375 A1 | 7/2016 | Kitchen et al. |
| 2016/0200819 A1 | 7/2016 | Morgan et al. |
| 2016/0200824 A1 | 7/2016 | Chmielewski et al. |
| 2016/0208015 A1 | 7/2016 | Ho et al. |
| 2016/0208018 A1 | 7/2016 | Chen et al. |
| 2016/0208021 A1 | 7/2016 | Chang et al. |
| 2016/0215059 A1 | 7/2016 | Liu et al. |
| 2016/0215261 A1 | 7/2016 | Li et al. |
| 2016/0229919 A1 | 8/2016 | Ho et al. |
| 2016/0237139 A1 | 8/2016 | Pulé et al. |
| 2016/0250258 A1 | 9/2016 | Delaney et al. |
| 2016/0257762 A1 | 9/2016 | Kwon et al. |
| 2016/0264662 A1 | 9/2016 | Dimitrov et al. |
| 2016/0264674 A1 | 9/2016 | Eenennaam et al. |
| 2016/0280798 A1 | 9/2016 | Orentas et al. |
| 2016/0296562 A1 | 10/2016 | Pulé et al. |
| 2016/0296563 A1 | 10/2016 | Sourdive et al. |
| 2016/0297884 A1 | 10/2016 | Kuo et al. |
| 2016/0303166 A1 | 10/2016 | Katz et al. |
| 2016/0304615 A1 | 10/2016 | Kirshner et al. |
| 2016/0304619 A1 | 10/2016 | Kipps et al. |
| 2016/0311907 A1 | 10/2016 | Brogdon et al. |
| 2016/0311910 A1 | 10/2016 | Qin et al. |
| 2016/0311917 A1 | 10/2016 | Beatty et al. |
| 2016/0319020 A1 | 11/2016 | Hansen et al. |
| 2016/0319022 A1 | 11/2016 | Yang et al. |
| 2016/0326265 A1 | 11/2016 | June et al. |
| 2016/0333094 A1 | 11/2016 | Duchateau et al. |
| 2016/0333108 A1 | 11/2016 | Forman et al. |
| 2016/0333114 A1 | 11/2016 | Williams et al. |
| 2016/0333422 A1 | 11/2016 | Feldman et al. |
| 2016/0340406 A1 | 11/2016 | Zhao et al. |
| 2016/0340442 A1 | 11/2016 | Kufe et al. |
| 2016/0340649 A1 | 11/2016 | Brown et al. |
| 2016/0347815 A1 | 12/2016 | Sahin et al. |
| 2016/0347854 A1 | 12/2016 | Hornbach et al. |
| 2016/0355589 A1 | 12/2016 | Williams et al. |
| 2016/0355599 A1 | 12/2016 | Sagert et al. |
| 2017/0000900 A1 | 1/2017 | Romanelli et al. |
| 2017/0000901 A1 | 1/2017 | Stull et al. |
| 2017/0002072 A1 | 1/2017 | Powell et al. |
| 2017/0005308 A1 | 1/2017 | Fujii |
| 2017/0008963 A1 | 1/2017 | Brogdon et al. |
| 2018/0044686 A1 | 2/2018 | Nagy et al. |
| 2018/0273903 A1 | 9/2018 | Zhang et al. |
| 2019/0010514 A1 | 1/2019 | Poirot et al. |
| 2019/0019269 A1 | 1/2019 | Itagaki et al. |
| 2019/0054122 A1 | 2/2019 | Moriarity et al. |
| 2019/0060363 A1 | 2/2019 | Moriarity et al. |
| 2019/0060364 A1 | 2/2019 | Moriarity et al. |
| 2019/0062394 A1 | 2/2019 | Yarlagadda et al. |
| 2019/0062735 A1 | 2/2019 | Welstead et al. |
| 2019/0091310 A1 | 3/2019 | Wright et al. |
| 2019/0144515 A1 | 5/2019 | Sievers et al. |
| 2019/0161530 A1 | 5/2019 | Certo et al. |
| 2019/0183936 A1 | 6/2019 | Shum, Shum et al. |
| 2019/0202918 A1 | 7/2019 | Lim et al. |
| 2019/0314418 A1 | 10/2019 | Mukherjee et al. |
| 2019/0338309 A1 | 11/2019 | Vallier et al. |
| 2019/0365876 A1 | 12/2019 | Russell et al. |
| 2019/0375850 A1 | 12/2019 | Themeli et al. |
| 2020/0054675 A1 | 2/2020 | DiPersio et al. |
| 2020/0063100 A1 | 2/2020 | Terrett et al. |
| 2020/0095543 A1 | 3/2020 | Bhattacharya et al. |
| 2020/0147134 A1 | 5/2020 | Qin et al. |
| 2020/0172879 A1 | 6/2020 | Suri et al. |
| 2020/0181228 A1 | 6/2020 | Bachmann et al. |
| 2020/0224163 A1 | 7/2020 | Busser et al. |
| 2020/0283489 A1 | 9/2020 | Winston et al. |
| 2020/0283522 A1 | 9/2020 | Orentas et al. |
| 2020/0289571 A1 | 9/2020 | Moriarity et al. |
| 2020/0318067 A1 | 10/2020 | Gilham et al. |
| 2020/0325235 A1* | 10/2020 | Tabi ..................... C40B 40/10 |
| 2021/0015859 A1 | 1/2021 | valamehr et al. |
| 2021/0024959 A1 | 1/2021 | valamehr et al. |
| 2021/0060072 A1 | 3/2021 | Terrett et al. |
| 2021/0062227 A1 | 3/2021 | Qi et al. |
| 2021/0069242 A1 | 3/2021 | Genkin et al. |
| 2021/0079347 A1 | 3/2021 | Terrett et al. |
| 2021/0087537 A1 | 3/2021 | valamehr et al. |
| 2021/0115404 A1 | 4/2021 | Campana et al. |
| 2021/0138051 A1 | 5/2021 | O'Dwyer |
| 2021/0139935 A1 | 5/2021 | Carson et al. |
| 2021/0161954 A1 | 6/2021 | Smith et al. |
| 2021/0163895 A1 | 6/2021 | valamehr et al. |
| 2021/0187025 A1 | 6/2021 | DiPierro et al. |
| 2021/0198342 A1 | 7/2021 | Boissel et al. |
| 2021/0205362 A1 | 7/2021 | Davila |
| 2021/0230289 A1 | 7/2021 | Chen et al. |
| 2021/0230548 A1 | 7/2021 | Daher et al. |
| 2021/0252073 A1 | 8/2021 | Mukherjee et al. |
| 2021/0254005 A1 | 8/2021 | Kang et al. |
| 2021/0260116 A1 | 8/2021 | Boissel et al. |
| 2021/0260117 A1 | 8/2021 | Moriarity et al. |
| 2021/0261919 A1 | 8/2021 | Terrett et al. |
| 2021/0309713 A1 | 10/2021 | Xie |
| 2021/0347850 A1 | 11/2021 | Boissel et al. |
| 2021/0363212 A1 | 11/2021 | Ghonime et al. |
| 2021/0386785 A1 | 12/2021 | Klingemann et al. |
| 2022/0002424 A1 | 1/2022 | Trager et al. |
| 2022/0017594 A1 | 1/2022 | Navarro et al. |
| 2022/0025329 A1 | 1/2022 | Lee et al. |
| 2022/0047634 A1 | 2/2022 | Marasco et al. |
| 2022/0054544 A1 | 2/2022 | Lin et al. |
| 2022/0074945 A1 | 3/2022 | Sadelain et al. |
| 2022/0127328 A1 | 4/2022 | valamehr et al. |
| 2022/0127366 A1 | 4/2022 | Fotakis et al. |
| 2022/0162301 A1 | 5/2022 | Wang et al. |
| 2022/0184142 A1 | 6/2022 | valamehr et al. |

FOREIGN PATENT DOCUMENTS

| | | |
|---|---|---|
| EP | 3057994 A1 | 8/2015 |
| EP | 2990416 A1 | 3/2016 |
| EP | 2997134 A4 | 3/2016 |
| EP | 3048112 A1 | 7/2016 |
| EP | 3049812 A2 | 8/2016 |
| EP | 3071687 A1 | 9/2016 |
| EP | 3074419 A2 | 10/2016 |
| EP | 3083671 A1 | 10/2016 |
| EP | 3098237 A1 | 11/2016 |
| EP | 3421590 A1 | 1/2019 |
| EP | 3434762 A1 | 1/2019 |
| EP | 3459560 A1 | 3/2019 |
| EP | 3789487 A1 | 3/2021 |

(56) References Cited

FOREIGN PATENT DOCUMENTS

| | | |
|---|---|---|
| EP | 3791892 A2 | 3/2021 |
| EP | 3845638 A1 | 7/2021 |
| WO | 1994009699 A1 | 5/1994 |
| WO | 1995007358 A1 | 3/1995 |
| WO | 2000029447 A1 | 5/2000 |
| WO | 2000034337 A1 | 6/2000 |
| WO | 2000058363 A1 | 10/2000 |
| WO | 2003075840 A2 | 9/2003 |
| WO | 2004002431 A2 | 1/2004 |
| WO | 2004/094475 | 11/2004 |
| WO | 2005030124 A2 | 4/2005 |
| WO | 2005042780 A1 | 5/2005 |
| WO | 2005118643 A2 | 12/2005 |
| WO | 2006012688 A1 | 2/2006 |
| WO | 2007024921 A2 | 3/2007 |
| WO | 2007070538 A2 | 6/2007 |
| WO | 2007118214 A2 | 10/2007 |
| WO | 2008127735 A1 | 10/2008 |
| WO | 2009070753 A2 | 6/2009 |
| WO | 2009080830 A1 | 7/2009 |
| WO | 2009121847 A2 | 10/2009 |
| WO | 2010037041 A2 | 4/2010 |
| WO | 2010065962 A2 | 6/2010 |
| WO | 2010132659 A2 | 11/2010 |
| WO | 2011041441 A1 | 4/2011 |
| WO | 2011069019 A2 | 6/2011 |
| WO | 2011097513 A1 | 8/2011 |
| WO | 2011116212 A2 | 9/2011 |
| WO | 2012007167 A1 | 1/2012 |
| WO | 2012019061 A1 | 2/2012 |
| WO | 2012027723 A2 | 3/2012 |
| WO | 2012031273 A1 | 3/2012 |
| WO | 2012/082841 | 6/2012 |
| WO | 2012079000 A1 | 6/2012 |
| WO | 2012099973 A1 | 7/2012 |
| WO | 2012112943 A1 | 8/2012 |
| WO | 2012118547 A1 | 9/2012 |
| WO | 2012138475 A1 | 10/2012 |
| WO | 2012145384 A1 | 10/2012 |
| WO | 2012145714 A2 | 10/2012 |
| WO | 2013006490 A2 | 1/2013 |
| WO | 2013014668 A1 | 1/2013 |
| WO | 2013023162 A2 | 2/2013 |
| WO | 2013052745 A1 | 4/2013 |
| WO | 2013059593 A1 | 4/2013 |
| WO | 2013063419 A2 | 5/2013 |
| WO | 2013067492 A1 | 5/2013 |
| WO | 2013074596 A1 | 5/2013 |
| WO | 2013098813 A1 | 7/2013 |
| WO | 2013120012 A2 | 8/2013 |
| WO | 2013123061 A1 | 8/2013 |
| WO | 2013128194 A1 | 9/2013 |
| WO | 2013142034 A1 | 9/2013 |
| WO | 2013154760 A1 | 10/2013 |
| WO | 2013158292 A1 | 10/2013 |
| WO | 2013176915 A1 | 11/2013 |
| WO | 2013176916 A1 | 11/2013 |
| WO | 2014039682 | 3/2014 |
| WO | 2014055648 | 4/2014 |
| WO | 2014066532 | 5/2014 |
| WO | 2014089493 | 6/2014 |
| WO | 2014130657 | 8/2014 |
| WO | 2014130657 A1 | 8/2014 |
| WO | 2014143765 A1 | 9/2014 |
| WO | 2014144722 A2 | 9/2014 |
| WO | 2014153270 A1 | 9/2014 |
| WO | 2014165707 A2 | 10/2014 |
| WO | 2014179759 A1 | 11/2014 |
| WO | 2014184143 A1 | 11/2014 |
| WO | 2014184741 A1 | 11/2014 |
| WO | 2014184744 A1 | 11/2014 |
| WO | 2014186469 | 11/2014 |
| WO | 2014186469 A2 | 11/2014 |
| WO | 2015009740 | 1/2015 |
| WO | 2015032598 A1 | 3/2015 |
| WO | 2015042246 A1 | 3/2015 |
| WO | 2015052538 A1 | 4/2015 |
| WO | 2015054441 | 4/2015 |
| WO | 2015057834 | 4/2015 |
| WO | 2015057852 A1 | 4/2015 |
| WO | 2015069922 | 5/2015 |
| WO | 2015070061 | 5/2015 |
| WO | 2015073575 | 5/2015 |
| WO | 2015075175 | 5/2015 |
| WO | 2015075195 | 5/2015 |
| WO | 2015075468 | 5/2015 |
| WO | 2015077789 | 5/2015 |
| WO | 2015/095895 | 6/2015 |
| WO | 2015080981 | 6/2015 |
| WO | 2015084513 A1 | 6/2015 |
| WO | 2015091655 A1 | 6/2015 |
| WO | 2015092024 A2 | 6/2015 |
| WO | 2015097536 A2 | 7/2015 |
| WO | 2015112830 A1 | 7/2015 |
| WO | 2015112900 A1 | 7/2015 |
| WO | WO 2015103479 * | 7/2015 |
| WO | 2015116753 A1 | 8/2015 |
| WO | 2015118030 A2 | 8/2015 |
| WO | 2015120180 A1 | 8/2015 |
| WO | 2015121454 A1 | 8/2015 |
| WO | 2015124715 A1 | 8/2015 |
| WO | 2015132604 A1 | 9/2015 |
| WO | 2015133817 A1 | 9/2015 |
| WO | 2015136001 A1 | 9/2015 |
| WO | 2015140268 A1 | 9/2015 |
| WO | 2015142675 A2 | 9/2015 |
| WO | 2015143382 A1 | 9/2015 |
| WO | 2015150526 A2 | 10/2015 |
| WO | 2015153912 A1 | 10/2015 |
| WO | 2015155341 A1 | 10/2015 |
| WO | 2015157252 A1 | 10/2015 |
| WO | 2015157399 A1 | 10/2015 |
| WO | 2015158671 A1 | 10/2015 |
| WO | 2015158868 A2 | 10/2015 |
| WO | 2015166056 A1 | 11/2015 |
| WO | 2015174928 A1 | 11/2015 |
| WO | 2015187528 A1 | 12/2015 |
| WO | 2015188141 A2 | 12/2015 |
| WO | 2015191997 A1 | 12/2015 |
| WO | 2016/014576 | 1/2016 |
| WO | 2016008973 A1 | 1/2016 |
| WO | 2016014535 A1 | 1/2016 |
| WO | 2016014565 A2 | 1/2016 |
| WO | 2016014789 A2 | 1/2016 |
| WO | 2016016341 A1 | 2/2016 |
| WO | 2016016343 A1 | 2/2016 |
| WO | 2016016344 A1 | 2/2016 |
| WO | 2016020502 A1 | 2/2016 |
| WO | 2016022939 A1 | 2/2016 |
| WO | 2016026742 A1 | 2/2016 |
| WO | 2016028896 A1 | 2/2016 |
| WO | 2017025323 A1 | 2/2016 |
| WO | 2016033225 A2 | 3/2016 |
| WO | 2016033570 A1 | 3/2016 |
| WO | 2016034666 A1 | 3/2016 |
| WO | 2016040321 A1 | 3/2016 |
| WO | 2016040683 A1 | 3/2016 |
| WO | 2016040892 A1 | 3/2016 |
| WO | 2016041947 A1 | 3/2016 |
| WO | 2016042461 A1 | 3/2016 |
| WO | 2016044383 A1 | 3/2016 |
| WO | 2016049459 A1 | 3/2016 |
| WO | 2016054555 A2 | 4/2016 |
| WO | 2016055551 A1 | 4/2016 |
| WO | 2016055609 A1 | 4/2016 |
| WO | 2016061142 A1 | 4/2016 |
| WO | 2016069919 A1 | 5/2016 |
| WO | 2016073629 A1 | 5/2016 |
| WO | 2016073649 A1 | 5/2016 |
| WO | 2016077638 A1 | 5/2016 |
| WO | 2016089916 A1 | 6/2016 |
| WO | 2016090034 A2 | 6/2016 |
| WO | 2016090312 A1 | 6/2016 |
| WO | 2016090320 A1 | 6/2016 |

(56) References Cited

FOREIGN PATENT DOCUMENTS

| | | |
|---|---|---|
| WO | 2016090337 A1 | 6/2016 |
| WO | 2016090365 A1 | 6/2016 |
| WO | 2016090369 A1 | 6/2016 |
| WO | 2016094304 A2 | 6/2016 |
| WO | 2016097231 A2 | 6/2016 |
| WO | 2016097370 A2 | 6/2016 |
| WO | 2016100236 A2 | 6/2016 |
| WO | 2016109410 A2 | 7/2016 |
| WO | 2016112870 A1 | 7/2016 |
| WO | 2016115482 A1 | 7/2016 |
| WO | 2016116035 A1 | 7/2016 |
| WO | 2016120216 A1 | 8/2016 |
| WO | 2016120217 A1 | 8/2016 |
| WO | 2016120218 A1 | 8/2016 |
| WO | 2016120219 A1 | 8/2016 |
| WO | 2016120220 A1 | 8/2016 |
| WO | 2016122147 A1 | 8/2016 |
| WO | 2016122701 A1 | 8/2016 |
| WO | 2016123143 A1 | 8/2016 |
| WO | 2016124930 A1 | 8/2016 |
| WO | 2016126213 A1 | 8/2016 |
| WO | 2016130598 A1 | 8/2016 |
| WO | 2016130726 A1 | 8/2016 |
| WO | 2016134284 A1 | 8/2016 |
| WO | 2016138491 A1 | 9/2016 |
| WO | 2016139487 A1 | 9/2016 |
| WO | 2016141480 A1 | 9/2016 |
| WO | 2016142532 A1 | 9/2016 |
| WO | 2016149368 A1 | 9/2016 |
| WO | 2016149578 A1 | 9/2016 |
| WO | 2016150400 A1 | 9/2016 |
| WO | 2016154047 | 9/2016 |
| WO | 2016160618 A2 | 10/2016 |
| WO | 2016160620 | 10/2016 |
| WO | 2016160622 A2 | 10/2016 |
| WO | 2016161390 A1 | 10/2016 |
| WO | 2016164429 A1 | 10/2016 |
| WO | 2016164580 A1 | 10/2016 |
| WO | 2016164731 A2 | 10/2016 |
| WO | 2016168595 A1 | 10/2016 |
| WO | 2016168766 A1 | 10/2016 |
| WO | 2016168769 A1 | 10/2016 |
| WO | 2016168773 A2 | 10/2016 |
| WO | 2016172537 A1 | 10/2016 |
| WO | 2016172703 A2 | 10/2016 |
| WO | 2016174409 A1 | 11/2016 |
| WO | 2016179319 A1 | 11/2016 |
| WO | 2016182957 A1 | 11/2016 |
| WO | 2016185035 A1 | 11/2016 |
| WO | 2016187216 A1 | 11/2016 |
| WO | 2016187349 A1 | 11/2016 |
| WO | 2016191246 A2 | 12/2016 |
| WO | 2016196228 A1 | 12/2016 |
| WO | 2016201394 A1 | 12/2016 |
| WO | 2017004091 A1 | 1/2017 |
| WO | 2017004254 A1 | 1/2017 |
| WO | 2017017184 A1 | 2/2017 |
| WO | 2017040945 A1 | 3/2017 |
| WO | 2017/078807 | 5/2017 |
| WO | 2017075478 A2 | 5/2017 |
| WO | 2017112784 A1 | 6/2017 |
| WO | 2018023100 A2 | 2/2018 |
| WO | 2018096343 A1 | 5/2018 |
| WO | 2018126074 A1 | 7/2018 |
| WO | 2018156791 A1 | 8/2018 |
| WO | 2018156802 A1 | 8/2018 |
| WO | 2018161038 A1 | 9/2018 |
| WO | 2018213731 A1 | 11/2018 |
| WO | 2018/231759 | 12/2018 |
| WO | 2018226958 A1 | 12/2018 |
| WO | 2019/024979 | 2/2019 |
| WO | 2019060695 A1 | 3/2019 |
| WO | 2019067805 A1 | 4/2019 |
| WO | 2019/112899 | 6/2019 |
| WO | 2019126724 A1 | 6/2019 |
| WO | 2019126748 A1 | 6/2019 |
| WO | 2019149743 A1 | 8/2019 |
| WO | 2019161035 A1 | 8/2019 |
| WO | 2019161271 A1 | 8/2019 |
| WO | 2019191495 A1 | 10/2019 |
| WO | 2019204643 A2 | 10/2019 |
| WO | 2019204661 A1 | 10/2019 |
| WO | 2019205403 A1 | 10/2019 |
| WO | 2019220109 A1 | 11/2019 |
| WO | 2019220110 A1 | 11/2019 |
| WO | 2019238722 A1 | 12/2019 |
| WO | 2019241688 A1 | 12/2019 |
| WO | 2019246563 A1 | 12/2019 |
| WO | 2020000035 A1 | 1/2020 |
| WO | 2020006126 A1 | 1/2020 |
| WO | 2020010235 A1 | 1/2020 |
| WO | 2020088631 A1 | 5/2020 |
| WO | 2020092467 A1 | 5/2020 |
| WO | 2020097395 A1 | 5/2020 |
| WO | 2020223445 A1 | 5/2020 |
| WO | 2020123716 A1 | 6/2020 |
| WO | 2020124021 A1 | 6/2020 |
| WO | 2020150702 A1 | 7/2020 |
| WO | 2020168300 A1 | 8/2020 |
| WO | 2020172177 A1 | 8/2020 |
| WO | 2020247392 A1 | 12/2020 |
| WO | 2020261219 A1 | 12/2020 |
| WO | 2021013950 A1 | 1/2021 |
| WO | 2021015997 A1 | 1/2021 |
| WO | 2021041316 A1 | 3/2021 |
| WO | 2021069508 A1 | 4/2021 |
| WO | 2021076427 A1 | 4/2021 |
| WO | 2021077117 A1 | 4/2021 |
| WO | 2021081133 A1 | 4/2021 |
| WO | 2021087466 A1 | 5/2021 |
| WO | 2021092252 A1 | 5/2021 |
| WO | 2021095009 A1 | 5/2021 |
| WO | 2021099944 A1 | 5/2021 |
| WO | 2021127594 A1 | 6/2021 |
| WO | 2021146627 A1 | 7/2021 |
| WO | 2021154218 A1 | 8/2021 |
| WO | 2021226151 A2 | 11/2021 |
| WO | 2021252804 A1 | 12/2021 |
| WO | 2021258016 A1 | 12/2021 |
| WO | WO 2021/258016 * | 12/2021 |
| WO | 2022036041 A1 | 2/2022 |
| WO | 2022038158 A1 | 2/2022 |
| WO | 2022/087453 | 4/2022 |
| WO | 2022076910 A1 | 4/2022 |
| WO | 2022093825 A1 | 5/2022 |
| WO | 2022099297 A1 | 5/2022 |

OTHER PUBLICATIONS

Seki et al.; Generation of induced pluripotent stem cells from human terminally differentiated circulating T cells; Cell Stem Cell; Jul. 2, 2010; 7 (1); 11-14.

Skerra; Alternative non-antibody scaffolds for molecular recognition; Curr. Opin. Biotech.; Aug. 2007: 18 (4); 295-304.

Staerk et al.; Reprogramming of human peripheral blood cells to induced pluripotent stem cells; Cell Stem Cell; Jul. 2, 2010; 7 (1); 20-4.

Stanova et al.; Anti-Idiotypic 1-63 Agonistic Antibodies: Candidates for the Role of Universal Remedy; Antibodies; vol. 9, No. 2, May 28, 2020; p. 19; Retrieved from the Internet: URL: https://www.ncbi.nlm.nih.gov/pmc/articles/PMC7345059/pdf/antibodies-09-00019.pdf> abstract, figure 1.

Stone et al.; The assembly of single domain antibodies into bispecific decavalent molecules; J. Immunol. Methods; Jan. 10; 2007; 318 (1-2); 88-94.

Sutherland et al.; Modular Chimeric Antigen Receptor Systems for Universal CAR T Cell Retargeting; Int. J. Mol. Sci. 21 (19); Sep. 30, 2022; p. 7222. Retrieved from the Internet: https://www.ncbi.nlm.nih.goc/pmc/articles/PMC7582510/pdf/ijms-21-07222.pdf>.

Takahashi et al.; Induction of pluripotent stem cells from mouse embryonic and adult fibroblast cultures by defined factors; Cell; Aug. 25, 2006; 126 (4); 663-76.

(56) References Cited

OTHER PUBLICATIONS

Tessier et al.; PCR-assisted mutagenesis for site-directed insertion/deletion of large DNA segments; Methods Mol. Biol.; 1996; 57; 229-37.
Tur-Kaspa et al.; Use of electroporation to introduce biologically active foreign genes into primary rat hepatocytes; Mol. Cell Biol.; Feb. 1986; 6 (2); 716-8.
Van der Schans et al.; Dual Targeting to Overcome Current Challenges in Multiple Myeloma CAR T-Cell Treatment Frontiers in Oncology; 10 (5) Aug. 5, 2020; 8 pages.
Vitale et al.; NK-active cytokines IL-2, IL-12, and IL-15 selectively modulate specific protein kinase C (PKC) isoforms in primary human NK cells; Anat. Rec.; Feb. 1, 2002; 266 (2); 87-92.
Wada et al.; Successful differentiation to T cells, but unsuccessful B-cell generation, from B-cell-derived induced pluripotent stem cells; Int. Immunol.; 23 (1); 65-74.
Wagner et al.; Transferrin-polycation conjugates as carriers for DNA uptake into cells; Proc. Natl. Acad. Sci. USA; May 1990; 87 (9); 3410-14.
Wang et al.; Multiple mutant cDNAs from one reaction mixture using asymmetric primers in PCR; Biotechniques; Oct. 1995; 19 (4); 556-9.
Wang et al.; Site-directed mutagenesis of large (13-kb) plasmids in a single-PCR procedure; Biotechniques; Nov. 2000; 29 (5); 976-8.
Wang et al.; Two-stage PCR protocol allowing introduction of multiple mutations, deletions and insertions using QuikChange Site-Directed Mutagenesis; Biotechniques; Apr. 1999; 26 (4); 680-2.
Watarai et al.; Murine induced pluripotent stem cells can be derived from and differentiate into natural killer T cells; J. Clin. Invest.; Jul. 2010; 120 (7); 2610-8.
Wikman et al.; Selection and characterization of HER2/neu-binding affibody ligands; Prot. Eng. Des. Sel.; May 2004; 17 (5); 455-62.
Wilson et al.; Implantation of vascular grafts lined with genetically modified endothelial cells; Jun. 16, 1989; 244 (4910); 1344-6.
Wörn et al.; Stability engineering of antibody single-chain Fv fragments; J. Mo.l Biol.; Feb. 2, 2001; 305 (5); 989-1010.
Wu and Wu "Liver-directed gene delivery," Adv. Drug Delivery Rev., 12:159-167, 1993.
Wu et al.; Receptor-mediated in vitro gene transformation by a soluble DNA carrier system; J. Biol. Chem.; Apr. 5, 1987; 262 (10); 4429-32.
Xu et al.; Adaptation of inverse PCR to generate an internal deletion; Biotechniques; Apr. 1999; 26 (4); 639-41.
Xu et al.; Directed evolution of high-affinity antibody mimics using mRNA display; Chem. Biol.; Aug. 2002; 9 (8); 933-42.
Yang et al.; A common pathway for T lymphocyte activation involving both the CD3-Ti complex and CD2 sheep erythrocyte receptor determinants; J. Immunol.; Aug. 15, 1986; 137 (4); 1097-1100.
Yang et al.; In vivo and in vitro gene transfer to mammalian somatic cells by particle bombardment; Proc. Natl. Acad. Sci. USA; Dec. 1, 1990; 87 (24); 9568-72.
Bibeau et al.; Impact of Fcgamma RIIa-Fcgamma RIIIa polymorphisms and KRAS mutations on the clinical outcome of patients with metastatic colorectal cancer treated with cetuximab plus irinotecan. J Clin Oncol (2009) 27(7):1122-9.doi:10.1200/JCO.2008.18.0463.
Blázquez-Moreno et al. Transmembrane features governing Fc receptor CD16A assembly with CD16A signaling adaptor molecules. PNAS. 2017.
Clemenceau et al.; CD16-FceR1G CAR: Antibody-dependent cellular cytotoxicity (ADCC) is mediated by genetically modified antigen-specific human T lymphocytes. Blood 2006.
Challita et al.; Multiple modifications in cis elements of the long terminal repeat of retroviral vectors lead to increased expression and decreased DNA methylation in embryonic carcinoma cells. J Virol. Feb. 1995;69(2):748-55. https://doi.org/10.1128/JVI.69.2.748-55. 1995 PMID: 7815539; PMCID: PMC188638.
Chen et al.; Bispecific antibody (HER2 × mPEG) enhances anticancer effects by precise targeting and accumulation of mPEGylated liposomes. Acta Biomater. Jul. 15, 2020;111:386-97. doi: 10.1016/j.actbio.2020.04.029. Epub May 15, 2020. PMID: 32417267.
Zhang et al.; Enhanced efficacy and limited systemic cytokine exposure with membrane-anchored interleukin-12 T-cell therapy in murine tumor models. J Immunother Cancer; Jan. 2020;8(1).
Halene et al.; Improved expression in hematopoietic and lymphoid cells in mice after transplantation of bone marrow transduced with a modified retroviral vector. Blood. Nov. 15, 1999;94(10):3349-57. https://doi.org/10.1182/blood.V94.10.3349.422k05_3349_3357 PMID: 10552944.
Hara et al.; "Neuron-like differentiation and selective ablation of undifferentiated embryonic stem cells containing suicide gene with Oct-4 promoter." Stem Cells and Develop., 2008, vol. 17, pp. 619-628.
Ho et al.; Double attack strategy for leukemia using a pre-targeting bispecific antibody (CD20 Ab-mPEG scFv) and actively attracting PEGylated liposomal doxorubicin to enhance anti-tumor activity. J Nanobiotechnol 19, 16 (2021). https://doi.org/10.1186/S12951-020-00752-w.
Huang et al.; Engineering Chimeric Receptors to Investigate the Size- and Rigidity-Dependent Interaction of PEGylated Nanoparticles with Cells. ACS Nano. Jan. 26, 2016;10(1):648-62. doi: 10.1021/acsnano.5b05661. Epub Jan. 13, 2016. PMID: 26741147.
Mirlekar et al.; IL-12 Family Cytokines in Cancer and Immunotherapy; Cancers (Basel); Jan. 2021; 13(2): 167.
Inniss et al. "A Novel Bxb1 Integrase RMCE System for High Fidelity Site-Specific Integration of mAb Expression Cassette in CHO cells" (http://onlinelibrary.wiley.com/doi/10.1002/bit.26268/abstract). DOI 10.1002/bit.26268. Biotechnology and Bioengineering 114(8); Aug. 2017.
Lasek et al.; Interleukin 12: still a promising candidate for tumor immunotherapy? Cancer Immunol Immunother. 2014; 63(5): 419-35.
Jing et al. Identification of an ADAM17 clavage region in human CD16 and the engineering of a non-cleavable version in NK cells. Plos One 2015; 10(3).
Koene et al.; 158V/F polymorphism influences the binding of IgG by natural killer cell Fc gammaRIIIa, independently of the Fc gammaRIIIa-48L/R/H phenotype. Blood. 1997; 90: 1109-14.
Kudo et al.; T lymphocytes expressing a CD16 signaling receptor exert antibody-dependent cancer cell killing. Cancer Res (2014) 74(1):93-103. doi:10 1158/0008-5472. CAN-13-1365.
Kyba, et al. "Enhanced hematopoietic differentiation of embryonic stem cells conditionally expressing Stat5." PNAS, 2003, vol. 100, pp. 11904-11910.
Li et al.; The unique cytoplasmic domain of human FcγRIIIA regulates receptor-mediated function. J Immunol.; vol. 189; 2012; 4284-94.
Matreyek et al. "A platform for functional assessment of large variant libraries in mammalian cells" Nucleic Acids Research, 2017, vol. 45, No. 11 e102 doi: 10.1093/nar/gkx183.
Ochi et al.; Genemodified human α/β-T cells expressing a chimeric CD16-CD3ζ receptor as adoptively transferable effector cells for anticancer monoclonal antibody therapy. Cancer Immunol Res (2014) 2(3):249-62. doi:10.1158/2326-6066. CIR-13-0099-T.
Qin et al.; "Preclinical Development of Bivalent Chimeric Antigen Receptors Targeting Both CD19 and CD22" https://linkinghub.elsevier.com/retrieve/pii/S2372770518300305; Molecular Therapy: Oncolytics vol. Dec. 11, 2018.
Rong et al.; "A scalable approach to prevent teratoma formation of human embryonic stem cells." J. Biol. Chem., 2012, vol. 287, pp. 32338-32345.
Sarin et al.; Conditional telomerase induction causes proliferation of hair follicle stem cells. Nature, 2005, vol. 436, pp. 1048-1052.
Suri et al.; "Small Molecule Regulated Cytokine Expression Enables Potent and Durable Responses to Engineered T-Cell Therapy." <https://ashpublications.org/blood/article/132/Supplement%201/2045/261668/Small-Molecule-Regulated-Cytokine-Expression>. Adoptive Immunotherapy: Poster; Nov. 29, 2018; 3 pages.
Tanaka et al.; Development of engineered T cells expressing a chimeric CD16-CD3ζ receptor to improve the clinical efficacy of mogamulizumab therapy against adult T cell leukemia. Clin Cancer Res (2016) 22:4405-16. doi:10.1158/1078-0432. CCR-15-2714.

(56) References Cited

OTHER PUBLICATIONS

Wilken et al.; Regulatory DNA keyholes enable specific and persistent multi-gene expression programs in primary T cells without genome modification. BioRxiv 2020.02.19.956730; doi: https://doi.org/10.1101/2020.02.19.956730. Feb. 20, 2020; 19 pages.
Wu et al.; A novel polymorphism of FcgammaRllla (CD16) alters receptor function and predisposes to autoimmune disease. J Clin Invest. 1997; 100: 1059-70.
Zenatti et al.; "Oncogenic IL7R gain-of-function mutations in childhood T-cell acute lymphoblastic leukemia"; https://pubmed.ncbi.nlm.nih.gov/21892159/ PMID: 21892159. Nat Genet. Sep. 4, 2011;43(10):932-9.
Zhu et al.; Pluripotent stem cell-derived NK cells with high-affinity noncleavable CD16a mediate improved antitumor activity. Blood. 2020; 135 (6): 399-410.
US 9,028,812, Jan. 9, 2001, Ishii et al. (withdrawn).
Angag et al.; General Method for Site-Directed Mutagenesis; Biotechniques; Mar. 30, 2001; 30 (3): 486-8.
Baranova et al.; SbsB structure and lattice reconstruction unveil Ca2+ triggered S-layer assembly; Nature; 487 (7405); Jun. 10, 2012; Retrieved from the Internet: URL:http://www.nature.com/articles/nature11155>.
Barettino et al.; Improved method for PCR-mediated site-directed mutagenesis; Nuc. Acids. Res. 22: 541-542 (1993).
Battalia et al.; Interleukin-21 (IL-21) synergizes with IL-2 to enhance T-cell receptor-induced human T-cell proliferation and counteracts IL-2/transforming growth factor-β-induced regulatory T-cell development; May 2013, Immunology, 139(1):109-120.
Bazdar and Sieg; Interieukin-7 enhances proliferation responses to T-cell receptor stimulation in naive CD4+ T cells from human immunodeficiency virus-infected persons; J. Virol.; Nov. 8, 2007; 81(22):12670-4.
Binz et al.; Engineering novel binding proteins from nonimmunoglobulin domains; Nat. Biolechnol. 23 (10); Oct. 2005; 1257-68.
Boles et al.; A rapid and highly efficient method for PCR-based site-directed mutagenesis using only one new primer; Curr. Genet.; 28 (2); Jul. 1995; 197-8.
Brown et al.; Lipocalin-7 Is a Matricellular Regulator of Angiogenesis; PLoS ONE; Nov. 2010; 5 (11); e13905; 11 pages.
Byla et al.; Selection of a novel and highly specific tumor necrosis factor alpha (TNFalpha) antagonist: insight from the crystal structure of the antagonist-TNFalpha complex; J. Biol. Chem; 285 (16); Apr. 16, 2010; 12096-100.
Carmeliet et al.; Angiogenesis in cancer and other diseases; Nature; Sep. 14, 2000; 407 (6801) 249-57.
Chen et al.; High-efficiency transformation of mammalian cells by plasmid DNA; Mol. Cell. Biol.; Aug. 1987; 7 (8); 2745-52.
Cornish et al.; Differential regulation of T-cell growth by IL-2 and IL-15; Blood; Jul. 15, 2006; 108 (2); 600-8.
Dijkema et al.; Cloning and expression of the chromosomal immune interferon gene of the rat; Embo J.; Mar. 1985; 4 (3) 761-7.
Fechheimer et al.; Transfection of mammalian cells with plasmid DNA by scrape loading and sonication loading; Proc. Natl. Acad. Sci. USA; Dec. 1987; 84 (23); 8463-7.
Ferraro et al.; Co-delivery of PSA and PSMA DNA vaccines with electroporation induces potent immune responses; Hum. Vaccin.; Feb. 2011.
Fukuoka et al.; Ligand binding sites on guinea pig C3aR: point and deletion mutations in the large extracellular loop and vicinity; Biochem. Biophys. Res. Commun.; 263 (2); 357-60; Sep. 24, 1999; 357-60.
Gene et al.; High anti-Internalin B VHH antibody fragments isolated from naturally and artificially immunized repertoires; J. Immuno. Meth. 416 (8); Nov. 8, 2014; pp. 29-39.
Ghosh et al.; In: Liver Diseases, Targeted Diagnosis and Therapy Using Specific Receptors and Ligands; 1991; 87-104.
Gill et al.; Biopharmaceutical drug discovery using novel protein scaffolds; Curr. Opin. Biotech.; Dec. 2006; 17 (6); 653-8.

Gopal; Gene transfer method for transient gene expression, stable transformation, and cotransformation of suspension cell cultures; Mol. Cell. Biol.; May 1985; 5 (5); 1188-90.
Gorman et al.; The Rous sarcoma virus long terminal repeat is a strong promoter when introduced into a variety of eukaryotic cells by DNA-mediated transfection; Proc. Natl. Acad. Sci. USA; Nov. 1982; 79 (22); 6777-81.
Graham et al.; A new technique for the assay of infectivity of human adenovirus 5 DNA; Virology; Apr. 1973; 52 (2); 546-67.
Hanna et al.; Direct reprogramming of terminally differentiated mature B lymphocytes to pluripotency; Cell; Apr. 18, 2008; 133 (2); 250-64.
Hey et al.; Artificial, non-antibody binding proteins for pharmaceutical and industrial applications; Trends Biotechnol.; Oct 2005; 23 (10); 514-22.
Holliger et al.; Engineered Antibody Fragments and the Rise of Single Domains; Nat. Biotechno.; Sep. 2005; 23 (9); 1126-36.
Holt et al.; A peroxidase-coupled continuous absorbance plate-reader assay for flavin monoamine oxidases, copper-containing amine oxidases and related enzymes Domain antibodies: proteins for therapy; Nov. 2003; 21 (11); 484-90.
International Search Report and Written Opinion dated Mar. 31, 2022 in Application No. PCT/021/063955.
Jang et al.; Initiation of protein synthesis by internal entry of ribosomes into the 5' nontranslated region of encephalomyocarditis virus RNA in vivo; J. Virol.; Apr. 1989; 63 (4); 1651-60.
Kang et al.; Transient Gene Transfer into Myotubes Following Differentiation in Culture Biotech; BioTechniques; Jan. 1996; 20(1) 40-6.
Kim et al.; Multiple site mutagenesis with high targeting efficiency in one cloning step; Biotechniques; Feb. 2000; 28 (2); 196-8.
Kirsch et al.; An improved PCR-mutagenesis strategy for two-site mutagenesis or sequence swapping between related genes; Nucleic Acids Res.; Apr. 1, 1998; 26 (7); 1848-50.
Klein et al., "High-velocity microprojectiles for delivering nucleic acids into living cells" (1987) Nature, 327, 70-3.
Koide et al.; Monobodies: antibody mimics based on the scaffold of the fibronectin type III domain; Methods Mol. Biol. 2007; 95-109.
Kunkel; Rapid and efficient site-specific mutagenesis without phenotypic selection Proc. Natl. Acad. Sci. USA 82: 488-92 (1985).
Kuo et al.; Efficient gene transfer into primary murine lymphocytes obviating the need for drug selection; Blood; Aug. 1, 1993; 82 (3); 845-52.
Loh et al.; Reprogramming of T cells from human peripheral blood; Cell Stem Cell; Jul. 2, 2010; 7 (1); 15-19.
Mann et al.; Construction of a retrovirus packaging mutant and its use to produce helper-free defective retrovirus; Cell; May 1983; 33 (1); 153-9.
Markowitz et al.; A safe packaging line for gene transfer: separating viral genes on two different plasmids; J. Virol.; Apr. 1988; 62 (4); 1120-4.
Meuer et al.; An alternative pathway of T-cell activation: a functional role for the 50 kd T11 sheep erythrocyte receptor protein; Cell; Apr. 1984; 36 (4); 897-906.
Nabel et al.; Recombinant gene expression in vivo within endothelial cells of the arterial wall; Jun. 16, 1989; 244(4910); 1342-4.
Nicolau et al.; Liposomes as carriers for in vivo gene transfer and expression; Methods EnzymoL; 1987; 149; 157-76.
Noguchi; Pancreatic Islet Purification from Large Mammals and Humans Using a COBE 2991 Cell Processor versus Large Plastic Bottles; J. Clin. Med.; Dec. 23, 2020; 10 (1); 10 pages.
Ogel et al.; Efficient deletion mutagenesis by PCR; Protein Eng. Jul. 1992; 5 (5); 467-8.
Parikh et al.; Random mutagenesis by whole-plasmid PCR amplification; Biotechniques; Mar. 1998; 24 (3) 428-31.
Perales et al.; Gene transfer in vivo: sustained expression and regulation of genes introduced into the liver by receptor-targeted uptake; Proc. Natl. Acad. Sci. USA; Apr. 26, 1994; 91 (9); 4086-90.
Pons et al.; PCR site-directed mutagenesis using *Pyrococcus* sp GB-D polymerase coupled to a rapid screening procedure. Application to a beta-glucanase gene; Methods Mol. Biol.; 1997; 67; 209-18.

(56) References Cited

OTHER PUBLICATIONS

Potter et al.; Enhancer-dependent expression of human kappa immunoglobulin genes introduced into mouse pre-B lymphocytes by electroporation; Proc. Natl. Acad. Sci. USA; Nov. 1984; 81 (22); 7161-5.
Rhem et al.; Membrane topology of the outer membrane protein OprH from Pseudomonas aeruginosa: PCR-mediated site-directed insertion and deletion mutagenesis; J. Bacteriol.; Jun. 1996; 178 (11); 3346-9.
Richards et al.; Exploring alternative antibody scaffolds: Antibody fragments and antibody mimics for targeted drug delivery; Drug Discovery Today: Technologies; 30; Nov. 8, 2018; 35-46.
Rippe et al.; DNA-mediated gene transfer into adult rat hepatocytes in primary culture; Mol. Cell Biol.; Feb. 1990; 10(2); 689-95.
Zoller et al., Miniproteins as Phage Display-Scaffolds for Clinical Applications, Molecules, 2011, vol. 16, pp. 2467-2485.
Wypych et al., "Hman IgG2 Antibodies Display Disulfide-mediated Structural Isoforms", The Journal of Biological Chemistry, 2008, vol. 283, No. 23, pp. 16194-16205.
Brown et al., "Derivation of Induced Pluripotent Stem Cells from Human Peripheral Blood T Lymphocytes", PloS One, 2010, vol. 5, Issue 6, e11373, 9 pages.
Illades et al., "Triabodies: single chain Fv fragments without a linker form trivalent trimers", FEBS Letters, 1997, vol. 409, pp. 437-441.
Hoshino et al., "Activation via the CD3 and CD16 Pathway Mediates Interleukin-2-Dependent Autocrine Proliferation of Granular Lymphocytes in Patients With Granular Lyphocyte Proliferative Disorders", Blood, 1991, vol. 78, No. 12, pp. 3232-3240.

\* cited by examiner

Bridge Molecules:

Universal CAR

- Herceptin scFv (Trastuzumab)
- Anti-idiotype scFv (ScFv69)
- 9G8 VHH targets EGFR

FIG. 11F

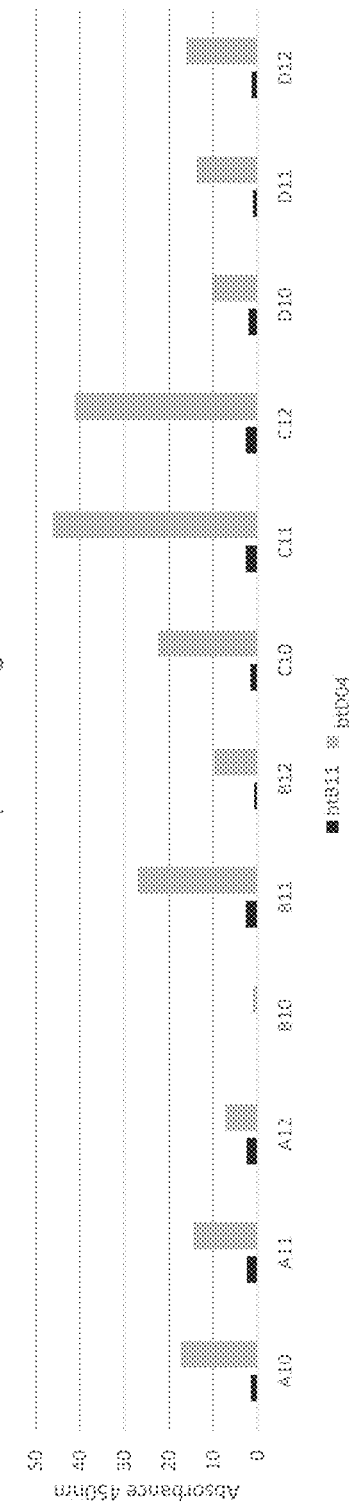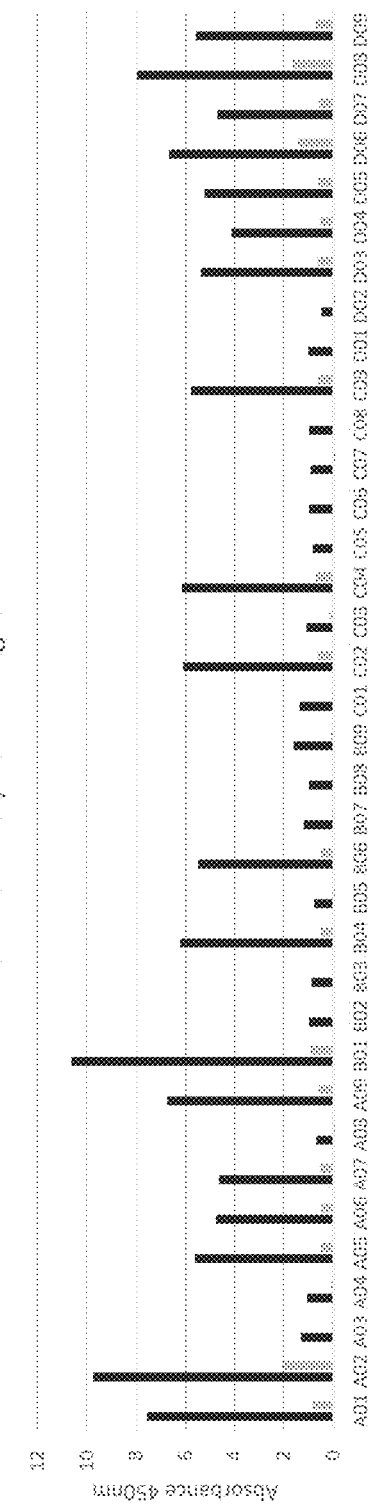
FIG. 16B
FIG. 16C

SEQUENCE LISTING

```
<160> NUMBER OF SEQ ID NOS: 134

<210> SEQ ID NO 1
<211> LENGTH: 22
<212> TYPE: PRT
<213> ORGANISM: Homo sapiens

<400> SEQUENCE: 1

Met Leu Leu Leu Val Thr Ser Leu Leu Cys Glu Leu Pro His Pro
1               5                   10                  15

Ala Phe Leu Leu Ile Pro
            20

<210> SEQ ID NO 2
<211> LENGTH: 120
<212> TYPE: PRT
<213> ORGANISM: Artificial Sequence
<220> FEATURE:
<223> OTHER INFORMATION: FMC63 VH

<400> SEQUENCE: 2

Glu Val Lys Leu Gln Glu Ser Gly Pro Gly Leu Val Ala Pro Ser Gln
1               5                   10                  15

Ser Leu Ser Val Thr Cys Thr Val Ser Gly Val Ser Leu Pro Asp Tyr
            20                  25                  30

Gly Val Ser Trp Ile Arg Gln Pro Pro Arg Lys Gly Leu Glu Trp Leu
        35                  40                  45

Gly Val Ile Trp Gly Ser Glu Thr Thr Tyr Tyr Asn Ser Ala Leu Lys
    50                  55                  60

Ser Arg Leu Thr Ile Ile Lys Asp Asn Ser Lys Ser Gln Val Phe Leu
65                  70                  75                  80

Lys Met Asn Ser Leu Gln Thr Asp Asp Thr Ala Ile Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Ser Val Thr Val Ser Ser
        115                 120

<210> SEQ ID NO 3
<211> LENGTH: 18
<212> TYPE: PRT
<213> ORGANISM: Artificial Sequence
<220> FEATURE:
<223> OTHER INFORMATION: Whitlow Linker

<400> SEQUENCE: 3

Gly Ser Thr Ser Gly Ser Gly Lys Pro Gly Ser Gly Glu Gly Ser Thr
1               5                   10                  15

Lys Gly
```

-continued

```
<210> SEQ ID NO 4
<211> LENGTH: 107
<212> TYPE: PRT
<213> ORGANISM: Artificial Sequence
<220> FEATURE:
<223> OTHER INFORMATION: FMC63 VL

<400> SEQUENCE: 4
```

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr
            100                 105

```
<210> SEQ ID NO 5
<211> LENGTH: 107
<212> TYPE: PRT
<213> ORGANISM: Homo sapiens

<400> SEQUENCE: 5
```

Ile Glu Val Met Tyr Pro Pro Pro Tyr Leu Asp Asn Glu Lys Ser Asn
1               5                   10                  15

Gly Thr Ile Ile His Val Lys Gly Lys His Leu Cys Pro Ser Pro Leu
            20                  25                  30

Phe Pro Gly Pro Ser Lys Pro Phe Trp Val Leu Val Val Val Gly Gly
        35                  40                  45

Val Leu Ala Cys Tyr Ser Leu Leu Val Thr Val Ala Phe Ile Ile Phe
    50                  55                  60

Trp Val Arg Ser Lys Arg Ser Arg Leu Leu His Ser Asp Tyr Met Asn
65                  70                  75                  80

Met Thr Pro Arg Arg Pro Gly Pro Thr Arg Lys His Tyr Gln Pro Tyr
                85                  90                  95

Ala Pro Pro Arg Asp Phe Ala Ala Tyr Arg Ser
            100                 105

```
<210> SEQ ID NO 6
<211> LENGTH: 112
<212> TYPE: PRT
<213> ORGANISM: Homo sapiens

<400> SEQUENCE: 6
```

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 7
<211> LENGTH: 245
<212> TYPE: PRT
<213> ORGANISM: Artificial Sequence
<220> FEATURE:
<223> OTHER INFORMATION: FMC63 scFV

<400> SEQUENCE: 7

Glu Val Lys Leu Gln Glu Ser Gly Pro Gly Leu Val Ala Pro Ser Gln
1               5                   10                  15

Ser Leu Ser Val Thr Cys Thr Val Ser Gly Val Ser Leu Pro Asp Tyr
            20                  25                  30

Gly Val Ser Trp Ile Arg Gln Pro Pro Arg Lys Gly Leu Glu Trp Leu
        35                  40                  45

Gly Val Ile Trp Gly Ser Glu Thr Thr Tyr Tyr Asn Ser Ala Leu Lys
    50                  55                  60

Ser Arg Leu Thr Ile Ile Lys Asp Asn Ser Lys Ser Gln Val Phe Leu
65                  70                  75                  80

Lys Met Asn Ser Leu Gln Thr Asp Asp Thr Ala Ile Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Ser Val Thr Val Ser Ser Gly Ser Thr Ser Gly Ser Gly Lys
        115                 120                 125

Pro Gly Ser Gly Glu Gly Ser Thr Lys Gly Asp Ile Gln Met Thr Gln
    130                 135                 140

Thr Thr Ser Ser Leu Ser Ala Ser Leu Gly Asp Arg Val Thr Ile Ser
145                 150                 155                 160

Cys Arg Ala Ser Gln Asp Ile Ser Lys Tyr Leu Asn Trp Tyr Gln Gln
                165                 170                 175

Lys Pro Asp Gly Thr Val Lys Leu Leu Ile Tyr His Thr Ser Arg Leu
            180                 185                 190

His Ser Gly Val Pro Ser Arg Phe Ser Gly Ser Gly Ser Gly Thr Asp
        195                 200                 205

Tyr Ser Leu Thr Ile Ser Asn Leu Glu Gln Glu Asp Ile Ala Thr Tyr
    210                 215                 220

Phe Cys Gln Gln Gly Asn Thr Leu Pro Tyr Thr Phe Gly Gly Gly Thr
225                 230                 235                 240

Lys Leu Glu Ile Thr
                245

<210> SEQ ID NO 8
<211> LENGTH: 42
<212> TYPE: PRT
<213> ORGANISM: Homo sapiens

<400> SEQUENCE: 8

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe

```
                20                  25                  30

Pro Glu Glu Glu Gly Gly Cys Glu Leu
        35                  40

<210> SEQ ID NO 9
<211> LENGTH: 94
<212> TYPE: PRT
<213> ORGANISM: Homo sapiens

<400> SEQUENCE: 9

Asn Cys Arg Asn Thr Gly Pro Trp Leu Lys Lys Val Leu Lys Cys Asn
1               5                   10                  15

Thr Pro Asp Pro Ser Lys Phe Phe Ser Gln Leu Ser Ser Glu His Gly
            20                  25                  30

Gly Asp Val Gln Lys Trp Leu Ser Ser Pro Phe Pro Ser Ser Ser Phe
        35                  40                  45

Ser Pro Gly Gly Leu Ala Pro Glu Ile Ser Pro Leu Glu Val Leu Glu
    50                  55                  60

Arg Asp Lys Val Thr Gln Leu Leu Pro Leu Asn Thr Asp Ala Tyr Leu
65                  70                  75                  80

Ser Leu Gln Glu Leu Gln Gly Gln Asp Pro Thr His Leu Val
                85                  90

<210> SEQ ID NO 10
<211> LENGTH: 62
<212> TYPE: PRT
<213> ORGANISM: Homo sapiens

<400> SEQUENCE: 10

Lys Lys Val Ala Lys Lys Pro Thr Asn Lys Ala Pro His Pro Lys Gln
1               5                   10                  15

Glu Pro Gln Glu Ile Asn Phe Pro Asp Asp Leu Pro Gly Ser Asn Thr
            20                  25                  30

Ala Ala Pro Val Gln Glu Thr Leu His Gly Cys Gln Pro Val Thr Gln
        35                  40                  45

Glu Asp Gly Lys Glu Ser Arg Ile Ser Val Gln Glu Arg Gln
    50                  55                  60

<210> SEQ ID NO 11
<211> LENGTH: 42
<212> TYPE: PRT
<213> ORGANISM: Homo sapiens

<400> SEQUENCE: 11

Ala Leu Tyr Leu Leu Arg Arg Asp Gln Arg Leu Pro Pro Asp Ala His
1               5                   10                  15

Lys Pro Pro Gly Gly Gly Ser Phe Arg Thr Pro Ile Gln Glu Glu Gln
            20                  25                  30

Ala Asp Ala His Ser Thr Leu Ala Lys Ile
        35                  40

<210> SEQ ID NO 12
<211> LENGTH: 25
<212> TYPE: PRT
<213> ORGANISM: Homo sapiens

<400> SEQUENCE: 12

Thr Tyr Cys Phe Ala Pro Arg Cys Arg Glu Arg Arg Asn Glu Arg
1               5                   10                  15
```

Leu Arg Arg Glu Ser Val Arg Pro Val
            20                  25

<210> SEQ ID NO 13
<211> LENGTH: 61
<212> TYPE: PRT
<213> ORGANISM: Homo sapiens

<400> SEQUENCE: 13

Lys Trp Lys Lys Lys Arg Pro Arg Asn Ser Tyr Lys Cys Gly Thr
1               5                   10                  15

Asn Thr Met Glu Arg Glu Glu Ser Glu Gln Thr Lys Lys Arg Glu Lys
            20                  25                  30

Ile His Ile Pro Glu Arg Ser Asp Glu Ala Gln Arg Val Phe Lys Ser
        35                  40                  45

Ser Lys Thr Ser Ser Cys Asp Lys Ser Asp Thr Cys Phe
50                  55                  60

<210> SEQ ID NO 14
<211> LENGTH: 48
<212> TYPE: PRT
<213> ORGANISM: Homo sapiens

<400> SEQUENCE: 14

Gln Arg Arg Lys Tyr Arg Ser Asn Lys Gly Glu Ser Pro Val Glu Pro
1               5                   10                  15

Ala Glu Pro Cys His Tyr Ser Cys Pro Arg Glu Glu Glu Gly Ser Thr
            20                  25                  30

Ile Pro Ile Gln Glu Asp Tyr Arg Lys Pro Glu Pro Ala Cys Ser Pro
        35                  40                  45

<210> SEQ ID NO 15
<211> LENGTH: 38
<212> TYPE: PRT
<213> ORGANISM: Homo sapiens

<400> SEQUENCE: 15

Cys Trp Leu Thr Lys Lys Lys Tyr Ser Ser Ser Val His Asp Pro Asn
1               5                   10                  15

Gly Glu Tyr Met Phe Met Arg Ala Val Asn Thr Ala Lys Lys Ser Arg
            20                  25                  30

Leu Thr Asp Val Thr Leu
        35

<210> SEQ ID NO 16
<211> LENGTH: 51
<212> TYPE: PRT
<213> ORGANISM: Homo sapiens

<400> SEQUENCE: 16

Met Gly Trp Ile Arg Gly Arg Arg Ser Arg His Ser Trp Glu Met Ser
1               5                   10                  15

Glu Phe His Asn Tyr Asn Leu Asp Leu Lys Lys Ser Asp Phe Ser Thr
            20                  25                  30

Arg Trp Gln Lys Gln Arg Cys Pro Val Val Lys Ser Lys Cys Arg Glu
        35                  40                  45

Asn Ala Ser
50

<210> SEQ ID NO 17

<211> LENGTH: 24
<212> TYPE: PRT
<213> ORGANISM: Homo sapiens

<400> SEQUENCE: 17

Leu Cys Ala Arg Pro Arg Arg Ser Pro Ala Gln Glu Asp Gly Lys Val
1               5                   10                  15

Tyr Ile Asn Met Pro Gly Arg Gly
            20

<210> SEQ ID NO 18
<211> LENGTH: 52
<212> TYPE: PRT
<213> ORGANISM: Homo sapiens

<400> SEQUENCE: 18

Tyr Phe Leu Gly Arg Leu Val Pro Arg Gly Arg Gly Ala Ala Glu Ala
1               5                   10                  15

Ala Thr Arg Lys Gln Arg Ile Thr Glu Thr Glu Ser Pro Tyr Gln Glu
            20                  25                  30

Leu Gln Gly Gln Arg Ser Asp Val Tyr Ser Asp Leu Asn Thr Gln Arg
        35                  40                  45

Pro Tyr Tyr Lys
    50

<210> SEQ ID NO 19
<211> LENGTH: 120
<212> TYPE: PRT
<213> ORGANISM: Homo sapiens

<400> SEQUENCE: 19

Trp Arg Arg Lys Arg Lys Glu Lys Gln Ser Glu Thr Ser Pro Lys Glu
1               5                   10                  15

Phe Leu Thr Ile Tyr Glu Asp Val Lys Asp Leu Lys Thr Arg Arg Asn
            20                  25                  30

His Glu Gln Glu Gln Thr Phe Pro Gly Gly Gly Ser Thr Ile Tyr Ser
        35                  40                  45

Met Ile Gln Ser Gln Ser Ser Ala Pro Thr Ser Gln Glu Pro Ala Tyr
    50                  55                  60

Thr Leu Tyr Ser Leu Ile Gln Pro Ser Arg Lys Ser Gly Ser Arg Lys
65                  70                  75                  80

Arg Asn His Ser Pro Ser Phe Asn Ser Thr Ile Tyr Glu Val Ile Gly
                85                  90                  95

Lys Ser Gln Pro Lys Ala Gln Asn Pro Ala Arg Leu Ser Arg Lys Glu
            100                 105                 110

Leu Glu Asn Phe Asp Val Tyr Ser
        115                 120

<210> SEQ ID NO 20
<211> LENGTH: 41
<212> TYPE: PRT
<213> ORGANISM: Homo sapiens

<400> SEQUENCE: 20

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser

-continued

```
                35                  40

<210> SEQ ID NO 21
<211> LENGTH: 47
<212> TYPE: PRT
<213> ORGANISM: Homo sapiens

<400> SEQUENCE: 21

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
                20                  25                  30

Gly Ala Val His Thr Arg Gly Leu Asp Phe Ala Cys Asp Ile Tyr
            35                  40                  45

<210> SEQ ID NO 22
<211> LENGTH: 39
<212> TYPE: PRT
<213> ORGANISM: Homo sapiens

<400> SEQUENCE: 22

Ile Glu Val Met Tyr Pro Pro Pro Tyr Leu Asp Asn Glu Lys Ser Asn
1               5                   10                  15

Gly Thr Ile Ile His Val Lys Gly Lys His Leu Cys Pro Ser Pro Leu
                20                  25                  30

Phe Pro Gly Pro Ser Lys Pro
            35

<210> SEQ ID NO 23
<211> LENGTH: 21
<212> TYPE: PRT
<213> ORGANISM: Homo sapiens

<400> SEQUENCE: 23

Ile Tyr Ile Trp Ala Pro Leu Ala Gly Thr Cys Gly Val Leu Leu Leu
1               5                   10                  15

Ser Leu Val Ile Thr
            20

<210> SEQ ID NO 24
<211> LENGTH: 27
<212> TYPE: PRT
<213> ORGANISM: Homo sapiens

<400> SEQUENCE: 24

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 25
<211> LENGTH: 15
<212> TYPE: PRT
<213> ORGANISM: Artificial Sequence
<220> FEATURE:
<223> OTHER INFORMATION: (GGGGS)3

<400> SEQUENCE: 25

Gly Gly Gly Gly Ser Gly Gly Gly Gly Ser Gly Gly Gly Gly Ser
1               5                   10                  15

<210> SEQ ID NO 26
```

```
<211> LENGTH: 20
<212> TYPE: PRT
<213> ORGANISM: Artificial Sequence
<220> FEATURE:
<223> OTHER INFORMATION: Linker 3

<400> SEQUENCE: 26

Gly Gly Ser Glu Gly Lys Ser Ser Gly Ser Gly Ser Glu Ser Lys Ser
1               5                   10                  15

Thr Gly Gly Ser
            20

<210> SEQ ID NO 27
<211> LENGTH: 8
<212> TYPE: PRT
<213> ORGANISM: Artificial Sequence
<220> FEATURE:
<223> OTHER INFORMATION: Linker 4

<400> SEQUENCE: 27

Gly Gly Gly Ser Gly Gly Gly Ser
1               5

<210> SEQ ID NO 28
<211> LENGTH: 12
<212> TYPE: PRT
<213> ORGANISM: Artificial Sequence
<220> FEATURE:
<223> OTHER INFORMATION: Linker 5

<400> SEQUENCE: 28

Gly Gly Gly Ser Gly Gly Gly Ser Gly Gly Gly Ser
1               5                   10

<210> SEQ ID NO 29
<211> LENGTH: 16
<212> TYPE: PRT
<213> ORGANISM: Artificial Sequence
<220> FEATURE:
<223> OTHER INFORMATION: Linker 6

<400> SEQUENCE: 29

Gly Gly Gly Ser Gly Gly Gly Ser Gly Gly Gly Ser Gly Gly Gly Ser
1               5                   10                  15

<210> SEQ ID NO 30
<211> LENGTH: 20
<212> TYPE: PRT
<213> ORGANISM: Artificial Sequence
<220> FEATURE:
<223> OTHER INFORMATION: Linker 7

<400> SEQUENCE: 30

Gly Gly Gly Ser Gly Gly Gly Ser Gly Gly Gly Ser Gly Gly Gly Ser
1               5                   10                  15

Gly Gly Gly Ser
            20

<210> SEQ ID NO 31
<211> LENGTH: 20
<212> TYPE: PRT
<213> ORGANISM: Artificial Sequence
<220> FEATURE:
<223> OTHER INFORMATION: Linker 8

<400> SEQUENCE: 31
```

```
Gly Gly Gly Gly Ser Gly Gly Gly Gly Ser Gly Gly Gly Ser Gly
1               5                   10                  15

Gly Gly Gly Ser
            20
```

<210> SEQ ID NO 32
<211> LENGTH: 25
<212> TYPE: PRT
<213> ORGANISM: Artificial Sequence
<220> FEATURE:
<223> OTHER INFORMATION: Linker 9

<400> SEQUENCE: 32

```
Gly Gly Gly Gly Ser Gly Gly Gly Gly Ser Gly Gly Gly Ser Gly
1               5                   10                  15

Gly Gly Gly Ser Gly Gly Gly Gly Ser
            20                  25
```

<210> SEQ ID NO 33
<211> LENGTH: 14
<212> TYPE: PRT
<213> ORGANISM: Artificial Sequence
<220> FEATURE:
<223> OTHER INFORMATION: Linker 10

<400> SEQUENCE: 33

```
Ile Arg Pro Arg Ala Ile Gly Gly Ser Lys Pro Arg Val Ala
1               5                   10
```

<210> SEQ ID NO 34
<211> LENGTH: 15
<212> TYPE: PRT
<213> ORGANISM: Artificial Sequence
<220> FEATURE:
<223> OTHER INFORMATION: Linker 11

<400> SEQUENCE: 34

```
Gly Lys Gly Gly Ser Gly Lys Gly Gly Ser Gly Lys Gly Gly Ser
1               5                   10                  15
```

<210> SEQ ID NO 35
<211> LENGTH: 15
<212> TYPE: PRT
<213> ORGANISM: Artificial Sequence
<220> FEATURE:
<223> OTHER INFORMATION: Linker 12

<400> SEQUENCE: 35

```
Gly Gly Lys Gly Ser Gly Gly Lys Gly Ser Gly Gly Lys Gly Ser
1               5                   10                  15
```

<210> SEQ ID NO 36
<211> LENGTH: 15
<212> TYPE: PRT
<213> ORGANISM: Artificial Sequence
<220> FEATURE:
<223> OTHER INFORMATION: Linker 13

<400> SEQUENCE: 36

```
Gly Gly Gly Lys Ser Gly Gly Gly Lys Ser Gly Gly Gly Lys Ser
1               5                   10                  15
```

<210> SEQ ID NO 37
<211> LENGTH: 15
<212> TYPE: PRT
<213> ORGANISM: Artificial Sequence

```
<220> FEATURE:
<223> OTHER INFORMATION: Linker 14

<400> SEQUENCE: 37

Gly Lys Gly Lys Ser Gly Lys Gly Lys Ser Gly Lys Gly Lys Ser
1               5                   10                  15

<210> SEQ ID NO 38
<211> LENGTH: 15
<212> TYPE: PRT
<213> ORGANISM: Artificial Sequence
<220> FEATURE:
<223> OTHER INFORMATION: Linker 15

<400> SEQUENCE: 38

Gly Gly Gly Lys Ser Gly Gly Lys Gly Ser Gly Lys Gly Gly Ser
1               5                   10                  15

<210> SEQ ID NO 39
<211> LENGTH: 15
<212> TYPE: PRT
<213> ORGANISM: Artificial Sequence
<220> FEATURE:
<223> OTHER INFORMATION: Linker 16

<400> SEQUENCE: 39

Gly Lys Pro Gly Ser Gly Lys Pro Gly Ser Gly Lys Pro Gly Ser
1               5                   10                  15

<210> SEQ ID NO 40
<211> LENGTH: 20
<212> TYPE: PRT
<213> ORGANISM: Artificial Sequence
<220> FEATURE:
<223> OTHER INFORMATION: Linker 17

<400> SEQUENCE: 40

Gly Lys Pro Gly Ser Gly Lys Pro Gly Ser Gly Lys Pro Gly Ser Gly
1               5                   10                  15

Lys Pro Gly Ser
            20

<210> SEQ ID NO 41
<211> LENGTH: 20
<212> TYPE: PRT
<213> ORGANISM: Artificial Sequence
<220> FEATURE:
<223> OTHER INFORMATION: Linker 18

<400> SEQUENCE: 41

Gly Lys Gly Lys Ser Gly Lys Gly Lys Ser Gly Lys Gly Lys Ser Gly
1               5                   10                  15

Lys Gly Lys Ser
            20

<210> SEQ ID NO 42
<211> LENGTH: 14
<212> TYPE: PRT
<213> ORGANISM: Artificial Sequence
<220> FEATURE:
<223> OTHER INFORMATION: Linker 19

<400> SEQUENCE: 42

Ser Thr Ala Gly Asp Thr His Leu Gly Gly Glu Asp Phe Asp
1               5                   10
```

```
<210> SEQ ID NO 43
<211> LENGTH: 15
<212> TYPE: PRT
<213> ORGANISM: Artificial Sequence
<220> FEATURE:
<223> OTHER INFORMATION: Linker 20

<400> SEQUENCE: 43

Gly Glu Gly Gly Ser Gly Glu Gly Gly Ser Gly Glu Gly Gly Ser
1               5                   10                  15

<210> SEQ ID NO 44
<211> LENGTH: 15
<212> TYPE: PRT
<213> ORGANISM: Artificial Sequence
<220> FEATURE:
<223> OTHER INFORMATION: Linker 21

<400> SEQUENCE: 44

Gly Gly Glu Gly Ser Gly Gly Glu Gly Ser Gly Gly Glu Gly Ser
1               5                   10                  15

<210> SEQ ID NO 45
<211> LENGTH: 15
<212> TYPE: PRT
<213> ORGANISM: Artificial Sequence
<220> FEATURE:
<223> OTHER INFORMATION: Linker 22

<400> SEQUENCE: 45

Gly Glu Gly Glu Ser Gly Glu Gly Glu Ser Gly Glu Gly Glu Ser
1               5                   10                  15

<210> SEQ ID NO 46
<211> LENGTH: 15
<212> TYPE: PRT
<213> ORGANISM: Artificial Sequence
<220> FEATURE:
<223> OTHER INFORMATION: Linker 23

<400> SEQUENCE: 46

Gly Gly Gly Glu Ser Gly Gly Glu Gly Ser Gly Glu Gly Gly Ser
1               5                   10                  15

<210> SEQ ID NO 47
<211> LENGTH: 20
<212> TYPE: PRT
<213> ORGANISM: Artificial Sequence
<220> FEATURE:
<223> OTHER INFORMATION: Linker 24

<400> SEQUENCE: 47

Gly Glu Gly Glu Ser Gly Glu Gly Glu Ser Gly Glu Gly Glu Ser Gly
1               5                   10                  15

Glu Gly Glu Ser
            20

<210> SEQ ID NO 48
<211> LENGTH: 18
<212> TYPE: PRT
<213> ORGANISM: Artificial Sequence
<220> FEATURE:
<223> OTHER INFORMATION: Linker 25

<400> SEQUENCE: 48

Gly Ser Thr Ser Gly Ser Gly Lys Pro Gly Ser Gly Glu Gly Ser Thr
```

```
1               5                   10                  15

Lys Gly

<210> SEQ ID NO 49
<211> LENGTH: 19
<212> TYPE: PRT
<213> ORGANISM: Artificial Sequence
<220> FEATURE:
<223> OTHER INFORMATION: Linker 26

<400> SEQUENCE: 49

Pro Arg Gly Ala Ser Lys Ser Gly Ser Ala Ser Gln Thr Gly Ser Ala
1               5                   10                  15

Pro Gly Ser

<210> SEQ ID NO 50
<211> LENGTH: 19
<212> TYPE: PRT
<213> ORGANISM: Artificial Sequence
<220> FEATURE:
<223> OTHER INFORMATION: Linker 27

<400> SEQUENCE: 50

Gly Thr Ala Ala Ala Gly Ala Gly Ala Ala Gly Gly Ala Ala Ala Gly
1               5                   10                  15

Ala Ala Gly

<210> SEQ ID NO 51
<211> LENGTH: 19
<212> TYPE: PRT
<213> ORGANISM: Artificial Sequence
<220> FEATURE:
<223> OTHER INFORMATION: Linker 28

<400> SEQUENCE: 51

Gly Thr Ser Gly Ser Ser Gly Ser Gly Ser Gly Gly Ser Gly Ser Gly
1               5                   10                  15

Gly Gly Gly

<210> SEQ ID NO 52
<211> LENGTH: 20
<212> TYPE: PRT
<213> ORGANISM: Artificial Sequence
<220> FEATURE:
<223> OTHER INFORMATION: Linker 29

<400> SEQUENCE: 52

Gly Lys Pro Gly Ser Gly Lys Pro Gly Ser Gly Lys Pro Gly Ser Gly
1               5                   10                  15

Lys Pro Gly Ser
            20

<210> SEQ ID NO 53
<211> LENGTH: 4
<212> TYPE: PRT
<213> ORGANISM: Artificial Sequence
<220> FEATURE:
<223> OTHER INFORMATION: Linker 30

<400> SEQUENCE: 53

Gly Ser Gly Ser
1
```

```
<210> SEQ ID NO 54
<211> LENGTH: 10
<212> TYPE: PRT
<213> ORGANISM: Artificial Sequence
<220> FEATURE:
<223> OTHER INFORMATION: Linker 31

<400> SEQUENCE: 54

Ala Pro Ala Pro Ala Pro Ala Pro Ala Pro
1               5                   10

<210> SEQ ID NO 55
<211> LENGTH: 20
<212> TYPE: PRT
<213> ORGANISM: Artificial Sequence
<220> FEATURE:
<223> OTHER INFORMATION: Linker 32

<400> SEQUENCE: 55

Ala Pro Ala Pro Ala Pro Ala Pro Ala Pro Ala Pro Ala Pro Ala Pro
1               5                   10                  15

Ala Pro Ala Pro
            20

<210> SEQ ID NO 56
<211> LENGTH: 32
<212> TYPE: PRT
<213> ORGANISM: Artificial Sequence
<220> FEATURE:
<223> OTHER INFORMATION: Linker 33

<400> SEQUENCE: 56

Ala Glu Ala Ala Ala Lys Glu Ala Ala Ala Lys Glu Ala Ala Ala Ala
1               5                   10                  15

Lys Glu Ala Ala Ala Ala Lys Glu Ala Ala Ala Lys Ala Ala Ala Ala
                20                  25                  30

<210> SEQ ID NO 57
<211> LENGTH: 15
<212> TYPE: PRT
<213> ORGANISM: Homo sapiens

<400> SEQUENCE: 57

Glu Pro Lys Ser Cys Asp Lys Thr His Thr Cys Pro Pro Cys Pro
1               5                   10                  15

<210> SEQ ID NO 58
<211> LENGTH: 12
<212> TYPE: PRT
<213> ORGANISM: Homo sapiens

<400> SEQUENCE: 58

Glu Arg Lys Cys Cys Val Glu Cys Pro Pro Cys Pro
1               5                   10

<210> SEQ ID NO 59
<211> LENGTH: 62
<212> TYPE: PRT
<213> ORGANISM: Homo sapiens

<400> SEQUENCE: 59

Glu Leu Lys Thr Pro Leu Gly Asp Thr Thr His Thr Cys Pro Arg Cys
1               5                   10                  15

Pro Glu Pro Lys Ser Cys Asp Thr Pro Pro Pro Cys Pro Arg Cys Pro
                20                  25                  30
```

-continued

Glu Pro Lys Ser Cys Asp Thr Pro Pro Cys Pro Arg Cys Pro Glu
             35                   40                  45

Pro Lys Ser Cys Asp Thr Pro Pro Cys Pro Arg Cys Pro
     50                  55                  60

<210> SEQ ID NO 60
<211> LENGTH: 12
<212> TYPE: PRT
<213> ORGANISM: Homo sapiens

<400> SEQUENCE: 60

Glu Ser Lys Tyr Gly Pro Pro Cys Pro Ser Cys Pro
1               5                   10

<210> SEQ ID NO 61
<211> LENGTH: 63
<212> TYPE: DNA
<213> ORGANISM: Mus musculus

<400> SEQUENCE: 61
atggccagga gccccgccca gctgctgggc ctgctgctgc tgtggctgag cggcgccagg      60
tgc                                                                    63

<210> SEQ ID NO 62
<211> LENGTH: 21
<212> TYPE: PRT
<213> ORGANISM: Mus musculus

<400> SEQUENCE: 62

Met Ala Arg Ser Pro Ala Gln Leu Leu Gly Leu Leu Leu Leu Trp Leu
1               5                   10                  15

Ser Gly Ala Arg Cys
            20

<210> SEQ ID NO 63
<211> LENGTH: 36
<212> TYPE: DNA
<213> ORGANISM: Artificial Sequence
<220> FEATURE:
<223> OTHER INFORMATION: Short Hinge

<400> SEQUENCE: 63
gagagcaagt atgggccccc ttgtcctcct tgtccg                                36

<210> SEQ ID NO 64
<211> LENGTH: 12
<212> TYPE: PRT
<213> ORGANISM: Artificial Sequence
<220> FEATURE:
<223> OTHER INFORMATION: Short Hinge

<400> SEQUENCE: 64

Glu Ser Lys Tyr Gly Pro Pro Cys Pro Pro Cys Pro
1               5                   10

<210> SEQ ID NO 65
<211> LENGTH: 357
<212> TYPE: DNA
<213> ORGANISM: Artificial Sequence
<220> FEATURE:
<223> OTHER INFORMATION: Medium Hinge

<400> SEQUENCE: 65

```
gagagcaagt atgggccccc ttgtcctcct tgtccggggc agccccgaga gccacaggtg    60
tacactctgc caccaagtca ggaggagatg accaagaacc aggtcagcct gacctgcctg   120
gtcaaaggct tctaccccag cgacatcgcc gtggagtggg agagcaatgg cagccggag    180 aacaactaca agaccacgcc tcccgtgctg gactccgacg gctccttctt cctctacagc   240
aggctcaccg tggacaagag caggtggcag gaggggaatg tcttctcatg ctccgtgatg   300
catgaggctc tgcacaacca ctacacacag aagagcctct ccctgtctct gggaaag     357
```

```
<210> SEQ ID NO 66
<211> LENGTH: 119
<212> TYPE: PRT
<213> ORGANISM: Artificial Sequence
<220> FEATURE:
<223> OTHER INFORMATION: Medium Hinge

<400> SEQUENCE: 66

Glu Ser Lys Tyr Gly Pro Pro Cys Pro Pro Cys Pro Gly Gln Pro Arg
1               5                   10                  15

Glu Pro Gln Val Tyr Thr Leu Pro Pro Ser Gln Glu Glu Met Thr Lys
            20                  25                  30

Asn Gln Val Ser Leu Thr Cys Leu Val Lys Gly Phe Tyr Pro Ser Asp
        35                  40                  45

Ile Ala Val Glu Trp Glu Ser Asn Gly Gln Pro Glu Asn Asn Tyr Lys
    50                  55                  60

Thr Thr Pro Pro Val Leu Asp Ser Asp Gly Ser Phe Phe Leu Tyr Ser
65                  70                  75                  80

Arg Leu Thr Val Asp Lys Ser Arg Trp Gln Gln Gly Asn Val Phe Ser
                85                  90                  95

Cys Ser Val Met His Glu Ala Leu His Asn His Tyr Thr Gln Lys Ser
                100                 105                 110

Leu Ser Leu Ser Leu Gly Lys
        115
```

```
<210> SEQ ID NO 67
<211> LENGTH: 684
<212> TYPE: DNA
<213> ORGANISM: Artificial Sequence
<220> FEATURE:
<223> OTHER INFORMATION: Long Hinge

<400> SEQUENCE: 67
gagtctaagt atgggccccc ttgtcctcct tgtccggcac ctcccgtggc tggaccaagt    60
gtattcttat ttcccccaaa acccaaagat actctcatga tttcccggac ccctgaggtt   120
acatgcgtgg tggtggatgt gagccaggaa gaccccgaag tccagtttaa ctggtacgtg   180
gatggagtgg aggtgcataa tgcaaagaca aagcctcggg aagaacagtt tcagagcaca   240
taccgtgtgg ttagtgtcct cacagttctg caccaggact ggctgaacgg caaggagtat   300
aagtgtaagg tctccaataa aggcctcccg tcatcgatcg aaaaaaccat cagtaaagcc   360
aaagggcagc caaggagcc acaggtgtat actttaccac caagtcagga ggaaatgacc   420
aagaaccagg tatctctgac ctgcctagtc aaaggctttt accccagcga tatcgctgtg   480
gagtgggagt ctaatgggca gccagagaac aactacaaga ccacacctcc tgtgctggac   540
tccgatggct ccttctttct atacagcagg ttaaccgtgg ataagagcag gtggcaggag   600
gggaatgtct ctcatgctc tgtgatgcat gaggctctgc acaaccacta cacacagaag   660
agcctctccc tgtctctggg aaag                                         684
```

<210> SEQ ID NO 68
<211> LENGTH: 228
<212> TYPE: PRT
<213> ORGANISM: Artificial Sequence
<220> FEATURE:
<223> OTHER INFORMATION: Long Hinge

<400> SEQUENCE: 68

```
Glu Ser Lys Tyr Gly Pro Pro Cys Pro Pro Cys Pro Ala Pro Pro Val
1               5                   10                  15

Ala Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

Gln Glu Asp Pro Glu Val Gln Phe Asn Trp Tyr Val Asp Gly Val Glu
    50                  55                  60

Val His Asn Ala Lys Thr Lys Pro Arg Glu Glu Gln Phe Gln Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Gly Leu Pro Ser Ser
            100                 105                 110

Ile Glu Lys Thr Ile Ser Lys Ala Lys Gly Gln Pro Arg Glu Pro Gln
        115                 120                 125

Val Tyr Thr Leu Pro Pro Ser Gln Glu Glu Met Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Arg Leu Thr
            180                 185                 190

Val Asp Lys Ser Arg Trp Gln Glu Gly Asn Val Phe Ser Cys Ser Val
        195                 200                 205

Met His Glu Ala Leu His Asn His Tyr Thr Gln Lys Ser Leu Ser Leu
    210                 215                 220

Ser Leu Gly Lys
225
```

<210> SEQ ID NO 69
<211> LENGTH: 735
<212> TYPE: DNA
<213> ORGANISM: Artificial Sequence
<220> FEATURE:
<223> OTHER INFORMATION: Herceptin scFv

<400> SEQUENCE: 69

| | | |
|---|---|---|
| gacatccaga tgactcagtc accatcaagc ctgagtgcat ccgtgggcga tcgagtgaca | 60 |
| ataacatgta gagcgagcca ggatgtaaat acggcagtag cgtggtacca acagaaaccc | 120 |
| ggcaaggctc ctaagctgtt aatctacagc gccagcttcc tttatagtgg agtgccttca | 180 |
| aggttctcag gatctaggtc cggtactgac ttcacgctga caatctcgag cctacaaccc | 240 |
| gaggacttcg ccacttatta ctgccagcag cattacacta ctcctcccac attcggacag | 300 |
| ggaaccaaag tcgagatcaa aggatcaacc tctggatctg caagcccgg gagcggggaa | 360 |
| ggctctacta agggtgaggt gcaactagtg gagagtggcg gagggctcgt ccagccagga | 420 |

```
ggttccctga ggctgagttg cgctgcaagc ggattcaata tcaaggacac gtacatacac    480
tgggtgcgcc aggcccccgg aaagggactg gagtgggtcg cccgaatcta tcctactaat    540
ggctacacca gtatgctga ttcagtgaaa ggaaggttta caatctctgc cgatacttca    600
aagaatacag cttatctaca gatgaattca cttagagccg aggatacagc cgtgtattat    660
tgctcccgat ggggaggaga tgggttctac gctatggact actggggtca aggaaccctg    720
gtgaccgtta gttca                                                    735
```

```
<210> SEQ ID NO 70
<211> LENGTH: 245
<212> TYPE: PRT
<213> ORGANISM: Artificial Sequence
<220> FEATURE:
<223> OTHER INFORMATION: Herceptin scFv

<400> SEQUENCE: 70
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Gly Ser Thr Ser Gly
            100                 105                 110

Ser Gly Lys Pro Gly Ser Gly Glu Ser Thr Lys Gly Glu Val Gln
        115                 120                 125

Leu Val Glu Ser Gly Gly Gly Leu Val Gln Pro Gly Gly Ser Leu Arg
130                 135                 140

Leu Ser Cys Ala Ala Ser Gly Phe Asn Ile Lys Asp Thr Tyr Ile His
145                 150                 155                 160

Trp Val Arg Gln Ala Pro Gly Lys Gly Leu Glu Trp Val Ala Arg Ile
                165                 170                 175

Tyr Pro Thr Asn Gly Tyr Thr Arg Tyr Ala Asp Ser Val Lys Gly Arg
            180                 185                 190

Phe Thr Ile Ser Ala Asp Thr Ser Lys Asn Thr Ala Tyr Leu Gln Met
        195                 200                 205

Asn Ser Leu Arg Ala Glu Asp Thr Ala Val Tyr Tyr Cys Ser Arg Trp
    210                 215                 220

Gly Gly Asp Gly Phe Tyr Ala Met Asp Tyr Trp Gly Gln Gly Thr Leu
225                 230                 235                 240

Val Thr Val Ser Ser
                245

```
<210> SEQ ID NO 71
<211> LENGTH: 107
<212> TYPE: PRT
<213> ORGANISM: Artificial Sequence
<220> FEATURE:
<223> OTHER INFORMATION: Herceptin scFv VL
```

-continued

<400> SEQUENCE: 71

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105

<210> SEQ ID NO 72
<211> LENGTH: 120
<212> TYPE: PRT
<213> ORGANISM: Artificial Sequence
<220> FEATURE:
<223> OTHER INFORMATION: Herceptin scFv VH

<400> SEQUENCE: 72

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
        115                 120

<210> SEQ ID NO 73
<211> LENGTH: 732
<212> TYPE: DNA
<213> ORGANISM: Artificial Sequence
<220> FEATURE:
<223> OTHER INFORMATION: scFv69 (Herceptin anti-ID)

<400> SEQUENCE: 73
tcttctgagc tgactcagga ccctgctgtg tctgtggcct tgggacagac agtcaggatc        60
acatgccaag agacagcct cagaagctat tatgcaagct ggtaccagca gaagccagga        120
caggcccctg tacttgtcat ctatggtaaa acaaccggc cctcaggat cccagaccga        180 ttctctggct ccagctcagg aaacacagct tccttgacca tcactgggc tcaggcggaa       240 gatgaggctg actattactg taacagcagt gaaccaaccc caccaagagt ggtcttcggc       300
ggcggaacaa aactgacagt gctgggctct acaagcggca gcggcaaacc tggatctggc      360

```
gagggatcta ccaagggcga ggtgcaacta ttggaaagtg gtggcgggct ggtccaaccg    420
ggcgggtcct tgaggctgtc ctgtgcagcc agcgggttta cttttcttc ctacgccatg     480 tcttgggtac gacaggctcc cggaaaaggg ctcgagtggg tgagtgcaat ctccgggagt    540
gggggctcta cctactacgc cgattctgtc aagggtaggt tcactatctc agggataat    600 tcaaagaata ctttatacct gcagatgaat tcactgcgag cggaagatac agcagtgtac    660
tattgtgcca agaacgtgca catccagccc tttgattact ggggccaggg caccagcgtg    720
accgtgtcta gc                                                        732
```

<210> SEQ ID NO 74
<211> LENGTH: 244
<212> TYPE: PRT
<213> ORGANISM: Artificial Sequence
<220> FEATURE:
<223> OTHER INFORMATION: scFv69 (Herceptin anti-ID)

<400> SEQUENCE: 74

```
Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
                20                  25                  30

Ser Trp Tyr Gln Gln Lys Pro Gly Gln Ala Pro Val Leu Val Ile Tyr
            35                  40                  45

Gly Lys Asn Asn Arg Pro Ser Gly Ile Pro Asp Arg Phe Ser Gly Ser
        50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Ser Glu Pro Thr Pro Pro Arg
                85                  90                  95

Val Val Phe Gly Gly Gly Thr Lys Leu Thr Val Leu Gly Ser Thr Ser
                100                 105                 110

Gly Ser Gly Lys Pro Gly Ser Gly Glu Gly Ser Thr Lys Gly Glu Val
            115                 120                 125

Gln Leu Leu Glu Ser Gly Gly Gly Leu Val Gln Pro Gly Gly Ser Leu
        130                 135                 140

Arg Leu Ser Cys Ala Ala Ser Gly Phe Thr Phe Ser Ser Tyr Ala Met
145                 150                 155                 160

Ser Trp Val Arg Gln Ala Pro Gly Lys Gly Leu Glu Trp Val Ser Ala
                165                 170                 175

Ile Ser Gly Ser Gly Gly Ser Thr Tyr Tyr Ala Asp Ser Val Lys Gly
            180                 185                 190

Arg Phe Thr Ile Ser Arg Asp Asn Ser Lys Asn Thr Leu Tyr Leu Gln
        195                 200                 205

Met Asn Ser Leu Arg Ala Glu Asp Thr Ala Val Tyr Tyr Cys Ala Lys
210                 215                 220

Asn Val His Ile Gln Pro Phe Asp Tyr Trp Gly Gln Gly Thr Ser Val
225                 230                 235                 240

Thr Val Ser Ser
```

<210> SEQ ID NO 75
<211> LENGTH: 108
<212> TYPE: PRT
<213> ORGANISM: Artificial Sequence
<220> FEATURE:
<223> OTHER INFORMATION: scFv69 VL

<400> SEQUENCE: 75

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Ser Glu Pro Thr Pro Pro Arg
                85                  90                  95

Val Val Phe Gly Gly Gly Thr Lys Leu Thr Val Leu
            100                 105

<210> SEQ ID NO 76
<211> LENGTH: 118
<212> TYPE: PRT
<213> ORGANISM: Artificial Sequence
<220> FEATURE:
<223> OTHER INFORMATION: scFv69 VH

<400> SEQUENCE: 76

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asn Val His Ile Gln Pro Phe Asp Tyr Trp Gly Gln Gly Thr
            100                 105                 110

Ser Val Thr Val Ser Ser
        115

<210> SEQ ID NO 77
<211> LENGTH: 381
<212> TYPE: DNA
<213> ORGANISM: Artificial Sequence
<220> FEATURE:
<223> OTHER INFORMATION: 9G8 VHH (anti-EGFR)

<400> SEQUENCE: 77
gaagtgcagc ttgtggagag tggcggtggt ttagttcaac aggggggcag cctgcgcttg    60
agttgtgccg catcgggtcg tacctttttct agctacgcaa tggggtggtt tcgtcaagct   120
cctgggaagg aacgtgagtt tgtggtcgcc attaattggt catcagggag tacatactac   180
gctgattccg tcaaagggcg ctttacaatc tcacgcgata acagcaagaa tacccttttat  240 ttacaaatga atagtctgcg tgcagaagat acggctgtgt attactcgcg tgcggggtac   300
caaatcaact ctgggaatta aactttaag gactacgagt atgattattg gggccagggc    360

```
actcaggtta cagtctcgag c                                              381
```

<210> SEQ ID NO 78
<211> LENGTH: 127
<212> TYPE: PRT
<213> ORGANISM: Artificial Sequence
<220> FEATURE:
<223> OTHER INFORMATION: 9G8 VHH (anti-EGFR)

<400> SEQUENCE: 78

```
Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Ser Tyr
            20                  25                  30

Ala Met Gly Trp Phe Arg Gln Ala Pro Gly Lys Glu Arg Glu Phe Val
        35                  40                  45

Val Ala Ile Asn Trp Ser Ser Gly Ser Thr Tyr Tyr Ala Asp Ser Val
    50                  55                  60

Lys Gly Arg Phe Thr Ile Ser Arg Asp Asn Ala Lys Asn Thr Met Tyr
65                  70                  75                  80

Leu Gln Met Asn Ser Leu Lys Pro Glu Asp Thr Ala Val Tyr Tyr Cys
                85                  90                  95

Ala Ala Gly Tyr Gln Ile Asn Ser Gly Asn Tyr Asn Phe Lys Asp Tyr
            100                 105                 110

Glu Tyr Asp Tyr Trp Gly Gln Gly Thr Gln Val Thr Val Ser Ser
        115                 120                 125
```

<210> SEQ ID NO 79
<211> LENGTH: 66
<212> TYPE: DNA
<213> ORGANISM: Artificial Sequence
<220> FEATURE:
<223> OTHER INFORMATION: T2A Sequence

<400> SEQUENCE: 79

```
ggatccggcg ccacaaactt cagcctgctg aaacaggccg gcgacgtgga ggaaaaccca    60
ggccca                                                               66
```

<210> SEQ ID NO 80
<211> LENGTH: 22
<212> TYPE: PRT
<213> ORGANISM: Artificial Sequence
<220> FEATURE:
<223> OTHER INFORMATION: T2A Sequence

<400> SEQUENCE: 80

```
Gly Ser Gly Ala Thr Asn Phe Ser Leu Leu Lys Gln Ala Gly Asp Val
1               5                   10                  15

Glu Glu Asn Pro Gly Pro
            20
```

<210> SEQ ID NO 81
<211> LENGTH: 714
<212> TYPE: DNA
<213> ORGANISM: Artificial Sequence
<220> FEATURE:
<223> OTHER INFORMATION: GFP

<400> SEQUENCE: 81

```
gtgtccaagg gcgaagaact gttcaccggc gtggtgccca ttctggtgga actggacggg    60
gatgtgaacg gccacaagtt cagcgttaga ggcgaaggcg aaggggatgc cacaaacggc   120
```

-continued

```
aagctgaccc tgaagttcat ctgcaccacc ggaaagctgc ccgtgccttg gcctacactg      180
gtcaccacac tgacatacgg cgtgcagtgc ttcagcagat accccgacca tatgaagcag      240
cacgacttct tcaagagcgc catgcctgag ggctacgtgc aagagagaac catcaccttc      300
aaggacgacg gcacctacaa gaccagagcc gaagtgaagt tcgagggcga caccctggtc      360
aaccggatcg agctgaaggg catcgacttc aaagaggacg gcaacatcct gggccacaaa      420
cttgagtaca acttcaacag ccacaacgtg tatatcaccg ccgacaagca gaagaacggc      480
atcaaggcca acttcaagat ccggcacaac gtggaagatg gcagcgtgca gctggccgat      540
cactaccagc agaacacacc catcggagat ggccctgtgc tgctgcccga taaccactac      600
ctgagcaccc agagcaagct gagcaaggac cccaacgaga gcgggaccca tggtgctg       660 ctggaatttg tgacagccgc cggaatcacc cacggcatgg atgagctgta caag           714
```

```
<210> SEQ ID NO 82
<211> LENGTH: 238
<212> TYPE: PRT
<213> ORGANISM: Artificial Sequence
<220> FEATURE:
<223> OTHER INFORMATION: GFP

<400> SEQUENCE: 82
```

Val Ser Lys Gly Glu Glu Leu Phe Thr Gly Val Val Pro Ile Leu Val
1               5                   10                  15

Glu Leu Asp Gly Asp Val Asn Gly His Lys Phe Ser Val Arg Gly Glu
            20                  25                  30

Gly Glu Gly Asp Ala Thr Asn Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Thr Tyr Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Thr Phe Lys Asp Asp Gly Thr Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Phe Asn Ser His Asn Val Tyr Ile Thr Ala Asp Lys Gln Lys Asn Gly
145                 150                 155                 160

Ile Lys Ala Asn Phe Lys Ile Arg His Asn Val Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Lys Leu Ser
        195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Lys
225                 230                 235

```
<210> SEQ ID NO 83
<211> LENGTH: 354
```

-continued

```
<212> TYPE: DNA
<213> ORGANISM: Artificial Sequence
<220> FEATURE:
<223> OTHER INFORMATION: Listeria internalin 6dyx

<400> SEQUENCE: 83
caggtgaagt tggaagagtc tggtggtggc ctcgtccagg ctggggggag tcttcgcctt     60
agttgcgcag cttcaggtcg gacatacagc acttacgcga tggggtggtt tcgccagact    120
ccggggaagg agagagaatt ggtggcagca ataaattggt caggggggcaa cacgcactat   180 gcagactctg taaaaggccg gttcacgatc agtagagata cgccaagag caccgtctac     240 ctccagatga attccctgaa acctgaggac acagcagttt attactgtgc cgctccgaaa    300
ggccacacag gggatcatta ctggggaccc ggcacccaag tgactgtgag ctcg          354

<210> SEQ ID NO 84
<211> LENGTH: 118
<212> TYPE: PRT
<213> ORGANISM: Artificial Sequence
<220> FEATURE:
<223> OTHER INFORMATION: Listeria internalin 6dyx

<400> SEQUENCE: 84

Gln Val Lys Leu Glu Glu Ser Gly Gly Gly Leu Val Gln Ala Gly
 1               5                   10                  15

Ser Leu Arg Leu Ser Cys Ala Ala Ser Gly Arg Thr Tyr Ser Thr Tyr
            20                  25                  30

Ala Met Gly Trp Phe Arg Gln Thr Pro Gly Lys Glu Arg Glu Leu Val
        35                  40                  45

Ala Ala Ile Asn Trp Ser Gly Gly Asn Thr His Tyr Ala Asp Ser Val
    50                  55                  60

Lys Gly Arg Phe Thr Ile Ser Arg Asp Asn Ala Lys Ser Thr Val Tyr
65                  70                  75                  80

Leu Gln Met Asn Ser Leu Lys Pro Glu Asp Thr Ala Val Tyr Tyr Cys
                85                  90                  95

Ala Ala Pro Lys Gly His Thr Gly Asp His Tyr Trp Gly Pro Gly Thr
            100                 105                 110

Gln Val Thr Val Ser Ser
        115

<210> SEQ ID NO 85
<211> LENGTH: 372
<212> TYPE: DNA
<213> ORGANISM: Artificial Sequence
<220> FEATURE:
<223> OTHER INFORMATION: Naja kaouthia phospholipase A2 P3-3

<400> SEQUENCE: 85
caggtgcaac tcgttgaaag tggaggcggt agcgttcagg caggtggaag cctcaggctg     60
tcctgtgcgg ccagtagaga cacgtatgat tcacactgta tggggtggtt ccggcaagcg    120
cccggaaaag agagggaaca ggtggcggca cataacggtg gccgaaacac atattacgca    180
gatagcgtta aggacgatt tacaatatct caggacaatg ctaagaatac gatgtatctc     240
caaatgaata gccttaaacc tgaagataca gccatttact actgcgccgc ggacatgtcc    300
gcgagaaggg tcgcaaacac aggatgcaga tacaattatt ggggccaagg cactttggta    360
actgtgagct cg                                                         372

<210> SEQ ID NO 86
```

<210> SEQ ID NO 86
<211> LENGTH: 124
<212> TYPE: PRT
<213> ORGANISM: Artificial Sequence
<220> FEATURE:
<223> OTHER INFORMATION: Naja kaouthia phospholipase A2 P3-3

<400> SEQUENCE: 86

Gln Val Gln Leu Val Glu Ser Gly Gly Gly Ser Val Gln Ala Gly Gly
1               5                   10                  15

Ser Leu Arg Leu Ser Cys Ala Ala Ser Arg Asp Thr Tyr Asp Ser His
            20                  25                  30

Cys Met Gly Trp Phe Arg Gln Ala Pro Gly Lys Glu Arg Glu Gln Val
        35                  40                  45

Ala Ala His Asn Gly Gly Arg Asn Thr Tyr Tyr Ala Asp Ser Val Lys
    50                  55                  60

Gly Arg Phe Thr Ile Ser Gln Asp Asn Ala Lys Asn Thr Met Tyr Leu
65                  70                  75                  80

Gln Met Asn Ser Leu Lys Pro Glu Asp Thr Ala Ile Tyr Tyr Cys Ala
                85                  90                  95

Ala Asp Met Ser Ala Arg Arg Val Ala Asn Thr Gly Cys Arg Tyr Asn
            100                 105                 110

Tyr Trp Gly Gln Gly Thr Leu Val Thr Val Ser Ser
        115                 120

<210> SEQ ID NO 87
<211> LENGTH: 345
<212> TYPE: DNA
<213> ORGANISM: Artificial Sequence
<220> FEATURE:
<223> OTHER INFORMATION: Ebola nucleoprotein anti-Z C

<400> SEQUENCE: 87
caggtgcaac ttcaacaaag cggcggggga tccgtaacgc caggtggatc actgcggctt     60
tcttgtgctg cttccggatc catttcagac tttgctgcta tggcatggta tcggcaggcc    120
cctggcaaag aaagggattg gttttttgga accatattct cagcaggtgc tttgttgtac    180
gcagaaccag ttaaaggtcg gtttaccata tcaagggata cgctaagaa tactgtatat     240
cttcaaatga acagtttgaa accagaggat actgccgtat actattgtcg cctctatgct    300
aaggcaattt attggggtca gggcacacag gtaacggtga gctcg                    345

<210> SEQ ID NO 88
<211> LENGTH: 115
<212> TYPE: PRT
<213> ORGANISM: Artificial Sequence
<220> FEATURE:
<223> OTHER INFORMATION: Ebola nucleoprotein anti-Z C

<400> SEQUENCE: 88

Lys Val Gln Leu Gln Gln Ser Gly Gly Gly Ser Val Thr Pro Gly Gly
1               5                   10                  15

Ser Leu Arg Leu Ser Cys Ala Ala Ser Gly Ser Ile Ser Asp Phe Ala
            20                  25                  30

Ala Met Ala Trp Tyr Arg Gln Ala Pro Gly Lys Glu Arg Asp Trp Val
        35                  40                  45

Phe Gly Thr Ile Phe Ser Ala Gly Ala Leu Leu Tyr Ala Glu Pro Val
    50                  55                  60

Lys Gly Arg Phe Thr Ile Ser Arg Asp Asn Ala Lys Asn Thr Val Tyr
65                  70                  75                  80

```
Leu Gln Met Asn Ser Leu Lys Pro Glu Asp Thr Ala Val Tyr Tyr Cys
                85                  90                  95

Arg Leu Tyr Ala Lys Ala Ile Tyr Trp Gly Gln Gly Thr Gln Val Thr
            100                 105                 110

Val Ser Ser
        115

<210> SEQ ID NO 89
<211> LENGTH: 372
<212> TYPE: DNA
<213> ORGANISM: Artificial Sequence
<220> FEATURE:
<223> OTHER INFORMATION: Herpes simplex virus: Glycoprotein D

<400> SEQUENCE: 89
caggtgcaac ttcaggctag tggaggggga ctggtgcaag ctggcgggtc tttgcgactg    60
tcctgtgcag cctcaggccg agctacaggc aattatccca tgggatggtt ccgccaggcc   120
cctggaaaag aacgcgagtt cgttgcagcc atcagtcggg acgcgacag tacatactac    180 cgggatagtg ttaaaggccg atttaccata tcccgagaca atacgaaaaa tacggcatat   240
cttcagatga acagtcttaa gccggaggac acagccgtct actattgtgc agctgaccgg   300
ctgacagcat atcgatacaa tccagggcag attgactatt ggggacaggg tacacaagtt   360
acggtgagct cg                                                       372

<210> SEQ ID NO 90
<211> LENGTH: 124
<212> TYPE: PRT
<213> ORGANISM: Artificial Sequence
<220> FEATURE:
<223> OTHER INFORMATION: Herpes simplex virus: Glycoprotein D

<400> SEQUENCE: 90

Glu Val Gln Leu Gln Ala Ser Gly Gly Gly Leu Val Gln Ala Gly Gly
1               5                   10                  15

Ser Leu Arg Leu Ser Cys Ala Ala Ser Gly Arg Ala Thr Gly Asn Tyr
            20                  25                  30

Pro Met Gly Trp Phe Arg Gln Ala Pro Gly Lys Glu Arg Glu Phe Val
        35                  40                  45

Ala Ala Ile Ser Arg Asp Gly Asp Ser Thr Tyr Tyr Arg Asp Ser Val
    50                  55                  60

Lys Gly Arg Phe Thr Ile Ser Arg Asp Asn Thr Lys Asn Thr Ala Tyr
65                  70                  75                  80

Leu Gln Met Asn Ser Leu Lys Pro Glu Asp Thr Ala Val Tyr Tyr Cys
                85                  90                  95

Ala Ala Asp Arg Leu Thr Ala Tyr Arg Tyr Asn Pro Gly Gln Ile Asp
            100                 105                 110

Tyr Trp Gly Gln Gly Thr Gln Val Thr Val Ser Ser
        115                 120

<210> SEQ ID NO 91
<211> LENGTH: 369
<212> TYPE: DNA
<213> ORGANISM: Artificial Sequence
<220> FEATURE:
<223> OTHER INFORMATION: Lacotococcal phage: RBP

<400> SEQUENCE: 91
caggtgcaac tggtcgaaag tggtgggggg ctcgttcaag ccggtggcag tttgcgcttg    60
```

```
tcatgcgccg ctagtgaaag taccttctct aactacgcga tgggatggtt caggcaagca    120
ccaggccctg aaagggaatt tgtggctacg atttctcaaa cagggtccca cacctactac    180
cgcaattctg tgaagggacg cttcacgatt agtcgggata acgccaagaa cacagtgtac    240
cttcaaatga acaatatgaa gcctgaagac acggccgtgt attattgtgc agccggagac    300
aactattact ataccagaac ttatgagtac gactactggg gccagggtac tcaggtcact    360
gtgagctcg                                                             369
```

<210> SEQ ID NO 92
<211> LENGTH: 123
<212> TYPE: PRT
<213> ORGANISM: Artificial Sequence
<220> FEATURE:
<223> OTHER INFORMATION: Lacotococcal phage: RBP

<400> SEQUENCE: 92

```
Gln Val Gln Leu Val Glu Ser Gly Gly Gly Leu Val Gln Ala Gly Gly
1               5                   10                  15

Ser Leu Arg Leu Ser Cys Ala Ala Ser Glu Ser Thr Phe Ser Asn Tyr
            20                  25                  30

Ala Met Gly Trp Phe Arg Gln Ala Pro Gly Pro Glu Arg Glu Phe Val
        35                  40                  45

Ala Thr Ile Ser Gln Thr Gly Ser His Thr Tyr Tyr Arg Asn Ser Val
    50                  55                  60

Lys Gly Arg Phe Thr Ile Ser Arg Asp Asn Ala Lys Asn Thr Val Tyr
65                  70                  75                  80

Leu Gln Met Asn Asn Met Lys Pro Glu Asp Thr Ala Val Tyr Tyr Cys
                85                  90                  95

Ala Ala Gly Asp Asn Tyr Tyr Tyr Thr Arg Thr Tyr Glu Tyr Asp Tyr
            100                 105                 110

Trp Gly Gln Gly Thr Gln Val Thr Val Ser Ser
        115                 120
```

<210> SEQ ID NO 93
<211> LENGTH: 375
<212> TYPE: DNA
<213> ORGANISM: Artificial Sequence
<220> FEATURE:
<223> OTHER INFORMATION: RSV: F-protein

<400> SEQUENCE: 93

```
caggtgcagt tggtcgagtc aggtggaggg tcagtgcagc caggggggtc ccttcgactt     60
agttgtgcag ccagtggttt tacactggat tactattaca ttgggtggtt tcgacaggcc    120
cccgggaagg aacgcgaggg tgtttcttgt atttccagct cacatggctc aacctattat    180
gctgactcag taaaggtcg gtttacgata agccgggata atgcaaagaa taccgtgtat    240
cttcaaatga atagccttaa accagaagat accgctgtgt actattgtgc cactatacgc    300
tctagctcat ggggggctg tgtccactac gggatggatt attgggggaa gggcacgcaa    360
gtcacggtga gctcg                                                      375
```

<210> SEQ ID NO 94
<211> LENGTH: 125
<212> TYPE: PRT
<213> ORGANISM: Artificial Sequence
<220> FEATURE:
<223> OTHER INFORMATION: RSV: F-protein

<400> SEQUENCE: 94

```
Gln Val Gln Leu Val Glu Ser Gly Gly Gly Ser Val Gln Pro Gly Gly
1               5                   10                  15

Ser Leu Arg Leu Ser Cys Ala Ala Ser Gly Phe Thr Leu Asp Tyr Tyr
            20                  25                  30

Tyr Ile Gly Trp Phe Arg Gln Ala Pro Gly Lys Glu Arg Glu Gly Val
        35                  40                  45

Ser Cys Ile Ser Ser Ser His Gly Ser Thr Tyr Tyr Ala Asp Ser Val
50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Thr Ile Arg Ser Ser Ser Trp Gly Gly Cys Val His Tyr Gly Met
            100                 105                 110

Asp Tyr Trp Gly Lys Gly Thr Gln Val Thr Val Ser Ser
            115                 120                 125

<210> SEQ ID NO 95
<211> LENGTH: 372
<212> TYPE: DNA
<213> ORGANISM: Artificial Sequence
<220> FEATURE:
<223> OTHER INFORMATION: Geobacillus stearothermophilus: SbsB

<400> SEQUENCE: 95
caggtgcagt tgcaagaaag tggaggggga ttggtgcagg caggtggatc tttgaggctg      60
tcctgtgcag cctctggtcg cactagctct gcgtacgcta tgggttggtt tcgacaggcc    120
cctgggaaag aacgcgagtt cgttgccggc atttcaagca aaggcggtag cacgtattat    180
ggtgccagca tgaaaggacg ctttacgata tcacgggata acgcgaaaaa tacggtctac    240
ttgcagatga acggtctggc cccagaagac acggcagtgt actactgcgc tgcgagcgac    300
aagtataatt tcgacaccag ccatgcggga tacggctatt ggggccaagg gacccaggtt    360
acagtgagct cg                                                       372

<210> SEQ ID NO 96
<211> LENGTH: 124
<212> TYPE: PRT
<213> ORGANISM: Artificial Sequence
<220> FEATURE:
<223> OTHER INFORMATION: Geobacillus stearothermophilus: SbsB

<400> SEQUENCE: 96

Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Thr Ser Ser Ala Tyr
            20                  25                  30

Ala Met Gly Trp Phe Arg Gln Ala Pro Gly Lys Glu Arg Glu Phe Val
        35                  40                  45

Ala Gly Ile Ser Ser Lys Gly Gly Ser Thr Tyr Tyr Gly Ala Ser Met
50                  55                  60

Lys Gly Arg Phe Thr Ile Ser Arg Asp Asn Ala Lys Asn Thr Val Tyr
65                  70                  75                  80

Leu Gln Met Asn Gly Leu Ala Pro Glu Asp Thr Ala Val Tyr Tyr Cys
                85                  90                  95

Ala Ala Ser Asp Lys Tyr Asn Phe Asp Thr Ser His Ala Gly Tyr Gly
            100                 105                 110
```

Tyr Trp Gly Gln Gly Thr Gln Val Thr Val Ser Ser
        115                 120

<210> SEQ ID NO 97
<211> LENGTH: 360
<212> TYPE: DNA
<213> ORGANISM: Artificial Sequence
<220> FEATURE:
<223> OTHER INFORMATION: Ricin (V5E4)

<400> SEQUENCE: 97
caggtgcaac tcgtggagac gggtggagga cttgtgcaag cgggcggaag ccttaggttg      60
agctgtgctg cgtctggatt tacatttagt agctatgcaa tgggctggtt cgccaggcg     120 ccggggaagg aacgcgactt cgttgcgggt atctcactta gcggcgccgg gacgtactat     180
gtaaaaggaa ggttcaccat ttcacgcgat aacgctaaaa acactgtcta tttgcagatg     240
aacagcctca aaccagagga tactgcagta tattactgta aggccacagg agaaaggggg     300
tatggagatc agggatatct tgaagtctgg gggagaggga cgctggttac cgtgagctcg     360

<210> SEQ ID NO 98
<211> LENGTH: 120
<212> TYPE: PRT
<213> ORGANISM: Artificial Sequence
<220> FEATURE:
<223> OTHER INFORMATION: Ricin (V5E4)

<400> SEQUENCE: 98

Gln Val Gln Leu Val Glu Thr Gly Gly Gly Leu Val Gln Ala Gly Gly
1               5                   10                  15

Ser Leu Arg Leu Ser Cys Ala Ala Ser Gly Phe Thr Phe Ser Ser Tyr
            20                  25                  30

Ala Met Gly Trp Phe Arg Gln Ala Pro Gly Lys Glu Arg Asp Phe Val
        35                  40                  45

Ala Gly Ile Ser Leu Ser Gly Ala Gly Thr Tyr Tyr Val Lys Gly Arg
    50                  55                  60

Phe Thr Ile Ser Arg Asp Asn Ala Lys Asn Thr Val Tyr Leu Gln Met
65                  70                  75                  80

Asn Ser Leu Lys Pro Glu Asp Thr Ala Val Tyr Tyr Cys Lys Ala Thr
                85                  90                  95

Gly Glu Arg Gly Tyr Gly Asp Gln Gly Tyr Leu Glu Val Trp Gly Arg
            100                 105                 110

Gly Thr Leu Val Thr Val Ser Ser
        115                 120

<210> SEQ ID NO 99
<211> LENGTH: 384
<212> TYPE: DNA
<213> ORGANISM: Artificial Sequence
<220> FEATURE:
<223> OTHER INFORMATION: Lyso CW P01 B10

<400> SEQUENCE: 99
caggtgcaac ttgtggagag cggggtggt ctcgtccagg ctggtggctc acttcgcctc      60
tcctgcgcgg ctagcggcgg gatattctca ggtggaagaa tgggctggtt cagacaagct     120
ccaggtaaag agagagagtt cgtagcggcg gtaatcactc gcgggggtc tacttattat     180 gcggactctg tgaagggtag atttacaatt tcacgggaca cgcaaagaa tactgtgtac     240 cttcaaatga actcacttaa acctgaggac acggcggttt attactgcgc tgcaagcgag     300

```
gtaacctatg acgagggaca ttacatcgga accaaatcca cttacgacac ttggggacag    360
ggcacgcagg taactgtgag ctcg                                           384
```

<210> SEQ ID NO 100
<211> LENGTH: 128
<212> TYPE: PRT
<213> ORGANISM: Artificial Sequence
<220> FEATURE:
<223> OTHER INFORMATION: Lyso CW P01 B10

<400> SEQUENCE: 100

```
Gln Val Gln Leu Val Glu Ser Gly Gly Gly Leu Val Gln Ala Gly Gly
1               5                   10                  15

Ser Leu Arg Leu Ser Cys Ala Ala Ser Gly Gly Ile Phe Ser Gly Gly
            20                  25                  30

Arg Met Gly Trp Phe Arg Gln Ala Pro Gly Lys Glu Arg Glu Phe Val
        35                  40                  45

Ala Ala Val Ile Thr Arg Gly Gly Ser Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Ser Glu Val Thr Tyr Asp Glu Gly His Tyr Ile Gly Thr Lys
            100                 105                 110

Ser Thr Tyr Asp Thr Trp Gly Gln Gly Thr Gln Val Thr Val Ser Ser
        115                 120                 125
```

<210> SEQ ID NO 101
<211> LENGTH: 384
<212> TYPE: DNA
<213> ORGANISM: Artificial Sequence
<220> FEATURE:
<223> OTHER INFORMATION: Lyso CW P01 B11

<400> SEQUENCE: 101

```
caggtgcagc tcgtagagtc cggggggaggt ctggtgcaag ctggaggttc cttgcgattg     60
tcatgtgcgg caagcggagg aatttttttct ggaggacgaa tggggtggtt ccgacaggca   120
ccgggaaaag agagggagtt cgtagctgcc gtgattacaa ggggtggtag cacatactat   180
gcagatagcg taaagggtag gtttacgata tccagggata cgcaagaa cacggtctac     240 ctgcagatga actcccttaa accagaagat actgccgttt attattgcgc cgcatcagag   300
gtaacttacg atgaaggtcg atacattggg acgaagagca cctatgacac atgggggcag   360
ggtactcaag tgaccgtgag ctcg                                            384
```

<210> SEQ ID NO 102
<211> LENGTH: 128
<212> TYPE: PRT
<213> ORGANISM: Artificial Sequence
<220> FEATURE:
<223> OTHER INFORMATION: Lyso CW P01 B11

<400> SEQUENCE: 102

```
Gln Val Gln Leu Val Glu Ser Gly Gly Gly Leu Val Gln Ala Gly Gly
1               5                   10                  15

Ser Leu Arg Leu Ser Cys Ala Ala Ser Gly Gly Ile Phe Ser Gly Gly
            20                  25                  30
```

Arg Met Gly Trp Phe Arg Gln Ala Pro Gly Lys Glu Arg Glu Phe Val
         35                  40                  45

Ala Ala Val Ile Thr Arg Gly Ser Thr Tyr Tyr Ala Asp Ser Val
 50                  55                  60

Lys Gly Arg Phe Thr Ile Ser Arg Asp Asn Ala Lys Asn Thr Val Tyr
 65                  70                  75                  80

Leu Gln Met Asn Ser Leu Lys Pro Glu Asp Thr Ala Val Tyr Tyr Cys
                 85                  90                  95

Ala Ala Ser Glu Val Thr Tyr Asp Glu Gly Arg Tyr Ile Gly Thr Lys
             100                 105                 110

Ser Thr Tyr Asp Thr Trp Gly Gln Gly Thr Gln Val Thr Val Ser Ser
         115                 120                 125

<210> SEQ ID NO 103
<211> LENGTH: 351
<212> TYPE: PRT
<213> ORGANISM: Artificial Sequence
<220> FEATURE:
<223> OTHER INFORMATION: Lyso CW P01 D04

<400> SEQUENCE: 103

Cys Ala Gly Gly Thr Gly Cys Ala Ala Cys Thr Gly Gly Thr Gly Gly
 1               5                   10                  15

Ala Ala Thr Cys Cys Gly Gly Gly Gly Thr Gly Gly Ala Cys Thr
             20                  25                  30

Gly Gly Thr Ala Cys Ala Ala Gly Cys Cys Gly Gly Ala Gly Gly Gly
         35                  40                  45

Ala Gly Thr Thr Gly Ala Gly Ala Cys Thr Cys Thr Cys Thr Thr
 50                  55                  60

Gly Cys Gly Cys Thr Gly Cys Thr Cys Cys Gly Gly Thr Ala Gly
 65                  70                  75                  80

Ala Ala Thr Thr Thr Thr Thr Cys Ala Ala Thr Ala Thr Ala Cys
                 85                  90                  95

Gly Ala Cys Ala Cys Cys Ala Thr Ala Gly Gly Ala Thr Gly Gly Thr
             100                 105                 110

Thr Thr Cys Gly Ala Cys Ala Ala Gly Cys Gly Cys Cys Thr Gly Gly
         115                 120                 125

Ala Ala Ala Gly Gly Ala Ala Gly Ala Gly Ala Gly Thr Thr Thr
 130                 135                 140

Gly Thr Ala Gly Cys Gly Gly Cys Cys Ala Cys Thr Ala Thr Cys Ala
 145                 150                 155                 160

Cys Ala Ala Cys Gly Gly Cys Gly Gly Thr Ala Thr Thr Ala Cys Cys
                 165                 170                 175

Gly Ala Cys Ala Thr Ala Thr Gly Ala Thr Ala Thr Ala Gly Cys
             180                 185                 190

Gly Thr Thr Ala Ala Gly Gly Ala Cys Gly Gly Thr Thr Cys Ala
         195                 200                 205

Cys Gly Ala Thr Ala Ala Gly Cys Gly Cys Gly Ala Cys Ala Ala
 210                 215                 220

Thr Gly Cys Cys Ala Ala Gly Ala Ala Cys Ala Cys Gly Gly Thr Gly
 225                 230                 235                 240

Thr Ala Cys Cys Thr Cys Cys Ala Ala Ala Thr Gly Ala Ala Thr Ala
                 245                 250                 255

Gly Cys Cys Thr Thr Ala Ala Gly Cys Cys Gly Ala Gly Gly Ala
             260                 265                 270

```
Thr Ala Cys Ala Gly Cys Cys Gly Thr Thr Ala Cys Thr Ala Thr
            275                 280                 285
Thr Gly Thr Thr Ala Cys Gly Thr Cys Cys Gly Ala Thr Thr Gly
            290                 295                 300
Gly Thr Cys Gly Cys Gly Thr Gly Ala Cys Thr Ala Cys Thr Gly
305                 310                 315                 320
Gly Gly Gly Thr Cys Ala Ala Gly Gly Thr Ala Cys Thr Cys Ala Gly
                325                 330                 335
Gly Thr Gly Ala Cys Thr Gly Thr Ala Ala Gly Cys Thr Cys Gly
            340                 345                 350
```

<210> SEQ ID NO 104
<211> LENGTH: 117
<212> TYPE: PRT
<213> ORGANISM: Artificial Sequence
<220> FEATURE:
<223> OTHER INFORMATION: Lyso CW P01 D04

<400> SEQUENCE: 104

```
Gln Val Gln Leu Val Glu Ser Gly Gly Gly Leu Val Gln Ala Gly Gly
1               5                   10                  15
Ser Leu Arg Leu Ser Cys Ala Ala Ser Gly Arg Ile Phe Ser Ile Tyr
            20                  25                  30
Asp Thr Ile Gly Trp Phe Arg Gln Ala Pro Gly Lys Glu Arg Glu Phe
        35                  40                  45
Val Ala Ala Thr Ile Thr Thr Ala Gly Ile Thr Thr Tyr Asp Asp Ser
    50                  55                  60
Val Lys Gly Arg Phe Thr Ile Ser Arg Asp Asn Ala Lys Asn Thr Val
65                  70                  75                  80
Tyr Leu Gln Met Asn Ser Leu Lys Pro Glu Asp Thr Ala Val Tyr Tyr
                85                  90                  95
Cys Tyr Val Arg Val Gly Arg Gly Asp Tyr Trp Gly Gln Gly Thr Gln
            100                 105                 110
Val Thr Val Ser Ser
        115
```

<210> SEQ ID NO 105
<211> LENGTH: 351
<212> TYPE: DNA
<213> ORGANISM: Artificial Sequence
<220> FEATURE:
<223> OTHER INFORMATION: Lyso CW P01 F11

<400> SEQUENCE: 105

```
caggtgcaac tggttgaatc tggtggtggg ctggtccaag cgggaggcag tcttcgactt    60
tcctgcgcag cctcagggag tatattcagc ttttacgacg taggttggtt ccgccaagcg   120
cccggtaaag aacgagagtt cgtcgctgcc agtataacga agggaggcgg gacgtactac   180
gtagattcag taaaagggag atttaccata gtagggaca atgcaaagaa cacggtctac   240
ctccagatga atagccttaa accagaagat acggcagtct attactgcgc cctggcaacc   300
ccccacggat atgacttttg gggccaaggt acgcaagtca cggtgagctc g            351
```

<210> SEQ ID NO 106
<211> LENGTH: 117
<212> TYPE: PRT
<213> ORGANISM: Artificial Sequence
<220> FEATURE:
<223> OTHER INFORMATION: Lyso CW P01 F11

<400> SEQUENCE: 106

Gln Val Gln Leu Val Glu Ser Gly Gly Gly Leu Val Gln Ala Gly Gly
1               5                   10                  15

Ser Leu Arg Leu Ser Cys Ala Ala Ser Gly Ser Ile Phe Ser Phe Tyr
            20                  25                  30

Asp Val Gly Trp Phe Arg Gln Ala Pro Gly Lys Glu Arg Glu Phe Val
        35                  40                  45

Ala Ala Ser Ile Thr Lys Gly Gly Thr Tyr Tyr Val Asp Ser Val
50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Leu Ala Thr Pro His Gly Tyr Asp Phe Trp Gly Gln Gly Thr Gln
            100                 105                 110

Val Thr Val Ser Ser
        115

<210> SEQ ID NO 107
<211> LENGTH: 354
<212> TYPE: DNA
<213> ORGANISM: Artificial Sequence
<220> FEATURE:
<223> OTHER INFORMATION: Lyso CW P01 F09

<400> SEQUENCE: 107

```
caggtgcagc tcgttgaaag cggggggtggc ttggtccaag cgggaggttc cctgagactg      60
tcctgcgctg cgtcaggatc aataatcacg atttatgtag tcggatggtt ccgacaagcc     120
ccaggtaaag agcgggaatt tgtggcctcc gacataggct ctggtgggtc aacttattac     180
agtgactccg taaaaggtcg gttcacaatc tcaagggata cgcaaagaa tacagtctac      240
ttgcaaatga attcattgaa gcctgaggat acagcagtgt actactgcgt tactggagat     300
ccctctactc cgtattcata ctggggtcaa ggcacacagg ttacagtgag ctcg           354
```

<210> SEQ ID NO 108
<211> LENGTH: 118
<212> TYPE: PRT
<213> ORGANISM: Artificial Sequence
<220> FEATURE:
<223> OTHER INFORMATION: Lyso CW P01 F09

<400> SEQUENCE: 108

Gln Val Gln Leu Val Glu Ser Gly Gly Gly Leu Val Gln Ala Gly Gly
1               5                   10                  15

Ser Leu Arg Leu Ser Cys Ala Ala Ser Gly Ser Ile Ile Thr Ile Tyr
            20                  25                  30

Val Val Gly Trp Phe Arg Gln Ala Pro Gly Lys Glu Arg Glu Phe Val
        35                  40                  45

Ala Ser Asp Ile Gly Ser Gly Ser Thr Tyr Tyr Ser Asp Ser Val
50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Val Thr Gly Asp Pro Ser Thr Pro Tyr Ser Tyr Trp Gly Gln Gly Thr
            100                 105                 110

```
Gln Val Thr Val Ser Ser
        115
```

<210> SEQ ID NO 109
<211> LENGTH: 363
<212> TYPE: DNA
<213> ORGANISM: Artificial Sequence
<220> FEATURE:
<223> OTHER INFORMATION: Lyso CW P01 C04

<400> SEQUENCE: 109

```
caggtgcaac tggtcgagag tgtggtggga ctggttcaag ctgggggcag cctgagattg      60
tcctgcgccg catctggctc ctccttctca atttacgacg tgggctggtt ccgccaagca     120
cctggaaagg aaagagagtt tgttgctgcg acaattgaga ctgggggaca cacgtcttac     180
gccgactcag tgaaaggtag atttacaatc tcaagggata cgctaaaaaa caccgtttat     240
ctgcaaatga actccctgaa accggaggat acagctgtgt actattgtta tgcgaagatt     300
gtctacgacc agggcccgag ctactactat tggggccagg ggacacaggt taccgtgagc     360
tcg                                                                   363
```

<210> SEQ ID NO 110
<211> LENGTH: 121
<212> TYPE: PRT
<213> ORGANISM: Artificial Sequence
<220> FEATURE:
<223> OTHER INFORMATION: Lyso CW P01 C04

<400> SEQUENCE: 110

```
Gln Val Gln Leu Val Glu Ser Gly Gly Gly Leu Val Gln Ala Gly Gly
1               5                   10                  15

Ser Leu Arg Leu Ser Cys Ala Ala Ser Gly Ser Ser Phe Ser Ile Tyr
            20                  25                  30

Asp Val Gly Trp Phe Arg Gln Ala Pro Gly Lys Glu Arg Glu Phe Val
        35                  40                  45

Ala Ala Thr Ile Glu Thr Gly Gly His Thr Ser Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Tyr Ala Lys Ile Val Tyr Asp Gln Gly Pro Ser Tyr Tyr Tyr Trp Gly
            100                 105                 110

Gln Gly Thr Gln Val Thr Val Ser Ser
        115                 120
```

<210> SEQ ID NO 111
<211> LENGTH: 128
<212> TYPE: PRT
<213> ORGANISM: Artificial Sequence
<220> FEATURE:
<223> OTHER INFORMATION: huLYSO_CW_P01_B11

<400> SEQUENCE: 111

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Gly Ile Phe Ser Gly Gly
            20                  25                  30

Arg Met Gly Trp Phe Arg Gln Ala Pro Gly Lys Glu Arg Glu Phe Val
        35                  40                  45
```

```
Ala Ala Val Ile Thr Arg Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Ala Ser Glu Val Thr Tyr Asp Glu Gly Arg Tyr Ile Gly Thr Lys
            100                 105                 110

Ser Thr Tyr Asp Thr Trp Gly Gln Gly Thr Gln Val Thr Val Ser Ser
            115                 120                 125

<210> SEQ ID NO 112
<211> LENGTH: 117
<212> TYPE: PRT
<213> ORGANISM: Artificial Sequence
<220> FEATURE:
<223> OTHER INFORMATION: huLYSO_CW_P01_D04

<400> SEQUENCE: 112

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Arg Ile Phe Ser Ile Tyr
             20                  25                  30

Asp Thr Ile Gly Trp Phe Arg Gln Ala Pro Gly Lys Glu Arg Glu Phe
         35                  40                  45

Val Ala Ala Thr Ile Thr Thr Ala Gly Ile Thr Thr Tyr Asp Asp Ser
     50                  55                  60

Val Lys Gly Arg Phe Thr Ile Ser Arg Asp Asn Ser Lys Asn Thr Leu
 65                  70                  75                  80

Tyr Leu Gln Met Asn Ser Leu Arg Ala Glu Asp Thr Ala Val Tyr Tyr
                 85                  90                  95

Cys Tyr Val Arg Val Gly Arg Gly Asp Tyr Trp Gly Gln Gly Thr Gln
            100                 105                 110

Val Thr Val Ser Ser
        115

<210> SEQ ID NO 113
<211> LENGTH: 130
<212> TYPE: PRT
<213> ORGANISM: Artificial Sequence
<220> FEATURE:
<223> OTHER INFORMATION: huD04_CNTY2_F09

<400> SEQUENCE: 113

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Arg Thr Phe Ser Ser Gly
             20                  25                  30

Ala Met Gly Trp Tyr Arg Gln Ala Pro Gly Lys Glu Arg Glu Leu Val
         35                  40                  45

Ser Ala Ile Ser Asn Arg Gly Ser Thr Val Tyr Ala Asp Ser Val Lys
     50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Ala Asp Arg Asn Pro Ser Ser Ala Gly Ala Gly Val Ala Ala Tyr Arg
            100                 105                 110
```

```
                    100                 105                 110
Leu Ile Ala Arg Phe Asn Tyr Trp Gly Gln Gly Thr Gln Val Thr Val
            115                 120                 125

Ser Ser
    130

<210> SEQ ID NO 114
<211> LENGTH: 131
<212> TYPE: PRT
<213> ORGANISM: Artificial Sequence
<220> FEATURE:
<223> OTHER INFORMATION: huD04_CNTY2_F08

<400> SEQUENCE: 114

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Leu Ser Ser Tyr
            20                  25                  30

Ala Met Gly Trp Tyr Arg Gln Ala Pro Gly Lys Glu Arg Glu Gly Val
        35                  40                  45

Ser Ser Ile Ser Tyr Ala Gly Val Thr Asn Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Ala Ala Leu Thr Gly Tyr Tyr Ala Tyr Arg Arg Leu Trp Ser Tyr Arg
            100                 105                 110

Ile Gly Ser Gln Ala Tyr Asp Tyr Trp Gly Gln Gly Thr Gln Val Thr
            115                 120                 125

Val Ser Ser
    130

<210> SEQ ID NO 115
<211> LENGTH: 133
<212> TYPE: PRT
<213> ORGANISM: Artificial Sequence
<220> FEATURE:
<223> OTHER INFORMATION: huD04_CNTY2_E03

<400> SEQUENCE: 115

Glu Val Gln Leu Leu Glu Ser Gly Gly Gly Leu Val Gln Pro Gly Gly
1               5                   10                  15

Ser Leu Arg Leu Ser Cys Ala Ala Ser Gly Leu Thr Tyr Thr Gly Tyr
            20                  25                  30

Ala Met Gly Trp Tyr Arg Gln Ala Pro Gly Lys Glu Arg Glu Leu Val
        35                  40                  45

Ser Ala Ile Ser Ser Arg Ser Ser Ile Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Ala Gly Arg Pro Val Ala Leu Gly Ser Trp Arg Arg Thr Ala Thr Trp
            100                 105                 110

Ser Ala Gly Leu Gly Ala Glu Tyr Ala Tyr Trp Gly Gln Gly Thr Gln
            115                 120                 125
```

```
Val Thr Val Ser Ser
    130

<210> SEQ ID NO 116
<211> LENGTH: 132
<212> TYPE: PRT
<213> ORGANISM: Artificial Sequence
<220> FEATURE:
<223> OTHER INFORMATION: huD04_CNTY2_F04

<400> SEQUENCE: 116

Glu Val Gln Leu Leu Glu Ser Gly Gly Gly Leu Val Gln Pro Gly Gly
1               5                   10                  15

Ser Leu Arg Leu Ser Cys Ala Ala Ser Gly Arg Thr Phe Ser Ser Tyr
            20                  25                  30

Gly Met Gly Trp Tyr Arg Gln Ala Pro Gly Lys Glu Arg Glu Leu Val
        35                  40                  45

Ser Ala Ile Ser Asn Arg Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Ala Ser Pro Ala Arg Val Gly Val Ser Gly His Ser Ser Ser Arg Arg
            100                 105                 110

Ser Tyr Tyr Gly Tyr Ser Tyr Asp Tyr Trp Gly Gln Gly Thr Gln Val
        115                 120                 125

Thr Val Ser Ser
    130

<210> SEQ ID NO 117
<211> LENGTH: 130
<212> TYPE: PRT
<213> ORGANISM: Artificial Sequence
<220> FEATURE:
<223> OTHER INFORMATION: huD04_CNTY2_H12

<400> SEQUENCE: 117

Glu Val Gln Leu Leu Glu Ser Gly Gly Gly Leu Val Gln Pro Gly Gly
1               5                   10                  15

Ser Leu Arg Leu Ser Cys Ala Ala Ser Gly Ser Ile Phe Ser Ser Asp
            20                  25                  30

Val Met Gly Trp Tyr Arg Gln Ala Pro Gly Lys Glu Arg Glu Leu Val
        35                  40                  45

Ser Ala Ile Ser Ser Gly Gly Ser Thr Arg Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Ala Thr Met Gly Lys Ser Lys Thr Asn Arg Arg Asn Tyr Gly Thr Trp
            100                 105                 110

Arg Tyr Gly Ala Tyr Ala Tyr Trp Gly Gln Gly Thr Gln Val Thr Val
        115                 120                 125

Ser Ser
    130

<210> SEQ ID NO 118
```

```
<211> LENGTH: 133
<212> TYPE: PRT
<213> ORGANISM: Artificial Sequence
<220> FEATURE:
<223> OTHER INFORMATION: huD04_CNTY2_F12

<400> SEQUENCE: 118
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Asn
            20                  25                  30

Ala Met Gly Trp Tyr Arg Gln Ala Pro Gly Lys Glu Arg Glu Phe Val
        35                  40                  45

Ser Ser Ile Ser Ser Gly Arg Ser Thr Thr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Ala His Gly Thr Lys Tyr Lys Trp Thr Arg Ala Arg Leu Arg Ser Ala
            100                 105                 110

Arg Gln Lys Gln Leu Glu Thr Tyr Arg Tyr Trp Gly Gln Gly Thr Gln
        115                 120                 125

Val Thr Val Ser Ser
    130

```
<210> SEQ ID NO 119
<211> LENGTH: 117
<212> TYPE: PRT
<213> ORGANISM: Artificial Sequence
<220> FEATURE:
<223> OTHER INFORMATION: huD04_CNTY1_A11

<400> SEQUENCE: 119
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Ser Ser Asn Tyr
            20                  25                  30

Val Met Gly Trp Tyr Arg Gln Ala Pro Gly Lys Glu Arg Glu Phe Val
        35                  40                  45

Ser Ala Ile Gly Ser Gly Gly Ser Thr Tyr Tyr Ala Asp Ser Val Lys
    50                  55                  60

Gly Arg Phe Thr Ile Ser Arg Asp Asn Ser Lys Asn Thr Tyr Leu Gln
65                  70                  75                  80

Met Asn Ser Leu Arg Ala Glu Asp Thr Ala Val Tyr Tyr Cys Ala Ala
                85                  90                  95

Glu Ile Tyr Thr Ser Gly Ala Arg Asp Tyr Trp Gly Gln Gly Thr Gln
            100                 105                 110

Val Thr Val Ser Ser
        115

```
<210> SEQ ID NO 120
<211> LENGTH: 129
<212> TYPE: PRT
<213> ORGANISM: Artificial Sequence
<220> FEATURE:
<223> OTHER INFORMATION: huD04_CNTY2_C03

<400> SEQUENCE: 120
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Leu Thr Phe Ser Arg Tyr
            20                  25                  30

Ala Met Gly Trp Tyr Arg Gln Ala Pro Gly Lys Glu Arg Glu Leu Val
        35                  40                  45

Ser Ala Ile Ser Ser Arg Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
            85                  90                  95

Ala Asp Tyr Arg Leu Thr Ser Leu Glu Arg Ala Arg Tyr Ala Ser Ala
            100                 105                 110

Ser Ile Thr Tyr Asp Tyr Trp Gly Gln Gly Thr Gln Val Thr Val Ser
            115                 120                 125

Ser

<210> SEQ ID NO 121
<211> LENGTH: 131
<212> TYPE: PRT
<213> ORGANISM: Artificial Sequence
<220> FEATURE:
<223> OTHER INFORMATION: huD04_CNTY2_B06

<400> SEQUENCE: 121

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asn Arg Tyr
            20                  25                  30

Ser Met Gly Trp Tyr Arg Gln Ala Pro Gly Lys Glu Arg Glu Leu Val
        35                  40                  45

Ser Ala Ile Ser Ser Gly Gly Ser Gly Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
            85                  90                  95

Ile Gln Asp Tyr Ser Arg Ile Trp Glu Tyr Ile Ala Leu Asp Arg Arg
            100                 105                 110

Arg Ser Tyr Tyr Gly Met Asp Tyr Trp Gly Gln Gly Thr Gln Val Thr
            115                 120                 125

Val Ser Ser
        130

<210> SEQ ID NO 122
<211> LENGTH: 130
<212> TYPE: PRT
<213> ORGANISM: Artificial Sequence
<220> FEATURE:
<223> OTHER INFORMATION: huD04_CNTY2_D02

<400> SEQUENCE: 122

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Ser Tyr
            20                  25                  30

-continued

```
Ala Met Gly Trp Tyr Arg Gln Ala Pro Gly Lys Glu Arg Glu Gly Val
            35                  40                  45

Ser Val Ile Ser Ser Gly Gly Thr Pro Ser Tyr Ala Asp Ser Val Lys
 50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Asp
                 85                  90                  95

Ala Ile Met Gly Leu Val Glu Ala Asp Tyr Val Ser Thr Gly Thr Tyr
            100                 105                 110

Glu Tyr Thr Ala Tyr Ala Tyr Trp Gly Gln Gly Thr Gln Val Thr Val
            115                 120                 125

Ser Ser
    130

<210> SEQ ID NO 123
<211> LENGTH: 130
<212> TYPE: PRT
<213> ORGANISM: Artificial Sequence
<220> FEATURE:
<223> OTHER INFORMATION: huD04_CNTY2_D04

<400> SEQUENCE: 123

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Leu Thr Phe Ser Gly Val
                 20                  25                  30

Cys Met Gly Trp Phe Arg Gln Ala Pro Gly Lys Glu Arg Glu Gly Val
            35                  40                  45

Ser Ala Ile Tyr Ser Ser Gly Ser Thr Tyr Tyr Ala Asp Ser Val Lys
 50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Ala Asp Arg Ile Pro Asp Leu Gly Glu Pro Cys Ile Gly Thr Thr Asn
            100                 105                 110

Leu Ala Arg Thr Tyr Asn Tyr Trp Gly Gln Gly Thr Gln Val Thr Val
            115                 120                 125

Ser Ser
    130

<210> SEQ ID NO 124
<211> LENGTH: 119
<212> TYPE: PRT
<213> ORGANISM: Artificial Sequence
<220> FEATURE:
<223> OTHER INFORMATION: huD04_CNTY1_B12

<400> SEQUENCE: 124

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Arg Thr Ser Ser Asn Tyr
                 20                  25                  30

Val Met Gly Trp Tyr Arg Gln Ala Pro Gly Lys Glu Arg Glu Gly Val
            35                  40                  45

Ser Ala Ile Thr Ser Gly Gly Ser Thr Tyr Tyr Ala Asp Ser Val Lys
 50                  55                  60
```

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
            85                  90                  95

Ala Asn Leu Tyr Ser Arg Thr Gly Ala Tyr Asp Tyr Trp Gly Gln Gly
        100                 105                 110

Thr Gln Val Thr Val Ser Ser
        115

<210> SEQ ID NO 125
<211> LENGTH: 129
<212> TYPE: PRT
<213> ORGANISM: Artificial Sequence
<220> FEATURE:
<223> OTHER INFORMATION: huD04_CNTY2_D05

<400> SEQUENCE: 125

Glu Val Gln Leu Leu Glu Ser Gly Gly Gly Leu Val Gln Pro Gly Gly
1               5                   10                  15

Ser Leu Arg Leu Ser Cys Ala Ala Ser Gly Tyr Ile Tyr Ser Ser Tyr
            20                  25                  30

Ser Met Gly Trp Tyr Arg Gln Ala Pro Ala Lys Asn Ala Ser Leu Ser
        35                  40                  45

Ala Ile Thr Ser Gly Glu Thr Tyr Tyr Ala Asp Ser Val Lys Gly
    50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Ala Ala
            85                  90                  95

Asp Ala Leu Asp Ala Pro Ile Ala Gly Asp Arg Tyr Tyr Arg Gly Ser
        100                 105                 110

Gly Ala Gly Tyr Ala Tyr Trp Gly Gln Gly Thr Gln Val Thr Val Ser
        115                 120                 125

Ser

<210> SEQ ID NO 126
<211> LENGTH: 133
<212> TYPE: PRT
<213> ORGANISM: Artificial Sequence
<220> FEATURE:
<223> OTHER INFORMATION: huD04_CNTY2_D12

<400> SEQUENCE: 126

Glu Val Gln Leu Leu Glu Ser Gly Gly Gly Leu Val Gln Pro Gly Gly
1               5                   10                  15

Ser Leu Arg Leu Ser Cys Ala Ala Ser Gly Ser Ala Phe Ser Ser Asn
            20                  25                  30

Ala Met Gly Trp Tyr Arg Gln Ala Pro Gly Lys Glu Arg Glu Leu Val
        35                  40                  45

Ser Ala Ile Ser Ser Gly Gly Ser Thr Asn Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
            85                  90                  95

Ala Arg Asn Pro Leu Thr Tyr Thr Ala Leu Val Ser Asn Ala Pro Ser
        100                 105                 110

```
Gly Asp Tyr Tyr Leu Phe Glu Tyr Arg Leu Trp Gly Gln Gly Thr Gln
        115                 120                 125

Val Thr Val Ser Ser
        130

<210> SEQ ID NO 127
<211> LENGTH: 119
<212> TYPE: PRT
<213> ORGANISM: Artificial Sequence
<220> FEATURE:
<223> OTHER INFORMATION: huD04_CNTY1_D12

<400> SEQUENCE: 127

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Ser Ser Asn Tyr
            20                  25                  30

Val Met Gly Trp Tyr Arg Gln Ala Pro Gly Lys Glu Arg Glu Gly Val
        35                  40                  45

Ser Ala Ile Ser Ser Ser Gly Arg Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Ala Ala Tyr Tyr Ser Gly Tyr Gly Glu Thr Asp Tyr Trp Gly Gln Gly
            100                 105                 110

Thr Gln Val Thr Val Ser Ser
        115

<210> SEQ ID NO 128
<211> LENGTH: 118
<212> TYPE: PRT
<213> ORGANISM: Artificial Sequence
<220> FEATURE:
<223> OTHER INFORMATION: huD04_CNTY1_D11

<400> SEQUENCE: 128

Glu Val Gln Leu Leu Glu Ser Gly Gly Gly Leu Val Gln Pro Gly Gly
1               5                   10                  15

Ser Leu Arg Leu Ser Cys Ala Ala Ser Gly Ser Thr Phe Ser Tyr Tyr
            20                  25                  30

Tyr Met Gly Trp Tyr Arg Gln Ala Pro Gly Lys Glu Arg Glu Leu Val
        35                  40                  45

Ser Ala Ile Ser Ser Gly Gly Ser Ile Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Arg Thr Tyr Tyr Gly Asp Glu Ala Asp Tyr Trp Gly Gln Gly Thr
            100                 105                 110

Gln Val Thr Val Ser Ser
        115

<210> SEQ ID NO 129
<211> LENGTH: 119
<212> TYPE: PRT
```

<213> ORGANISM: Artificial Sequence
<220> FEATURE:
<223> OTHER INFORMATION: huD04_CNTY1_D10

<400> SEQUENCE: 129

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Arg Thr Ser Ser Asn Tyr
            20                  25                  30

Val Ile Gly Trp Tyr Arg Gln Ala Pro Gly Lys Glu Arg Glu Phe Val
        35                  40                  45

Ser Ala Ile Ser Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Thr Arg Ile Tyr Thr Ala Arg Gly Ala Gly Asp Tyr Trp Gly Gln Gly
                100                 105                 110

Thr Gln Val Thr Val Ser Ser
        115
```

<210> SEQ ID NO 130
<211> LENGTH: 128
<212> TYPE: PRT
<213> ORGANISM: Artificial Sequence
<220> FEATURE:
<223> OTHER INFORMATION: huB11_CNTY3+4_A02

<400> SEQUENCE: 130

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Arg Thr Tyr Thr Gly Ser
            20                  25                  30

Ala Met Gly Trp Tyr Arg Gln Ala Pro Gly Lys Glu Arg Glu Leu Val
        35                  40                  45

Ser Ala Ile Ser Thr Gly Gly Glu Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Ala Gly Tyr Val Gly Leu Pro Tyr Thr Tyr Arg Pro Ala Thr Ser Arg
                100                 105                 110

Arg Gly Tyr Thr Tyr Trp Gly Gln Gly Thr Gln Val Thr Val Ser Ser
            115                 120                 125
```

<210> SEQ ID NO 131
<211> LENGTH: 127
<212> TYPE: PRT
<213> ORGANISM: Artificial Sequence
<220> FEATURE:
<223> OTHER INFORMATION: huB11_CNTY3+4_A01

<400> SEQUENCE: 131

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30
```

```
Ser Ile Gly Trp Tyr Arg Gln Ala Pro Gly Lys Glu Arg Glu Leu Val
            35                  40                  45

Ser Val Ile Ser Ser Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Ala Ser Asp Trp Ser Tyr Ser Trp Ile Thr Tyr Thr Gly Thr Trp Arg
                100                 105                 110

Leu Tyr Glu Tyr Trp Gly Gln Gly Thr Gln Val Thr Val Ser Ser
            115                 120                 125

<210> SEQ ID NO 132
<211> LENGTH: 118
<212> TYPE: PRT
<213> ORGANISM: Artificial Sequence
<220> FEATURE:
<223> OTHER INFORMATION: huB11_CNTY1_E11

<400> SEQUENCE: 132

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ala Phe Ser Asp Tyr
            20                  25                  30

Val Met Gly Trp Tyr Arg Gln Ala Pro Gly Lys Glu Arg Glu Phe Val
            35                  40                  45

Ser Ala Ile Arg Ser Thr Thr Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Ala Asp Val Trp Ser Gly Tyr Glu Tyr Asp Tyr Trp Gly Gln Gly Thr
                100                 105                 110

Gln Val Thr Val Ser Ser
            115

<210> SEQ ID NO 133
<211> LENGTH: 118
<212> TYPE: PRT
<213> ORGANISM: Artificial Sequence
<220> FEATURE:
<223> OTHER INFORMATION: huB11_CNTY1_B11

<400> SEQUENCE: 133

Glu Val Gln Leu Leu Glu Ser Gly Gly Gly Leu Val Gln Pro Gly Gly
1               5                   10                  15

Ser Leu Arg Leu Ser Cys Ala Ala Ser Gly Leu Ala Phe Ser Ser Tyr
            20                  25                  30

Ala Met Gly Trp Tyr Arg Gln Ala Pro Gly Lys Glu Arg Glu Phe Val
            35                  40                  45

Ser Val Ile Ser Gly Thr Gly Thr Leu Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
```

```
                    85                  90                  95
Ala Asp Val Trp Ser Gly Tyr Glu Tyr Asp Tyr Trp Gly Gln Gly Thr
                100                 105                 110

Gln Val Thr Val Ser Ser
        115

<210> SEQ ID NO 134
<211> LENGTH: 125
<212> TYPE: PRT
<213> ORGANISM: Artificial Sequence
<220> FEATURE:
<223> OTHER INFORMATION: Consensus Sequence
<220> FEATURE:
<221> NAME/KEY: misc_feature
<222> LOCATION: (31)..(31)
<223> OTHER INFORMATION: Xaa can be any naturally occurring amino acid
<220> FEATURE:
<221> NAME/KEY: misc_feature
<222> LOCATION: (33)..(33)
<223> OTHER INFORMATION: Xaa can be any naturally occurring amino acid
<220> FEATURE:
<221> NAME/KEY: misc_feature
<222> LOCATION: (51)..(51)
<223> OTHER INFORMATION: Xaa can be any naturally occurring amino acid
<220> FEATURE:
<221> NAME/KEY: misc_feature
<222> LOCATION: (54)..(54)
<223> OTHER INFORMATION: Xaa can be any naturally occurring amino acid
<220> FEATURE:
<221> NAME/KEY: misc_feature
<222> LOCATION: (61)..(61)
<223> OTHER INFORMATION: Xaa can be any naturally occurring amino acid
<220> FEATURE:
<221> NAME/KEY: misc_feature
<222> LOCATION: (99)..(100)
<223> OTHER INFORMATION: Xaa can be any naturally occurring amino acid
<220> FEATURE:
<221> NAME/KEY: misc_feature
<222> LOCATION: (102)..(102)
<223> OTHER INFORMATION: Xaa can be any naturally occurring amino acid
<220> FEATURE:
<221> NAME/KEY: misc_feature
<222> LOCATION: (104)..(104)
<223> OTHER INFORMATION: Xaa can be any naturally occurring amino acid
<220> FEATURE:
<221> NAME/KEY: misc_feature
<222> LOCATION: (106)..(111)
<223> OTHER INFORMATION: Xaa can be any naturally occurring amino acid
<220> FEATURE:
<221> NAME/KEY: misc_feature
<222> LOCATION: (113)..(114)
<223> OTHER INFORMATION: Xaa can be any naturally occurring amino acid

<400> SEQUENCE: 134

Gln Val Gln Leu Val Glu Ser Gly Gly Gly Leu Val Gln Ala Gly Gly
1               5                   10                  15

Ser Leu Arg Leu Ser Cys Ala Ser Gly Arg Ile Phe Ser Xaa Tyr
            20                  25                  30

Xaa Met Gly Trp Phe Arg Gln Ala Pro Gly Lys Glu Arg Glu Phe Val
            35                  40                  45

Ala Ala Xaa Ile Thr Xaa Gly Gly Ser Thr Tyr Tyr Xaa Asp Ser Val
        50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Val Xaa Xaa Asp Xaa Gly Xaa Tyr Xaa Xaa Xaa Xaa Xaa Xaa Tyr
                100                 105                 110
```

```
Xaa Xaa Trp Gly Gln Gly Thr Gln Val Thr Val Ser Ser
    115             120                 125
```

CHIMERIC ANTIGEN RECEPTOR SYSTEM WITH ADAPTABLE RECEPTOR SPECIFICITY

CROSS REFERENCE TO RELATED APPLICATIONS

This application claims the benefit of U.S. Provisional Patent Application No. 63/127,587 filed Dec. 18, 2020, which is incorporated by reference herein in its entirety.

FIELD OF THE INVENTION

The application relates to chimeric antigen receptors (CARs), particularly CARs with an adaptable receptor specificity (arCARs), and their uses in immunotherapy (e.g., adoptive cell therapy).

REFERENCE TO SEQUENCE LISTING SUBMITTED ELECTRONICALLY

This application contains a sequence listing, which is submitted electronically via EFS-Web as an ASCII formatted sequence listing with a file name "SequenceListing_ST25.txt" and a creation date of Dec. 15, 2021 and having a size of 103,886 bytes. The sequence listing submitted via EFS-Web is part of the specification and is herein incorporated by reference in its entirety.

BACKGROUND

Adoptive cell therapy (ACT) typically involves isolating cells from a donor, culturing and/or manipulating cells in vitro, and then transferring the cells to a patient for the treatment of a disease. To enable the cells to target a specific antigen, the cells are often engineered with a chimeric antigen receptor (CAR). A conventional CAR has a fixed design; thus, one type of CAR T cell usually can only target one antigen epitope. This rigid design limits clinical application and leads to exceptionally high manufacturing cost. While there are various approaches for switch-CAR platforms, these antigen-specific CARs are typically generated on a custom-made basis.

Accordingly, there remains a need for an improved universal CAR platform with a built-in and convenient mechanism for modulating the CAR to easily adapt the CAR's specificity to improve therapies and methods for treating diseases using adoptive cell therapy.

SUMMARY OF THE INVENTION

In one aspect, provided herein is a universal chimeric antigen receptor system having an adaptable receptor specificity component (arCAR) comprising:
(i) an immune effector cell having a chimeric antigen receptor comprising a first polypeptide comprising (a) an extracellular tag-binding domain, (b) a transmembrane domain, and (c) at least one intracellular signaling domain; and
(ii) a second polypeptide comprising (a) an antigen-binding domain that binds to at least one antigen on a target cell, and (b) a tag that is recognized by the tag-binding domain of the first polypeptide of the chimeric antigen receptor;
wherein: (i) the tag comprises an antibody, or antigen-binding fragment thereof, or an alternative scaffold and the tag-binding domain comprises an anti-idiotype molecule that binds to the tag, or
(ii) the tag comprises an anti-idiotype molecule that binds to the tag-binding domain and the tag-binding domain comprises an antibody, or antigen-binding fragment thereof, or an alternative scaffold.

In some embodiments, the anti-idiotype molecule binds to at least one antigen binding region of the antibody, antigen-binding fragment thereof or alternative scaffold. In some embodiments, the anti-idiotype molecule binds to at least one complementarity determining region (CDR) of the antibody, or antigen-binding fragment thereof.

In some embodiments, the antigen-binding domain of the second polypeptide comprises an antibody, or antigen-binding fragment thereof, or an alternative scaffold. In some embodiments, the anti-idiotype molecule is an anti-idiotype antibody, or antigen-binding fragment thereof, or an anti-idiotype alternative scaffold.

In some embodiments, the antigen-binding fragment is an Fab fragment, an Fab' fragment, an F(ab')2 fragment, an scFv fragment, an Fv fragment, a dsFv diabody, a VHH, a VNAR, a single-domain antibody (sdAb) or nanobody, a dAb fragment, a Fd' fragment, a Fd fragment, a heavy chain variable region, an isolated complementarity determining region (CDR), a diabody, a triabody, or a decabody.

In some embodiments, at least one of the extracellular tag-binding domain, the antigen-binding domain, or the tag comprises a single-domain antibody or nanobody. In some embodiments, at least one of the extracellular tag-binding domain, the antigen-binding domain, or the tag comprises a VHH. In some embodiments, the extracellular tag-binding domain and the tag each comprise a VHH. In some embodiments, the extracellular tag-binding domain, the tag, and the antigen-binding domain each comprise a VHH.

In some embodiments, one or more of the antigen-binding fragment, the extracellular tag-binding domain, the antigen-binding domain, and the tag comprise at least in part a polypeptide sequence having at least 90%, 91%, 92%, 93%, 94%, 95%, 96%, 97%, 98%, 99% or 100% sequence identity to a sequence selected from the group consisting of SEQ ID NOs.: 84, 86, 88, 90, 92, 94, 96, 98, 100, 102, 104, 106, 108, and 110-133.

In some embodiments, at least one of the extracellular tag-binding domain, the antigen-binding domain, or the tag comprises an scFv.

In some embodiments, the alternative scaffold is Affilin or Centyrin.

In some embodiments, the tag comprises an antibody, or antigen-binding fragment thereof, or an alternative scaffold. In some embodiments, the antibody, or antigen-binding fragment thereof, or alternative scaffold binds to a polypeptide from a non-human source. In some embodiments, the polypeptide derived from a non-human source is respiratory syncytial virus (RSV) F-protein, *Listeria* internalin, Cobra phospholipase A2, Ebola nucleoprotein, herpes simplex virus (HSV) glycoprotein D, lactococcal phage receptor binding protein (RBP), *Geobacillus stearothermophilus*, ricin, or chicken egg white lysozyme.

In some embodiments, the antigen-binding domain binds to at least one tumor antigen or autoimmune antigen. In some embodiments, the at least one antigen are associated with the same tumor or autoimmune disease. In some embodiments, the tumor antigen is associated with glioblastoma, ovarian cancer, cervical cancer, head and neck cancer, liver cancer, prostate cancer, pancreatic cancer, renal cell carcinoma, bladder cancer, or hematologic malignancy. In some embodiments, the tumor antigen associated with glioblastoma is HER2, EGFRvIII, EGFR, CD133, PDGFRA, FGFR1, FGFR3, MET, or IL13Ra2. In some embodiments, the tumor antigen associated with ovarian cancer is FOLR1, FSHR, MUC16, MUC1, Mesothelin, CA125, EpCAM, EGFR, PDGFRα, or B7H4. In some embodiments, the tumor antigen associated with cervical cancer or head and neck cancer is GD2, MUC1, Mesothelin, HER2, or EGFR. In some embodiments, the tumor antigen associated with liver cancer is Claudin 18.2, GPC-3, EpCAM, cMET, or AFP.

In some embodiments, the transmembrane domain further comprises a hinge domain. In some embodiments, the transmembrane domain and/or hinge domain is derived from CD8 or CD28.

In some embodiments, the at least one intracellular signaling domain comprises a CD3 signaling domain.

In some embodiments, the at least one intracellular signaling domain comprises one or more co-stimulatory signaling domains. In some embodiments, the one or more co-stimulatory signaling domains are derived from CD28, 41BB, IL2Rb, CD40, OX40, CD80, CD86, CD27, ICOS, NKG2D, DAP10, DAP12, or 2B4 (CD244).

In various embodiments, the second polypeptide comprises the antigen-binding domain at the N-terminus and the tag at the C-terminus. In some embodiments, the second polypeptide comprises the antigen-binding domain at the C-terminus and the tag at the N-terminus.

In various embodiments, the second polypeptide is a soluble polypeptide.

In various embodiments of the arCAR described herein, the immune effector cell is a T cell, a Natural Killer (NK) cell, a cytotoxic T lymphocyte (CTL), a regulatory T cell or a tumor-infiltrating lymphocyte (TIL), a dendritic cell or a macrophage. In some embodiments, the immune effector cell is derived from an induced pluripotent stem cell (iPSC). In some embodiments, the immune effector cell is a T cell or NK cell derived from an induced pluripotent stem cell (iPSC).

In various embodiments of the arCAR described herein, the arCAR further comprises one or more polypeptides each comprising (a) an antigen-binding domain that binds to a unique antigen and (b) a tag that is recognized by the tag-binding domain of the first polypeptide.

In another aspect, provided herein is an arCAR system comprising two or more arCARs described herein, wherein each arCAR comprises a unique pair of tag and tag-binding domain.

In another aspect, provided herein is a polynucleotide encoding the first polypeptide of the arCAR system described herein.

In another aspect, provided herein is a polynucleotide encoding the second polypeptide of the arCAR system described herein.

In another aspect, provided herein is a polynucleotide encoding the first polypeptide and the second polypeptide of the arCAR system described herein.

In some embodiments of the polynucleotide described herein, one or more of the antigen-binding fragment, the extracellular tag-binding domain, the antigen-binding domain, and the tag are encoded at least in part by a polynucleotide sequence having at least 90%, 91%, 92%, 93%, 94%, 95%, 96%, 97%, 98%, 99% or 100% sequence identity to a sequence selected from the group consisting of SEQ ID NOs.: 83, 85, 87, 89, 91, 93, 95, 97, 99, 101, 103, 105, 107, and 109.

In another aspect, provided herein is a recombinant vector comprising the polynucleotide described herein. In some embodiments, the vector is a plasmid.

In another aspect, provided herein is a host cell comprising a polynucleotide that expresses the first polypeptide of the arCAR system described herein.

In another aspect, provided herein is a host cell comprising a polynucleotide that expresses the second polypeptide of the arCAR system described herein.

In another aspect, provided herein is a pharmaceutical composition comprising the immune effector cell of the arCAR system described herein and a pharmaceutically acceptable carrier and/or excipient.

In another aspect, provided herein is a pharmaceutical composition comprising the second polypeptide of the arCAR system described herein and a pharmaceutically acceptable carrier and/or excipient.

In another aspect, provided herein is a kit comprising the pharmaceutical composition comprising the immune effector cell of the arCAR system described herein and the pharmaceutical composition comprising the second polypeptide of the arCAR system in combination.

In another aspect, provided herein is a method of preparing the host cell comprising a polynucleotide that expresses the first polypeptide, comprising introducing the polynucleotide encoding the first polypeptide of the arCAR system, or a recombinant vector comprising the polynucleotide, into the cell.

In another aspect, provided herein is a method of preparing the host cell comprising a polynucleotide that expresses the second polypeptide, comprising introducing the polynucleotide encoding the second polypeptide of the arCAR system, or a recombinant vector comprising the polynucleotide, into the cell.

In another aspect, provided herein is a method of treating a disease in a subject in need thereof, comprising administering to the subject a therapeutically effective amount of
(i) an immune effector cell comprising a chimeric antigen receptor comprising the first polypeptide of the arCAR described herein, and
(ii) the second polypeptide of said arCAR, or a polynucleotide encoding said second polypeptide, or a host cell comprising said second polypeptide.

In some embodiments, the second polypeptide is administered before, after or in conjunction with the immune effector cell.

In another aspect, provided herein is a method of treating a disease in a subject in need thereof, comprising administering to the subject an therapeutically effective amount of
(i) An immune effector cell comprising the first polypeptides of two or more arCARs, wherein the two or more arCARs each comprise a unique pair of tag and tag-binding domain, and
(ii) the second polypeptides of said two or more arCARs, or one or more polynucleotide encoding said second polypeptides, or one or more host cells comprising said second polypeptides.

In some embodiments of the treatment methods described herein, the immune effector cell is a T cell, a Natural Killer (NK) cell, a cytotoxic T lymphocyte (CTL), a regulatory T cell or a tumor-infiltrating lymphocyte (TIL), dendritic cell or macrophage. In some embodiments, the immune effector cell is derived from an iPSC. In some embodiments, the immune effector cell constitutively expresses the first polypeptide.

In some embodiments, the disease is a cancer or autoimmune disease. In some embodiments, the cancer is glioblastoma, ovarian cancer, cervical cancer, head and neck cancer, liver cancer, prostate cancer, pancreatic cancer, renal cell carcinoma, bladder cancer, or hematologic malignancy.

In some embodiments, the immune effector cell and the second polypeptide(s) are administered simultaneously. In some embodiments, the immune effector cell and the second polypeptide(s) are administered sequentially.

In some embodiments, the immune effector cell is an autologous cell. In some embodiments, the immune effector cell is an allogeneic cell.

In some embodiments, the subject is a mammal. In some embodiments, the subject is a human.

BRIEF DESCRIPTION OF THE DRAWINGS

FIG. 11F shows alignment of the amino acid sequences of VHHs targeting *Geobacillus stearothermophilus* (SEQ ID NO: 96), LYSO_CW_P01_B11 (SEQ ID NO: 102) and LYSO_CW_P01_D04 (SEQ ID NO: 104). A consensus sequence is shown above the aligned sequences (SEQ ID NO: 134).

FIGS. 16A-16D show periplasmic extract (PPE) ELISA outputs (absorbance at 450 nm) the colonies achieved for each CNTY library. Black bars represent ELISA responses against the B11 protein, while gray bars represent responses against the D04 protein.

(FIG. 19A) GFP expression of B11 and D04 CAR Nurkat cells, as well as parental Nurkat cells after overnight coculture with anti-idiotype Fc-fusion proteins. (FIG. 19B) Detection of biotinylated protein via streptavidin-APC after the overnight incubation. Controls include PMA/Ionomycin (a TCR-crosslinker that results in robust Nurkat cell activation), biotinylated protein A, and a sample with no protein added. The samples shown in the graphs for each protein appear in the order as specified in the legend.

DETAILED DESCRIPTION

Figure 1:
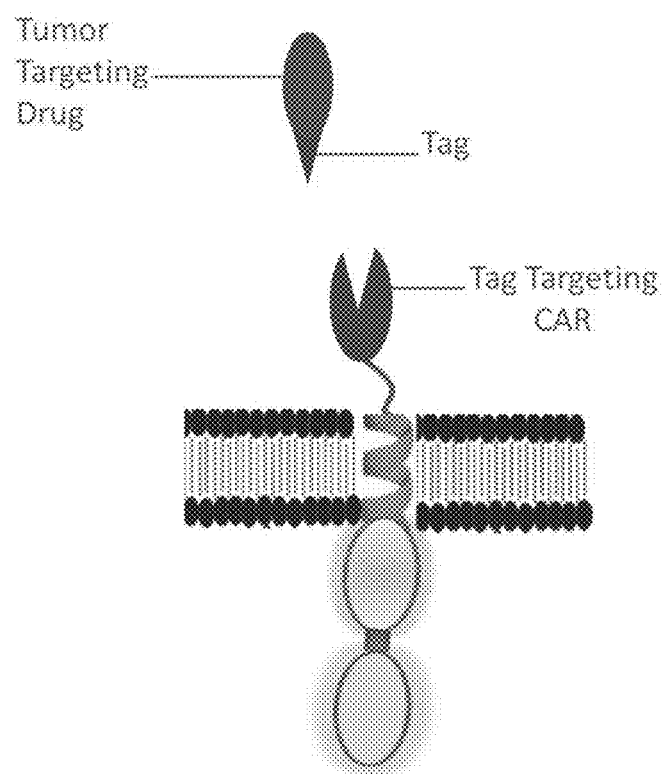
FIG. 1 depicts a schematic representation of an exemplary CAR having an adaptable receptor specificity (arCAR) of the present disclosure. The CAR binds to a "tag" on a soluble drug. The soluble drug can be an antibody or antibody fragment (e.g., VHH, scFv, Fab, mAb) or an alternative scaffold. Tumor specificity and CAR activation is driven by the soluble drug.
Figure 2A:
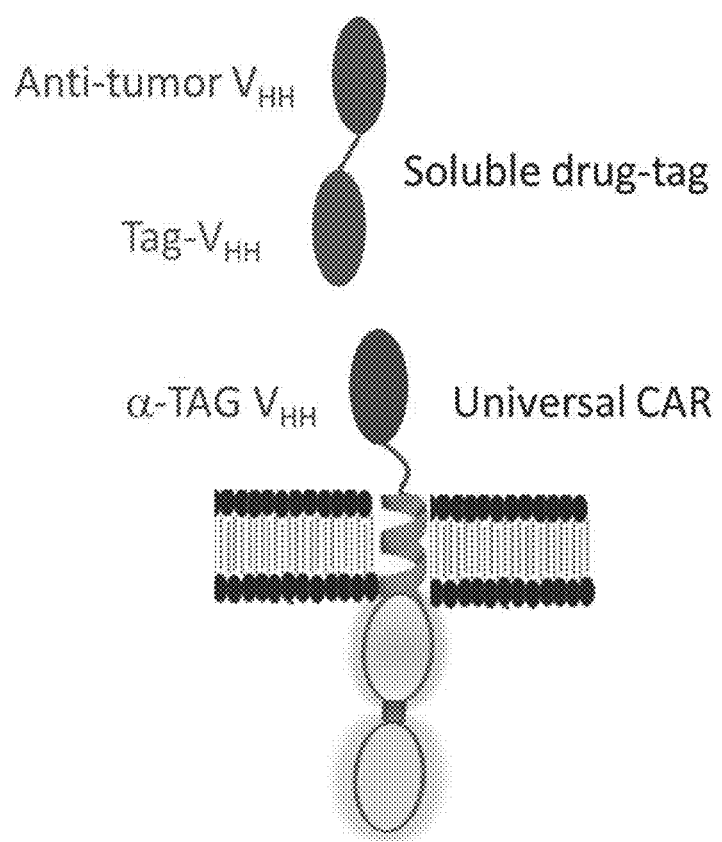
FIG. 2A depicts a schematic representation of another exemplary arCAR of the present disclosure. A VHH is used in both the antigen-binding domain and the tag in the soluble drug, as well as the tag-binding domain (α-tag) of the arCAR.
Figure 2B:
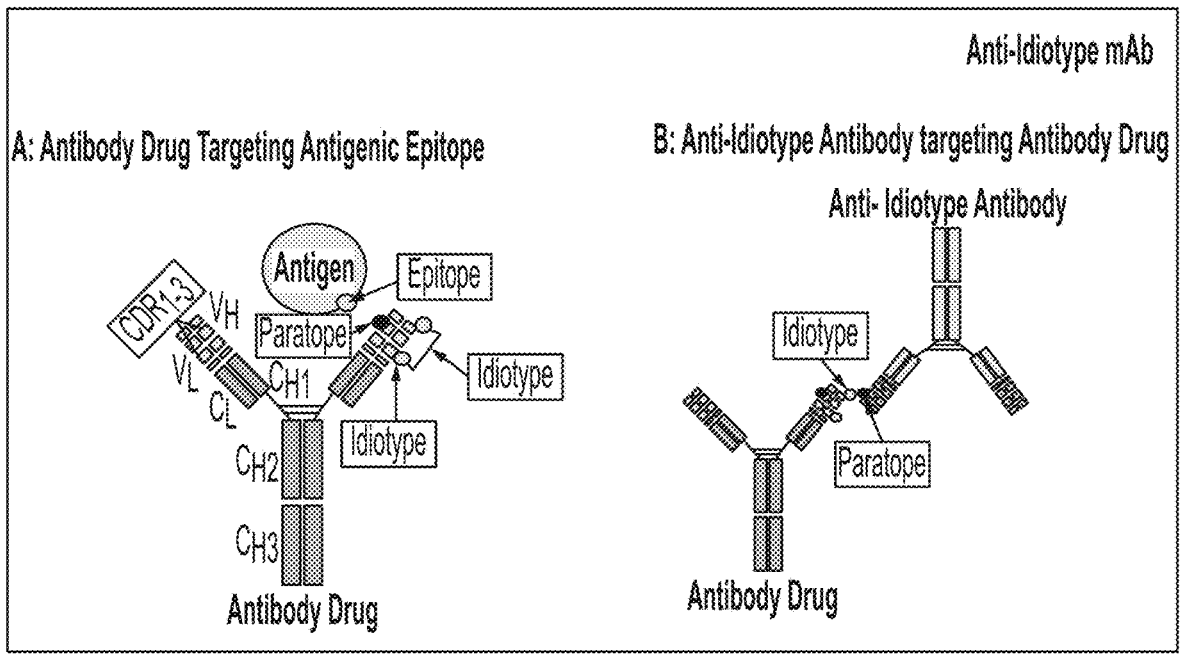
FIG. 2B illustrates the structural characteristics of an anti-idiotype mAb.
Figure 2C:
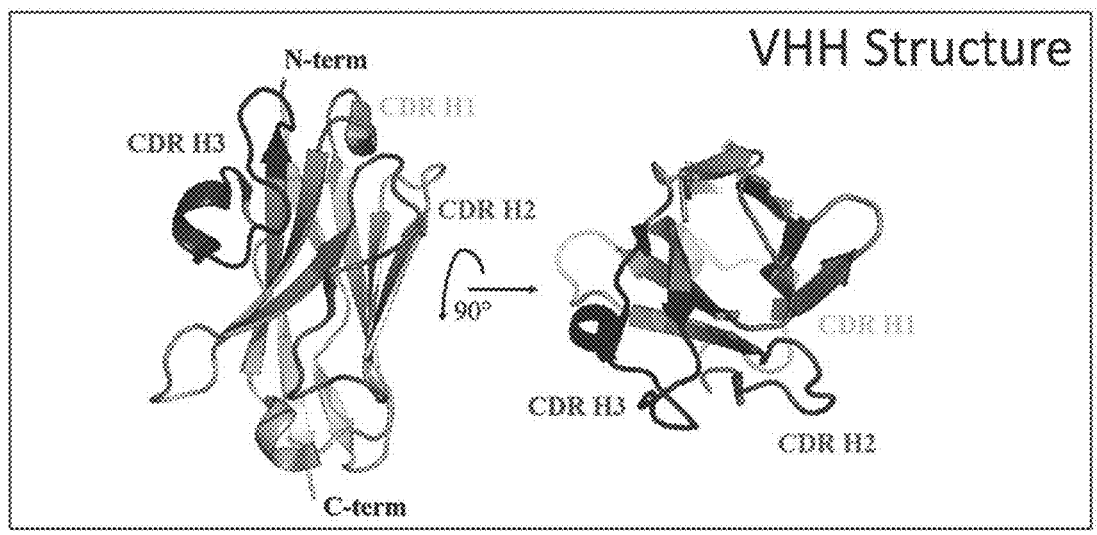
FIG. 2C illustrates the structural characteristics of an exemplary VHH structure.
Figure 2D:
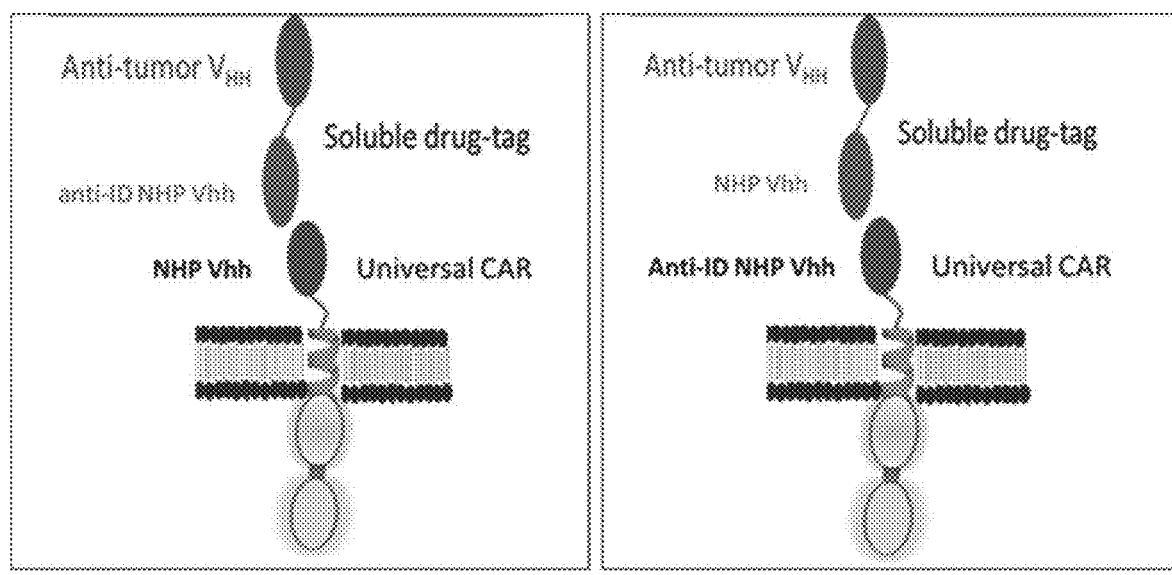
FIG. 2D depicts a schematic representation of another exemplary arCAR of the present disclosure. A non-human primate (NHP) VHH and an anti-idiotype NHP VHH are used in the soluble drug, as well as the tag-binding domain of the arCAR.

Various publications, articles and patents are cited or described in the background and throughout the specification; each of these references is herein incorporated by reference in its entirety. Discussion of documents, acts, materials, devices, articles or the like which has been included in the present specification is for the purpose of providing context for the invention. Such discussion is not an admission that any or all of these matters form part of the prior art with respect to any inventions disclosed or claimed.

The present application provides, among other things, universal chimeric antigen receptor systems having an adaptable receptor specificity component (arCARs) and their uses in immunotherapy (e.g., adoptive cell therapy). This arCAR platform provides a built-in and convenient mechanism for modulation of the receptor using tag polypeptide affinity and allowing for multiple receptors to be present on a cell therapy. Such arCARs can enable fit-for-purpose cell therapy.

Definitions

The term "chimeric antigen receptor" or "CAR" as used herein generally refers to a cell-surface receptor comprising an extracellular target-binding domain, a transmembrane domain, and a cytoplasmic domain comprising a signaling domain and optionally at least one costimulatory signaling domain, all in a combination that is not naturally found together on a single protein. This particularly includes receptors wherein the extracellular domain and the cytoplasmic domain are not naturally found together on a single receptor protein.

The term "chimeric antigen receptor having an adaptable receptor specificity component" or "arCAR" as used herein refers to a two-component CAR system wherein the extracellular target-binding domain of the receptor can be coupled with a variety of different antigen-binding moieties. Except as otherwise indicated, the term "chimeric antigen receptor" or "CAR" used herein is meant to encompass the "chimeric antigen receptor having an adaptable receptor specificity component" or "arCAR" described herein. The arCAR system of the present disclosure may be used with immune effector cells such as lymphocytes including T cells and natural killer (NK) cells, which may be derived from stem cells such as induced pluripotent stem cells (iPSCs).

The term "immune effector cell" as used herein means a cell that has differentiated into a form capable of modulating or effecting a specific immune response. Such cells may include mature lymphocytes suitable for therapy, including, but not limited to, cytotoxic T-cells, helper T-cells, natural killer cells, and tumor-infiltrating lymphocytes (TILs), and may also include dendritic cells or macrophages.

The term "antibody" herein is used in the broadest sense and includes polyclonal and monoclonal antibodies, including intact antibodies and functional (antigen-binding) antibody fragments, including fragment antigen binding (Fab) fragments, F(ab')2 fragments, Fab' fragments, Fv fragments, scFv fragments, recombinant IgG (rIgG) fragments, single chain antibody fragments, including single chain variable fragments (scFv), and single domain antibodies (e.g., VHH, VNAR, sdAb, sdFv) fragments or nanobodies, Fd' fragments, Fd fragments, heavy chain variable regions, or isolated complementarity determining regions (CDRs). The term encompasses genetically engineered and/or otherwise modified forms of immunoglobulins, such as intrabodies, peptibodies, chimeric antibodies, fully human antibodies, humanized antibodies, and heteroconjugate antibodies, multispecific, e.g., bispecific, antibodies, diabodies, triabodies, tetrabodies, decabodies, tandem di-scFv, and tandem tri-scFv. Unless otherwise stated, the term "antibody" should be understood to encompass functional antibody fragments thereof. The term also encompasses intact or full-length antibodies, including antibodies of any class or sub-class, including IgG and sub-classes thereof (e.g., IgG1, IgG2, IgG3, IgG4), IgM, IgY, IgE, IgA, and IgD.

The term "anti-idiotype molecule" refers to a molecule (e.g., peptide, protein, antibody or antibody fragment, alternative scaffold) that specifically recognizes, is specifically targeted to, and/or specifically binds to an idiotope of an antibody, such as an antigen-binding fragment. The idiotopes of an antibody may include, but are not necessarily limited to, residues within one or more of complementarity determining region(s) (CDRs) of the antibody, variable regions of the antibody, and/or partial portions or portions of such variable regions and/or of such CDRs, and/or any combination of the foregoing. The CDR may be one or more selected from the group consisting of CDR-H1, CDR-H2, CDR-H3, CDR-L1, CDR-L2, and CDR-L3. The variable regions of the antibody may be heavy chain variable regions, light chain variable regions, or a combination of the heavy chain variable regions and the light chain variable regions. The partial fragments or portions of the heavy chain variable regions and/or the light chain variable regions of the antibody may be fragments including 2 or more, 5 or more, or 10 or more contiguous amino acids, for example, from about 2 to about 100, from about 5 to about 100, from about 10 to about 100, from about 2 to about 50, from about 5 to about 50, or from about 10 to about 50 contiguous amino acids within the heavy chain variable regions or the light chain variable regions of the antibody; the idiotope may include multiple non-contiguous stretches of amino acids. The partial fragments of the heavy chain variable regions and the light chain variable regions of the antibody may be fragments including 2 or more, 5 or more, or 10 or more contiguous amino acids, for example, from about 2 to about 100, from about 5 to about 100, from about 10 to about 100, from about 2 to about 50, from about 5 to about 50, or from about 10 to about 50 contiguous amino acids within the variable regions, and in some embodiments contain one or more CDRs or CDR fragments. The CDR fragments may be consecutive or non-consecutive 2 or more, or 5 or more amino acids within the CDR. Therefore, the idiotopes of the antibody may be from about 2 to about 100, from about 5 to about 100, from about 10 to about 100, from about 2 to about 50, from about 5 to about 50, or from about 10 to about 50 contiguous amino acids containing one or more CDR or one or more CDR fragments within the heavy chain variable regions or the light chain variable regions of the antibody. In another embodiment, the idiotopes may be a single amino acid which is located at the variable regions of the antibody, for example, CDR sites.

In some embodiments, the idiotope is any single antigenic determinant or epitope within the variable portion of an antibody. In some cases, it can overlap the actual antigen-binding site of the antibody, and in some cases, it may comprise variable region sequences outside of the antigen-binding site of the antibody. The set of individual idiotopes of an antibody is in some embodiments referred to as the "idiotype" of such antibody.

As used herein, the term "antigen" refers to any agent (e.g., protein, peptide, polysaccharide, glycoprotein, glycolipid, nucleic acid, portions thereof, or combinations thereof) molecule capable of being bound by an antibody or antibody fragment, T-cell receptor or alternative scaffold. An antigen is also able to provoke an immune response. An example of an immune response may involve, without limitation, antibody production, or the activation of specific immunologically competent cells, or both. A skilled artisan will understand that an antigen need not be encoded by a "gene" at all. It is readily apparent that an antigen can be generated synthesized or can be derived from a biological sample, or might be macromolecule besides a polypeptide. Such a biological sample can include, but is not limited to a tissue sample, a tumor sample, a cell or a fluid with other biological components, organisms, subunits of proteins/antigens, killed or inactivated whole cells or lysates.

The terms "vector", "expression vector", and "expression construct" are used interchangeably to refer to a composition of matter which can be used to deliver a nucleic acid of interest to the interior of a cell and mediate its expression within the cell. Most commonly used examples of vectors are autonomously replicating plasmids and viruses (such as, e.g., adenoviral vectors, adeno-associated virus vectors (AAV), lentiviral vectors, Sindbis virus vectors, etc.). An expression construct can be replicated in a living cell, or it can be made synthetically. In one embodiment, an expression vector comprises a promoter operably linked to a polynucleotide (e.g., a polynucleotide encoding the first polypeptide and/or second polypeptide of an arCAR described herein) which promoter controls the initiation of transcription by RNA polymerase and expression of the polynucleotide. Typical promoters for mammalian cell expression include, e.g., SV40 early promoter, CMV immediate early promoter (see, e.g., U.S. Pat. Nos. 5,168,062 and 5,385,839, both of which are incorporated herein by reference in their entirety), mouse mammary tumor virus LTR promoter, adenovirus major late promoter (Ad MLP), herpes simplex virus promoter, murine metallothionein gene promoter, and U6 or H1 RNA pol III promoter. Non-limiting examples of promoters useful for expressing first polypeptide and/or second polypeptide of an arCAR described herein in the methods of the present disclosure include, e.g., Synapsin promoter (neuron specific), CamKIIa promoter (specific for excitatory neurons), ubiquitin promoter, CAG promoter, CMV promoter, and β-actin promoter. These and other promoters can be obtained from commercially available plasmids, using techniques well known in the art. See, e.g., Sambrook et al., supra. Enhancer elements may be used in association with promoters to increase expression levels of the vectors. Examples include the SV40 early gene enhancer, as described in Dijkema et al., EMBO J. (1985) 4:761, the enhancer/promoter derived from the long terminal repeat (LTR) of the Rous Sarcoma Virus, as described in Gorman et al., Proc. Natl. Acad. Sci. USA (1982b) 79:6777, which is incorporated herein by reference in its entirety, and elements derived from human CMV, as described in Boshart et al., Cell (1985) 41:521, which is incorporated herein by reference in its entirety, such as elements included in the CMV intron A sequence.

Transcription terminator/polyadenylation signals may also be present in the expression vector. Examples of such sequences include, but are not limited to, those derived from SV40, as described in Sambrook et al., supra, as well as a bovine growth hormone terminator sequence (see, e.g., U.S. Pat. No. 5,122,458, which is incorporated herein by reference in its entirety). Additionally, 5'-UTR sequences can be placed adjacent to the coding sequence in order to enhance expression of the same. Such sequences include UTRs which include, e.g., an Internal Ribosome Entry Site (IRES) present in the leader sequences of picornaviruses such as the encephalomyocarditis virus (EMCV) UTR (fang et al. J. Virol. (1989) 63:1651-1660, which is incorporated herein by reference in its entirety). Other useful picornavirus UTR sequences include, e.g., the polio leader sequence, hepatitis A virus leader and the hepatitis C IRES.

The term "host cell" means any cell that contains a heterologous nucleic acid. The heterologous nucleic acid can be a vector (e.g., an expression vector). For example, a host cell can be a cell from any organism that is selected, modified, transformed, grown, used or manipulated in any way, for the production of a substance by the cell, for example the expression by the cell of a gene, a DNA or RNA sequence, a protein or an enzyme. An appropriate host may be determined. For example, the host cell may be selected based on the vector backbone and the desired result. By way of example, a plasmid or cosmid can be introduced into a prokaryote host cell for replication of several types of vectors. Bacterial cells such as, but not limited to DH5α, JM109, and KCB, SURE® Competent Cells, and SOLO-PACK Gold Cells, can be used as host cells for vector replication and/or expression. Additionally, bacterial cells such as E. coli LE392 could be used as host cells for phage viruses. Eukaryotic cells that can be used as host cells include, but are not limited to yeast (e.g., YPH499, YPH500 and YPH501), insects and mammals. Examples of mammalian eukaryotic host cells for replication and/or expression of a vector include, but are not limited to, HeLa, NIH3T3, Jurkat, 293, COS, CHO, Saos, and PC12.

Host cells of the present disclosure include T cells and natural killer cells that contain the DNA or RNA sequences encoding the CAR and/or express the CAR on the cell surface. Host cells may be used for enhancing T cell activity, natural killer cell activity, treatment of cancer, and treatment of autoimmune disease.

The terms "T cell" and "T lymphocyte" are interchangeable and used synonymously herein. As used herein, T cell includes thymocytes, naive T lymphocytes, immature T lymphocytes, mature T lymphocytes, resting T lymphocytes, or activated T lymphocytes. A T cell can be a T helper (Th) cell, for example a T helper 1 (Th1) or a T helper 2 (Th2)

cell. The T cell can be a helper T cell (HTL; CD4+ T cell) CD4+ T cell, a cytotoxic T cell (CTL; CD8+ T cell), a tumor infiltrating cytotoxic T cell (TIL; CD8+ T cell), CD4+CD8+ T cell, or any other subset of T cells. Other illustrative populations of T cells suitable for use in particular embodiments include naive T cells and memory T cells. Also included are "NKT cells", which refer to a specialized population of T cells that express a semi-invariant T-cell receptor, but also express a variety of molecular markers that are typically associated with NK cells, such as NK1.1. NKT cells include NK1.1+ and NK1.1−, as well as CD4+, CD4−, CD8+ and CD8− cells. The TCR on NKT cells is unique in that it recognizes glycolipid antigens presented by the MHC I-like molecule CD Id. NKT cells can have either protective or deleterious effects due to their abilities to produce cytokines that promote either inflammation or immune tolerance. Also included are "gamma-delta T cells (γδ T cells)," which refer to a specialized population that to a small subset of T cells possessing a distinct TCR on their surface, and unlike the majority of T cells in which the TCR is composed of two glycoprotein chains designated α- and β-TCR chains, the TCR in γδ T cells is made up of a γ-chain and a δ-chain. γδ T cells can play a role in immunosurveillance and immunoregulation, and were found to be an important source of IL-17 and to induce robust CD8+ cytotoxic T cell response. Also included are "regulatory T cells" or "Tregs" refers to T cells that suppress an abnormal or excessive immune response and play a role in immune tolerance. Tregs cells are typically transcription factor Foxp3-positive CD4+ T cells and can also include transcription factor Foxp3-negative regulatory T cells that are IL-10-producing CD4+ T cells.

The terms "natural killer cell" and "NK cell" are used interchangeable and used synonymously herein. As used herein, NK cell refers to a differentiated lymphocyte with a CD 16+ CD56+ and/or CD57+ TCR− phenotype. NKs are characterized by their ability to bind to and kill cells that fail to express "self" MHC/HLA antigens by the activation of specific cytolytic enzymes, the ability to kill tumor cells or other diseased cells that express a ligand for NK activating receptors, and the ability to release protein molecules called cytokines that stimulate or inhibit the immune response.

In certain embodiments of the disclosure, the cells containing nucleic acid constructs of the present disclosure may be identified in vitro or in vivo by including a marker in the expression vector. Such markers would confer an identifiable change to the cell permitting easy identification of cells containing the expression vector. Usually the inclusion of a drug selection marker aids in cloning and in the selection of transformants, for example, genes that confer resistance to neomycin, puromycin, hygromycin, DHFR, GPT, zeocin and histidinol are useful selectable markers. Alternatively, enzymes such as herpes simplex virus thymidine kinase (tk) or chloramphenicol acetyltransferase (CAT) may be employed. Fluorescent markers (e.g., green fluorescent protein (GFP), EGFP, or Dronpa), or immunologic markers can also be employed. Further examples of selectable markers are well known to one of skill in the art.

As used herein, the term "variant" in the context of proteins or polypeptides (e.g., arCAR polypeptides or domains thereof) refer to: (a) a polypeptide that has at least 40%, 45%, 50%, 55%, 60%, 65%, 70%, 75%, 80%, 85%, 90%, 95%, 98% or 99% sequence identity to the polypeptide it is a variant of; (b) a polypeptide encoded by a nucleotide sequence that has at least 40%, 45%, 50%, 55%, 60%, 65%, 70%, 75%, 80%, 85%, 90%, 95%, 98% or 99% sequence identity to a nucleotide sequence encoding the polypeptide it is a variant of; (c) a polypeptide that contains 1, 2, 3, 4, 5, 6, 7, 8, 9, 10, 11, 12, 13, 14, 15, 16, 17, 18, 19, 20 or more amino acid mutations (i.e., additions, deletions and/or substitutions) relative to the polypeptide it is a variant of; (d) a polypeptide encoded by nucleic acids can hybridize under high, moderate or typical stringency hybridization conditions to nucleic acids encoding the polypeptide it is a variant of; (e) a polypeptide encoded by a nucleotide sequence that can hybridize under high, moderate or typical stringency hybridization conditions to a nucleotide sequence encoding a fragment of the polypeptide, it is a variant of, of at least 20 contiguous amino acids, at least 30 contiguous amino acids, at least 40 contiguous amino acids, at least 50 contiguous amino acids, at least 75 contiguous amino acids, at least 100 contiguous amino acids, at least 125 contiguous amino acids, or at least 150 contiguous amino acids; or (f) a fragment of the polypeptide it is a variant of.

Percent sequence identity can be determined using any method known to one of skill in the art. In a specific embodiment, the percent identity is determined using the "Best Fit" or "Gap" program of the Sequence Analysis Software Package (Version 10; Genetics Computer Group, Inc., University of Wisconsin Biotechnology Center, Madison, Wis.). Information regarding hybridization conditions (e.g., high, moderate, and typical stringency conditions) have been described, see, e.g., U.S. Patent Application Publication No. US 2005/0048549 (e.g., paragraphs 72-73).

In the context of the present disclosure insofar as it relates to any of the disease conditions recited herein, the terms "treat", "treatment", and the like mean to prevent, relieve or alleviate at least one symptom associated with such condition, or to slow or reverse the progression of such condition, or to arrest, delay the onset (i.e., the period prior to clinical manifestation of a disease) and/or reduce the risk of developing or worsening a disease.

As used herein the term "therapeutically effective" applied to dose or amount refers to that quantity of a compound or pharmaceutical composition that is sufficient to result in a desired activity (e.g., alleviation of symptoms associated with cancer or autoimmune disease) upon administration to a subject in need thereof. Note that when a combination of active ingredients is administered, the effective amount of the combination may or may not include amounts of each ingredient that would have been effective if administered individually. The exact amount required will vary from subject to subject, depending on the species, age, and general condition of the subject, the severity of the condition being treated, the particular drug or drugs employed, the mode of administration, and the like. An appropriate "effective" amount in any individual case may be determined by one of ordinary skill in the art using routine experimentation, based upon the information provided herein.

The phrase "pharmaceutically acceptable", as used in connection with compositions of the disclosure, refers to molecular entities and other ingredients of such compositions that are physiologically tolerable and do not typically produce untoward reactions when administered to a mammal (e.g., a human). Preferably, as used herein, the term "pharmaceutically acceptable" means approved by a regulatory agency of the Federal or a state government or listed in the U.S. Pharmacopeia or other generally recognized pharmacopeia for use in mammals, and more particularly in humans.

As used herein, the term "combination" of a composition of the disclosure and at least an additional therapeutic agent means at least two, but any desired combination of agents can be delivered simultaneously or sequentially. It is contemplated that when used to treat various diseases, the compositions and methods of the present disclosure can be utilized with other therapeutic methods/agents suitable for the same or similar diseases. Such other therapeutic methods/agents can be co-administered (simultaneously or sequentially) to generate additive or synergistic effects. Suitable therapeutically effective dosages for each agent may be lowered due to the additive action or synergy.

The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Alternatively, the carrier can be a solid dosage form carrier, including but not limited to one or more of a binder (for compressed pills), a glidant, an encapsulating agent, a flavorant, and a colorant. Suitable pharmaceutical carriers are described in "Remington's Pharmaceutical Sciences" by E. W. Martin.

An "individual" or "subject" or "animal", as used herein, refers to humans, veterinary animals (e.g., cats, dogs, cows, horses, sheep, pigs, etc.) or experimental animal models of a disease or disorder (e.g., cancer or autoimmune disease). In a preferred embodiment, the subject is a human.

The term "associated with" is used to encompass any correlation, co-occurrence and any cause-and-effect relationship.

The term "about" means within an acceptable error range for the particular value as determined by one of ordinary skill in the art, which will depend in part on how the value is measured or determined, i.e., the limitations of the measurement system. For example, "about" can mean within an acceptable standard deviation, per the practice in the art. Alternatively, "about" can mean within an order of magnitude, preferably within 50%, more preferably within 20%, still more preferably within 10%, even more preferably within 5%, and most preferably within 1% of a given value or range. Alternatively, particularly with respect to biological systems or processes, the term can mean within an order of magnitude, preferably within 2-fold, of a value. Where particular values are described in the application and claims, unless otherwise stated, the term "about" is implicit and in this context means within an acceptable error range for the particular value.

It must be noted that, as used in this specification and the appended claims, the singular forms "a," "an" and "the" include plural referents unless the content clearly dictates otherwise.

In accordance with the present disclosure there may be employed conventional molecular biology, microbiology, and recombinant DNA techniques within the skill of the art. Such techniques are explained fully in the literature. See, e.g., Sambrook, Fritsch & Maniatis, Molecular Cloning: A Laboratory Manual, Second Edition. Cold Spring Harbor, N.Y.: Cold Spring Harbor Laboratory Press, 1989 (herein "Sambrook et al., 1989"); DNA Cloning: A Practical Approach, Volumes I and II (D. N. Glover ed. 1985); Oligonucleotide Synthesis (M. J. Gait ed. 1984); Nucleic Acid Hybridization [B. D. Hames & S. J. Higgins eds. (1985)]; Transcription And Translation [B. D. Hames & S. J. Higgins, eds. (1984)]; Animal Cell Culture [R. I. Freshney, ed. (1986)]; Immobilized Cells And Enzymes [IRL Press, (1986)]; B. Perbal, A Practical Guide To Molecular Cloning (1984); Ausubel, F. M. et al. (eds.). Current Protocols in Molecular Biology. John Wiley & Sons, Inc., 1994. These techniques include site directed mutagenesis as described in Kunkel, Proc. Natl. Acad. Sci. USA 82: 488-492 (1985), U.S. Pat. No. 5,071,743, Fukuoka et al., Biochem. Biophys. Res. Commun. 263: 357-360 (1999); Kim and Maas, BioTech. 28: 196-198 (2000); Parikh and Guengerich, BioTech. 24: 428-431 (1998); Ray and Nickoloff, BioTech. 13: 342-346 (1992); Wang et al., BioTech. 19: 556-559 (1995); Wang and Malcolm, BioTech. 26: 680-682 (1999); Xu and Gong, BioTech. 26: 639-641 (1999), U.S. Pat. Nos. 5,789,166 and 5,932,419, Hogrefe, Strategies 14. 3: 74-75 (2001), U.S. Pat. Nos. 5,702,931, 5,780,270, and 6,242,222, Angag and Schutz, Biotech. 30: 486-488 (2001), Wang and Wilkinson, Biotech. 29: 976-978 (2000), Kang et al., Biotech. 20: 44-46 (1996), Ogel and McPherson, Protein Engineer. 5: 467-468 (1992), Kirsch and Joly, Nucl. Acids. Res. 26: 1848-1850 (1998), Rhem and Hancock, J. Bacteriol. 178: 3346-3349 (1996), Boles and Miogsa, Curr. Genet. 28: 197-198 (1995), Barrenttino et al., Nuc. Acids. Res. 22: 541-542 (1993), Tessier and Thomas, Meths. Molec. Biol. 57: 229-237, and Pons et al., Meth. Molec. Biol. 67: 209-218.

Chimeric Antigen Receptors Having an Adaptable Receptor Specificity Component (arCARs)

In one aspect, provided herein is a universal chimeric antigen receptor system having an adaptable receptor specificity component (arCAR) comprising:
  (i) an immune effector cell having a chimeric antigen receptor comprising a first polypeptide comprising (a) an extracellular tag-binding domain, (b) a transmembrane domain, and (c) at least one intracellular signaling domain; and
  (ii) a second polypeptide comprising (d) an antigen-binding domain that binds to at least one antigen on a target cell, and (e) a tag that is recognized by the tag-binding domain of the first polypeptide of the chimeric antigen receptor;
  wherein: (i) the tag comprises an antibody, or antigen-binding fragment thereof, or an alternative scaffold and the tag-binding domain comprises an anti-idiotype molecule that binds to the tag, or
    (ii) the tag comprises an anti-idiotype molecule that binds to the tag-binding domain and the tag-binding domain comprises an antibody, or antigen-binding fragment thereof, or an alternative scaffold.

In some embodiments, the anti-idiotype molecule binds to at least one antigen binding region or non-framework region of the antibody, or antigen-binding fragment thereof.

In some embodiments, the tag comprises an antibody, or antigen-binding fragment thereof, or an alternative scaffold that binds to a polypeptide derived from a non-human source. Alternatively, the tag-binding domain comprises an antibody, or antigen-binding fragment thereof, or an alternative scaffold that binds to a polypeptide derived from a non-human source.

In some embodiments, the anti-idiotype molecule binds to at least one complementarity determining region (CDR) of the antibody, or antigen-binding fragment thereof.

In some embodiments, the anti-idiotype molecule is an anti-idiotype antibody, or antigen-binding fragment thereof, or an alternative scaffold.

In some embodiments, the antigen-binding domain of the second polypeptide comprises an antibody, or antigen-binding fragment thereof, or an alternative scaffold.

In various embodiments, antibodies or antibody fragments suitable for use in the arCAR system of the present disclosure include, but are not limited to, monoclonal antibodies, bispecific antibodies, multispecific antibodies, chimeric antibodies, polypeptide-Fc fusions, single-chain Fvs (scFv), single chain antibodies, Fab fragments, F(ab') fragments, disulfide-linked Fvs (sdFv), masked antibodies (e.g., Probodies®), Small Modular ImmunoPharmaceuticals ("SMIPs™"), intrabodies, minibodies, single domain antibody variable domains, nanobodies, VHHs, diabodies, tandem diabodies (TandAb®), and epitope-binding fragments of any of the above. Antibodies and/or antibody fragments may be derived from murine antibodies, rabbit antibodies, human antibodies, fully humanized antibodies, camelid antibody variable domains and humanized versions, shark antibody variable domains and humanized versions, and camelized antibody variable domains.

In some embodiments, the antigen-binding fragment is an Fab fragment, an Fab' fragment, an F(ab')2 fragment, an scFv fragment, an Fv fragment, a dsFv diabody, a VHH, a VNAR, a single-domain antibody (sdAb) or nanobody, a dAb fragment, a Fd' fragment, a Fd fragment, a heavy chain variable region, an isolated complementarity determining region (CDR), a diabody, a triabody, or a decabody. In some embodiments, the antigen-binding fragment is an scFv fragment. In some embodiments, the antigen-binding fragment is a VHH.

In some embodiments, at least one of the extracellular tag-binding domain, the antigen-binding domain, or the tag comprises a single-domain antibody or nanobody.

In some embodiments, at least one of the extracellular tag-binding domain, the antigen-binding domain, or the tag comprises a VHH.

In some embodiments, the extracellular tag-binding domain and the tag each comprise a VHH.

In some embodiments, the extracellular tag-binding domain, the tag, and the antigen-binding domain each comprise a VHH.

In some embodiments, at least one of the extracellular tag-binding domain, the antigen-binding domain, or the tag comprises an scFv.

In some embodiments, the extracellular tag-binding domain and the tag each comprise an scFv.

In some embodiments, the extracellular tag-binding domain, the tag, and the antigen-binding domain each comprise a scFv.

In some embodiments, the antibodies or antigen-binding fragments (e.g., VHH, scFv) used herein are humanized. Humanized proteins have the potential to reduce the risk of immunogenicity.

Alternative scaffolds to immunoglobulin domains that exhibit similar functional characteristics, such as high-affinity and specific binding of target biomolecules, may also be used in the arCARs of the present disclosure. Such scaffolds have been shown to yield molecules with improved characteristics, such as greater stability or reduced immunogenicity. Non-limiting examples of alternative scaffolds that may be used in the arCAR system of the present disclosure include engineered, tenascin-derived, tenascin type III domain (e.g., Centyrin™); engineered, gamma-B crystallin-derived scaffold or engineered, ubiquitin-derived scaffold (e.g., Affilins); engineered, fibronectin-derived, 10th fibronectin type III (10Fn3) domain (e.g., monobodies, AdNectins™, or AdNexins™); engineered, ankyrin repeat motif containing polypeptide (e.g., DARPins™); engineered, low-density-lipoprotein-receptor-derived, A domain (LDLR-A) (e.g., Avimers™); lipocalin (e.g., anticalins); engineered, protease inhibitor-derived, Kunitz domain (e.g., EETI-II/AGRP, BPTI/LACI-D1/ITI-D2); engineered, Protein-A-derived, Z domain (Affibodies™); Sac7d-derived polypeptides (e.g., Nanoffitins® or affitins); engineered, Fyn-derived, SH2 domain (e.g., Fynomers®); CTLD3 (e.g., Tetranectin); thioredoxin (e.g., peptide aptamer); KALBITOR®; the β-sandwich (e.g., iMab); miniproteins; C-type lectin-like domain scaffolds; engineered antibody mimics; and any genetically manipulated counterparts of the foregoing that retains its binding functionality (Worn A, Pluckthun A, J Mol Biol 305: 989-1010 (2001); Xu L et al., Chem Biol 9: 933-42 (2002); Wikman M et al., Protein Eng Des Sel 17: 455-62 (2004); Binz H et al., Nat Biolechnol 23: 1257-68 (2005); Hey T et al., Trends Biotechnol 23:514-522 (2005); Holliger P, Hudson P, Nat Biotechnol 23: 1126-36 (2005); Gill D, Damle N, Curr Opin Biotech 17: 653-8 (2006); Koide A, Koide S, Methods Mol Biol 352: 95-109 (2007); Skerra, Current Opin. in Biotech., 2007 18: 295-304; Byla P et al., J Biol Chem 285: 12096 (2010); Zoller F et al., Molecules 16: 2467-85 (2011), each of which is incorporated by reference in its entirety).

In some embodiments, the alternative scaffold is Affilin or Centyrin.

The molecule derived from a non-human source may be derived from any non-human organisms, including but not limited to, viruses, bacteria, yeast, fungi, plants, and non-human animals.

In some embodiments, the molecule derived from a non-human source is a polypeptide. In some embodiments, the source of the protein is from a non-human polypeptide that does not have a human homolog.

In some embodiments, the polypeptide derived from a non-human source is respiratory syncytial virus (RSV) F-protein, *Listeria* internalin, Cobra phospholipase A2, Ebola nucleoprotein, herpes simplex virus (HSV) glycoprotein D, lactococcal phage receptor binding protein (RBP), *Geobacillus stearothermophilus*, ricin, or chicken egg white lysozyme.

In some embodiments, the first polypeptide of the arCARs of the present disclosure comprises a leader sequence. The leader sequence may be positioned at the N-terminus of the extracellular tag-binding domain. The leader sequence may be optionally cleaved from the extracellular tag-binding domain during cellular processing and localization of the CAR to the cellular membrane. Any of various leader sequences known to one of skill in the art may be used as the leader sequence. Non-limiting examples of peptides from which the leader sequence may be derived include granulocyte-macrophage colony-stimulating factor (GMCSF), FcɛR, human immunoglobulin (IgG) heavy chain (HC) variable region, CD8a, mouse Ig-kappa signal peptide, or any of various other proteins secreted by T cells. In various embodiments, the leader sequence is compatible with the secretory pathway of a T cell. In certain embodiments, the leader sequence is derived from human immunoglobulin heavy chain (HC).

In some embodiments, the leader sequence is derived from GMCSF. In one embodiment, the GMCSF leader sequence comprises the amino acid sequence set forth in SEQ ID NO: 1, or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NO: 1.

In some embodiments, the leader sequence is derived from the mouse Ig-kappa signal peptide. In one embodiment, the mouse Ig-kappa signal peptide comprises the amino acid sequence set forth in SEQ ID NO: 61, or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NO: 61.

In some embodiments, the first polypeptide of the arCARs of the present disclosure comprise a transmembrane domain, fused in frame between the extracellular tag-binding domain and the cytoplasmic domain.

The transmembrane domain may be derived from the protein contributing to the extracellular tag-binding domain, the protein contributing the signaling or co-signaling domain, or by a totally different protein. In some instances, the transmembrane domain can be selected or modified by amino acid substitution, deletions, or insertions to minimize interactions with other members of the arCAR complex. In some instances, the transmembrane domain can be selected or modified by amino acid substitution, deletions, or insertions to avoid binding of proteins naturally associated with the transmembrane domain. In certain embodiments, the transmembrane domain includes additional amino acids to allow for flexibility and/or optimal distance between the domains connected to the transmembrane domain.

The transmembrane domain may be derived either from a natural or from a synthetic source. Where the source is natural, the domain may be derived from any membrane-bound or transmembrane protein. Non-limiting examples of transmembrane domains of particular use in this disclosure may be derived from (i.e. comprise at least the transmembrane region(s) of) the α, β or ζ chain of the T-cell receptor (TCR), NKG2D, CD28, CD3 epsilon, CD45, CD4, CD5, CD8, CD8α, CD9, CD16, CD22, CD33, CD37, CD40, CD64, CD80, CD86, CD134, CD137, or CD154. Alternatively, the transmembrane domain may be synthetic, in which case it will comprise predominantly hydrophobic residues such as leucine and valine. For example, a triplet of phenylalanine, tryptophan and/or valine can be found at each end of a synthetic transmembrane domain.

In some embodiments, it will be desirable to utilize the transmembrane domain of the η or FcεR1γ chains which contain a cysteine residue capable of disulfide bonding, so that the resulting chimeric protein will be able to form disulfide linked dimers with itself, or with unmodified versions of the ζ, η or FcεR1γ chains or related proteins. In some instances, the transmembrane domain will be selected or modified by amino acid substitution to avoid binding of such domains to the transmembrane domains of the same or different surface membrane proteins to minimize interactions with other members of the receptor complex. In other cases, it will be desirable to employ the transmembrane domain of ζ, η or FcεR1γ and -β, MB1 (Igα), B29 or CD3-γ, ζ, or η, in order to retain physical association with other members of the receptor complex.

In some embodiments, the transmembrane domain is derived from CD8 or CD28. In one embodiment, the CD8 transmembrane domain comprises the amino acid sequence set forth in SEQ ID NO: 23, or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NO: 23. In one embodiment, the CD28 transmembrane domain comprises the amino acid sequence set forth in SEQ ID NO: 24, or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NO: 24.

In some embodiments, the first polypeptide of the arCAR system of the present disclosure comprises a spacer region between the extracellular tag-binding domain and the transmembrane domain, wherein the tag-binding domain, linker, and the transmembrane domain are in frame with each other.

The term "spacer region" as used herein generally means any oligo- or polypeptide that functions to link the tag-binding domain to the transmembrane domain. A spacer region can be used to provide more flexibility and accessibility for the tag-binding domain. A spacer region may comprise up to 300 amino acids, preferably 10 to 100 amino acids and most preferably 25 to 50 amino acids. A spacer region may be derived from all or part of naturally occurring molecules, such as from all or part of the extracellular region of CD8, CD4 or CD28, or from all or part of an antibody constant region. Alternatively, the spacer region may be a synthetic sequence that corresponds to a naturally occurring spacer region sequence, or may be an entirely synthetic spacer region sequence. Non-limiting examples of spacer regions which may be used in accordance to the disclosure include a part of human CD8a chain, partial extracellular domain of CD28, FcγRIIIa receptor, IgG, IgM, IgA, IgD, IgE, an Ig hinge, or functional fragment thereof. In some embodiments, additional linking amino acids are added to the spacer region to ensure that the antigen-binding domain is an optimal distance from the transmembrane domain. In some embodiments, when the spacer is derived from an Ig, the spacer may be mutated to prevent Fc receptor binding.

In some embodiments, the spacer region comprises a hinge domain. The hinge domain may be derived from CD8a, CD28, or an immunoglobulin (IgG). For example, the IgG hinge may be from IgG1, IgG2, IgG3, IgG4, IgM1, IgM2, IgA1, IgA2, IgD, IgE, or a chimera thereof.

In certain embodiments, the hinge domain comprises an immunoglobulin IgG hinge or functional fragment thereof. In certain embodiments, the IgG hinge is from IgG1, IgG2, IgG3, IgG4, IgM1, IgM2, IgA1, IgA2, IgD, IgE, or a chimera thereof. In certain embodiments, the hinge domain comprises the CH1, CH2, CH3 and/or hinge region of the immunoglobulin. In certain embodiments, the hinge domain comprises the core hinge region of the immunoglobulin. The term "core hinge" can be used interchangeably with the term "short hinge" (a.k.a "SH"). Non-limiting examples of suitable hinge domains are the core immunoglobulin hinge regions include EPKSCDKTHTCPPCP (SEQ ID NO: 57) from IgG1, ERKCCVECPPCP (SEQ ID NO: 58) from IgG2, ELKTPLGDTTHTCPRCP(EPKSCDTPPPCPRCP)$_3$ (SEQ ID NO: 59) from IgG3, and ESKYGPPCPSCP (SEQ ID NO: 60) from IgG4 (see also Wypych et al., *JBC* 2008 283(23): 16194-16205, which is incorporated herein by reference in its entirety for all purposes). In certain embodiments, the hinge domain is a fragment of the immunoglobulin hinge.

In some embodiments, the hinge domain is derived from CD8 or CD28. In one embodiment, the CD8 hinge domain comprises the amino acid sequence set forth in SEQ ID NO: 21, or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NO: 21. In one embodiment, the CD28 hinge domain comprises the amino acid sequence set forth in SEQ ID NO: 22, or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NO: 22.

In some embodiments, the transmembrane domain and/or hinge domain is derived from CD8 or CD28. In some embodiments, both the transmembrane domain and hinge domain are derived from CD8. In some embodiments, both the transmembrane domain and hinge domain are derived from CD28.

In certain aspects, the first polypeptide of arCARs of the present disclosure comprise a cytoplasmic domain, which comprises at least one intracellular signaling domain. In some embodiments, cytoplasmic domain also comprises one or more co-stimulatory signaling domains.

The cytoplasmic domain is responsible for activation of at least one of the normal effector functions of the host cell (e.g., T cell) in which the arCAR has been placed in. The term "effector function" refers to a specialized function of a cell. Effector function of a T-cell, for example, may be cytolytic activity or helper activity including the secretion of cytokines. Thus, the term "signaling domain" refers to the portion of a protein which transduces the effector function signal and directs the cell to perform a specialized function. While usually the entire signaling domain is present, in many cases it is not necessary to use the entire chain. To the extent that a truncated portion of the intracellular signaling domain is used, such truncated portion may be used in place of the intact chain as long as it transduces the effector function signal. The term intracellular signaling domain is thus meant to include any truncated portion of the signaling domain sufficient to transduce the effector function signal.

Non-limiting examples of signaling domains which can be used in the arCARs of the present disclosure include, e.g., signaling domains derived from DAP10, DAP12, Fc epsilon receptor I γ chain (FCER1G), FcR β, NKG2D, CD3δ, CD3ε, CD3γ, CD3ζ, CD5, CD22, CD226, CD66d, CD79A, or CD79B.

In some embodiments, the cytoplasmic domain comprises a CD3ζ signaling domain. In one embodiment, the CD3ζ signaling domain comprises the amino acid sequence set forth in SEQ ID NO: 6, or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NO: 6.

In some embodiments, the cytoplasmic domain further comprises one or more co-stimulatory signaling domains. In some embodiments, the one or more co-stimulatory signaling domains are derived from CD28, 41BB, IL2Rb, CD40, OX40 (CD134), CD80, CD86, CD27, ICOS, NKG2D, DAP10, DAP12, 2B4 (CD244), BTLA, CD30, GITR, CD226, CD79A, or HVEM.

In one embodiment, the co-stimulatory signaling domain is derived from 41BB. In one embodiment, the 41BB co-stimulatory signaling domain comprises the amino acid sequence set forth in SEQ ID NO: 8, or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NO: 8.

In one embodiment, the co-stimulatory signaling domain is derived from IL2Rb. In one embodiment, the IL2Rb co-stimulatory signaling domain comprises the amino acid sequence set forth in SEQ ID NO: 9, or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NO: 9.

In one embodiment, the co-stimulatory signaling domain is derived from CD40. In one embodiment, the CD40 co-stimulatory signaling domain comprises the amino acid sequence set forth in SEQ ID NO: 10, or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NO: 10.

In one embodiment, the co-stimulatory signaling domain is derived from OX40. In one embodiment, the OX40 co-stimulatory signaling domain comprises the amino acid sequence set forth in SEQ ID NO: 11, or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NO: 11.

In one embodiment, the co-stimulatory signaling domain is derived from CD80. In one embodiment, the CD80 co-stimulatory signaling domain comprises the amino acid sequence set forth in SEQ ID NO: 12, or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NO: 12.

In one embodiment, the co-stimulatory signaling domain is derived from CD86. In one embodiment, the CD86 co-stimulatory signaling domain comprises the amino acid sequence set forth in SEQ ID NO: 13, or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NO: 13.

In one embodiment, the co-stimulatory signaling domain is derived from CD27. In one embodiment, the CD27 co-stimulatory signaling domain comprises the amino acid sequence set forth in SEQ ID NO: 14, or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NO: 14.

In one embodiment, the co-stimulatory signaling domain is derived from ICOS. In one embodiment, the ICOS co-stimulatory signaling domain comprises the amino acid sequence set forth in SEQ ID NO: 15, or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NO: 15.

In one embodiment, the co-stimulatory signaling domain is derived from NKG2D. In one embodiment, the NKG2D co-stimulatory signaling domain comprises the amino acid sequence set forth in SEQ ID NO: 16, or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NO: 16.

In one embodiment, the co-stimulatory signaling domain is derived from DAP10. In one embodiment, the DAP10 co-stimulatory signaling domain comprises the amino acid sequence set forth in SEQ ID NO: 17, or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NO: 17.

In one embodiment, the co-stimulatory signaling domain is derived from DAP12. In one embodiment, the DAP12 co-stimulatory signaling domain comprises the amino acid sequence set forth in SEQ ID NO: 18, or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NO: 18.

In one embodiment, the co-stimulatory signaling domain is derived from 2B4 (CD244). In one embodiment, the 2B4 (CD244) co-stimulatory signaling domain comprises the amino acid sequence set forth in SEQ ID NO: 19, or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NO: 19.

In one embodiment, the co-stimulatory signaling domain is derived from CD28. In one embodiment, the CD28 co-stimulatory signaling domain comprises the amino acid sequence set forth in SEQ ID NO: 20, or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NO: 20.

In some embodiments, the arCAR of the present disclosure comprises one costimulatory signaling domains. In some embodiments, the arCAR of the present disclosure comprises two or more costimulatory signaling domains. In certain embodiments, the arCAR of the present disclosure comprises two, three, four, five, six or more costimulatory signaling domains.

In some embodiments, the signaling domain(s) and costimulatory signaling domain(s) can be placed in any order. In some embodiments, the signaling domain is upstream of the costimulatory signaling domains. In some embodiments, the signaling domain is downstream from the costimulatory signaling domains. In the cases where two or more costimulatory domains are included, the order of the costimulatory signaling domains could be switched.

Non-limiting exemplary CAR regions and sequences are provided in Table 1.

TABLE 1

| CAR regions | Sequence | UniProt Id | SEQ ID NO |
|---|---|---|---|
| CD19 CAR: | | | |
| GMCSF Signal Peptide | MLLLVTSLLLCELPHPAFLLIP | | 1 |
| FMC63 VH | EVKLQESGPGLVAPSQSLSVTCTVSGVSLPDYGVSW IRQPPRKGLEWLGVIWGSETTYYNSALKSRLTIIKD NSKSQVFLKMNSLQTDDTAIYYCAKHYYYGGSYAMD YWGQGTSVTVSS | | 2 |
| Whitlow Linker | GSTSGSGKPGSGEGSTKG | | 3 |
| FMC63 VL | DIQMTQTTSSLSASLGDRVTISCRASQDISKYLNWY QQKPDGTVKLLIYHTSRLHSGVPSRFSGSGSGTDYS LTISNLEQEDIATYFCQQGNTLPYTFGGGTKLEIT | | 4 |
| CD28 (AA 114-220) | IEVMYPPPYLDNEKSGNTIIHVKGKHLCPSPLFPGP SKPFWVLVVVGGVLACYSLLVTVAFIIFWVRSKRSR LLHSDYMNMTPRRGPTRKHYQPYAPPRDFAAYRS | | 5 |
| CD3-zeta isoform 3 (AA 52-163) | RVKFSRSADAPAYQQGQNQLYNELNLGRREEYDVLD KRRGRDPEMGGKPRRKNPQEGLYNELQKDKMAEAYS EIGMKGERRRGKGHDGLYQGLSTATKDTYDALHMQA LPPR | | 6 |
| FMC63 scFV | EVKLQESGPGLVAPSQSLSVTCTVSGVSLPDYGVSW IRQPPRKGLEWLGVIWGSETTYYNSALKSRLTIIKD NSKSQVFLKMNSLQTDDTAIYYCAKHYYYGGSYAMD YWGQGTSVTVSSGSTSGSGKPGSGEGSTKGDIQMTQ TTSSLSASLGDRVTISCRASQDISKYLNWYQQKPDG TVKLLIYHTSRLHSGVPSRFSGSGSGTDYSLTISNL EQEDIATYFCQQGNTLPYTFGGGTKLEIT | | 7 |
| Signaling Domains: | | | |
| 41BB (AA 214-255) | KRGRKKLLYIFKQPFMRPVQTTQEEDGCSCRFPEEE EGGCEL | Q07011 | 8 |
| IL2Rb (AA 266-551) | NCRNTGPWLKKVLKCNTPDPSKFFSQLSSEHGGDVQ KWLSSPFPSSSFSPGGLAPEISPLEVLERDKVTQLL PLNTDAYLSLQELQGQDPTHLV | P14784 | 9 |
| CD40 (AA 216-277) | KKVAKKPTNKAPHPKQEPQEINFPDDLPGSNTAAPV QETLHGCQPVTQEDGKESRISVQERQ | P25942 | 10 |
| OX40 (AA 236-277) | ALYLLRRDQRLPPDAHKPPGGGSFRTPIQEEQADHS TLAKI | P43489 | 11 |
| CD80 (AA 264-288) | TYCFAPRCRERRRNERLRRESVRPV | P33681 | 12 |
| CD86 (AA269-329) | KWKKKKRPRNSYKCGTNTMEREESEQTKKREKIHIP ERSDEAQRVFKSSKTSSCDKSDTCF | P42081 | 13 |
| CD27 (AA 213-260) | QRRKYRSNKGESPVEPAEPCHYSCPREEEGSTIPIQ ESYRKPEPACSP | P26842 | 14 |
| ICOS (AA 162-199) | CWLTKKKYSSSVHDPNGEYMFMRAVNTAKKSRLTDV TL | Q9Y6W8 | 15 |
| NKG2D (AA 1-51) | MGWIRGRRSR HSWEMSEFHN YNLDLKKSDF STRWQKQRCP VVKSKCRENAS | P26718 | 16 |
| DAP10 (AA 70-93) | LCARPRRSPAQEDGKVYINMPGRG | Q9UBK5 | 17 |
| DAP12 (AA 62-113) | YFLGRLVPRGRGAAEAATRKQRITETESPYQELQGQ RSDVYSDLNTQRPYYK | O54885 | 18 |
| 2B4/CD244 (AA 251-370) | WRRKRKEKQSETSPKEFLTIYEDVKDLKTRRNHEQE QTFPGGGSTIYSMIQSQSSAPTSQEPAYTLYSLIQP SRKSGSRKRNHSPSFNSTIYEVIGKSQPKAQNPARL SRKELENFDVYS | Q9BZW8 | 19 |

TABLE 1-continued

| CAR regions | Sequence | UniProt Id | SEQ ID NO |
|---|---|---|---|
| CD3-zeta isoform 3 (AA 52-163) | RVKFSRSADAPAYQQGQNQLYNELNLGRREEYDVLD KRRGRDPEMGGKPRRKNPQEGLYNELQKDKMAEAYS EIGMKGERRRGKGHDGLYQGLSTATKDTYDALHMQA LPPR | P20963-3 | 6 |
| CD28 (AA 180-220) | RSKRSRLLHSDYMNMTPRRPGPTRKHYQPYAPPRDF AAYRS | A10747-1 | 20 |
| Spacer/Hinge: | | | |
| CD8 (AA 136-182) | TTTPAPRPPTPAPTIASQPLSLRPEACRPAAGGAVH TRGLDFACDIY | P01732 | 21 |
| CD28 (AA 114-151) | IEVMYPPPYLDNEKSNGTIIHVKGKHLCPSPLFPGP SKP | P10747-1 | 22 |
| Short Hinge (nucleotide sequence) | GAGAGCAAGTATGGGCCCCCTTGTCCTCCTTGTCCG | | 63 |
| Short Hinge (amino acid sequence) | ESKYGPPCPPCP | | 64 |
| Medium Hinge (nucleotide sequence) | GAGAGCAAGTATGGGCCCCCTTGTCCTCCTTGTCCG GGGCAGCCCCGAGAGCCACAGGTGTACACtCTGCCa CCAAGTCAGGAGGAGATGACCAAGAACCAGGTCAGC CTGACCTGCCTGGTCAAAGGCTTCTACCCCAGCGAC ATCGCCGTGGAGTGGGAGAGCAATGGGCAGCCGGAG AACAACTACAAGACCACGCCTCCCGTGCTGGACTCC GACGGCTCCTTCTTCCTCTACAGCAGGCTCACCGTG GACAAGAGCAGGTGGCAGGAGGGGAATGTCTTCTCA TGCTCCGTGATGCATGAGGCTCTGCACAACCACTAC ACACAGAAGAGCCTCTCCCTGTCTCTGGGAAAG | | 65 |
| Medium Hinge (amino acid sequence) | ESKYGPPCPPCPGQPREPQVYTLPPSQEEMTKNQVS LTCLVKGFYPSDIAVEWESNGQPENNYKTTPPVLDS DGSFFLYSRLTVDKSRWQEGNVFSCSVMHEALHNHY QTKSLSLSLGK | | 66 |
| Long Hinge (nucleotide sequence) | GAGTCTAAGTATGGGCCCCCTTGTCCTCCTTGTCCG GCACCTCCCGTGGCTGGACCAAGTGTATTCATTTCC CCCAAAACCCAAAGATACTCTCATGATTTCCCGGAC CCCTGAGGTTACATGCGTGGTGGTGGATGTGAGCCA GGAAGACCCCGAAGTCCAGTTTAACTGGTACGTGGA TGGAGTGGAGGTGCATAATGCAAAGACAAAGCCTCG GGAAGAACAGTTTCAGAGCACATACCGTGTGGTTAG TGTCCTCACAGTTCTGCACCAGGACTGGCTGAACGG CAAGGAGTATAAGTGTAAGGTCTCCAATAAAGGCCT CCCGTCATCGATCGAAAAAAACCATCAGTAAAGCCAA AGGGCAGCCAAGGGAGCCACAGGTGTATACTTTACC ACCAAGTCAGGAGGAAATGACCAAGAACCAGGTATC TCTGACCTGCCTAGTCAAAGGCTTTTACCCCAGCGA TATCGCTGTGGAGTGGGAGTCTAATGGGCAGCCAGA GAACAACTACAAGACCACACCTCCTGTGCTGGACTC CGATGGCTCCTTCTTTCTATACAGCAGGTTAACCGT GGATAAGAGCAGGTGGCAGGAGGGGAATGTCTTCTC ATGCTCTGTGATGCATGAGGCTCTGCACAACCACTA CACACAGAAGAGCCTCTCCCTGTCTCTGGGAAAG | | 67 |
| Long Hinge (amino acid sequence) | ESKYGPPCPPCPAPPVAGPSVFLFPPKPKDLTMLIS RTPEVTCVVVDVSQEDPEVQFNWYVDGVEVHNAKTK PREEQFQSTYRVVSVLTVLHQDWLNGKEYKCKVSNK GLPSSIEKTISKAKGQPREPQVYTLPPSQEEMTKNQ VSLTCLVKGFYPSDIAVEWESNGQPENNYKTTPPVL DSDGSFFLYSRLTVDKSRWQEGNVFSCSVMHEALHN HYTQKSLSLSLGK | | 68 |
| Leader Sequence/Signal Peptide: | | | |
| GMCSF Signal Peptide | MLLLVTSLLLCELPHPAFLLIP | | 1 |
| Mouse Ig-Kappa Signal Peptide (nucleotide sequence) | ATGGCCAGGAGCCCCGCCCAGCTGCTGGGCCTGCTG CTGCTGTGGCTGAGCGGCGCCAGGTGC | | 61 |
| Mouse Ig-Kappa Signal Peptide (amino acid sequence) | MARSPAQLLGLLLLWLSGARC | | 62 |

TABLE 1-continued

| CAR regions | Sequence | UniProt Id | SEQ ID NO |
|---|---|---|---|
| Transmembrane: | | | |
| CD8 (AA 183-203) | IYIWAPLAGTGCGVLLLSLVIT | P10732 | 23 |
| CD28 (AA 153-179) | FWVLVVVGGVLACYSLLVTVAFIIFWV | P10747-1 | 24 |
| Linkers: | | | |
| Whitlow Linker | GSTSGSGKPGSGEGSTKG | | 3 |
| (G$_4$S)$_3$ | GGGGSGGGGSGGGGS | | 25 |
| Linker 3 | GGSEGKSSGSGSESKSTGGS | | 26 |
| Linker 4 | GGGSGGGS | | 27 |
| Linker 3 | GGGSGGGSGGGS | | 28 |
| Linker 4 | GGGSGGGSGGGSGGGS | | 29 |
| Linker 5 | GGGSGGGSGGGSGGGSGGGS | | 30 |
| Linker 6 | GGGGSGGGGSGGGGSGGGGS | | 31 |
| Linker 7 | GGGGSGGGGSGGGGSGGGGSGGGGS | | 32 |
| Linker 8 | IRPRAIGGSKPRVA | | 33 |
| Linker 9 | GKGGSGKGGSGKGGS | | 34 |
| Linker 10 | GGKGSGGKGSGGKGS | | 35 |
| Linker 11 | GGGKSGGGKSGGGKS | | 36 |
| Linker 12 | GKGKSGKGKSGKGKS | | 37 |
| Linker 13 | GGGKSGGKGSGKGGS | | 38 |
| Linker 14 | GKPGSGKPGSGKPGS | | 39 |
| Linker 15 | GKPGSGKPGSGKPGSGKPGS | | 40 |
| Linker 16 | GKGKSGKGKSGKGKSGKGKS | | 41 |
| Linker 17 | STAGDTHLGGEDFD | | 42 |
| Linker 18 | GEGGSGEGGSGEGGS | | 43 |
| Linker 19 | GGEGSGGEGSGGEGS | | 44 |
| Linker 20 | GEGESGEGESGEGES | | 45 |
| Linker 21 | GGGESGGEGSGEGGS | | 46 |
| Linker 22 | GEGESGEGESGEGESGEGES | | 47 |
| Linker 23 | GSTSGSGKPGSGEGSTKG | | 48 |
| Linker 24 | PRGASKSGSASQTGSAPGS | | 49 |
| Linker 25 | GTAAAGAGAAGGAAAGAAG | | 50 |
| Linker 26 | GTSGSSGSGSGGSGSGGG | | 51 |
| Linker 27 | GKPGSGKPGSGKPGSGKPGS | | 52 |
| Linker 28 | GSGS | | 53 |
| Linker 29 | APAPAPAPAP | | 54 |
| Linker 30 | APAPAPAPAPAPAPAPAPAP | | 55 |
| Linker 31 | AEAAAKEAAAKEAAAAKEAAAAKEAAAAKAAA | | 56 |

In some embodiments, the antigen-binding domain of the second polypeptide binds to an antigen. The antigen-binding domain of the second polypeptide may bind to more than one antigen or more than one epitope in an antigen. For example, the antigen-binding domain of the second polypeptide may bind to two, three, four, five, six, seven, eight or more antigens. As another example, the antigen-binding domain of the second polypeptide may bind to two, three, four, five, six, seven, eight or more epitopes in the same antigen.

The choice of antigen-binding domain may depend upon the type and number of antigens that define the surface of a target cell. For example, the antigen-binding domain may be chosen to recognize an antigen that acts as a cell surface marker on target cells associated with a particular disease state. In certain embodiments, the arCARs of the present disclosure can be genetically modified to target a tumor antigen of interest by way of engineering a desired antigen-binding domain that specifically binds to an antigen (e.g., on a tumor cell). Non-limiting examples of cell surface markers that may act as targets for the antigen-binding domain in the arCAR of the disclosure include those associated with tumor cells or autoimmune diseases.

In some embodiments, the antigen-binding domain binds to at least one tumor antigen or autoimmune antigen.

In some embodiments, the antigen-binding domain binds to at least one tumor antigen. In some embodiments, the antigen-binding domain binds to two or more tumor antigens. In some embodiments, the two or more tumor antigens are associated with the same tumor. In some embodiments, the two or more tumor antigens are associated with different tumors.

In some embodiments, the antigen-binding domain binds to at least one autoimmune antigen. In some embodiments, the antigen-binding domain binds to two or more autoimmune antigens. In some embodiments, the two or more autoimmune antigens are associated with the same autoimmune disease. In some embodiments, the two or more autoimmune antigens are associated with different autoimmune diseases.

In some embodiments, the tumor antigen is associated with glioblastoma, ovarian cancer, cervical cancer, head and neck cancer, liver cancer, prostate cancer, pancreatic cancer, renal cell carcinoma, bladder cancer, or hematologic malignancy. Non-limiting examples of tumor antigen associated with glioblastoma include HER2, EGFRvIII, EGFR, CD133, PDGFRA, FGFR1, FGFR3, MET, CD70, ROBO1 and IL13Rα2. Non-limiting examples of tumor antigens associated with ovarian cancer include FOLR1, FSHR, MUC16, MUC1, Mesothelin, CA125, EpCAM, EGFR, PDGFRα, Nectin-4 and B7H4. Non-limiting examples of the tumor antigens associated with cervical cancer or head and neck cancer include GD2, MUC1, Mesothelin, HER2, and EGFR. Non-limiting examples of tumor antigen associated with liver cancer include Claudin 18.2, GPC-3, EpCAM, cMET, and AFP. Non-limiting examples of tumor antigens associated with hematological malignancies include CD19, CD22, CD79, BCMA, GPRC5D, SLAM F7, CD33, CLL1, CD123, and CD70. Non-limiting examples of tumor antigens associated with bladder cancer include Nectin-4 and SLITRK6. Non-limiting examples of tumor antigens associated with renal cancer include CD70 and FOLR1.

Additional examples of antigens that may be targeted by the antigen-binding domain include, but are not limited to, alpha-fetoprotein, A3, antigen specific for A33 antibody, Ba 733, BrE3-antigen, carbonic anhydrase EX, CD1, CD1a, CD3, CD5, CD15, CD16, CD19, CD20, CD21, CD22, CD23, CD25, CD30, CD33, CD38, CD45, CD74, CD79a, CD80, CD123, CD138, colon-specific antigen-p (CSAp), CEA (CEACAM5), CEACAM6, CSAp, EGFR, EGP-I, EGP-2, Ep-CAM, EphA1, EphA2, EphA3, EphA4, EphA5, EphA6, EphA7, EphA8, EphA10, EphB1, EphB2, EphB3, EphB4, EphB6, Flt-I, Flt-3, folate receptor, HLA-DR, human chorionic gonadotropin (HCG) and its subunits, hypoxia inducible factor (HIF-I), Ia, IL-2, IL-6, IL-8, insulin growth factor-1 (IGF-I), KC4-antigen, KS-1-antigen, KS1-4, Le-Y, macrophage inhibition factor (MIF), MAGE, MUC2, MUC3, MUC4, NCA66, NCA95, NCA90, antigen specific for PAM-4 antibody, placental growth factor, p53, prostatic acid phosphatase, PSA, PSMA, RS5, S100, TAC, TAG-72, tenascin, TRAIL receptors, Tn antigen, Thomson-Friedenreich antigens, tumor necrosis antigens, VEGF, ED-B fibronectin, 17-1A-antigen, an angiogenesis marker, an oncogene marker or an oncogene product.

In one embodiment, the antigen targeted by the antigen-binding domain is CD19. In one embodiment, the antigen-binding domain comprises an anti-CD19 scFv. In one embodiment, the anti-CD19 scFv comprises a heavy chain variable region (VH) comprising the amino acid sequence set forth in SEQ ID NO: 2, or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NO: 2. In one embodiment, the anti-CD19 scFv comprises a light chain variable region (VL) comprising the amino acid sequence set forth in SEQ ID NO: 4, or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NO: 4. In one embodiment, the anti-CD19 scFv comprises the amino acid sequence set forth in SEQ ID NO: 7, or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NO: 7.

In some embodiments, the antigen is associated with an autoimmune disease or disorder. Such antigens may be derived from cell receptors and cells which produce "self"-directed antibodies. In some embodiments, the antigen is associated with an autoimmune disease or disorder such as Rheumatoid arthritis (RA), multiple sclerosis (MS), Sjögren's syndrome, Systemic lupus erythematosus, sarcoidosis, Type 1 diabetes mellitus, insulin dependent diabetes mellitus (IDDM), autoimmune thyroiditis, reactive arthritis, ankylosing spondylitis, scleroderma, polymyositis, dermatomyositis, psoriasis, vasculitis, Wegener's granulomatosis, Myasthenia gravis, Hashimoto's thyroiditis, Graves' disease, chronic inflammatory demyelinating polyneuropathy, Guillain-Barre syndrome, Crohn's disease or ulcerative colitis.

In some embodiments, autoimmune antigens that may be targeted by the arCAR disclosed herein include but are not limited to platelet antigens, myelin protein antigen, Sm antigens in snRNPs, islet cell antigen, Rheumatoid factor, and anticitrullinated protein. citrullinated proteins and peptides such as CCP-1, CCP-2 (cyclical citrullinated peptides), fibrinogen, fibrin, vimentin, filaggrin, collagen I and II peptides, alpha-enolase, translation initiation factor 4G1, perinuclear factor, keratin, Sa (cytoskeletal protein vimentin), components of articular cartilage such as collagen II, IX, and XI, circulating serum proteins such as RFs (IgG, IgM), fibrinogen, plasminogen, ferritin, nuclear components such as RA33/hnRNP A2, Sm, eukaryotic translation elongation factor 1 alpha 1, stress proteins such as HSP-65, -70, -90, BiP, inflammatory/immune factors such as B7-H1, IL-1 alpha, and IL-8, enzymes such as calpastatin, alpha-enolase, aldolase-A, dipeptidyl peptidase, osteopontin, glucose-6-phosphate isomerase, receptors such as lipocortin 1, neutrophil nuclear proteins such as lactoferrin and 25-35 kD nuclear protein, granular proteins such as bactericidal permeability increasing protein (BPI), elastase, cathepsin G, myeloperoxidase, proteinase 3, platelet antigens, myelin protein antigen, islet cell antigen, rheumatoid factor, histones, ribosomal P proteins, cardiolipin, vimentin, nucleic acids such as dsDNA, ssDNA, and RNA, ribonuclear particles and proteins such as Sm antigens (including but not limited to SmD's and SmB'/B), U1RNP, A2/B1 hnRNP, Ro (SSA), and La (SSB) antigens.

Non-limiting exemplary antigen targets are provided in Tables 2-4.

TABLE 2

The antigen-binding domain may comprise a VH sequence, a VL sequence, and/or CDRs thereof, such as those described in the cited publications, the contents of each publication are incorporated herein by reference in their entirety for all purposes.

| Antigen target | Type | Examples of Source | Type | Examples of Source |
| --- | --- | --- | --- | --- |
| 5T4 | VH | Identifier 2, 4 in WO2016022939 | VL | Identifier 1, 3 in WO2016022939 |
| AGR2 | VH | Identifier 10, 18 in WO2016040321 | VL | Identifier 11, 19 in WO2016040321 |
| ALK | VH | Identifier 1, 11, 13, 15, 3, 5, 7, 9 in US20160280798A1; Identifier 9, 1, 3, 5, 11, 13, 15, 7, 9 in WO2015069922 | VL | Identifier 10, 12, 14, 16, 2, 4, 6, 8 in US20160280798A1; Identifier 10, 12, 14, 16, 8 in WO2015069922; Identifier 2, 4, 6 in WO2015069922 |

TABLE 2-continued

The antigen-binding domain may comprise a VH sequence, a VL sequence, and/or CDRs thereof, such as those described in the cited publications, the contents of each publication are incorporated herein by reference in their entirety for all purposes.

| Antigen target | Type | Examples of Source | Type | Examples of Source |
|---|---|---|---|---|
| AMC | VH | Identifier 17, 18, 19, 20, 21, 22, 23, 24, 25, 26 in WO2016161390 | VL | Identifier 27, 28, 29, 31, 32, 33, 34, 35, 36 in WO2016161390 |
| ANG2 | VH | Identifier 1, 3 in WO2015091655 | VL | Identifier 2, 4 in WO2015091655 |
| APCDD1 | VH | Identifier 10, 102, 106, 110, 114, 118, 122, 126, 130, 134, 14, 6, 98 in WO2012019061 | VL | Identifier 136, 100, 104, 108, 112, 116, 12, 120, 124, 128, 132, 16, 8 in WO2012019061 |
| APRIL | VH | Identifier 12, 14, 16. 18. 3. 32, 34, 36, 38, 40, 42, 44, 46, 48, 52 in US20160264674 | VL | Identifier 20, 22, 24, 26, 28, 30, 4, 50 in US2016026467 |
| AXL | VH | Identifier 21, 3, 45 in WO2016097370 | VL | Identifier 22, 4 in WO2016097370 |
| B2MG | VH | Identifier 28 in WO2016126213A1 | VL | Identifier 29 in WO2016126213A1 |
| B7H1 | VH | Identifier 12, 32, 42, 52, 72, 2, 62 in US20130034559 | VL | Identifier 17, 37, 47, 57, 7, 77, 27, 67 in US20130034559 |
| B7H3 | VH | Identifier 10, 11, 12, 13, 14, 15, 16, 9 in WO2016033225 | VL | Identifier 1, 2, 3, 4, 5, 6, 7, 8 in WO2016033225 |
| B7H3 (CD276) | VH | Identifier 17, 26, 7 in WO20160443 83 | VL | Identifier 18, 27, 8 in WO20160443 83 |
| B7H4 | VH | Identifier 100, 101, 102, 103, 107, 108, 109, 110, 111, 112, 113, 114, 12, 127, 130, 131, 132, 133, 137, 2, 20, 28, 36, 37, 38, 4, 56, 99, 144 in US20160159910; Identifier 13, 15, 17 in WO2016160620 | VL | Identifier 104, 11, 126, 134, 138, 19, 27, 3, 35, 55, 93, 95, 97, 98, 145, 146, 147, 148 in US20160159910; Identifier 29, 31, 33 in WO2016160620 |
| BAT1 | VH | Identifier 5, 6, 7, 8, 9 in WO2013014668 | VL | Identifier 1, 2, 3, 4 in WO2013014668 |
| BCMA | VH | Identifier 26 in WO2016168773 A3; Identifier 142, 148, 154, 160, 166, 172, 178, 184, 190, 196, 202, 208, 214, 220, 226, 232, 238, 244, 250, 256, 262, 268, 274, 280, 286, 292, 298, 304, 310, 316, 322, 328, 334, 340, 346, 352 in WO2016168595A1; Identifier 8 in WO2016094304A3; Identifier 171, 172, 173, 174, 175, 176, 177, 178, 179, 180, 181, 182, 183, 184, 185, 186, 187, 190, 255, 257, 258, 69, 70, 71, 72, 73, 74, 75, 76, 77, 78, 79, 80, 81 WO2016014565; Identifier 38 in EP3057994A1; Identifier 55 in WO2016187349A1; Identifier 1, 13, 17, 21, 25, 29, 33, 37, 41, 45, 49, 5, 53, 57, 61, 65, 9 in WO2016090320; Identifier 101, 743, 174, 758, 95, 759, 97, 760, 99 in WO2016120216; Identifier 11, 741, 17 in WO2015158671A1; Identifier 10, 11, 12, 13, 14 in WO2016014789; Identifier 15 in WO2016168766A1 | VL | Identifier 25 in WO2016168773 A3; Identifier 42 in WO2016097231; Identifier 143, 149, 155, 161, 167, 173, 179, 185, 191, 197, 203, 209, 215, 221, 227, 233, 239, 245, 251, 257, 263, 269, 275, 281, 287, 293, 299, 305, 311, 317, 323, 329, 335, 341, 347, 353 in WO2016168595 A1; Identifier 192, 193, 194, 195, 196, 197, 198, 199, 200, 201, 204, 205, 207, 208, 211, 259, 260, 84, 85, 86, 87, 88, 89, 90, 91, 92, 93, 94, 95, 96, 97, 98 in WO2016014565; Identifier 53 in WO2016187349A1; Identifier 7 in WO2016094304 A3; Identifier 10, 14, 18, 2, 22, 26, 30, 34, 38, 42, 46, 50, 54, 58, 6, 62, 66 in WO2016090320; Identifier 100, 102, 175, 96, 98 in WO2016120216; Identifier 12, 14, 16, 18 in WO2015158671A1; Identifier 7, 8, 9 in WO2016014789; Identifier 14 in WO2016168766A1 |
| BMPR1A | VH | Identifier 12 in WO2011116212 | — | — |
| CA19.9 | VH | Identifier 117 in US20160333114A1 | VL | Identifier 118 in US20160333114A1 |

TABLE 2-continued

The antigen-binding domain may comprise a VH sequence, a VL sequence, and/or CDRs thereof, such as those described in the cited publications, the contents of each publication are incorporated herein by reference in their entirety for all purposes.

| Antigen target | Type | Examples of Source | Type | Examples of Source |
|---|---|---|---|---|
| Campath 1 | VH | Identifier 34 in US20160333114A1 | VL | Identifier 31, 33 in US20160333114A1 |
| CD105 | VH | Identifier 13, 14, 16 in WO2014039682 | VL | Identifier 1, 17, 20, 22, 23 in WO2014039682 |
| CD123 | VH | Identifier 11, 13, 14, 21 in WO2015140268A1; Identifier 113, 115, 57, 59, 63 in WO2016120216; Identifier 12, 123, 24, 25, 26, 27, 28, 29, 30, 9 in WO2016120220; Identifier 216, 217, 218, 219, 274 in WO2016028896 | VL | Identifier 9, 11, 18, 19, 20, 21, 22, 23 in WO2016120220; Identifier 12, 16, 18, 19, 22 in WO2015140268A1; Identifier 275, 276, 277, 278, 307, 308, 309, 310 in WO2016028896; Identifier 5 in US20160333108A1; Identifier 114, 116, 58, 60, 64 in WO2016120216 |
| CD148 | VH | Identifier 10, 14, 18, 2, 22, 26, 30, 6 in WO2005118643 | VL | Identifier 12, 16, 20, 24, 28, 32, 4, 8 in WO2005118643 |
| CD16 | VH | Identifier 25 in WO2015158868 | VL | Identifier 26 in WO2015158868 |
| CD19 | VH | Identifier 53, 55 in WO2016120216 | VL | Identifier 27, 31 in WO2016168773 A3; Identifier 49 in WO2016187349A1; Identifier 11 in WO2016134284; Identifier 194 in US20140134142A1; Identifier 54, 56 in WO2016120216; Identifier 13, 14, 15, 16, 17, 186, 187, 188, 189, 192, 196, 197, 198, 199, 200, 201, 202, 203, 204, 205, 64, 66, 67, 68, 69, 70, 71, 91 US20160152723; Identifier 22 in US20160039942; 3361 Identifier 63 in WO2016097231; Identifier 3 in US20160145337A1; Identifier 112 in US20160333114A1; Identifier 114 in US20160333114A1; Identifier 13, 6 US20160319020 |
| CD19H 803 | VH | Identifier 28, 29, 32, 33, 34, 35 in WO2016168773 A3; Identifier 51 in WO2016187349A1; Identifier 20 in US20160039942; Identifier 1 in WO2014184143; Identifier 5 in US20160145337A1; Identifier 166, 167, 168, 172, 176, 177, 181, 183, 184, 185, 62 in US20160152723; Identifier 15 US20160319020; Identifier 17, 33, 34, 35 in EP3057994A1; Identifier 62 in WO2016097231; Identifier 12 in WO2016134284; Identifier 111, 113 in US20160333114A1 | — | — |
| CD2 | VH | Identifier 103, 117, 119 in WO2016122701 | VL | Identifier 102, 116 in WO2016122701 |
| CD20 | VH | Identifier 45 in WO2016097231; Identifier 11, 13, 14, 15, 16, 17, 18, 19, 20, 21, 22, 23, 24, 25, 26, 27, 28, 29, 30, 31, 32, 33, 7, 9 in WO2017004091; | VL | Identifier 46 in WO2016097231; Identifier 10, 12, 8 in WO2017004091; Identifier 51 in US20160333114A1 |

TABLE 2-continued

The antigen-binding domain may comprise a VH sequence, a VL sequence, and/or CDRs thereof, such as those described in the cited publications, the contents of each publication are incorporated herein by reference in their entirety for all purposes.

| Antigen target | Type | Examples of Source | Type | Examples of Source |
|---|---|---|---|---|
| | | Identifier 26 in US20170000900; Identifier 54 in US20160333114A1; Identifier 25 in US20170000900; Identifier 24 in US20170000900; Identifier 23 in US20170000900 | | |
| CD22 | VH | Identifier 3 in WO2013059593; Identifier 10, 11, 12, 7, 9, 8 in US20150299317; Identifier 201 in WO2016164731; CD22 VH 869 Identifier 671 in WO2016164731; Identifier 672 in WO2016164731; Identifier 673 in WO2016164731; Identifier 676 in WO2016164731; Identifier 678 in WO2016164731; Identifier 679 in WO2016164731; Identifier 680 in WO2016164731; Identifier 700 in WO2016164731; Identifier 701 in WO2016164731; Identifier 702 in WO2016164731; Identifier 703 in WO2016164731; Identifier 704 in WO2016164731; Identifier 705 in WO2016164731; Identifier 706 in WO2016164731; Identifier 707 in WO2016164731; Identifier 708 in WO2016164731, Identifier 709 in WO2016164731; Identifier 711 in WO2016164731; Identifier 712 in WO2016164731; Identifier 713 in WO2016164731; Identifier 714 in WO2016164731; Identifier 715 in WO2016164731; Identifier 716 in WO2016164731; Identifier 717 in WO2016164731; Identifier 718 in WO2016164731; Identifier 719 in WO2016164731; Identifier 720 in WO2016164731; Identifier 721 in WO2016164731; Identifier 722 in WO2016164731; Identifier 723 in WO2016164731; Identifier 724 in WO2016164731; Identifier 725 in WO2016164731; Identifier 726 in WO2016164731; Identifier 727 in WO2016164731; Identifier 728 in WO2016164731; Identifier 729 in WO2016164731; Identifier 730 in WO2016164731; Identifier 731 in WO2016164731; Identifier 732 in WO2016164731; | VL | Identifier 17, 8, 14, 15 in US20150239974; Identifier 7 in US20150299317; Identifier 681 in WO2016164731; Identifier 682 in WO2016164731; Identifier 683, 2020 in WO2016164731; Identifier 684 in WO2016164731; Identifier 685 in WO2016164731; Identifier 686 in WO2016164731; Identifier 687 in WO2016164731; Identifier 688 in WO2016164731; Identifier 690 in WO2016164731; Identifier 740 in WO2016164731; Identifier 741 in WO2016164731; Identifier 742 in WO2016164731; Identifier 743 in WO2016164731; Identifier 744 in WO2016164731; Identifier 745 in WO2016164731; Identifier 746 in WO2016164731; Identifier 747 in WO2016164731; Identifier 748 in WO2016164731; Identifier 749 in WO2016164731; Identifier 750 in WO2016164731; Identifier 752 in WO2016164731; Identifier 753 in WO2016164731; Identifier 754 in WO2016164731; Identifier 755 in WO2016164731; Identifier 756 in WO2016164731; Identifier 757 in WO2016164731; Identifier 758 in WO2016164731; Identifier 759 in WO2016164731; Identifier 760 in WO2016164731; Identifier 761 in WO2016164731; Identifier 762 in WO2016164731; Identifier 763 in WO2016164731; Identifier 764 in WO2016164731; Identifier 765 in WO2016164731; Identifier 766 in WO2016164731; Identifier 767 in WO2016164731; Identifier 768 in WO2016164731; Identifier 769 in WO2016164731; Identifier 770 in WO2016164731; Identifier 771 in WO2016164731; Identifier 772 in |

TABLE 2-continued

The antigen-binding domain may comprise a VH sequence, a VL sequence, and/or CDRs thereof, such as those described in the cited publications, the contents of each publication are incorporated herein by reference in their entirety for all purposes.

| Antigen target | Type | Examples of Source | Type | Examples of Source |
|---|---|---|---|---|
| | | Identifier 733 in WO2016164731; Identifier 734 in WO2016164731; Identifier 735 in WO2016164731; Identifier 736 in WO2016164731; Identifier 737 in WO2016164731; Identifier 738 in WO2016164731 | | WO2016164731; Identifier 773 in WO2016164731; Identifier 774 in WO2016164731; Identifier 775 in WO2016164731; Identifier 776 in WO2016164731; Identifier 777 in WO2016164731; Identifier 124 in WO2016122701 |
| CD276 | VH | Identifier 17, 26, 7 in US20160053017 | VL | Identifier 18, 27 in US20160053017 |
| CD28 | VH | Identifier 19 in WO2015158868 | VL | Identifier 20 in WO2015158868 |
| CD3 | VH | Identifier 108, 112, 115 in WO2016122701; Identifier 29 in WO2014144722 A2; Identifier 12 in WO2016126213A1 | VL | Identifier 104 in WO2016122701; Identifier 13 in WO2016126213A1 |
| CD30 | VH | Identifier 14, 16 in WO2016134284 | VL | Identifier 13, 15 in WO2016134284 |
| CD324 | VH | Identifier 21, 23, 25, 27, 29, 31, 33, 35, 37, 39, 41, 43, 45, 47, 49, 51, 53, 55, 57, 59, 61, 63, 65, 67, 69, 71 in U.S. Pat. No. 9,534,058 | VL | Identifier 20, 22, 24, 26, 28, 30, 32, 34, 36, 38, 40, 42, 44, 46, 48, 50, 52, 54, 56, 58, 60, 62, 64, 66, 68, 70 in U.S. Pat. No. 9,534,058 |
| CD32B | VH | Identifier 127 in WO2016122701 | VL | Identifier 126 in WO2016122701 |
| CD33 | VH | Identifier 65, 67, 69, 71, 77, 79, 81, 83, 84 in WO2016120216; Identifier 11, 13, 15; 17 in WO2015150526A2; Identifier 57, 58, 59, 60, 61, 62, 63, 64, 65 in WO2016014576 | VL | Identifier 12, 14, 16, 18 in WO2015150526A2; Identifier 66, 68, 70, 72, 78, 80, 82 in WO2016120216; Identifier 66, 67, 68, 69, 70, 71, 72, 73, 74 in WO2016014576 |
| CD37 | VH | Identifier 11, 12, 18 in US20170000900 | VL | Identifier 14, 15 in US20170000900 |
| CD38 | VH | Identifier 2 in WO2009080830; Identifier 10 in WO2015121454 | VL | Identifier 1, 11 in WO2009080830 |
| CD3s | VH | Identifier 7 in WO2014144722A2 | VL | Identifier 8 in WO2014144722A2 |
| CD40 | VH | Identifier 1 in WO2016069919; Identifier 5, 7, 8 in WO2015091655 | VL | Identifier 2 in WO2016069919; Identifier 6 in WO2015091655 |
| CD45 | VH | Identifier 24 in WO2016126213A1 | VL | Identifier 25 in WO2016126213A1 |
| CD46 | VH | Identifier 39, 47, 59, 15, 19, 23, 27, 31, 35, 43, 51, 55, 63, 67, 71, 75, 79, 83, 69, 71, 83 in WO2012031273; Identifier 1, 10, 11, 12, 13, 14,15,16,17,3,5, 6, 7, 9, 18, 19, 20, 21 in WO2016040683 | VL | Identifier 41, 61, 21, 25, 29, 33, 37, 45, 49, 53, 57, 65, 69, 73, 77, 81, 85, 17, 73, 77 in WO2012031273; Identifier 23, 24, 25, 26, 27, 28, 29, 30, 31, 32, 33, 34, 35, 36, 37, 38, 39, 40, 41,42 in WO2016040683 |
| CD4BS | VH | Identifier 15, 3 in US20160194375A1 | VL | Identifier 14, 2 in US20160194375A1 |
| CD4i | VH | Identifier 5 in US20160194375A1 | VL | Identifier 4 in US20160194375A1 |
| CD52 | VH | Identifier 103, 136, 137 in WO2010132659 | VL | Identifier 102, 138 in WO2010132659 |
| CD64 | VH | Identifier 129 in WO2016122701 | VL | Identifier 128 in WO2016122701 |
| CD7 | VH | Identifier 16, 20 in WO2016126213A1 | VL | Identifier 17, 21 in WO2016126213A1 |
| CD70 | VH | Identifier 81, 85, 89 in WO2015121454 | VL | Identifier 83, 87, 91 in WO2015121454; Identifier 83 in WO2015121454; Identifier 87 in WO2015121454; Identifier 91 in WO2015121454 |

TABLE 2-continued

The antigen-binding domain may comprise a VH sequence, a VL sequence, and/or CDRs thereof, such as those described in the cited publications, the contents of each publication are incorporated herein by reference in their entirety for all purposes.

| Antigen target | Type | Examples of Source | Type | Examples of Source |
|---|---|---|---|---|
| CD71 | VH | Identifier 1, 3, 325, 4, 5, 699 in US20160355599 | VL | Identifier 2,327, 329, 331, 333, 335, 337, 6, 650, 652, 654, 656, 658, 660, 670, 671, 672, 673, 7, 701, 702, 703, 704, 705, 706, 707, 708, 709, 710, 711, 712, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784 785, 786, 787, 788, 8, 810, 811, 812, 813, 814, 815, 816, 817, 818, 819, 820, 821, 822, 823, 824, 825, 826, 827, 828, 829, 830, 831, 832, 833, 834, 835, 836, 810, 842, 843, 844, 845, 846, 847, 848, 849, 850, 851, 852, 853, 854, 855, 856, 857, 858, 859, 860, 861, 862, 863, 864, 865, 866, 867, 868, 869, 870, 871, 872, 873, 874, 875, 876, 877, 879, 879, 880, 881, 882, 883, 884, 885, 886, 887, 888, 889, 890, 891, 892, 893, 894, 895, 896, 897, 898, 899, 900, 901, 902, 903, 904, 905, 906, 907, 908 in US20160355599 |
| CD73 | VH | Identifier 100, 103, 107, 109, 112, 114, 116, 119, 121, 16, 32, 4, 52, 60, 68, 80, 88 in US20160145350; Identifier 135, 40, 21, 3, 28, 36 in WO2016055609A1 | VL | Identifier 12. 20, 44, 72, 76, 8, 84, 92 in US20160145350; Identifier 22, 29, 37, 4 in WO2016055609A1; Identifier 101, 102, 104, 106, 110, 117, 118, 120, 122 in US20160145350 |
| CD74 | VH | Identifier 6 in US20100284906A1; Identifier 10, 11, 9 in US20040115193A1; Identifier 23, 27, 30, 33 in US20130171064 | VL | Identifier 25, 29, 31, 35 in US20130171064; Identifier 12, 13, 14, 11, 4 in US20040115193A1 |
| CD76b | VH | Identifier 15, 17, 19, 23, 27, 29, 37, 57, 59, 61 in US20160159906 | VL | Identifier 16, 18, 22, 38, 58, 60, 62 in US20160159906 |
| CD79 | VH | Identifier 131 in WO2016122701 | VL | Identifier 130 in WO2016122701 |
| CDIM | VH | Identifier 1, 10, 11, 12, 13, 14, 15, 16, 17, 18, 19, 2, 20, 21,22,3,4, 5, 6, 7, 8, 9 in WO2013120012 | VL | Identifier 28, 29, 30, 31, 32, 33, 34, 35, 36, 37, 38, 39, 40, 41, 42, 43, 44, 45, 46, 47, 48, 49 in WO2013120012 |
| CEA | VH | Identifier 8 in U.S. Pat. No. 8,287,865 | VL | Identifier 10, 38, 39, 7, 9 in U.S. Pat. No. 8,287,865 |
| Claudin | VH | Identifier 101, 103, 105, 107, 109, 111, 113, 115, 117, 119, 121, 122, 123, 124, 125, 126, 127, 128, 129, 130, 131, 132, 133, 134, 135, 136, 137, 138, 139, 140, 141, 142, 143, 144, 145, 146, 147, 148, | VL | Identifier 114, 116, 118, 120, 22, 25, 29, 33, 37, 41, 45, 49, 53, 57, 61, 65, 69, 73, 77 in WO2016073649A1 |

TABLE 2-continued

The antigen-binding domain may comprise a VH sequence, a VL sequence, and/or CDRs thereof, such as those described in the cited publications, the contents of each publication are incorporated herein by reference in their entirety for all purposes.

| Antigen target | Type | Examples of Source | Type | Examples of Source |
|---|---|---|---|---|
| | | 149, 150, 23, 27, 31, 35, 39, 43, 47, 51, 55, 59, 63, 67, 71, 75, 79, 81, 83, 85, 87, 89, 91, 93, 95, 97, 99 in WO2016073649A1 | | |
| CLDN18.2 | VH | Identifier 12, 2 in US20160347815A1 | VL | Identifier 13, 3 in US20160347815A1 |
| CLL1 | VH | Identifier 13, 14, 15, 17, 19, 21, 23, 25, 27, 29, 31, 33, 35 in WO2016120219; Identifier 195, 65, 66, 67, 68, 69, 70, 71, 72, 73, 74, 75, 76, 77 in WO2016014535; Identifier 31, 33, 34, 36, 38, 40, 42, 46 in US20160075787; Identifier 150, 103, 105, 107, 109, 111, 113, 115, 117 in WO2016179319A1 | VL | Identifier 16, 18, 20, 22, 24, 26, 28, 30, 32, 24, 36 in WO2016120219; Identifier 196, 78, 79, 80, 81, 82, 83, 84, 85, 86, 87, 88, 89, 90 in WO2016014535; Identifier 30, 32, 35, 37, 39, 41 in US20160075787; Identifier 152, 104, 106, 108, 110, 112, 114, 116, 118 in WO2016179319A1 |
| CLL3 | VH | Identifier 101, 103, 105, 107, 109, 111, 113, 115, 117, 119, 121, 123, 125, 127, 129, 131, 133, 135, 137, 139, 141, 145, 147, 149, 151, 153, 155, 157, 159, 161, 163, 165, 167, 169, 171, 173, 175, 177, 179, 181, 183, 185, 187, 191, 193, 195, 197, 199, 201, 203, 205, 207, 209, 21, 211, 213, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99 in US20170000901 | VL | Identifier 100, 102, 104, 106, 108, 110, 112, 114, 116, 118, 120, 122, 124, 126, 128, 130, 132, 134, 136, 138, 140, 144, 146, 148, 150, 152, 154, 156, 158, 160, 162, 164, 166, 170, 172, 174, 176, 178, 180, 182, 184, 186, 190, 192, 194, 196, 198, 20, 200, 202, 204, 206, 208, 210, 212, 22, 24, 26, 28, 30, 32, 34, 36, 38, 40, 42, 44, 46, 48, 50, 54, 56, 58, 60, 62, 64, 66, 68, 70, 72, 74, 76, 78, 80, 82, 84, 86, 88, 90, 92, 94, 96, 98 in US20170000901 |
| collagen | VH | Identifier 21, 4, 15, 17, 18, 19, 20, 5, 6, 7, 1, 2, 3 in WO2007024921 | VL | Identifier 11, 12, 14, 23, 25, 26, 27, 8, 9 in WO2007024921 |
| CS1 | VH | Identifier 22 in WO2016168773 A3; 103, 105, 107, 109 in WO2016120216; Identifier 13, 15, 17, 19 in WO2015166056A1; Identifier 38, 40, 42, 44, 46 in WO2015121454; Identifier 26 in US20160075784A1 | VL | Identifier 104, 106, 108 in WO2016120216; Identifier 14, 16, 18, 20, 22 in WO2015166056A1; Identifier 39, 41, 43, 45, 47 in WO2015121454; Identifier 110, 112 in WO2016120216 |
| CSF | VH | Identifier 10, 102, 14, 18, 2, 22, 26, 30, 34, 38, 46, 50, 54, 58, 6, 62, 66, 70, 74, 78, 82, 86, 90, 94, 98 in US20050059113A1 | VL | Identifier 12, 32, 44, 48, 60 in US20050059113A1 |
| CSPG4 | VH | Identifier 10, 16, 18, 4, 6, 8 in WO2016077638; Identifier 8 in WO2016164429 | VL | Identifier 7 in WO2016164429; Identifier 12, 14 in WO2016077638 |
| CTLA4 | VH | Identifier 3, 31, 32, 33, 34, 35, 41, 42, 43, 44, 45, 7 in US20140105914; Identifier 4 in U.S. Pat. No. 8,697,845; Identifier 19 in US20150283234; Identifier 17 in WO2014066532 | VL | Identifier 36, 37, 38, 39, 40, 46, 47, 48, 49, 50, 8, 4 in US20140105914; Identifier 2 in U.S. Pat. No. 8,697,845; Identifier 20 in US20150283234; Identifier 18 in WO2014066532 |
| CXCR4 | VH | Identifier 72, 73, 74, 75, 84 in US20110020218 | VL | Identifier 76, 77, 78, 79, 80, 81, 82, 87, 88, 90, 91, 92, 93 in US20110020218 |
| Daclizumab | VH | Identifier 44, 46 in US20160333114A1 | VL | Identifier 43, 45 in US20160333114A1 |

TABLE 2-continued

The antigen-binding domain may comprise a VH sequence, a VL sequence, and/or CDRs thereof, such as those described in the cited publications, the contents of each publication are incorporated herein by reference in their entirety for all purposes.

| Antigen target | Type | Examples of Source | Type | Examples of Source |
|---|---|---|---|---|
| DR5 | VH | Identifier 18, 82, 90, 98, 8 in WO2016122701 | VL | Identifier 13, 23, 25, 27, 3, 78, 86, 94, 29 in WO2016122701; Identifier 62 in WO2016122701; Identifier 54 in WO2016122701; Identifier 70 in WO2016122701 |
| E7MC | VH | Identifier 15, 16, 17, 18, 19, 20, 21, 22, 23, 233, 234, 235, 236, 237, 24, 25, 26, 27, 28, 29, 30, 31, 32, 33, 34, 35 in WO2016182957A1 | VL | Identifier 238, 239, 240, 241, 242, 243, 36, 37, 38, 39, 41, 42, 43, 44, 45, 46, 47, 48, 49, 50, 51, 52, 53, 54, 55, 56 in WO2016182957A1 |
| EFNA | VH | Identifier 149, 153, 157, 161 in US20150125472 | VL | Identifier 151, 155, 159, 163 in WO2012118547; Identifier 27, 53 in US20150125472 |
| EFNA4 | VH | Identifier 13, 39 in US20150125472 | — | — |
| EGFR | VH | Identifier 14, 50, 9 in WO2015143382; Identifier 12, 14, 15, 21 in US20100008978A1; Identifier 2123 in WO2018231759 | VL | Identifier 15 in WO2015143382; Identifier 14 in WO2014143765; Identifier 4051, 4052, 4053, 4054, 4055, 4056, 4057, 4058, 4059, 4060, 4061, 4062, 4063, 4064, 4065, 4066, 4067, 4068, 4069, 4070, 4071, 4072, 4073, 4074, 4075, 4076, 4077, 4078, 4079, 4080, 4081, 4082, 4083, 4084, 4085, 4086, 4087, 4088, 4089. 4090, 4091, 4092, 4093, 4094, 4095, 4096, 4097, 4098, 4099, 4100, 4101, 4102, 4103, 4104, 4105, 4106, 4107, 4108, 4109, 4110, 4111, 4112, 4113, 4114, 4115, 4116, 4117, 4118, 4119, 4120, 4121, 4122, 4123, 4124, 4125, 4126, 4127, 4128, 4129, 4130, 4131, 4132, 4133, 4134, 4135, 4136, 4137, 4138, 4139, 4140, 4141, 4142, 4143, 4144, 4145, 4146, 4147, 4148, 4149, 4150, 4151, 4152, 4153, 4154, 4155, 4156, 4157, 4158, 4159, 4160, 4161, 4162, 4163, 4164, 4165, 4166, 4167, 4168, 4169, 4170, 4171, 4172, 4173, 4174, 4175, 4176, 4177, 4178, 4179, 4180, 4181, 4182, 4183, 4184, 4185, 4186, 4187, 4188, 4189, 4190, 4191, 4192, 4193, 4194, 4195, 4196, 4197, 4198, 4199, 4200, 4201, 4202, 4203, 4204, 4205, , 4206, 4207, 4208, 4209, 4210, 4211, 4212, 4213, 4214, 4215, 4216, 4217, 4218, 4219, 4220, 4221, 4222, 4223, 4224, 4225, 4226, 4227, 4228, 4229, 4230, 4231, 4232, 4233, 4234, 4235, 4236, 4237, 4238, 4239, 4240, 4241, 4242, 4243, 4244, 4245, 4246, 4247, 4248, 4249, 4250, 4251, 4252, 4253, 4254, 4255, 4256, |

TABLE 2-continued

The antigen-binding domain may comprise a VH sequence, a VL sequence, and/or CDRs thereof, such as those described in the cited publications, the contents of each publication are incorporated herein by reference in their entirety for all purposes.

| Antigen target | Type | Examples of Source | Type | Examples of Source |
|---|---|---|---|---|
| | | | | 4257, 4258, 4259, 4260, 4261, 4262, 4263, 4264, 4265, 4266, 4267, 4268, 4269, 4270, 4271, 4272, 4273, 4274, 4275, 4276, 4277, 4278, 4279, 42870, 4281, 4282, 42834284, 4285, 4286, 4287, 4288, 4289, 4290, 4291, 4292, 4293, 4294, 4295, 4296, 4297, 4298, 4299, 4300, 4301, 4302, 4303, 4304, 4305, 4306, 4307, 4308, 4309, 4310, 4311, 4312, 4313, 4314, 4315, 4316, 4317, 4318, 4319, 4320, 4321, 4322, 4323, 4324, 4325, 4326, 4327, 4328, 4329, 4330, 4331, 4332, 4333, 4334, 4335, 4336, 4337, 4338, 4339, 4340, 4341, 4342, 4343, 4344, 4345, 4346, 4347, 4348, 4349, 4350, 4351, 4352, 4353, 4354, 4355, 4356, 4357, 4358, 4359, 4360, 4361, 4362, 4363, 4364, 4365, 4366, 4367, 4368, 4369, 4370, 4371, 4372, 4373, 4374, 4375, 4376, 4377, 4378, 4379, 4380, 4381, 4382, 4383, 4384, 4385, 4386, 4387, 4388, 4389, 4390, 4391, 4392, 4393, 4394, 4395, 4396, 4397, 4398, 4399, 4400, 4401, 4402, 4403, 4404, 4405, 4406, 4407, 4408, 4409, 4410, 4411, 4412, 4413, 4414, 4415, 4416, 4417, 4418, 4419, 4420, 4421, 4422, 4423, 4424, 4425, 4426, 4427, 4428, 4429, 4430, 4431, 4432, 4433, 4434, 4435, 4436, 4437, 4438, 4439, 4440, 4441, 4442, 4443, 4444, 4445, 4446, 4447, 4448, 4449, 4450, 4451, 4452, 4453, 4454, 4455, 4456, 4457, 4458, 4459, 4460, 4461, 4462, 4463, 4464, 4465, 4466, 4467, 4468, 4469, 4470, 4471, 4472, 4473, 4474, 4475, 4476, 4477, 4478, 4479, 4480, 4481, 4482, 4483, 4484, 4485, 4486, 4487, 4488, 4489, 4490, 4491, 4492, 4493, 4494, 4495, 4496, 4497, 4498, 4499, 4500, 4501, 4502, 4503, 4504, 4505, 4506, 4507, 4508, 4509, 4510, 4511, 4512, 4513, 4514, 4515, 4516, 4517, 4518, 4519, 4520, 4521, 4522, 4523, 4524, 4525, 4526, 4527, 4528, 4529, 4530, 4531, 4532, 4533, 4534, 4535, 4536, 4537, 4538, 4539, 4540, 4541, 4542, 4543, 4544, 4545, 4546, 4547, 4548, 4549, 4550, 4551, 4552, |

TABLE 2-continued

The antigen-binding domain may comprise a VH sequence, a VL sequence, and/or CDRs thereof, such as those described in the cited publications, the contents of each publication are incorporated herein by reference in their entirety for all purposes.

| Antigen target | Type | Examples of Source | Type | Examples of Source |
|---|---|---|---|---|
| | | | | 4553, 4554, 4555, 4556, 4557, 4558, 4559, 4560, 4561, 4562, 4563, 4564, 4565, 4566, 4567, 4568, 4569, 4570, 4571, 4572, 4573, 4574, 4575, 4576, 4577, 4578, 4579, 4580, 4581, 4582, 4583, 4584, 4585, 4586, 4587, 4588, 4589, 4590, 4591, 4592, 4593, 4594, 4595, 4596, 4597, 4598, 4599, 4600, 4601, 4602, 4603, 4604, 4605, 4606, 4607, 4608, 4609, 4610, 4611, 4612, 4613, 4614, 4615, 4616, 4617, 4618, 4619, 4620, 4621, 4622, 4623, 4624, 4625, 4626, 4627, 4629, 4629, 4630, 4631, 4632, 4633, 4634, 4635, 4636, 4637, 4638, 4639 in WO2018231759 |
| EGFR (EGFRvIII) | VH | Identifier 2124 in WO2018231759; Identifier 13 in WO2016016341; Identifier 24 in WO2016168773 A3; Identifier 34 in US20160304615; Identifier 2 in US20160200819A1; Identifier 91, 93 in WO2016120216 | VL | 4640, 4641, 4642, 4643, 4644, 4645, 4646, 4647, 4648, 4649, 4650, 4651, 4652, 4653, 4654, 4655, 4656, 4657, 4658 in WO2018231759; Identifier 14 in WO2016016341; Identifier 23 in WO2016168773 A3; Identifier 42 in US20160304615; Identifier 1 in US20160200819A1; Identifier 92, 94 in WO2016120216 |
| Endoglin | VH | Identifier 41, 42, 43, 71, 73, 75, 88, 89, 90, 91, 92 in US20160009811 | VL | Identifier 103, 88, 89, 90, 91, 92, 93, 94, 95, 96, 97, 102, 100 in WO2011041441; Identifier 100, 102, 103, 3, 4, 5, 70, 72, 74, 93, 94, 95, 96, 97 in US20160009811 |
| EphA2 receptor | VH | Identifier 20, 22, 24, 32, 34, 36, 37, 38, 40, 42, 43, 45, 74, 76 in US20150274824 | VL | Identifier 26, 28, 30, 47, 48, 49, 50, 52, 78, 80 in US20150274824 |
| ERBB2 | VH | Identifier 2, 4 in US20110129464; Identifier 10, 2, 26, 30, 38, 4, 40, 42, 52, 54, 56, 57, 58, 6 in US20130089544; Identifier 8 in US20130266564; Identifier 1 in US20150104443 | VL | Identifier 1 in US20110129464; Identifier 12, 16, 20, 24, 32, 36, 44, 50, 51, 53, 8 in US20130089544; Identifier 7 in US20130266564; Identifier 3 in US20110129464 |
| Factor D | VH | Identifier 17, 20, 27, 29, 30, 31, 32, 33, 4 in US20160017052 | VL | Identifier 16, 18, 19, 26, 3 in US20160017052 |
| Factor XII | VH | Identifier 15 in WO2014089493 | VL | Identifier 17 in WO2014089493 |
| FAP | VH | Identifier 1, 5 in WO2015118030; Identifier 170, 172 in WO2016120216; Identifier 8 in US20160326265 A1 | VL | Identifier 2, 6 in WO2015118030; Identifier 171, 173 in WO2016120216; Identifier 9 in US20160326265A1 |
| FcRL5 (FcReceptorLike 5) | VH | Identifier 12, 16, 20, 24, 28, 32, 36, 4, 40, 44, 48, 8, 915, 919 in WO2016090337 | VL | Identifier 11, 15, 19, 23, 27, 3, 31, 35, 39, 43, 47, 7, 917, 921 WO2016090337 |
| FGFR3 | VH | Identifier 132, 134, 136 in U.S. Pat. No. 9,499,623 | VL | Identifier 133, 135, 137, 139 in U.S. Pat. No. 9,499,623 |
| Frizzled Receptor | VH | Identifier 10 in WO2010037041 | VL | Identifier 12, 14 in WO2010037041 |
| GAH | VH | Identifier 7 in US20060057147A1 | VL | Identifier 8 in US20060057147A1 |

TABLE 2-continued

The antigen-binding domain may comprise a VH sequence, a VL sequence, and/or CDRs thereof, such as those described in the cited publications, the contents of each publication are incorporated herein by reference in their entirety for all purposes.

| Antigen target | Type | Examples of Source | Type | Examples of Source |
|---|---|---|---|---|
| GCC1 | VH | Identifier 1 in US20160030595A1 | VL | Identifier 4, 2 in US20160030595A1 |
| GD2 | VH | Identifier 17 in WO2016134284; Identifier 1 in US20130216528; Identifier 10, 9 in WO2015132604; Identifier 3, 4, 6, 8 in US20130216528 | VL | Identifier 10, 2, 5, 7, 9 in US20130216528; Identifier 11, 12 in WO2015132604; Identifier 18 in WO2016134284 |
| GD3 | VH | Identifier 11, 13, 15, 17 in WO2016185035A1 | VL | Identifier 12, 14, 16, 18 in WO2016185035A1 |
| Glyco epitope and ErbBB I Specific | VH | Identifier 7 in WO2012007167A1 | VL | Identifier 10 in WO2012007167A1 |
| GM2 | VH | Identifier 20, 22, 23, 26, 27, 28, 29, 30 in US20090028877 | VL | Identifier 21, 24, 25, 31, 32, 33, 34, 35 in US20090028877 |
| GPC3 | VH | Identifier 10, 14, 2, 3, 4, 5, 6, 7, 8, 9 in US20160208015 A1; Identifier 22 in WO2016049459; Identifier 12, 16, 20, 37, 8 in U.S. Pat. No. 9,409,994B2 | VL | Identifier 10, 14, 18, 22, 24, 26 in U.S. Pat. No. 9,409,994B2; Identifier 16, 31 in US20160208015A1; Identifier 23 in WO2016049459 |
| GPDL1 | VH | Identifier 20 in US20160108123 | — | — |
| GPRC5D | VH | Identifier 13, 17, 21, 25, 29, 314, 326, 33, 338, 350, 362, 37, 374, 386, 41, 45, 49, 5, 53, 57, 61, 65, 69, 73, 77, 81, 85, 89, 93, 1, 9 in WO2016090312 | VL | Identifier 10, 14, 18, 2, 22, 26, 30, 303, 315, 327, 339, 34, 351, 363, 375, 38, 387, 42, 46, 50, 54, 58, 6, 62, 66, 70, 74, 78, 82, 86, 94 in WO2016090312 |
| Her2 | VH | Identifier 141, 262, 264, 266, 268, 270 in WO2016168773A3; Identifier 11 in U.S. Pat. No. 9,518,118; Identifier 62 in US20160333114A1; Identifier 19, 24 in U.S. Pat. No. 9,518,118 | VL | Identifier 140 in WO2016054555A2; Identifier 261, 263, 265, 267, 269 in WO2016168773A3; Identifier 10, 18, 23 in U.S. Pat. No. 9,518,118; Identifier 3 in WO2016168769A1; Identifier 59, 61 in US20160333114A1 |
| Herl/her3 | VH | Identifier 8 of WO2016073629 | VL | Identifier 4 of WO2016073629 |
| HLAG | VH | Identifier 10, 8 in WO2016160622A2 | VL | Identifier 18, 20 in WO2016160622A2 |
| HSP70 | VH | Identifier 11, 12 in WO2016120217 | VL | Identifier 16, 17 in WO2016120217 |
| Human collagen VII | VH | Identifier 31 in WO2016112870 | VL | Identifier 32 in WO2016112870 |
| humanCD79b | VH | Identifier 27 in WO2016112870 humanCD79b VH 2304 Identifier 29 in WO2016112870 | VL | Identifier 28, 30 in WO2016112870 |
| humanERBB3 | VH | Identifier 19, 29, 38, 45, 55, 61, 9 in WO2013052745 | VL | Identifier 10, 20, 30, 39, 46, 56, 62 in WO2013052745 |
| ICOS | VH | Identifier 15, 16, 19, 23, 7 in US20160215059 | VL | Identifier 17, 18, 20, 24, 8 in US20160215059 |
| IGFI | VH | Identifier 1, 3, 7 in WO2007118214; Identifier 7 in WO2015073575 | VL | Identifier 2, 4, 6, 8 in WO2007118214 |
| IGFR1 | VH | Identifier 7 in WO2015073575 A2 | VL | Identifier 8 in WO2015073575 A2 |
| IL13 | VH | Identifier 302 in US20160168242 | VL | Identifier 303 in US20160168242 |
| IL13Ra2 | VH | Identifier 7, 8 in WO2016123143 | — | — |
| IL21 | VH | Identifier 2, 3 in US20160145332 | — | — |
| IL33 | VH | Identifier 134, 136, 138, 185, 187, 189, 216, 218, 220, 221,236, 246, 282, 284, | VL | Identifier 135, 137, 139, 184, 188, 217, 219, 237, 247, 283, 285, 287, 37, 39, |

TABLE 2-continued

The antigen-binding domain may comprise a VH sequence, a VL sequence, and/or CDRs thereof, such as those described in the cited publications, the contents of each publication are incorporated herein by reference in their entirety for all purposes.

| Antigen target | Type | Examples of Source | Type | Examples of Source |
|---|---|---|---|---|
| | | 286, 36, 38, 40, 84, 86, 88 in US20160168242 | | 41, 87 in US20160168242 |
| IL3alpha | VH | Identifier 22 in WO2008127735 | VL | Identifier 27, 37 in WO2008127735 |
| IL4R | VH | Identifier 10, 11, 14, 15, 9 in WO2009121847 | VL | Identifier 13, 7, 8 in WO2009121847 |
| IL1RAP | VH | Identifier 1, 10, 19, 8, 9 in WO2016020502; Identifier 120, 122, 124 in WO2016179319A1 | VL | Identifier 14, 15, 17, 18, 2, 20 in WO2016020502; Identifier 121, 123, 125 in WO2016179319A1 |
| Integrin | VH | Identifier 3, 4, 5 in US 20140161794 | VL | Identifier 10, 11, 8, 9 in US 20140161794 |
| KDR | VH | Identifier 20, 24, 26, 29, 31, 33 in WO2003075840 | VL | Identifier 22 in WO2003075840 |
| KIR (Lirilumab) | VH | Identifier 3 in US20150290316; 2371 Identifier 1 in WO2014055648 | VL | Identifier 5 in US20150290316; Identifier 2 in WO2014055648 |
| KIR2DL 1 | VH | Identifier 36 in WO2016126213A1 | VL | Identifier 37 in WO2016126213A1 |
| KIR2DL 2/3 | VH | Identifier 36 in WO2016126213A1 | VL | Identifier 37 in WO2016126213A1 |
| Klon43 | VH | Identifier 47 in WO2016097231 | VL | Identifier 48 in WO2016097231 |
| KMA | VH | Identifier 22 in WO2016172703 A2 | VL | Identifier 2, 21 in WO2016172703A2 |
| LAG3 | VH | Identifier 102, 106, 110, 113, 122, 18, 30, 66, 70, 74, 78 in US20150259420; Identifier 100, 104, 108, 28, 64, 68, 72, 76, 8, 80 in US20150259420; Identifier 1 in WO2015042246 | VL | Identifier 32, 36, 40, 44, 48, 52, 56, 60, 84, 88, 92, 96, 134, 34, 38, 42, 46, 50, 54, 58, 60, 86, 90, 94, 98 in US20150259420; Identifier 2 in WO2015042246 |
| leukocytegenA2 | VH | Identifier 25 in WO2010065962 A2 | — | — |
| leukocytegenA | VH | Identifier 9 in WO2010065962 A2 | VL | Identifier 24 in WO2010065962 A2 |
| LGR4 | VH | Identifier 12, 13, 5, 9 in US20160046723 | VL | Identifier 10, 11, 6 in US20160046723 |
| LGR5 | VH | Identifier 10, 12, 16, 18, 20, 22, 24, 26, 4 in US20160102146 | VL | Identifier 15, 19, 21, 23, 25, 3 in US20160102146 |
| LHR | VH | Identifier 1, 2, 3, 4, 5, 6, 7, 8 in WO2016160618A3 | — | — |
| Lymphotoxin beta receptor | VH | Identifier 10, 12, 14, 16, 2 in WO2004002431 | VL | Identifier 1, 15, 4, 6, 8 in WO2004002431 |
| Lysyloxidase-like 2 | VH | Identifier 42, 44 in WO2011097513 | VL | Identifier 43, 45 in WO2011097513 |
| Malignant Variable Receptor | VH | Identifier 1 in WO2015133817A1 | VL | Identifier 5 in WO2015133817A1 |
| MCAM | VH | Identifier 115, 116, 117, 118, 119, 157, 158, 159, 160, 161, 178, 179 in US20150259419; Identifier 35, 45, 55, 65, 77, 89 in US20150239980; Identifier 101, 102, 103, 104, 105, 106, 107 in US20150259419 | VL | Identifier 109, 110, 111, 112, 121, 122, 123 in US20150259419; Identifier 30, 40, 50, 60, 70, 71, 72 in US20150239980 |
| MCSF | VH | Identifier 102, 10, 14, 18, 2, 22, 26, 30, 34, 38, 46, 50, 54, 58, 6, 66, 70, 74, 78, 82, 86, 90, 94, 98 in WO2005030124 | VL | Identifier 8, 32, 52, 60, 28, 36, 4, 44, 48, 56, 62, 12, 16, 20, 24 in WO2005030124 |
| Mesothelin | VH | Identifier 1, 6 in WO2015188141; Identifier 119, 50 in US20160333114A1; Identifier 5, 6 in WO2013142034; Identifier 15, 2 in U.S. Pat. No. 9,416,190B2; Identifier 13, 17, 21, 25, 29, 9 in US20160229919A1 | VL | Identifier 3, 5 WO2015188141; Identifier 1, 2, 3 in WO2013142034; Identifier 11, 15, 19, 23, 27 in US20160229919A1; Identifier 120, 47, 49 in US20160333114A1 |

TABLE 2-continued

The antigen-binding domain may comprise a VH sequence, a VL sequence, and/or CDRs thereof, such as those described in the cited publications, the contents of each publication are incorporated herein by reference in their entirety for all purposes.

| Antigen target | Type | Examples of Source | Type | Examples of Source |
|---|---|---|---|---|
| MN | VH | Identifier 133, 135, 137, 139, 141, 143, 145, 147, 149, 151 in WO2007070538 | VL | Identifier 134, 136, 138, 140, 142, 144, 146, 148, 150, 152 in WO2007070538 |
| MPER | VH | Identifier 13 in US20160194375A1 | VL | Identifier 12 in US20160194375A1 |
| MUC1 | VH | Identifier 5 in US20160130357; Identifier 2, 14 in WO2013023162; Identifier 15, 19, 23, 60, 64, 68 in WO2015116753 | VL | Identifier 7 in US20160130357; Identifier 16, 7 in WO2013023162; Identifier 17, 21, 25, 62, 66, 70 in WO2015116753 |
| MUC16 | VH | Identifier 1, 21, 41, 81, 61 in WO2016149368; Identifier 11, 4, 6, 8 in US20130171152 | VL | Identifier 2, 22, 42, 62, 82 in WO2016149368 |
| MUC1C ECD | VH | Identifier 15, 19, 23, 60, 64, 68, 72 in US20160340442A1 | VL | Identifier 17, 21, 25, 62, 66, 70, 75 in US20160340442A1 |
| MUCIN1 | VH | Identifier 101, 106, 109, 115, 119, 123, 127, 141, 15, 23, 28, 33, 39, 42, 47, 5, 57, 66, 70, 75, 80, 83, 87, 92 in EP3049812A2 | VL | Identifier 148, 158, 162, 167, 170, 174, 184, 190, 193, 203, 208, 211, 220, 225, 229, 234, 242, 246, 250, 255, 261, 270, 275, 279, 283, 291, 297, 303, 308, 315, 319, 323, 333, 340 in EP3049812A2 |
| MVR | VH | Identifier 1 in US20160257762A1 | VL | Identifier 5 in US20160257762A1 |
| N Glycan | VH | Identifier 7, 9 in US20160194375A1 | VL | Identifier 6, 8 in US20160194375A1 N |
| NKG2A | VH | Identifier 32 in WO2016126213A1; Identifier 2, 3, 4, 5, 6 in WO2016041947 | VL | Identifier 33 in WO2016126213A1; Identifier 7 in WO2016041947 |
| NKG2D | VH | Identifier 135, 137 in WO2016122701 | VL | Identifier 134, 136 in WO2016122701 |
| NOTCH 1 | VH | Identifier 58 in US20160333114A1; Identifier 12 in WO2013074596 | VL | Identifier 16, 20 in WO2013074596; Identifier 55, 57 in US20160333114A1 |
| NOTCH 2/3 | VH | Identifier 29 in WO2013074596 | VL | Identifier 31 in WO2013074596 |
| Notum | VH | Identifier 56, 331 in WO2012027723 | VL | Identifier 332, 58 in WO2012027723 |
| NYBR1 | VH | Identifier 19 in US20160333422A1 | VL | Identifier 18 in US20160333422A1 |
| OlfmB | VH | Identifier 1 in WO2015054441A1 | VL | Identifier 2 in WO2015054441A1 |
| Olfml3 | VH | Identifier 19, 3 in WO2015054441A1 | VL | Identifier 20, 4 in WO2015054441A1 |
| Oncofetal fibronectin | — | — | VL | Identifier 1, 2, 7 in US20070202103A1 |
| Osteonectin | VH | Identifier 58 in WO2016112870 | VL | Identifier 59 in WO2016112870 |
| OTK3 | VH | Identifier 17 in WO2015158868 | VL | Identifier 18 in WO2015158868 |
| OX40 | VH | Identifier 101, 103, 105, 107, 109, 111, 113, 115, 117, 119, 121, 123, 124, 125, 17, 28, 318, 37, 48, 50, 58, 66 74, 85, 93, 95, 97, 99 in WO2016196228; Identifier 31, 34, 36, 38, 40, 42, 44, 46, 48, 50, 53, 54, 55, 58, 59, 61 in US20150190506; Identifier 33, 35, 37, 39, 41, 43, 45, 47, 49, 51, 53, 55, 57, 59, 61, 63, 65, 67, 71 in US20160137740; Identifier 44, 46, 48, 7, 9 in | VL | Identifier 10, 45, 47, 49, 8 in U.S. Pat. No. 8,283,450; Identifier 11, 7 in U.S. Pat. No. 9,428,570; Identifier 116, 120, 122, 30, 38, 49, 57, 65, 73, 84, 86, 94, 98 in WO2016196228; Identifier 24, 26, 27, 28, 30, 60, 8, 81, 82, 83, 84, 85, 86, 87, 88, 89 in U.S. Pat. No. 8,748,585; Identifier 30, 32 in US20160137740; Identifier 32, 35, 39, 41, 43, 45, 47, 49, 51, 52, 56, 57, 62 in US20150190506; Identifier |

TABLE 2-continued

The antigen-binding domain may comprise a VH sequence, a VL sequence, and/or CDRs thereof, such as those described in the cited publications, the contents of each publication are incorporated herein by reference in their entirety for all purposes.

| Antigen target | Type | Examples of Source | Type | Examples of Source |
|---|---|---|---|---|
| | | U.S. Pat. No. 8,283,450; Identifier 9, 15 in U.S. Pat. No. 9,428,570; Identifier 19, 21, 22, 23, 29, 58, 59, 7, 77, 78, 79, 80 in U.S. Pat. No. 8,748,585 | | 29, 37 in US20160137740 |
| PD1 | VH | Identifier 19 in US20150290316; Identifier 25, 26, 27, 28, 29 in US20130291136; Identifier 29, 3, 38 in US 20160159905; Identifier 38, 50 in WO2015112900; Identifier 4, 4, 6 in US 20160159905; Identifier 82, 86 in WO2015112900; Identifier 17 in WO2014055648; Identifier 4 in WO2016040892; Identifier 12 in US20150190506 | VL | Identifier 2, 39, 7, 8, 9 in US 20160159905; Identifier 21 in US20150290316; Identifier 30, 31, 32, 33 in US20130291136; Identifier 42, 46, 54 in WO2015112900; Identifier 58, 62, 66, 70, 74, 78 in WO2015112900; Identifier 18 in WO2014055648; Identifier 5 in WO2016040892; Identifier 13 in US20150190506 |
| PDK1 | VH | Identifier 2 in WO2016090365 | VL | Identifier 9 in WO2016090365 |
| PD1 (Nivolumab) | VH | Identifier 2 in WO2016040892; Identifier 10 in US20150190506 | VL | Identifier 11 in US20150190506 |
| PDL1 | VH | Identifier 10, 32, 8 in US20160319022; Identifier 18, 30, 38, 46, 50, 54, 62, 70, 78 in WO2016061142; Identifier 29, 7 in US20150190506; Identifier 16, 18, 197, 247, 248, 250, 251, 252, 253, 254, 255, 256, 257, 258, 259, 260, 30, 308, 310, 312, 319, 32, 324, 339, 356, 38, 40, 46, 48, 50, 52, 54, 6, 62, 70, 72, 78, 80, 91, 96 in US20160108123; Identifier 358, 56, 64 in US20160108123 | VL | Identifier 22, 26, 34, 42, 58, 66, 74, 82, 86 in WO2016061142; Identifier 30, 8, 9 in US20150190506; Identifier 7, 9 in US20160319022; Identifier 17, 22, 24, 249, 26, 28, 309, 311, 313, 320, 325, 34, 340, 357, 359, 36, 42, 44, 58, 60, 66, 68, 74, 76, 8, 82, 84, 86, 88 in US20160108123 |
| PDL2 | VH | Identifier 43, 44, 56, 46 in US20130291136 | VL | Identifier 47, 48, 49, 50, 51 in US20130291136 |
| PG16 | VH | Identifier 13 in EP3074419A2 | VL | Identifier 12 in EP3074419A2 |
| PG9 | VH | Identifier 11 in EP3074419A2 | VL | Identifier 10 in EP3074419A2 |
| PGT1 | VH | Identifier 15 in EP307441 | — | — |
| PGT2 | VH | Identifier 17 in EP3074419A2 | VL | Identifier 16 in EP3074419A2 |
| PGT3 | VH | Identifier 19 in EP3074419A2 | VL | Identifier 18 in EP3074419A2 |
| PGT4 | VH | Identifier 21 in EP3074419A2 | VL | Identifier 20 in EP3074419A2 |
| PGT5 | VH | Identifier 23 in EP3074419A2 | VL | Identifier 22 in EP3074419A2 |
| PRAME | VH | Identifier 50, 52, 54, 56, 58, 60, 62 in WO2016191246A2 | VL | Identifier 49, 51, 53, 55, 57, 59, 61 in WO2016191246A2 |
| PRP | VH | Identifier 42 in US20160333114A1 | VL | Identifier 39, 41 in US20160333114A1 |
| PSMA | VH | Identifier 43 in WO2016097231 | VL | Identifier 44 in WO2016097231; Identifier 44 in WO2016097231 |
| PTK7 | VH | Identifier 1, 25, 49 in US20150315293; Identifier 21, 23, 25, 27, 29, 31, 33, 35, 37, 39, 41, 43, 45, 47, 49, 51, 53, 55, 57, 59, 61, 63, 65, 67, 69 in WO2012112943A1 | VL | Identifier 20, 22, 24, 26, 28, 30, 32, 34, 36, 38, 40, 42, 44, 46, 48, 50, 52, 54, 56, 58, 60, 62, 64, 66, 68 in WO2012112943A1; Identifier 15, 39, 63 in US20150315293 |
| RAS | VH | Identifier 17, 47, 57, 67, 7, 77 in WO2016154047 | VL | Identifier 19, 49, 59, 69, 79, 9 in WO2016154047 |

TABLE 2-continued

The antigen-binding domain may comprise a VH sequence, a VL sequence, and/or CDRs thereof, such as those described in the cited publications, the contents of each publication are incorporated herein by reference in their entirety for all purposes.

| Antigen target | Type | Examples of Source | Type | Examples of Source |
| --- | --- | --- | --- | --- |
| RHAMM | VH | Identifier 4 in US20020127227A1 | — | — |
| RHAMM antagonist body | VH | Identifier 2 in WO2000029447 | VL | Identifier 4 in WO2000029447 |
| Rituximab | VH | Identifier 66 in US20160333114A1 | VL | Identifier 63, 65 in US20160333114A1 |
| ROR1 | VH | Identifier 12, 20, 28, 36, 44, 60, 68 WO2016016343Al; Identifier 57, 19, 31, 45, 53, 71 in WO2016016344A1; Identifier 85, 87, 89 in WO2016120216; Identifier 122, 125, 175, 176, 179, 180, 181, 182, 183, 184, 185, 186, 187, 188, 189, 190, 191, 192, 193, 194, 195, 196, 197, 197, 199, 200, 201, 202, 203, 204, 205, 206, 207, 208, 209 in US20160208018A1; Identifier 55 in EP3083671A1; Identifier 104, 112, 120, 128, 152, 16, 160, 168, 176, 184, 192, 200, 208, 216, 224, 232, 24, 240, 248, 256, 264, 272, 280, 288, 296, 304, 312, 32, 320, 336, 344, 352, 360, 40, 48, 56, 64, 72, 8, 80, 88 in WO2016187216A1 | VL | Identifier 16, 24, 32, 40, 56, 64, 72, 36, 62, 23, 49, 58 WO2016016343Al; Identifier 86, 88, 90 in WO2016120216; Identifier 126, 127, 234, 235, 236, 237, 238, 240, 241, 242, 243, 244, 245, 246, 247, 248 in US20160208018A1; Identifier 56 in EP3083671A1; Identifier 103, 111, 127, 135, 143, 15, 151, 159, 167, 175, 183, 191, 199, 207, 215, 223, 23, 231, 239, 247, 255, 263, 271, 279, 287, 295, 303, 31, 311, 319, 327, 335, 343, 351, 359, 39, 47, 55, 63, 7, 71, 79, 87, 95 in WO2016187216A1 |
| SEMAPHORIN 4D | VH | Identifier 10, 25, 9 in US20160115240A1 | VL | Identifier 17, 18, 29 in US20160115240A1 |
| TAG72 | VH | Identifier 115 in US20160333114A1 | VL | Identifier 116 in US20160333114A1 |
| TCR | VH | Identifier 133 in WO2016122701 | VL | Identifier 132 in WO2016122701 |
| TEM8 | VH | Identifier 1, 3, 5, 7 in US20160264662A1 | VL | Identifier 4, 6, 8 in US20160264662A1 |
| Tie | VH | Identifier 723 in US20060057138A1 | VL | Identifier 724 in US20060057138A1 |
| TIGIT | VH | Identifier 10, 11, 12, 124, 125, 126, 127, 128, 129, 13, 136, 138, 14, 143, 144, 149, 15, 150, 16, 17, 18, 19, 20, 21, 22, 23, 24, 37, 38, 39, 40, 41, 42, 43, 44, 45, 46, 47, 63, 94, 7, 9 in US20160355589 | VL | Identifier 130, 131, 132, 133, 137, 139, 145, 146, 151, 152, 25, 26, 27, 28, 29, 30, 50, 51, 52, 64, 95, 8 in US20160355589 |
| TIM3 | VH | Identifier 102, 112, 12, 2, 22, 32, 42, 52, 62, 72, 82, 91 in US20150086574; Identifier 82 in WO2013006490; Identifier 13, 21, 29, 37, 45, 5, 53, 61, 69, 77, 85, 93 in WO2016179319A1; Identifier 7 in WO2013006490; Identifier 107, 117, 17, 27, 37, 47, 57, 67, 7, 77, 87, 97 in US20150086574; Identifier 17, 25, 33, 41, 49, 57, 65, 73, 81, 89, 9, 97 in WO2016179319A1 | — | — |
| Tissue factor | VH | Identifier 10, 19, 23, 27, 29, 6 in WO2004094475; Identifier 38 in US20160333114A1 | VL | Identifier 25. 31 in US20040229301A1; Identifier 12, 21, 25, 31, 8 in WO2004094475; Identifier 35, 37 in US20160333114A1 |
| Tn Glycopeptide | VH | Identifier 19, 20 in WO2015120180 | — | — |

TABLE 2-continued

The antigen-binding domain may comprise a VH sequence, a VL sequence, and/or CDRs thereof, such as those described in the cited publications, the contents of each publication are incorporated herein by reference in their entirety for all purposes.

| Antigen target | Type | Examples of Source | Type | Examples of Source |
|---|---|---|---|---|
| TRBC1 | VH | Identifier 1 in WO2015132598 | VL | Identifier 2 in WO2015132598 |
| Trophoblast Glycoprotein 5T4 | VH | Identifier 17, 13, 15, 11 in WO2016034666A1 | VL | Identifier 18, 12, 14, 16 in WO2016034666A1 |
| Upar | VH | Identifier 72 in US20160333114A1 | VL | Identifier 71, 73 in US20160333114A1 |
| V2 | VH | Identifier 11 in US20160194375A1 | — | — |
| VEGF | VH | Identifier 4, 8, in WO2000034337; Identifier 12, 20, 4, 44 in WO2006012688A1; Identifier 7 in US20030175276A1; Identifier 152, 153, 154, 155, 156, 157, 158, 159 in US20160090427 | VL | Identifier 2, 6 in WO2000034337; Identifier 9 in US20030175276A1; Identifier 11, 19, 27, 28, 3, 43 in WO2006012688A1; Identifier 160, 161, 162, 163, 164, 165, 166, 167 in US20160090427 |
| VEGFR2 | VH | Identifier 100, 101, 102, 103, 114, 115, 116, 117, 118, 119, 120, 121, 122, 123, 124, 95, 96, 97, 98, 99 in WO2017004254 | VL | Identifier 107, 108, 109, 110, 111, 112, 113, 86, 87, 88, 89, 90, 91, 92, 93, 94 in WO2017004254 |
| VISTA | VH | Identifier 37, 38, 39, 40 in WO2015097536 | VL | Identifier 41, 42, 43, 44, 45 in WO2015097536 |
| VMS2 | VH | FIG. 1 in WO2000058363 | — | — |
| WT1/HLA Bispecific | VH | Identifier 104, 111, 128, 14, 32, 50, 68, 86 in WO2015070061 | VL | Identifier 106, 112, 130, 34, 52, 70, 88 in WO2015070061 |

TABLE 3

The antigen-binding domain may comprise an scFv derived from an antibody or antibody fragment that binds to an antigen target such as those described in the cited publications, the contents of each publication are incorporated herein by reference in their entirety for all purposes.

| Antigen Target | Examples of Source |
|---|---|
| Activated alpha v beta 3 | Identifier 8, 2, 4 in US20090117096A1 |
| Adalimunab | Identifier 41 in US20160208021; Identifier 41 in WO2016112870 |
| ALK | Identifier 17, 18, 19, 20, 21, 22, 23 in WO2015069922; Identifier 17, 18, 19, 20, 21, 22, 23, 24 in US20160280798Al; Identifier 24 in WO23015069922 |
| B7H3 | Identifier 99, 100, 101, 102, 103, 104, 102, 17, 18, 19, 20, 21, 22, 23, 24, 25, 26, 27, 87, 88, 89, 90, 91, 92, 94, 95, 96, 97, 98 in WO2016033225 |
| B7H4 | Identifier 1, 2, 3, 4 in WO2013067492; Identifier 1 in U.S. Pat. No. 9,422,351B2 |
| BCMA | Identifier 152, 158, 176, 185, 188, 200, 212, 218, 224, 284, 290, 296, 302, 314, 326, 344, 129, 130, 131, 132, 133, 134, 135, 136, 138, 139, 140, 141, 142, 143, 144, 145, 146, 147, 148, 149, 263, 264, 265, 266, 271, 273, 39, 40, 41, 42, 43, 44, 45, 46, 47, 48, 49, 50, 51, 52, 53, 64, 129, 130, 131, 132, 133, 134, 135, 136, 137, 138, 139, 140, 141, 142, 143, 144, 145, 146, 147, 148, 149, 263, 264, 265, 266, 39, 40, 41, 42, 43, 44, 45, 46, 47, 48, 49, 50, 51, 52, 53 in WO2016014565; Identifier 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 251 in US20160311907A1 |
| CCR4 | Identifier 7, 9 in WO2015191997 |
| CD123 | Identifier 157, 158, 159, 160, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 478, 480, 483, 485 in WO2016028896; Identifier 36 in WO2015092024A2; Identifier 57 in WO2016115482A1; Identifier 36 in EP3083691A2; Identifier 157 in US20160311907A1 |
| CD124 | Identifier 158 in US20160311907A1 |
| CD125 | Identifier 159 in US20160311907A1 |
| CD126 | Identifier 160 in US20160311907A1 |
| CD127 | Identifier 161 in US20160311907A1 |
| CD128 | Identifier 162 in US20160311907A1 |
| CD129 | Identifier 163 in US20160311907A1 |
| CD130 | Identifier 164 in US20160311907A1 |

TABLE 3-continued

The antigen-binding domain may comprise an scFv derived from an antibody or antibody fragment that binds to an antigen target such as those described in the cited publications, the contents of each publication are incorporated herein by reference in their entirety for all purposes.

| Antigen Target | Examples of Source |
|---|---|
| CD131 | Identifier 165 in US20160311907A1 |
| CD138 | Identifier 36 in WO2016130598A1 |
| CD19 | Identifier 53, 54, 37 in EP3083671A1; Identifier 1, 10, 11, 12, 2 in WO2015157252; Identifier 10, 2, 206, 207, 208, 209, 210, 211, 213, 214, 215, 216, 217, 218, 219, 220, 221, 222, 223, 224, 225, 4, 45, 47, 49, 51, 53, 55, 57, 51, 53, 55, 57, 59, 6, 8, 87 in WO2016033570; Identifier 3, 4, 5, 59, 6, 7, 8, 9 in WO2015157252; 5754 Identifier 5 in WO2015155341A1; Identifier 7 in WO2014184143; Identifier 9 in WO2016139487; Identifier 10, 2, 206, 207, 208, 209, 210, 211, 212, 213, 214, 215, 216, 217, 218, 219, 220, 221, 222, 223, 224, 225, 4, 45, 47, 49, 51, 53, 55, 57, 59, 6, 8, 87, 89 in US20160152723; Identifier 32, 35, 38 in EP3083691A2; Identifier 174 in WO2016115482A1; Identifier 20 in WO2012079000; Identifier 32, 33, 35, 38 in WO2015092024A2; Identifier 39, 40, 41, 42, 43, 44, 45, 46, 47, 48, 49, 50, 51 in WO2016109410; Identifier 5, 6 in WO2015155341A1; Identifier 7, 9 in US20160145337A1; Identifier 20 in U.S. Pat. No. 9,499,629B2; Identifier 73 in WO2016164580; Identifier 10, 2, 206, 207, 209, 210, 212, 216, 218, 219, 220, 221, 222, 223, 224, 225, 4, 45, 47, 49, 51, 53, 55, 57, 59, 6, 8, 87, 89 in US20160152723; Identifier 5 in WO2016055551 |
| CD19/CD22 Bispecific | Identifier 1303, 1307 in WO2016164731A2 |
| CD20 | Identifier 691 in WO2016164731A100; Identifier 692 in WO2016164731A101; Identifier 693 in WO2016164731A102; Identifier 694 in WO2016164731A103; Identifier 695 in WO2016164731A104; Identifier 696 in WO2016164731A105; Identifier 175 in WO2016115482A1 |
| CD22 | Identifier 5, 6 in WO2013059593; Identifier 9 in US20150299317; Identifier 131, 132, 133, 134, 135, 136, 137, 138, 139, 140, 203, 209, 215, 221, 227, 232, 238, 244, 250, 256, 262, 268, 274, 280, 286, 292, 298, 304, 310, 316, 322, 328, 334, 340, 346, 353, 358, 364, 370, 376, 383, 388, 394, 400, 406, 412, 418, 423 in WO2016164731A2 |
| CD276 | Identifier 10, 19, 28 in US20160053017 |
| CD3 | Identifier 46, 47 in WO2015153912A1 |
| CD30 | Identifier 20 in WO2016116035Al; Identifier 2 in US20160200824A1 |
| CD33 | Identifier 262, 263, 264, 265, 266, 267, 268, 39, 40, 41, 42, 43, 44, 45, 46, 47 in WO2016014576; Identifier 37 in WO2015092024 A2; Identifier 37 in EP3083691A2; Identifier 153, 154, 155, 156, 157, 158, 159, 160, 161, 162, 163 in WO2016115482A1 |
| CD33/CD3s bispecifc | Identifier 33, 34, 84 in WO2014144722A2 |
| CD37 | Identifier 21, 22 in US20170000900 |
| CD44 | Identifier 17 in WO2016042461A1 |
| CD46 | Identifier 1-42 in WO2016040683 |
| CD5 | Identifier 16 in WO2016138491 |
| CD79b | Identifier 33 in US20160208021 |
| CEA | Identifier 1 in US20160303166A1; Identifier 22 in US20140242701A1 |
| Centuxiamb | Identifier 37 in WO2016112870; Identifier 37 in US20160208021 |
| Claudin | Identifier 11, 5, 7, 9 in WO2016073649A1; Identifier 17 in WO2014179759A1 |
| Claudin6 | Identifier 164 in WO2016115482A1 |
| Claudin7 | Identifier 165 in WO2016115482A1 |
| Claudin8 | Identifier 166 in WO2016115482A1 |
| CLDN6 | Identifier 2 in WO2016150400 |
| CLDN7 | Identifier 4 in WO2016150400 |
| CLDN8 | Identifier 6 in WO2016150400 |
| CLL1 | Identifier 39, 40, 41, 42, 43, 44, 45, 46, 48, 49, 50, 51 in WO2016014535; Identifier 200, 201, 202, 203, 204, 205, 206, 207, 208, 209, 210, 211, 212, 213 in US20160311907A1 |
| CMet | Identifier 11, 12, 13, 14, 15, 16, 17, 18, 19, 2, 21, 22, 23, 25, 26, 27, 28, 3, 30, 31, 33, 34, 35, 36, 37, 38, 39, 4; 40, 41, 42, 43, 44, 48, 49, 5, 50, 51, 52, 53, 54, 55, 56, 57, 58, 6, 60, 7, 9, 29 in US20040166544; Identifier 26, 27, 28, 29, 30, 32 in US20150299326; Identifier 32 in US20130034559 |
| CS1 | Identifier 1 of WO2016090369; Identifier 17 in WO2014179759A1 |
| CSPG4 | Identifier 2 in WO2015080981; Identifier 2 in EP3074025A1 |
| CXCR4 | Identifier 83, 85, 86, 89 in US20110020218 |
| E7MC | Identifier 223, 224, 225, 226, 227, 228, 229, 230, 231, 232 in WO2016182957A1 |
| EGFR | Identifier 11, 38, 41, 44, 47, 50, 53, 56, 59, 62, 65, 68, 71, 74, 77, 80, 83, 88, 91, 94 in WO2014130657 |
| EGFR VIII | Identifier 5 in US20140037628; Identifier 174 in US20160311907A1; Identifier 38 in U.S. Pat. No. 9,394,368B2; Identifier 5 in US20160200819A1 |
| END 0180 | Identifier 6 in WO2013098813 |
| ERBB2 | Identifier 26, 27 in US20110059076A1; Identifier 1, 2 in U.S. Pat. No. 7,244,826 |
| ESKAVT | Identifier 173 in WO2016115482A1 |

TABLE 3-continued

The antigen-binding domain may comprise an scFv derived from an antibody or antibody fragment that binds to an antigen target such as those described in the cited publications, the contents of each publication are incorporated herein by reference in their entirety for all purposes.

| Antigen Target | Examples of Source |
| --- | --- |
| FcRL | Identifier 11, 15, 19, 23, 27, 31, 35, 39, 3, 43, 7, 594, 596, 598, 600, 602, 604, 606, 608, 610, 612, 614, 616, 618, 620, 622, 624, 626, 628, 630, 632, 634, 636, 638, 640, 642, 644, 646, 648, 652, 654, 656; 658, 660, 662, 664, 666, 668, 670, 672, 674, 676, 680, 682, 684, 686, 688, 690, 692, 694, 696, 700, 702, 704, 706, 708, 710, 712, 714, 716, 718, 720, 722, 724, 726, 728, 730, 732, 734, 736, 738, 740, 742, 744, 746, 748, 750, 752, 754, 756, 758, 760, 762, 764, 766, 768, 770, 772, 774, 776, 778, 780, 782, 784, 786, 788, 790, 792, 794, 796, 798, 800, 802, 804, 806, 808, 810, 812, 814, 816, 818, 820, 822, 824, 826, 828, 830, 832, 834, 836, 838, 840, 842, 844; 846, 848, 850, 852, 854, 856, 858, 860, 862, 864, 866, 868, 870, 874, 876, 878, 880, 882, 884, 886, 888, 890, 892, 894, 896, 650, 678 in WO2016090337 |
| Folate receptor | Identifier 15 in US20170002072A1 |
| Folate receptor alpha | Identifier 15, 23 in WO2012099973 |
| FOLR1/CD3s bispecific | Identifier 90 in WO2014144722A2 |
| GCN4 | Identifier 165, 166, 167, 168, 169, 170 in WO2016168773 A3 |
| GD2 | Identifier 19, 20, 21, in WO2016134284; Identifier 8 in WO2015132604 |
| GPC3 | Identifier 1 in WO2016049459; Identifier 12 in US20160208015A1 |
| GPC4 | Identifier 24 in WO2016049459 |
| GPRC5D | Identifier 100, 101, 102, 103, 104, 105, 106, 107, 108, 109, 110, 111, 112, 113, 114, 115, 116, 117, 118, 119, 120, 121, 122, 123, 301, 313, 325, 337, 349, 361, 373, 385 in WO2016090312 |
| HER2/CD3 | Identifier 9 in WO2014144722 A2 |
| Human CD79b | Identifier 33 in WO2016112870 |
| Human collagen VII | Identifier 34 in WO2016112870 |
| IL4 | Identifier 17, 16 in WO2009121847 |
| Integrin bivalent | Identifier 2, 1 in WO2009070753 |
| Ipilimumab | Identifier 39 in US20160208021; Identifier 39 in WO2016112870 |
| Mec/CD3s bispecific | Identifier 78 in WO2014144722A2 |
| Mesothelin | Identifier 7 WO2015188141; Identifier NO 47, 46, 57, 48, 49, 50, 51, 53, 54, 55, 56, 58, 59, 62, 64, 65, 66, 67, 68, 69, 70, 52, 60, 61, 63 in WO2016090034; Identifier 10, 11, 12 in WO2013142034; Identifier 11 in WO2013063419 |
| MUC1 | Identifier 15 in US20160130357 |
| MUC2 | Identifier 17 in US20160130357 |
| MUC3 | Identifier 15 in US20160130357 |
| MUC4 | Identifier 17 in US20160130357 |
| Nivolumab | Identifier 38 in US20160208021; Identifier 38 in WO2016112870 |
| NYBR1 | Identifier 21 in US20160333422A1; Identifier 21, 18, 19 in WO2015112830 |
| O-acetylated GD2 ganglioside | Identifier 29, 31 in US20150140023 |
| OX40 | Identifier 33 in US20150190506 |
| PD1 | Identifier 39, 40, 41, 42, 43, 44, 45, 46, 47, 48, 49, 50, 51, 52, 53, 54, 55, 56, 57, 58, 59, 60, 61 in US20160311917A1 |
| PDK1 | Identifier 15 in WO2016090365 |
| PDL1 nanobody | Identifier 22, 23, 24, 25, 26, 27 in US20110129458 |
| PDL2 nanobody 6462 | Identifier 28, 29, 30, 31, 32, 33 in US20110129458 |
| PRAME | Identifier 63, 64, 65, 66, 67, 68, 69 in WO2016191246A2 |
| PSMA | Identifier 19, 21, 30, 31, 34, 35 in WO2012145714 |
| PSMA diabody | Identifier 12, 13, 14, 15 in WO2011069019 |
| Radiation inducible neoantigen | Identifier 22, 24 in WO2005042780A1 |
| Ranibizuman | Identifier 40 in US20160208021; Identifier 40 in WO2016112870 |
| RAS | Identifier 81 in WO2016154047 |
| Rituximab | Identifier 36 in US20160208021; Identifier 36 in WO2016112870 |
| RORI | Identifier 34 in EP3083691A2; Identifier 249, 250 251, 252, 253, 254, 255, 256, 257, 258, 259, 260, 261, 262, 263, 264, 265, 266, 267, 268 in US20160208018A1; Identifier 57 in EP3083671A1; Identifier 1, 2 in US20160304619A1; Identifier 34 in WO2015092024A2 |
| Teplizumab | Identifier 42 in WO2016112870 |
| Teplizumab (mutated) | Identifier 42 in US20160208021 |
| TOSO | Identifier 2 in EP3098237A1 |
| Trastuzumab | Identifier 35 in US20160208021; Identifier 35 in WO2016112870 |
| TRBC1 | Identifier 13, 14, 15, 16, 17, 18, 19, 20, 21, 22, 3 in WO2015132598 |
| TRBC2 | Identifier 23, 24, 25, 26, 27, 28, 29, 30, 31, 32 in WO2015132598 |
| TSLPR | Identifier 1, 2 in US20160311910A1; Identifier 1, 2 in WO2015084513 |

TABLE 3-continued

The antigen-binding domain may comprise an scFv derived from an antibody or antibody fragment that binds to an antigen target such as those described in the cited publications, the contents of each publication are incorporated herein by reference in their entirety for all purposes.

| Antigen Target | Examples of Source |
| --- | --- |
| VEGF | Identifier 168, 169, 170, 171, 172, 173, 174, 175 in US20160090427; Identifier 498, 500, 502, 504, 506, 508 in US20110177074A1 |
| VEGFR2 | Identifier 1, 2 in US20120213783 |
| WT1/HLA bispecific | Identifier 108, 113, 18, 36, 54, 72, 90 in WO2015070061 |

TABLE 4

The antigen-binding domain may comprise an antigen-binding domain derived from a CAR that binds to an antigen target, such as those described in the cited publications, the contents of each publication are incorporated herein by reference in their entirety for all purposes.

| Antigen Target | Examples of Source |
| --- | --- |
| Acid/base leucine zipper | Identifier 34, 35 in WO2016124930 |
| ALK | Identifier 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 84, 85, 86, 87, 88, 89, 90 in WO2015069922 |
| APRIL-based CAR | Identifier 53 in US20160296562A1; Identifier 52 in US20160296562A1 |
| BCMA | Identifier 180, 162, 168, 174, 144, 150, 186, 192, 198, 204, 210, 156, 216, 222, 228, 234, 240, 246, 252, 258, 264, 270, 276 330, 282, 300, 306, 336, 354, 288, 312, 294, 342, 324, 318, 348 in WO2016168595A1; Identifier 48, 49, 50, 51, 52, 53, 54, 55, 56, 57, 58, 59, 19, 20, 21, 22, 23, 24, 25, 26, 27, 28, 29, 30, 31, 32, 33, 34, 35, 36, 37, 38, 39, 40, 41, 42 in WO2015158671A1; Identifier 124, 114, 115, 116, 117, 118, 119, 120, 121, 122, 123, 125, 126, 127, 128, 234, 235, 236, 237, 238, 239, 240, 241, 242, 243, 244, 245, 246, 247, 248, 249, 250, 251, 252, 253, 254, 267, 268, 269, 270 in WO2016014565; Identifier 1, 2, 3, 4, 5, 20 in WO2015052538; Identifier 1, 2, 3, 4, 5, 6 in US20160237139A1; Identifier 9 in WO2016094304 A3; Identifier 4, 5, 6, 8, 9, 10, 11, 12 in WO2013154760; Identifier 15, 16, 17, 18, 19, 20, 21, 22, 23, 24, 25, 26, 27, 28, 29, 71, 73 in WO2016014789; Identifier 125, 126, 127, 128, 129, 130, 131, 132, 133, 134, 135, 136, 137, 138, 139, 140, 141, 145, 146, 147, 148, 149, 150 in WO2016120216; Identifier 102, 106, 107, 108, 109, 110, 111, 112, 129, 130, 131, 132, 133, 134, 135, 136, 113, 114, 115, 116, 117, 118, 101, 100, 137, 119, 120, 121, 122, 123, 124, 125, 126, 127, 128, 103, 104, 105, 213 in WO2016097231 |
| CAR and gate (CD19 and CD33) CD148 phosphatase | Identifier 2 in US20160296562 |
| CAR and gate (CD19 and CD5) | Identifier 43 in US20160296562 |
| CAR and gate (CD19 and EGFR VIII) | Identifier 45 in US20160296562 |
| CAR and gate (CD19 and GD2) | Identifier 41 in US20160296562 |
| CAR and gate (CD19 or CD33) CD45 phosphatase | Identifier 3 in US20160296562 |
| CAR and not gate (CD19 and not CD33) | Identifier 4, 5 in US20160296562 |
| CAR and not gate (CD19 and not CD33) | Identifier 6 in US20160296562A1 |
| CAR and not gate 1 | Identifier 48 in US20160296562 |
| CAR and not gate 2 | Identifier 49 in US20160296562 |
| CAR and not gate 3 | Identifier 50 in US20160296562 |
| CAR or gate (DC19 or DC33) | Identifier 1 in US20160296562 |
| CAT19 CAR with CD28 zeta endodomain | Identifier 12 in WO2016139487 |
| CAT19 CAR with OX40 zeta endodomain | Identifier 11 in WO2016139487 |
| CAT19, campana architecture | Identifier 10 in WO2016139487 |

TABLE 4-continued

The antigen-binding domain may comprise an antigen-binding domain derived from a CAR that binds to an antigen target, such as those described in the cited publications, the contents of each publication are incorporated herein by reference in their entirety for all purposes.

| Antigen Target | Examples of Source |
|---|---|
| CD123 | Identifier 69 in WO2016142532; Identifier 23, 24, 25, 26, 27, 28, 29, 30, 31, 32, 33, 34, 35, 36, 37, 38, 39, 40, 41, 42, 44, 45, 46, 47, 48 in WO2015140268A1; Identifier 9, 10, 11, 12 in US20140271582; Identifier 56, 57, 58, 59, 60, 61 in WO2016097231; Identifier 98, 99, 100, 101, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156 in WO2016028896; Identifier 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 172, 173, 174, 175, 176, 177, 178, 179, 180, 181, 182, 183, 184, 185, 186, 187, 188, 189, 190, 191, 193, 194, 195, 196, 197 in WO2016120220; Identifier 1, 2, 3, 4, 5, 6, 7, 8, 9, 10, 142 in WO2016120216 |
| CD19 | Identifier 12 in US9499629B2; Identifier 24 in US20160333108A1; Identifier 25, 29 in US20160333108A1; Identifier 27 in US20160333108A1; Identifier 1 in EP2997134A4; Identifier 19, 20 in EP3071687A1; Identifier 181 in WO2016168773A3; Identifier 2 in WO2015157399A9; Identifier 56, 62 in WO2016744409A1; Identifier 145, 293, 294, 295, 296, 297, 298 in WO2016179319A1; Identifier 73 in WO2013176915A1; Identifier 73 in WO2013176916A1; Identifier 73 in US20130315884A1; Identifier 73 in US20140134142A1; Identifier 73 in US20150017136A1; Identifier 73 in US20150203817A1; Identifier 73 in US20160120905A1; Identifier 73 in US20160120906A1; Identifier 8, 5 in WO2015124715; Identifier 73 in WO2014184744; Identifier 73 in WO2014184741; Identifier 14, 15 in US20160145337A1; Identifier 14, 15 in WO2014184143; Identifier 15, 16 in WO2015075175; Identifier 16 in US20160145337A1; Identifier 16 in WO2014184143; Identifier 12 in WO2012079000; Identifier 31, 32, 33, 34, 35, 36, 37, 38, 39, 40, 41, 42, 58 in WO2016164580; Identifier 14, 15 in US20160296563A1; Identifier 31, 32, 33, 34, 35, 36, 37, 38, 39, 40, 41, 42 in WO2015157252; Identifier 14, 15 in WO2016139487; Identifier 53, 54, 55, 56, 57, 58 in US20160250258A1; Identifier 1, 2, 3, 4, 5, 6, 7, 8, 9, 10, 11, 12, 13 in WO2015187528; Identifier 31, 32, 33, 34, 35, 36, 37, 38, 39, 40, 41, 42, 58 in WO2015157252; Identifier 31, 32, 33, 34, 35, 36, 37, 38, 39, 40, 41, 42 in WO2014153270; WO2016134284 (no Identifier); Identifier 13 in WO2016139487 |
| CD19 or CD33 | Identifier 1 in WO2015075468 which recognizes CD19 OR CD33 |
| CD19/CD20 bispecific | Identifier 1308 in WO2016164731A2; Identifier 2, 8, 11 in US9447194B2 |
| CD19/IL13 bispecific | Identifier 10 in US20160340649A1 |
| CD2 | Identifier 10, 11 in WO2016138491 |
| CD20 | Identifier 25 in WO2015157399A9; Identifier 177, 181, 182, 183, 184, 185, 186, 187, 205, 206, 207, 208, 209, 210, 211, 188, 189, 190, 191, 192, 193, 176, 212, 194, 195, 196, 197, 198, 199, 200, 201, 202, 203, 178, 179, 180 in WO2016097231 |
| CD22 | Identifier 380, 204, 260, 266, 272, 278, 284, 290, 296, 302, 308, 341, 213, 320, 326, 332, 338, 347, 350, 356, 362, 368, 374, 219, 386, 392, 398, 404, 410, 416, 421, 427, 225, 230, 1109, 236, 242, 248, 254 in WO2016164731A2; Identifier 15, 16, 17, 18, 19, 20, 32 in WO2013059593; Identifier 22, 23, 24 in US20150299317 |
| CD22/CD19 bispecific | Identifier 29, 30 in WO2016149578; Identifier 1304 in WO2016164731A2 |
| CD276 | Identifier 39, 40, 41, 42, 43, 44, 45, 46, 47, 122, 123, 124, 125, 126, 127, 128, 129, 130 in US20160053017 |
| CD3 | Identifier 12 in WO2016138491 |
| CD30 | Identifier 20 in WO2016008973A1; Identifier 1 in WO2016116035A1; WO2016134284 (no Identifier); Identifier 2 in WO2016008973 |
| CD33 | Identifier 48, 49, 50, 51, 52, 53, 54, 55, 83 in WO2016014576; Identifier 19, 20, 21, 22, 23, 24, 25, 26, 27, 28, 29, 30, 31, 32, 33, 34, 35, 36, 37, 38, 39, 40, 41, 42, 48, 49, 50, 51, 52, 53, 54, 55, 56, 57, 58, 59, 60, 61, 62, 63, 64, 65, 66, 67, 68, 69, 70, 71 in WO2015150526A2 |
| CD38 | Identifier 70, 71, 72, 64, 65, 66, 67, 68, 69 in WO2016097231; Identifier 35, 36, 37 in WO2015121454 |

TABLE 4-continued

The antigen-binding domain may comprise an antigen-binding domain derived from a CAR that binds to an antigen target, such as those described in the cited publications, the contents of each publication are incorporated herein by reference in their entirety for all purposes.

| Antigen Target | Examples of Source |
| --- | --- |
| CD4 | Identifier 13, 14 in WO2016138491 |
| CD410 | Identifier 7 in EP3074419A2 |
| CD435 | Identifier 5 in EP3074419A2 |
| CD44 | Identifier 21, 22, 23, 24, 25, 26, 27, 28, 31, 32, 33, 34, 35 in WO2016042461A1 |
| CD4-DDY3 | Identifier 9 in EP3074419A2 |
| CD5 | Identifier 15, 13 in WO2016138491 |
| CD52 | Identifier 18 in WO2016138491 |
| CD7 | Identifier 17 in WO2016138491 |
| CD70 | Identifier 99 in WO2015121454 |
| CD70 | Identifier 100, 93, 94, 96, 101, 95, 97, 98 in WO2015121454 |
| CD8 stalk APRIL | Identifier 51 in US20160295562A1 |
| CEA | Identifier 4 in WO2016008973A1; Identifier 29, 30 in US20140242701A |
| CLDN6 | Identifier 22, 23, 24 in WO2016150400 |
| CLL1 | Identifier 148 in WO2016179319A1; Identifier 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112 in WO2016120218; Identifier 91, 92, 93, 94, 95, 96, 97, 98, 99, 100, 101, 102, 103, 197 in WO2016014535 |
| COM22 | Identifier 358, 359, 360 in US20160297884A1 |
| CS1 | Identifier 55, 57, 60, 54, 56, 48, 49, 50, 51, 52, 53, 58, 59, 61, 62 in WO2015121454; Identifier 28 in WO2014179759A1 |
| DDD1/AD1 zip | Identifier 37 in WO2016124930 |
| DDD1/AD1-based zip | Identifier 36 in WO2016124930 |
| EGFR | Identifier 3, 2in WO2014130657; Identifier 36, 37, 38, 39, 35 in US20140242701 A; Identifier 43, 96, 49, 55, 61, 67, 73, 79, 85, 90, 1 in WO2014130657 |
| EGFR vIII | Identifier 15, 16, 17, 18, 24, 25, 26, 27 in WO2016016341; Identifier 5, 10, 12, 8, 31, 30, 3 in US20160311907A1; Identifier 10 in US20160200819A1; Identifier 43, 49, 55, 61, 67, 73, 79, 85, 90, 96 in US9394368B2; Identifier 49, 55, 61, 67, 73, 79, 85, 90, 2, 1 in US20170008963A1; Identifier 10, 11 in US20140037628 |
| FcRL5 | Identifier 11 in US20170008963A1 |
| Folate receptor | Identifier 12 in US20170008963A1 |
| FR | Identifier 22 in US20170002072A1 |
| FR beta | Identifier 13, 22 in US9402865B2; Identifier 2, 4, 6 in US9446105B2 |
| FRa | Identifier 13, 14 in US20120213783 |
| Fra | Identifier 959 in WO2016090337; Identifier 13 in US20170002072A1 |
| GCN4 | Identifier 8, 10 in US9446105B2 |
| GD2 | Identifier 12 in US9446105B2; Identifier 273, 274 in WO2016168773A3; Identifier 26, 27, 28, 29, 30, 31, 32, 33, 34, 35, 36, 37 in WO2015132604; WO2016134284 (no Identifier) |
| GD3 | Identifier 19 in WO2016185035A1; Identifier 20, 21, 22, 23, 24, 25, 26 in WO2016185035A1; WO2016134284 (no Identifier) |
| GFR alpha | Identifier 27 in WO2016185035A1 |
| GPC3 | Identifier 28, 29 in WO2016185035A1; Identifier 3, 27, 10, 29, 14, 30, 31, 18, 33 in WO2016049459; Identifier 22 in US20160215261A1 |
| HER2 | Identifier 25 in US20160215261A1; Identifier 9, 10 of WO2016073629; Identifier 17, 28, 98, 110 in US20160333114A1; Identifier 271, 272 in WO2016168773A3; Identifier 5 in WO2016168769A1 |
| Her1/Her3 bispecific | Identifier 23, 24 in US20160215261A1 |
| HERVK | Identifier 6 in WO2016168769A1 |
| HIV Env | Identifier 48, 49 in WO2016168766A1; Identifier 4 in EP2997134A4; Identifier 7, 9, 47, 49 in WO2015077789 |
| HSP70 | Identifier 51, 53, 5 in WO2015077789; Identifier 21, 22, 23, 24, 25, 26, 27, 28, 29 in WO2016120217 |
| IL13 | Identifier 30, 31, 32 in WO2016120217 |
| IL13Ra2specific | Identifier 4, 5, 6 in WO2016089916A1; Identifier 47, 49 in WO2016123143; Identifier 51, 53, 55 in WO2016123143; Identifier 1, 31, 32, 33, 34, 35, 36, 37, 38, 39, 40, 41, 42, 43, 44, 45 in US20160340649A1 |
| KMA | Identifier 46 in US20160340649A1 |
| Mesothelin | Identifier 47, 48 in US20160340649A1; Identifier 48 in US20160340649A1; Identifier 27 in WO2016172703A2; Identifier 18, 19, 20, 21, 22, 23 in WO2013142034; Identifier 3 in WO2013067492 |

TABLE 4-continued

The antigen-binding domain may comprise an antigen-binding domain derived from a CAR that binds to an antigen target, such as those described in the cited publications, the contents of each publication are incorporated herein by reference in their entirety for all purposes.

| Antigen Target | Examples of Source |
|---|---|
| MUC1 | Identifier 5, 7 in WO2013063419; Identifier 51 in US20160340406A1; Identifier 30, 32, 34 in US20160130357; Identifier 295, 298, 301, 304, 307, 607, 609, 611, 613 in WO2016130726 |
| NCAR with RQR82 ACD 19 | Identifier 615 in WO2016130726 |
| NYBR1 | Identifier 617, 619 in WO2016130726; Identifier 218 in WO2016097231; Identifier 26, 29, 60 in WO2015112830; Identifier 1 in US20160333422A1 |
| P5A | Identifier 26, 29, 60 in US20160333422A1 |
| P5AC1 | Identifier 343, 344, 345, 346 in US20160297884A1 |
| P5AC16 | Identifier 347, 396, 348 in US20160297884A1 |
| P6AP | Identifier 349, 350, 351 in US20160297884A1 |
| P6DY | Identifier 364, 365, 366 in US20160297884A1 |
| PC1C12 | Identifier 352, 353, 354 in US20160297884A1 |
| PCI | Identifier 361, 362, 363 in US20160297884A1 |
| PD1 | Identifier 355, 356, 357 in US20160297884A1; Identifier 119 in WO2014153270; Identifier 121 in WO2014153270; Identifier 22, 24, 63, 64, 65, 66, 67, 68, 69, 70, 71, 72, 73, 74, 75, 76, 77, 78, 79, 80, 81, 82, 83, 84, 85, 86 in US20160311917A1; Identifier 26, 39 in WO2016172537A1; Identifier 40 in US20160311907A1; Identifier 121, 119 in WO2015157252; Identifier 24 in WO2016014565; Identifier 22 in WO2016014565 |
| PD1 | Identifier 23 in WO2016014565; Identifier 26 in WO2015142675 |
| PSMA | Identifier 39 in WO2015142675; Identifier 28, 29 in US20160311907A1; Identifier 140, 144, 145, 146, 147, 148, 149, 150, 167, 168, 169, 170, 171, 172, 173, 174, 151, 152, 153, 154, 155, 156, 139, 138, 175, 157, 158, 159, 160, 161, 162, 163, 164, 165, 166, 141, 142, 143, 214 in WO2016097231 |
| ROR1 | Identifier 216, 217, 215 in WO2016097231; Identifier 79, 80, 81, 82, 83, 84, 85, 86, 87, 88, 89, 90, 91, 92, 93, 94, 95, 96, 103, 104, 105, 106, 107, 108, 109, 110, 111, 112, 113, 114, 115, 116, 117, 118, 119, 120, 127, 128, 129, 130, 131, 132, 133, 134, 1335, 136, 137, 138, 97, 98, 99, 100, 101, 102, 121, 122, 123, 124, 125, 126 in WO2016016344A1; Identifier 386, 387, 388, 389, 390, 391, 392, 393, 394 in WO2016187216A1 |
| SNAP | Identifier 395 in WO2016187216A1 |
| SSEA4 | Identifier 396, 397 in WO2016187216A1 |
| Tan | Identifier 19 in US20160311907A1 recognizes CD19 AND CD33 using a CD45 phosphatase; Identifier 5 in WO2016026742A1 recognizes CD19 AND CD33 using a CD148 phosphatase; Identifier 6 in WO2016026742A1 which recognizes CD19 AND NOT CD33 and is based on an ITIM containing endodomain from LAIR1; Identifier 3 in WO2015075468 which recognizes CD19 AND NOT CD33 based on PTPN6 phosphatase; Identifier 2 in WO2015075468 which recognizes CD19 AND NOT CD33 and recruits a PTPN6/CD148 fusion protein to an ITIM containing endodomain |
| TOSO | Identifier 5, 4 in WO2015075468 |
| Trophoblast Glycoprotein 5T4 | Identifier 6 in WO2015075468; Identifier 4 in US20160347854A1; Identifier 4 in EP3098237A1; Identifier 19, 20, 21, 22, 23, 24, 25, 26, 27, 28, 29, 30, 31, 32, 33, 34, 35, 36, 37, 38, 39 in WO2016034666A1 |
| TSLPR | Identifier 40, 41, 42 in WO2016034666A1; Identifier 39, 40, 41, 42, 43, 44, 45, 46 in WO2015084513; Identifier 39, 40, 41, 42, 43 in US20160311910A1 |
| VEGFR2 | Identifier 44, 45, 46 in US20160311910A1; Identifier 10, 11, 12 in US20120213783 |
| VNAR | Identifier 105, 106, 107, 108, 109, 110 in US20160333094A1 |

In various embodiments, the scFv fragment used in the arCAR system of the present disclosure may include a linker between the VH and VL domains. The linker can be a peptide linker and may include any naturally occurring amino acid. Exemplary amino acids that may be included into the linker are Gly, Ser Pro, Thr, Glu, Lys, Arg, Ile, Leu, His and The. The linker should have a length that is adequate to link the VH and the VL in such a way that they form the correct conformation relative to one another so that they retain the desired activity, such as binding to an antigen. The linker may be about 5-50 amino acids long. In some embodiments, the linker is about 10-40 amino acids long. In some embodiments, the linker is about 10-35 amino acids long. In some embodiments, the linker is about 10-30 amino acids long. In some embodiments, the linker is about 10-25 amino acids long. In some embodiments, the linker is about 10-20 amino acids long. In some embodiments, the linker is about 15-20 amino acids long. Exemplary linkers that may be used are Gly rich linkers, Gly and Ser containing linkers, Gly and Ala containing linkers, Ala and Ser containing linkers, and other flexible linkers.

In one embodiment, the linker is a Whitlow linker. In one embodiment, the Whitlow linker comprises the amino acid sequence set forth in SEQ ID NO: 3, or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NO: 3. In another embodiment, the linker is a $(G_4S)_3$ linker. In one embodiment, the $(G_4S)_3$ linker comprises the amino acid sequence set forth in SEQ ID NO: 25, or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NO: 25.

Other linker sequences may include portions of immunoglobulin hinge area, CL or CH1 derived from any immunoglobulin heavy or light chain isotype. Exemplary linkers that may be used include any of SEQ ID NOs: 26-56 in Table 1. Additional linkers are described for example in Int. Pat. Publ. No. WO2019/060695, incorporated by reference herein in its entirety.

In some embodiments, the second polypeptide comprises the antigen-binding domain at the N-terminus and the tag at the C-terminus. In some embodiments, the second polypeptide comprises the antigen-binding domain at the C-terminus and the tag at the N-terminus.

In some embodiments, the second polypeptide is a soluble polypeptide.

In some embodiments, the arCAR system further comprises one or more additional polypeptides each comprising (a) an antigen-binding domain that binds to a unique antigen and (b) a tag that is recognized by the tag-binding domain of the first polypeptide.

In another aspect, provided herein is an arCAR system comprising two or more arCARs described herein, wherein each arCAR comprises a unique pair of tag and tag-binding domain.

In further aspects, provided herein is a polypeptide of an arCAR described herein. In one aspect, provided herein is a first polypeptide of an arCAR described herein. In one aspect, provided herein is a second polypeptide of an arCAR described herein.

Without wishing to be bound by theory, the arCAR systems of the present disclosure may have various advantages including:
  The high degree of specificity that the anti-ID molecule/antibody fragment minimizes off-target interactions, particularly in combination with the non-human protein target for the antibody specificity.
  Specificity to the binding loops on the tag avoids undesirable interacting with similar framework/scaffold proteins. True-IDs, which neutralize the binding to target, can also be employed.
  Inherent ability to develop a range of affinities to optimize and modulate the "tag" polypeptide and CAR interaction.
  The system is unlimited in possible pairs such that numerous optimized CAR/"tag" polypeptide pairs can be developed, each with a unique specificity to enable fit-for-purpose therapy including modulation of binding affinities, logic-gating, multiple specificities per cell and multiple soluble drugs per treatment.
  The approach is "platform agnostic" which allows one to incorporate a different scaffold (for example, replace an scFv with a VHH), if immunogenicity or other limitations towards one scaffold develop.

Polynucleotides and Vectors

In another aspect, provided herein are polynucleotides encoding one or more polypeptides in an arCAR system of the present disclosure.

In some embodiments, provided herein is a polynucleotide encoding the first polypeptide of an arCAR system of the present disclosure. In some embodiments, provided herein is a polynucleotide encoding the first polypeptides of two or more arCAR systems of the present disclosure. In some embodiments, the two or more arCAR systems each comprise a unique pair of tag and tag-binding domain.

In some embodiments, provided herein is a polynucleotide encoding the second polypeptide of an arCAR system of the present disclosure. In some embodiments, provided herein is a polynucleotide encoding the second polypeptides of two or more arCAR systems of the present disclosure. In some embodiments, the two or more arCAR systems each comprise a unique pair of tag and tag-binding domain.

In some embodiments, provided herein is a polynucleotide encoding both polypeptides of an arCAR system of the present disclosure. In some embodiments, the polynucleotide encodes both polypeptides of two or more arCAR systems of the present disclosure. In some embodiments, the two or more arCAR systems each comprise a unique pair of tag and tag-binding domain.

The polynucleotide can comprise any type of nucleotides, including, but not limited to DNA and RNA, which can be single-stranded or double-stranded, synthesized or obtained in part from natural sources, and which can contain natural, non-natural or altered nucleotides. The polynucleotide can comprise naturally-occurring or non-naturally-occurring internucleotide linkages, or both types of linkages.

In some embodiments, the polynucleotide described herein is a DNA molecule. In various embodiments, the polynucleotide described herein is an RNA molecule.

In one aspect, the present disclosure provides recombinant vectors comprising a polynucleotide described herein.

In some embodiments, the recombinant vector comprises a polynucleotide encoding the first polypeptide of an arCAR system of the present disclosure. In some embodiments, the recombinant vector comprises a polynucleotide encoding the first polypeptides of two or more arCARs of the present disclosure. In some embodiments, the two or more arCARs each comprise a unique pair of tag and tag-binding domain.

In some embodiments, the recombinant vector comprises a polynucleotide encoding the second polypeptide of an arCAR system of the present disclosure. In some embodiments, the recombinant vector comprises a polynucleotide encoding the second polypeptides of two or more arCARs of the present disclosure. In some embodiments, the two or more arCARs each comprise a unique pair of tag and tag-binding domain.

In some embodiments, the recombinant vector comprises a polynucleotide encoding both polypeptides of an arCAR system of the present disclosure. In some embodiments, the recombinant vector comprises a polynucleotide encoding both polypeptides of two or more arCARs of the present disclosure. In some embodiments, the two or more arCARs each comprise a unique pair of tag and tag-binding domain.

A recombinant vector can be any suitable recombinant expression vector. Suitable vectors include those designed for propagation and expansion or for expression or both, such as plasmids and viruses. For example, a vector can be selected from the pUC series (Fermentas Life Sciences, Glen Burnie, Md.), the pBluescript series (Stratagene, LaJolla, Calif.), the pET series (Novagen, Madison, Wis.), the pGEX series (Pharmacia Biotech, Uppsala, Sweden), and the pEX series (Clontech, Palo Alto, Calif.). Bacteriophage vectors, such as λGT10, λGT11, λZapII (Stratagene), λEMBL4, and λNM1149, can also be used. Examples of plant expression vectors useful in the context of the disclosure include pBI01, pBI101.2, pBI101.3, pBI121 and pBIN19 (Clontech). Examples of animal expression vectors useful in the context of the disclosure include pcDNA, pEUK-Cl, pMAM, and pMAMneo (Clontech). In some embodiments, a bicistronic IRES vector (e.g., from Clontech) can be used to include both a polynucleotide encoding the first polypeptide and the second polypeptide of an arCAR system described herein.

In some embodiments, the recombinant vector is a non-viral vector. The viral vector may be a plasmid or a transposon (such as a PiggyBac- or a Sleeping Beauty transposon). In one embodiment, the vector is a plasmid.

In some embodiments, the recombinant vector is a viral vector. Suitable viral vectors include, without limitation, retroviral vectors, lentiviral vectors, alphaviral vectors, adenoviral vectors, adeno-associated viral vectors (AAVs), herpes viral vectors, vaccinial vectors, and fowl pox viral vectors. In some embodiments, the viral vectors have a native or engineered capacity to transform a host cell (e.g., T cell).

Recombinant vectors can be prepared using standard recombinant DNA techniques described in, for example, Sambrook et al., Molecular Cloning: A Laboratory Manual, 3rd ed., Cold Spring Harbor Press, Cold Spring Harbor, N.Y. 2001; and Ausubel et al., Current Protocols in Molecular Biology, Greene Publishing Associates and John Wiley & Sons, N Y, 1994. Constructs of expression vectors, which are circular or linear, can be prepared to contain a replication system functional in a prokaryotic or eukaryotic host cell. Replication systems can be derived, e.g., from ColEl, 2μ plasmid, λ, SV40, bovine papilloma virus, and the like.

A recombinant vector can include one or more marker genes, which allow for selection of transformed or transfected hosts. Marker genes include biocide resistance, e.g., resistance to antibiotics, heavy metals, etc., complementation in an auxotrophic host to provide prototrophy, and the like. Suitable marker genes for the recombinant expression vectors include, for instance, neomycin/G418 resistance genes, puromycin resistance genes, hygromycin resistance genes, histidinol resistance genes, tetracycline resistance genes, and ampicillin resistance genes.

Vectors useful in the context of the disclosure can be "naked" nucleic acid vectors (i.e., vectors having little or no proteins, sugars, and/or lipids encapsulating them), or vectors complexed with other molecules. Other molecules that can be suitably combined with the vectors include without limitation viral coats, cationic lipids, liposomes, polyamines, gold particles, and targeting moieties such as ligands, receptors, or antibodies that target cellular molecules.

Vector DNA can be introduced into a host cell, e.g., an immune effector cell, via conventional transformation or transfection techniques. As used herein, the terms "transformation" and "transfection" are intended to refer to a variety of art-recognized techniques for introducing foreign nucleic acid (e.g., DNA) into a cell, including calcium phosphate or calcium chloride co-precipitation, DEAE-dextran-mediated transfection, lipofection, gene gun, or electroporation.

In various embodiments, the polynucleotide encoding the arCAR polypeptide (e.g., first polypeptide or second polypeptide) is operably linked to at least a regulatory element. The regulatory element can be capable of mediating expression of the arCAR polypeptide (e.g., first polypeptide or second polypeptide) in the host cell. Regulatory elements include, but are not limited to, promoters, enhancers, initiation sites, polyadenylation (polyA) tails, IRES elements, response elements, and termination signals. In certain embodiments, the regulatory element regulates arCAR polypeptide expression. In certain embodiments, the regulatory element increased the expression of the arCAR polypeptide (e.g., first polypeptide or second polypeptide). In certain embodiments, the regulatory element increased the expression of the arCAR polypeptide (e.g., first polypeptide or second polypeptide) once the host cell is activated. In certain embodiments, the regulatory element decreases expression of the arCAR polypeptide (e.g., first polypeptide or second polypeptide). In certain embodiments, the regulatory element decreases expression of the arCAR polypeptide (e.g., first polypeptide or second polypeptide) once the host cell is activated.

Modified Host Cells

In one aspect, provided herein are host cells modified to express one or more of the polypeptides of the arCARs of the present disclosure.

In some embodiments, provided herein is a host cell which is an immune effector cell comprising the first polypeptide of an arCAR system of the present disclosure. In some embodiments, provided herein is a host cell comprising the first polypeptides of two or more arCARs of the present disclosure. In some embodiments, the two or more arCARs each comprise a unique pair of tag and tag-binding domain.

In some embodiments, provided herein is a host cell comprising the second polypeptide of an arCAR of the present disclosure. In some embodiments, provided herein is a host cell comprising the second polypeptides of two or more arCARs of the present disclosure. In some embodiments, the two or more arCARs each comprise a unique pair of tag and tag-binding domain.

In some embodiments, provided herein is a host cell comprising both the first and the second polypeptides of an arCAR of the present disclosure.

In some embodiments, provided herein is a host cell comprising a polynucleotide, or a recombinant vector described herein.

In various embodiments, the cell having the chimeric antigen receptor comprising the first polypeptide is an immune-effector cell. In some embodiments, the cell is a T cell, a Natural Killer (NK) cell, a cytotoxic T lymphocyte (CTL), a regulatory T cell, a tumor-infiltrating lymphocyte (TIL), a dendritic cell or a macrophage.

In some embodiments, the immune effector cell is derived from a stem cell. In some embodiments, the cell is an induced pluripotent stem cell (iPSC), a hematopoietic stem cells (HSCs), or an embryonic stem cell (ESC). In some embodiments, the cell is an iPSC. In one embodiment, the cell is a T cell derived from an iPSC. In one embodiment, the cell is a NK cell derived from an iPSC.

In one aspect, provided herein are methods of preparing the modified host cells described herein.

In one embodiment, the method of preparing the modified host cell comprises introducing the polynucleotide encoding the first polypeptide of an arCAR of the present disclosure, or a recombinant vector comprising the polynucleotide, into the cell.

In one embodiment, the method of preparing the modified host cell comprises introducing the polynucleotide encoding the second polypeptide of an arCAR of the present disclosure, or a recombinant vector comprising the polynucleotide, into the cell.

In one embodiment, the method of preparing the modified host cell comprises introducing the polynucleotide encoding both the first polypeptide and the second polypeptide of an arCAR of the present disclosure, or a recombinant vector comprising the polynucleotide, into the cell.

In various embodiments, the modified cell constitutively expresses the first polypeptide of an arCAR described herein. In various embodiments, the modified cell inducibly expresses the first polypeptide of an arCAR described herein.

In various embodiments, the modified cell constitutively expresses the second polypeptide of an arCAR described herein. In various embodiments, the modified cell inducibly expresses the second polypeptide of an arCAR described herein.

In various embodiments, the host cells may be autologous/autogenic ("self") or non-autologous ("non-self," e.g., allogeneic, syngeneic or xenogeneic). In some embodiments, the host cells are obtained from a mammalian subject. In some embodiments, the host cells are obtained from a primate subject. In some embodiments, the host cells are obtained from a human subject.

In certain embodiments, immune cells such as lymphocytes are used. Lymphocytes can be obtained from sources such as, but not limited to, peripheral blood mononuclear cells, bone marrow, lymph nodes tissue, cord blood, thymus issue, tissue from a site of infection, ascites, pleural effusion, spleen tissue, and tumors. Lymphocytes may also be generated by differentiation of stem cells. In certain embodiments, lymphocytes can be obtained from blood collected from a subject using techniques generally known to the skilled person, such as sedimentation, e.g., FICOLL™ separation.

In certain embodiments, immune cells from the circulating blood of a subject are obtained by apheresis. An apheresis device typically contains lymphocytes, including T cells, monocytes, granulocytes, B cells, other nucleated white blood cells, red blood cells, and platelets. In certain embodiments, the cells collected by apheresis may be washed to remove the plasma fraction and to place the cells in an appropriate buffer or media for subsequent processing. The cells can be washed with PBS or with another suitable solution that lacks calcium, magnesium, and most, if not all other, divalent cations. A washing step may be accomplished by methods known to those in the art, such as, but not limited to, using a semiautomated flowthrough centrifuge (e.g., Cobe 2991 cell processor, or the Baxter CytoMate). After washing, the cells may be resuspended in a variety of biocompatible buffers, cell culture medias, or other saline solution with or without buffer.

In certain embodiments, T lymphocytes can be isolated from peripheral blood mononuclear cells (PBMCs) by lysing the red blood cells and depleting the monocytes. As an example, the cells can be sorted by centrifugation through a PERCOLL™ gradient. In certain embodiments, after isolation of PBMC, both cytotoxic and helper T lymphocytes can be sorted into naive, memory, and effector T-cell subpopulations either before or after activation, expansion, and/or genetic modification.

In certain embodiments, T lymphocytes can be enriched. For example, a specific subpopulation of T lymphocytes, expressing one or more markers such as, but not limited to, CD3, CD4, CD8, CD14, CD15, CD16, CD19, CD27, CD28, CD34, CD36, CD45RA, CD45RO, CD56, CD62, CD62L, CD122, CD123, CD127, CD235a, CCR7, HLA-DR or a combination thereof using either positive or negative selection techniques. In certain embodiments, the T lymphocytes for use in the compositions of the disclosure do not express or do not substantially express one or more of the following markers: CD57, CD244, CD160, PD-1, CTLA4, TIM3, and LAG3.

In certain embodiments, NK cells can be enriched. For example, a specific subpopulation of T lymphocytes, expressing one or more markers such as, but not limited to, CD2, CD16, CD56, CD57, CD94, CD122 or a combination thereof using either positive or negative selection techniques.

In certain embodiments, pluripotent stem cells (PSCs) such as induced pluripotent stem cells (iPSCs) and embryonic stem cells (ESCs) are used to generate the host cells such as NK cells or T lymphocytes. Human iPSCs and human ESCs can be produced by various methods known in the art. PSCs (e.g., iPSCs or ESCs) can be modified by an arCAR of the present disclosure by, e.g., contacting the cells with a polynucleotide or recombinant vector encoding a polypeptide of the arCAR, and the engineered PSC can be used to produce or generate immune cells (e.g., T cells) comprising the arCAR of the present disclosure.

iPSCs can be generated directly from adult cells (e.g., somatic cells). iPSCs can be derived or generated by introducing a specific set of pluripotency-associated genes, or "reprogramming factors", into a given cell type. Reprogramming factors include, but are not limited to, OCT4 (also known as "POUSFL"), SOX2, cMYC, and KLF4, which are also known as Yamanaka factors. See Takahashi, K; Yamanaka, S (2006). Cell 126 (4): 663-76. Each of the reprogramming factors can be functionally replaced by related transcription factors, miRNAs, small molecules, or even non-related genes such as lineage specifiers. Upon introduction of reprogramming factors, cells begin to form colonies that resemble PSCs, which can be isolated based on their morphology, conditions that select for their growth, or through expression of surface markers or reporter genes. In certain embodiments, the PSCs used in the methods of the present invention are subject-specific.

There are known technologies for producing PSCs from various types of somatic cells by reprogramming using the Yamanaka factors (OCT4, SOX2, KLF4, and cMYC). For example, reprogramming of mature lymphocytes into iPSCs was accomplished for murine B cells (Hanna et al., (2008) Cell, 133, pp. 250-264; Wada et al., (2011) Int. Immunol., 23, pp. 65-74), for murine T cells and mature NK T cells (Watarai et al., (2010) J. Clin. Invest., 120, pp. 2610-2618), and for human T cells (Loh et al., (2010) Cell Stem Cell, 7, pp. 15-19; Seki et al., (2010) Cell Stem Cell, 7, pp. 11-14). iPSCs can be produced from human T cells by using whole peripheral mononuclear cells (PBMCs) or $CD3^+$ cells as a source cell population (Loh et al., (2010) Cell Stem Cell, 7, pp. 15-19; Seki et al., (2010) Cell Stem Cell, 7, pp. 11-14; Staerk et al. (2010) Cell Stem Cell, 7, pp. 20-24; Brown et al, (2010) PloS One 5, el1373).

In order to reach sufficient therapeutic doses of host cell compositions, host cells are often subjected to one or more rounds of stimulation/activation. In certain embodiments, a method of producing host cells for administration to a subject comprises stimulating the host cells to become activated in the presence of one or more stimulatory signals or agents (e.g., compound, small molecule, e.g., small organic molecule, nucleic acid, polypeptide, or a fragment, isoform, variant, analog, or derivative thereof). In certain embodiments, a method of producing host cells for administration to a subject comprises stimulating the host cells to become activated and to proliferate in the presence of one or more stimulatory signals or agents.

Immune cells (e.g., T lymphocytes and NK cells) can be activated by inducing a change in their biologic state by which the cells express activation markers, produce cytokines, proliferate and/or become cytotoxic to target cells. All these changes can be produced by primary stimulatory signals. Co-stimulatory signals amplify the magnitude of the primary signals and suppress cell death following initial stimulation resulting in a more durable activation state and thus a higher cytotoxic capacity.

T cells can be activated generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; and 6,867,041, each of which is incorporated herein by reference in its entirety. In certain embodiments, the T cells are activated by binding to an agent that activates CD3ζ.

In some embodiments, a CD2-binding agent may be used to provide a primary stimulation signal to the T cells. For example, and not by limitation, CD2 agents include, but are not limited to, CD2 ligands and anti-CD2 antibodies, e.g., the Tl 1.3 antibody in combination with the Tl 1.1 or Tl 1.2 antibody (Meuer, S. C. et al. (1984) Cell 36:897-906) and the 9.6 antibody (which recognizes the same epitope as TI 1.1) in combination with the 9-1 antibody (Yang, S. Y. et al. (1986) J. Immunol. 137:1097-1100). Other antibodies which bind to the same epitopes as any of the above described antibodies can also be used.

In some embodiments, the immune cells are activated by administering phorbol myristate acetate (PMA) and ionomycine. In certain embodiments, the host cells are activated by administering an appropriate antigen that induces activation and then expansion. In certain embodiments, PMA, ionomycin, and/or appropriate antigen are administered with CD3 to induce activation and/or expansion.

In general, the activating agents used in the present disclosure includes, but is not limited to, an antibody, a fragment thereof and a proteinaceous binding molecule with antibody-like functions. Examples of (recombinant) antibody fragments are Fab fragments, Fv fragments, single-chain Fv fragments (scFv), a divalent antibody fragment such as an (Fab)2'-fragment, diabodies, triabodies (Iliades, P., et al., FEBS Lett (1997) 409, 437-441), decabodies (Stone, E., et al., Journal of Immunological Methods (2007) 318, 88-94) and other domain antibodies (Holt, L. J., et al., Trends Biotechnol. (2003), 21, 11, 484-490). The divalent antibody fragment may be an (Fab)2'-fragment, or a divalent single-chain Fv fragment while the monovalent antibody fragment may be selected from the group consisting of a Fab fragment, a Fv fragment, and a single-chain Fv fragment (scFv).

In certain embodiments, one or more binding sites of the CD3ζ agents may be a bivalent proteinaceous artificial binding molecule such as a dimeric lipocalin mutein (i.e., duocalin). In certain embodiments the receptor binding reagent may have a single second binding site, (i.e., monovalent). Examples of monovalent agents include, but are not limited to, a monovalent antibody fragment, a proteinaceous binding molecule with antibody-like binding properties or an MHC molecule. Examples of monovalent antibody fragments include, but are not limited to a Fab fragment, a Fv fragment, and a single-chain Fv fragment (scFv), including a divalent single-chain Fv fragment.

The agent that specifically binds CD3 includes, but is not limited to, an anti-CD3-antibody, a divalent antibody fragment of an anti-CD3 antibody, a monovalent antibody fragment of an anti-CD3-antibody, and a proteinaceous CD3-binding molecule with antibody-like binding properties. A proteinaceous CD3-binding molecule with antibody-like binding properties can be an aptamer, a mutein based on a polypeptide of the lipocalin family, a glubody, a protein based on the ankyrin scaffold, a protein based on the crystalline scaffold, an adnectin, and an avimer. It also can be coupled to a bead.

In certain embodiments, the activating agent (e.g., CD3-binding agents) can be present in a concentration of about 0.1 to about 10 µg/ml. In certain embodiments, the activating agent (e.g., CD3-binding agents) can be present in a concentration of about 0.2 µg/ml to about 9 µg/ml, about 0.3 µg/ml to about 8 µg/ml, about 0.4 µg/ml to about 7 µg/ml, about 0.5 µg/ml to about 6 µg/ml, about 0.6 µg/ml to about 5 µg/ml, about 0.7 µg/ml to about 4 µg/ml, about 0.8 µg/ml to about 3 µg/ml, or about 0.9 µg/ml to about 2 µg/ml. In certain embodiments, the activating agent (e.g., CD3-binding agents) is administered at a concentration of about 0.1 µg/ml, about 0.2 µg/ml, about 0.3 µg/ml, about 0.4 µg/ml, about 0.5 µg/ml, about 0.6 µg/ml, about 0.7 µg/ml, about 0.8 µM, about 0.9 µg/ml, about 1 µg/ml, about 2 µg/ml, about 3 µg/ml, about 4 µM, about 5 µg/ml, about 6 µg/ml, about 7 µg/ml, about 8 µg/ml, about 9 µg/ml, or about 10 µg/ml. In certain embodiments, the CD3-binding agents can be present in a concentration of 1 µg/ml.

NK cells can be activated generally using methods as described, for example, in U.S. Pat. Nos. 7,803,376, 6,949,520, 6,693,086, 8,834,900, 9,404,083, 9,464,274, 7,435,596, 8,026,097, 8,877,182; U.S. Patent Applications US2004/0058445, US2007/0160578, US2013/0011376, US2015/0118207, US2015/0037887; and PCT Patent Application WO2016/122147, each of which is incorporated herein by reference in its entirety.

In some embodiments, the NK cells are activated by, for example and not limitation, inhibition of inhibitory receptors on NK cells (e.g., KIR2DL1, KIR2DL2/3, KIR2DL4, KIR2DL5A, KIR2DL5B, KIR3DL1, KIR3DL2, KIR3DL3, LILRB1, NKG2A, NKG2C, NKG2E or LILRB5 receptor).

In certain embodiments, the NK cells are activated by, for example and not limitation, feeder cells (e.g., native K562 cells or K562 cells that are genetically modified to express 4-1BBL and cytokines such as IL15 or IL21).

In other embodiments, interferons or macrophage-derived cytokines can be used to activate NK cells. For example, such interferons include but are not limited to interferon alpha and interferon gamma, and such cytokines include but are not limited to IL-15, IL-2, IL-21.

In certain embodiments, the NK activating agent can be present in a concentration of about 0.1 to about 10 µg/ml. In certain embodiments, the NK activating agent can be present in a concentration of about 0.2 µg/ml to about 9 µg/ml, about 0.3 µg/ml to about 8 µg/ml, about 0.4 µg/ml to about 7 µg/ml, about 0.5 µg/ml to about 6 µg/ml, about 0.6 µg/ml to about 5 µg/ml, about 0.7 µg/ml to about 4 µg/ml, about 0.8 µg/ml to about 3 µg/ml, or about 0.9 µg/ml to about 2 µg/ml. In certain embodiments, the NK activating agent is administered at a concentration of about 0.1 µg/ml, about 0.2 µg/ml, about 0.3 µg/ml, about 0.4 µg/ml, about 0.5 µg/ml, about 0.6 µg/ml, about 0.7 µg/ml, about 0.8 µM, about 0.9 µg/ml, about 1 µg/ml, about 2 µg/ml, about 3 µg/ml, about 4 µM, about 5 µg/ml, about 6 µg/ml, about 7 µg/ml, about 8 µg/ml, about 9 µg/ml, or about 10 µg/ml. In certain embodiments, the NK activating agent can be present in a concentration of 1 µg/ml.

In certain embodiments, the activating agent is attached to a solid support such as, but not limited to, a bead, an absorbent polymer present in culture plate or well or other matrices such as, but not limited to, Sepharose or glass; may be expressed (such as in native or recombinant forms) on cell surface of natural or recombinant cell line by means known to those skilled in the art.

In certain embodiments, the host cells can be genetically modified after stimulation/activation. In certain embodiments, the host cells are modified within 12 hours, 16 hours, 24 hours, 36 hours, or 48 hours of stimulation/activation. In certain embodiments, the cells are modified within 16 to 24 hours after stimulation/activation. In certain embodiments, the host cells are modified within 24 hours. In certain embodiments, the host cells can be genetically modified before stimulation/activation.

In order to genetically modify the host cell to express the arCAR of the present disclosure, the arCAR polynucleotides or recombinant vectors must be transferred into the host cell. Polynucleotide transfer may be conducted via viral or non-viral delivery methods. Suitable methods for polynucleotide delivery for use with the current methods include any method known by those of skill in the art, by which a polynucleotide can be introduced into an organelle, cell, tissue or organism.

In various embodiments, genetic modification is conducted ex vivo. Various methods are available for transfecting cells and tissues removed from a subject via ex vivo modification. For example, retroviral gene transfer in vitro can be used to genetically modified cells removed from the subject and the cell transferred back into the subject. See e.g., Wilson et al., *Science,* 244:1344-1346, 1989 and Nabel et al., *Science,* 244(4910):1342-1344, 1989, both of which are incorporated herein by reference in their entity. In certain embodiments, the host cells may be removed from the subject and transfected ex vivo using the polynucleotides or recombinant vectors of the disclosure. In certain embodiments, the host cells obtained from the subject can be transfected or transduced with the polynucleotides or recombinant vectors of the disclosure and then administered back to the subject.

In some embodiments, the host cells can be transduced via retroviral transduction. References describing retroviral transduction of genes are Anderson et al., U.S. Pat. No. 5,399,346; Mann et al., Cell 33:153 (1983); Temin et al., U.S. Pat. No. 4,650,764; Temin et al., U.S. Pat. No. 4,980,289; Markowitz et al., J. Virol. 62:1120 (1988); Temin et al., U.S. Pat. No. 5,124,263; International Patent Publication No. WO 95/07358; and Kuo et al., Blood 82:845 (1993), each of which is incorporated herein by reference in its entirety.

Another suitable method of gene transfer includes injection. In certain embodiments, a polynucleotide or recombinant vector may be delivered to a cell, tissue, or organism via one or more injections (e.g., a needle injection). Non-limiting methods of injection include injection of a composition (e.g., a saline based composition). Polynucleotides or recombinant vectors can also be introduced by direct microinjection. Non-limiting sites of injection include, subcutaneous, intradermal, intramuscular, intranodal (allows for direct delivery of antigen to lymphoid tissues). intravenous, intraprotatic, intratumor, intralymphatic (allows direct administration of DCs) and intraperitoneal. It is understood that proper site of injection preparation is necessary (e.g., shaving of the site of injection to observe proper needle placement).

Electroporation is another suitable method of gene transfer. See e.g., Potter et al., (1984) *Proc. Nat'l Acad. Sci. USA,* 81, 7161-7165 and Tur-Kaspa et al., (1986) *Mol. Cell Biol.,* 6, 716-718, both of which are incorporated herein in their entirety for all purposes. Electroporation involves the exposure of a suspension of cells and DNA to a high-voltage electric discharge. In certain embodiments, cell wall-degrading enzymes, such as pectin-degrading enzymes, can be employed to render the host cells more susceptible to genetic modification by electroporation than untreated cells. See e.g., U.S. Pat. No. 5,384,253, incorporated herein by reference in its entirety for all purposes.

Methods of electroporation for use with this disclosure include, for example, Sardesai, N. Y., and Weiner, D. B., *Current Opinion in Immunotherapy* 23:421-9 (2011) and Ferraro, B. et al., *Human Vaccines* 7:120-127 (2011), both of which are hereby incorporated by reference herein in their entirety for all purposes.

Nucleic acid vaccines can be used to transfer arCAR polynucleotides or vectors into the host cells. Such vaccines include, but are not limited to non-viral vectors, "naked" DNA and RNA, and viral vectors. Methods of genetically modifying cells with these vaccines, and for optimizing the expression of genes included in these vaccines are known to those of skill in the art.

Additional methods of gene transfer include liposome-mediated transfection (e.g., polynucleotide entrapped in a lipid complex suspended in an excess of aqueous solution. See e.g., Ghosh and Bachhawat, (1991) In: *Liver Diseases, Targeted Diagnosis and Therapy Using Specific Receptors and Ligands.* pp. 87-104). Also contemplated is a polynucleotide complexed with Lipofectamine, or Superfect); DEAE-dextran (e.g., a polynucleotide is delivered into a cell using DEAE-dextran followed by polyethylene glycol. See e.g., Gopal, T. V., *Mol Cell Biol.* 1985 May; 5(5):1188-90); calcium phosphate (e.g., polynucleotide is introduced to the cells using calcium phosphate precipitation. See e.g., Graham and van der Eb, (1973) *Virology,* 52, 456-467; Chen and Okayama, *Mol. Cell Biol.,* 7(8):2745-2752, 1987), and Rippe et al., *Mol. Cell Biol.,* 10:689-695, 1990); sonication loading (introduction of a polynucleotide by direct sonic loading. See e.g., Fechheimer et al., (1987) *Proc. Nat'l Acad. Sci. USA,* 84, 8463-8467); microprojectile bombardment (e.g., one or more particles may be coated with at least one polynucleotide and delivered into cells by a propelling force. See e.g., U.S. Pat. Nos. 5,550,318; 5,538,880; 5,610,042; and PCT Application WO 94/09699; Klein et al., (1987) *Nature,* 327, 70-73, Yang et al., (1990) *Proc. Nat'l Acad. Sci. USA,* 87, 9568-9572); and receptor-mediated transfection (e.g., selective uptake of macromolecules by receptor-mediated endocytosis that will be occurring in a target cell using cell type-specific distribution of various receptors. See e.g., Wu and Wu, (1987) *J. Biol. Chem.,* 262, 4429-4432; Wagner et al., *Proc. Natl. Acad. Sci. USA,* 87(9):3410-3414, 1990; Perales et al., *Proc. Natl. Acad. Sci. USA,* 91:4086-4090, 1994; Myers, EPO 0273085; Wu and Wu, *Adv. Drug Delivery Rev.,* 12:159-167, 1993; Nicolau et al., (1987) *Methods Enzymol.,* 149, 157-176), each reference cited here is incorporated by reference in their entirety for all purposes.

In further embodiments, host cells are genetically modified using gene editing with homology-directed repair (HDR). Homology-directed repair (HDR) is a mechanism used by cells to repair double strand DNA breaks. In HDR, a donor polynucleotide with homology to the site of the double strand DNA break is used as a template to repair the cleaved DNA sequence, resulting in the transfer of genetic information from the donor polynucleotide to the DNA. As such, new nucleic acid material may be inserted or copied into a target DNA cleavage site. Double strand DNA breaks in host cells may be induced by a site-specific nuclease. The term "site-specific nuclease" as used herein refers to a nuclease capable of specifically recognizing and cleaving a nucleic acid (DNA or RNA) sequence. Suitable site-specific nucleases for use in the present disclosure include, but are not limited to, RNA-guided endonucleases (e.g., CRISPR-associated (Cas) proteins), zinc finger nucleases, TALEN nucleases, or mega-TALEN nucleases. For example, a site-specific nuclease (e.g., a Cas9+guide RNA) capable of inducing a double strand break in a target DNA sequence can be introduced to a host cell, along with a donor polynucleotide encoding a polypeptide of an arCAR of the present disclosure.

After the host cells are activated and transduced, the cells are cultured to proliferate.

T cells may be cultured for at least 1, 2, 3, 4, 5, 6, or 7 days, at least 2 weeks, at least 1, 2, 3, 4, 5, or 6 months or more with 1, 2, 3, 4, 5, 6, 7, 8, 9, or 10 or more rounds of expansion.

Agents that can be used for the expansion of T cells can include interleukins, such as IL-2, IL-7, IL-15, or IL-21 (see for example Cornish et al. 2006, Blood. 108(2):600-8, Bazdar and Sieg, 2007, Journal of Virology, 2007, 81(22): 12670-12674, Battalia et al, 2013, Immunology, 139(1):109-120). Other illustrative examples for agents that may be used for the expansion of T cells are agents that bind to CD8, CD45 or CD90, such as αCD8, αCD45 or αCD90 antibodies. Illustrative examples of T-cell population including antigen-specific T cells, T helper cells, cytotoxic T cells, memory T-cell (an illustrative example of memory T cells are CD62L|CD8| specific central memory T cells) or regulatory T cells (an illustrative example of Treg are CD4+CD25+CD45RA+ Treg cells).

Additional agents that can be used to expand T cells includes methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; and 6,867,041, each of which is incorporated herein by reference in its entirety.

In certain embodiments, the agent(s) used for expansion (e.g., IL-2) are administered at about 20 units/ml to about 200 units/ml. In certain embodiments, the agent(s) used for expansion (e.g., IL-2) are administered at about 25 units/ml to about 190 units/ml, about 30 units/ml to about 180 units/ml, about 35 units/ml to about 170 units/ml, about 40 units/ml to about 160 units/ml, about 45 units/ml to about 150 units/ml, about 50 units/ml to about 140 units/ml, about 55 units/ml to about 130 units/ml, about 60 units/ml to about 120 units/ml, about 65 units/ml to about 110 units/ml, about 70 units/ml to about 100 units/ml, about 75 units/ml to about 95 units/ml, or about 80 units/ml to about 90 units/ml. In certain embodiments, the agent(s) used for expansion (e.g., IL-2) are administered at about 20 units/ml, about 25 units/ml, about 30 units/ml, 35 units/ml, 40 units/ml, 45 units/ml, about 50 units/ml, about 55 units/ml, about 60 units/ml, about 65 units/ml, about 70 units/ml, about 75 units/ml, about 80 units/ml, about 85 units/ml, about 90 units/ml, about 95 units/ml, about 100 units/ml, about 105 units/ml, about 110 units/ml, about 115 units/ml, about 120 units/ml, about 125 units/ml, about 130 units/ml, about 135 units/ml, about 140 units/ml, about 145 units/ml, about 150 units/ml, about 155 units/ml, about 160 units/ml, about 165 units/ml, about 170 units/ml, about 175 units/ml, about 180 units/ml, about 185 units/ml, about 190 units/ml, about 195 units/ml, or about 200 units/ml. In certain embodiments, the agent(s) used for expansion (e.g., IL-2) are administered at about 5 mg/ml to about 10 ng/ml. In certain embodiments, the agent(s) used for expansion (e.g., IL-2) are administered at about 5.5 ng/ml to about 9.5 ng/ml, about 6 ng/ml to about 9 ng/ml, about 6.5 ng/ml to about 8.5 ng/ml, or about 7 ng/ml to about 8 ng/ml. In certain embodiments, the agent(s) used for expansion (e.g., IL-2) are administered at about 5 ng/ml, 6 ng/ml, 7 ng/ml, 8 ng/ml, 9, ng/ml, or 10 ng/ml.

NK cells may be cultured for at least 1, 2, 3, 4, 5, 6, or 7 days, at least 2 weeks, at least 1, 2, 3, 4, 5, or 6 months or more with 1, 2, 3, 4, 5, 6, 7, 8, 9, or 10 or more rounds of expansion.

Agents that can be used for the expansion of NK cells can include agents that bind to CD16 or CD56, such as for example aCD16 or aCD56 antibodies. In certain embodiments, the binding agent includes antibodies (see for example Hoshino et al, Blood. 1991 Dec. 15; 78(12):3232-40). Other agents that may be used for expansion of NK cells may be IL-15 (see for example Vitale et al. 2002. The Anatomical Record. 266:87-92, which is hereby incorporated by reference in its entirety for all purposes).

Conditions appropriate for T-cell culture include an appropriate media (e.g., Minimal Essential Media (MEM), RPMI Media 1640, Lonza RPMI 1640, Advanced RPMI, Clicks, AIM-V, DMEM, a-MEM, F-12, TexMACS, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion).

Examples of other additives for host cell expansion include, but are not limited to, surfactant, piasmanate, pH buffers such as HEPES, and reducing agents such as N-acetyl-cysteine and 2-mercaptoethanol, Antibiotics (e.g., penicillin and streptomycin), are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$).

In certain embodiments where PSCs (e.g., iPSCs or ESCs) are used as the starting cell population, the method may further comprise differentiating the PSCs into an immune cell such as a T cell. Applicable differentiation methods and compositions for obtaining iPSC derived hematopoietic cell lineages include those described in the art, for example, in International Patent Publication No. WO2017078807 and WO2019112899, the disclosure of which is incorporated herein by reference. The iPSC derived hematopoietic lineage cells may include, but not limited to, definitive hemogenic endothelium, hematopoietic multipotent progenitor cells, hematopoietic stem and progenitor cells, T cell progenitors, NK cell progenitors, T cells, NK cells, NKT cells, B cells, macrophages, and neutrophils.

In some embodiments, the present disclosure also provides methods to purify a polypeptide of an arCAR of the present disclosure. In some embodiments, the method involves purifying the second polypeptide of an arCAR from a host cell modified to express the second polypeptide of the arCAR. In some embodiments, the second polypeptide of an arCAR is a soluble protein.

Pharmaceutical Compositions

In one aspect, the compositions comprise one or more polypeptides of the arCARs described herein, polynucleotides, vectors comprising same, and cell compositions, as disclosed herein. In some embodiments, compositions of the present disclosure include, but are not limited to pharmaceutical compositions.

In one aspect, the present disclosure provides a pharmaceutical composition comprising a polypeptide of an arCAR described herein, and a pharmaceutically accepted carrier and/or excipient. In some embodiments, the pharmaceutical composition comprises the second polypeptide of an arCAR described herein, and a pharmaceutically accepted carrier and/or excipient. In some embodiments, the pharmaceutical composition comprises the second polypeptides of two or more arCARs described herein, and a pharmaceutically accepted carrier and/or excipient.

In another aspect, the present disclosure provides a pharmaceutical composition comprising a polynucleotide or a recombinant vector described herein, and a pharmaceutically accepted carrier and/or excipient. In some embodiments, the pharmaceutical composition comprises a polynucleotide encoding the second polypeptide of an arCAR described herein, and a pharmaceutically accepted carrier and/or excipient. In some embodiments, the pharmaceutical composition comprises a polynucleotide encoding the second polypeptides of two or more arCARs described herein, and a pharmaceutically accepted carrier and/or excipient. In some embodiments, the pharmaceutical composition comprises two or more polynucleotides each encoding the second polypeptides of an arCARs described herein, and a pharmaceutically accepted carrier and/or excipient. In some embodiments, the pharmaceutical composition comprises a recombinant vector comprising a polynucleotide encoding the second polypeptide of an arCAR described herein, and a pharmaceutically accepted carrier and/or excipient. In some embodiments, the pharmaceutical composition comprises a recombinant vector comprising a polynucleotide encoding the second polypeptides of two or more arCARs described herein, and a pharmaceutically accepted carrier and/or excipient. In various embodiments, the two or more arCARs each comprise a unique pair of tag and tag-binding domain.

In another aspect, the present disclosure provides pharmaceutical composition comprising the modified host cells described herein and a pharmaceutically acceptable carrier and/or excipient.

Examples of pharmaceutical carriers include but are not limited to sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions.

Compositions comprising modified host cells disclosed herein may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives.

Compositions comprising modified host cells disclosed herein may comprise one or more of the following: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose.

In some embodiments, the compositions are formulated for parenteral administration, e.g., intravascular (intravenous or intraarterial), intraperitoneal, intratumoral, intraventricular, intrapleural or intramuscular administration. The parenteral preparation can be enclosed in ampoules, disposable syringes or multiple dose vials made of glass or plastic. An injectable pharmaceutical composition is preferably sterile. In some embodiments, the composition is reconstituted from a lyophilized preparation prior to administration.

In some embodiments, the modified host cells may be mixed with substances that adhere or penetrate then prior to their administration, e.g., but not limited to, nanoparticles.

Treatment Methods

In some aspects, provided herein are methods of using the arCARs of the present disclosure for treatment of a disease.

In one aspect, provided herein is a method of treating a disease in a subject in need thereof, comprising administering to the subject a therapeutically effective amount of
  (i) an immune effector cell comprising a chimeric antigen receptor comprising the first polypeptide of an arCAR described herein, and
  (ii) the second polypeptide of said arCAR, or a polynucleotide encoding said second polypeptide, or a host cell comprising said second polypeptide.

In some embodiments, the method further comprises administering one or more additional polypeptides each comprising (a) an antigen-binding domain that binds to a unique antigen and (b) a tag that is recognized by the tag-binding domain of the first polypeptide.

In another aspect, provided herein is a method of treating a disease in a subject in need thereof, comprising administering to the subject a therapeutically effective amount of
  (i) an immune effector cell comprising chimeric antigen receptors comprising the first polypeptides of two or more arCARs, wherein the two or more arCARs are selected from the arCAR system described herein, and
  (ii) the second polypeptides of said two or more arCARs, or one or more polynucleotide encoding said second polypeptides, or one or more host cells comprising said second polypeptides.

In various embodiments of the treatment methods described herein, the cell is an immune effector cell. In some embodiments, the cell is a T cell, a Natural Killer (NK) cell, a cytotoxic T lymphocyte (CTL), a regulatory T cell or a tumor-infiltrating lymphocyte (TIL). In some embodiments, the cell is a T cell. In some embodiments, the cell is derived from an iPSC. In various embodiments, the cell constitutively expresses the first polypeptide.

In various embodiments of the treatment methods described herein, the host cell and/or the polypeptide(s) are administered as a pharmaceutical composition which also comprises a pharmaceutically accepted carrier and/or excipient as described herein.

In various embodiments of the treatment methods described herein, the disease is a cancer. The terms "cancer", "malignancy", "neoplasm", "tumor", and "carcinoma", are used interchangeably herein to refer to cells that exhibit relatively abnormal, uncontrolled, and/or autonomous growth, so that they exhibit an aberrant growth phenotype characterized by a significant loss of control of cell proliferation. In general, cells of interest for treatment in the present application include precancerous (e.g., benign), malignant, pre-metastatic, metastatic, and non-metastatic cells. The teachings of the present disclosure may be relevant to any and all cancers. To give but a few, non-limiting examples, in some embodiments, teachings of the present disclosure are applied to one or more cancers such as, for example, hematopoietic cancers including leukemias, lymphomas (Hodgkin's and non-Hodgkin's), myelomas and myeloproliferative disorders; sarcomas, melanomas, adenomas, carcinomas of solid tissue, squamous cell carcinomas of the mouth, throat, larynx, and lung, liver cancer, genitourinary cancers such as prostate, cervical, bladder, uterine, and endometrial cancer and renal cell carcinomas, bone cancer, pancreatic cancer, skin cancer, cutaneous or intraocular melanoma, cancer of the endocrine system, cancer of the thyroid gland, cancer of the parathyroid gland, head and neck cancers, breast cancer, gastro-intestinal cancers and nervous system cancers, benign lesions such as papillomas, and the like. In some embodiments, the cancer treated by methods of the present disclosure is a solid tumor. In some embodiments, the cancer treated by methods of the present disclosure is a hematologic malignancy.

In some embodiments, the cancer treated by methods of the present disclosure is a glioblastoma, ovarian cancer, cervical cancer, head and neck cancer, liver cancer, prostate cancer, pancreatic cancer, renal cell carcinoma, bladder cancer, or hematologic malignancy. In some embodiment, the hematologic malignancy is a leukemia (e.g., acute lymphocytic (ALL), chronic lymphocytic (CLL), acute myeloid (AML), chronic myeloid (CML)), myeloma, or lymphoma (e.g., Hodgkin's or non-Hodgkin's (NHL)).

In various embodiments of the treatment methods described herein, the disease is autoimmune disease or disorder. In some embodiments, the autoimmune disease or disorder is Rheumatoid arthritis (RA), multiple sclerosis (MS), Sjögren's syndrome, Systemic lupus erythematosus, sarcoidosis, Type 1 diabetes mellitus, insulin dependent diabetes mellitus (IDDM), autoimmune thyroiditis, reactive arthritis, ankylosing spondylitis, scleroderma, polymyositis, dermatomyositis, psoriasis, vasculitis, Wegener's granulomatosis, Myasthenia gravis, Hashimoto's thyroiditis, Graves' disease, chronic inflammatory demyelinating polyneuropathy, Guillain-Barre syndrome, Crohn's disease or ulcerative colitis.

When more than one polypeptides with unique antigen-binding specificities are administered, the methods can be used to target multiple antigens (or multiple epitopes in the same antigen) in the same disease (e.g., tumor or autoimmune disease), or multiple antigens in different diseases (e.g., tumor or autoimmune disease).

In some embodiments, the modified immune effector cell and the second polypeptide(s), or polynucleotide(s) encoding said second polypeptide(s), or host cell(s) comprising said second polypeptide(s), are administered simultaneously.

In some embodiments, the modified immune effector cell and the second polypeptide(s), or polynucleotide(s) encoding said second polypeptide(s), or host cell(s) comprising said second polypeptide(s), are administered sequentially. For example, the second polypeptide(s), or polynucleotide(s) encoding said second polypeptide(s), or host cell(s) comprising said second polypeptide(s), may be administered before or after the administration of the modified host cell.

In some embodiments, the immune effector cell is an autologous cell with respect to the subject receiving the treatment. In some embodiments, the immune effector cell is an allogeneic cell with respect to the subject receiving the treatment. When the immune effector cell is isolated from a donor, the method may further include a method to prevent graft vs host disease (GVHD) and the host cell rejection.

In some embodiments, additional steps can be performed prior to administration to a subject. For instance, an immune effector cell can be expanded in vitro after contacting (e.g., transducing or transfecting) the immune effector cell with a polynucleotide or recombinant vector described herein (e.g., a polynucleotide or recombinant vector encoding a first polypeptide of an arCAR), but prior to the administration to a subject. In vitro expansion can be carried out for 1 day or more, e.g., 2 days or more, 3 days or more, 4 days or more, 6 days or more, or 8 days or more, prior to the administration to a subject. Alternatively, or in addition, in vitro expansion can proceed for 21 days or less, e.g., 18 days or less, 16 days or less, 14 days or less, 10 days or less, 7 days or less, or 5 days or less, prior to administration to a subject. For example, in vitro expansion can be carried out for 1-7 days, 2-10 days, 3-5 days, or 8-14 days prior to the administration to a subject.

In some embodiments, during in vitro expansion, an immune effector host cell can be stimulated with an antigen (e.g., a TCR antigen). Antigen specific expansion optionally can be supplemented with expansion under conditions that non-specifically stimulate lymphocyte proliferation such as, for example, anti-CD3 antibody, anti-Tac antibody, anti-CD28 antibody, or phytohemagglutinin (PHA). The expanded host cells can be directly administered into a subject or can be frozen for future use, i.e., for subsequent administrations to a subject.

In some embodiments, an immune effector host cell is treated ex vivo with interleukin-2 (IL-2) prior to infusion into a subject, and/or the subject is treated with IL-2 after infusion. Furthermore, in some embodiments, a patient can undergo preparative lymphodepletion—the temporary ablation of the immune system—prior to administration of a modified host cell. A combination of IL-2 treatment and preparative lymphodepletion can enhance persistence of modified host cell.

In some embodiments, an immune effector host cell is transduced or transfected with a nucleic acid encoding a cytokine, which nucleic acid can be engineered to provide for constitutive, regulatable, or temporally-controlled expression of the cytokine. Suitable cytokines include, for example, cytokines which act to enhance the survival of T lymphocytes during the contraction phase, which can facilitate the formation and survival of memory T lymphocytes.

In some embodiments, a composition of the present disclosure (e.g., host cell or polypeptide) is administered in a therapeutically effective amount. The dosages of the composition administered in the methods of the disclosure will vary widely, depending upon the subject's physical parameters, the frequency of administration, the manner of administration, the clearance rate, and the like. The initial dose may be larger, and might be followed by smaller maintenance doses. The dose may be administered as infrequently as weekly or biweekly, or fractionated into smaller doses and administered daily, semi-weekly, etc., to maintain an effective dosage level. It is contemplated that a variety of doses will be effective to achieve in vivo persistence of modified host cells. It is also contemplated that a variety of doses will be effective to improve in vivo effector function of modified host cells.

In some embodiments, a composition comprising the modified host cells prepared by the methods described herein may be administered at a dosage of $10^2$ to $10^{10}$ cells/kg body weight, $10^5$ to $10^9$ cells/kg body weight, $10^5$ to $10^8$ cells/kg body weight, $10^5$ to $10^7$ cells/kg body weight, $10^7$ to $10^9$ cells/kg body weight, or $10^7$ to $10^8$ cells/kg body weight, including all integer values within those ranges. The number of modified host cells will depend on the therapeutic use for which the composition is intended for.

Modified host cells may be administered multiple times at dosages listed above. The modified host cells may be allogeneic, syngeneic, xenogeneic, or autologous to the patient undergoing therapy.

It is also contemplated that when used to treat various diseases/disorders, the compositions and methods of the present disclosure can be utilized with other therapeutic methods/agents suitable for the same or similar diseases/disorders. Such other therapeutic methods/agents can be co-administered (simultaneously or sequentially) to generate additive or synergistic effects. Suitable therapeutically effective dosages for each agent may be lowered due to the additive action or synergy.

In certain embodiments, a composition of the present disclosure (e.g., host cell or polypeptide) is administered prior to, substantially simultaneously with, or after the administration of an additional therapeutic agent such as a cancer therapeutic agent. The additional cancer therapeutic agent can be, e.g., a chemotherapeutic agent, a biological agent, surgery, gene therapy or radiation treatment. In some embodiments, a subject receiving a composition is not administered a treatment which is sufficient to cause a depletion of immune cells, such as lymphodepleting chemotherapy or radiation therapy.

In some embodiments of any of the above therapeutic methods, the method further comprises administering to the subject one or more additional compounds selected from the group consisting of immuno-suppressives, biologicals, probiotics, prebiotics, and cytokines (e.g., IFN or IL-2).

In some embodiments, the methods and compositions of the disclosure can be combined with other therapies that block inflammation (e.g., via blockage of ILL INFα/β, IL6, TNF, IL23, etc.).

The methods and compositions of the disclosure can be combined with other immunomodulatory treatments such as, e.g., therapeutic vaccines (including but not limited to GVAX, DC-based vaccines, etc.), checkpoint inhibitors (including but not limited to agents that block CTLA4, PD1, LAG3, TIM3, etc.) or activators (including but not limited to agents that enhance 4-1BB, OX40, etc.). The methods of the disclosure can be also combined with other treatments that possess the ability to modulate NKT function or stability, including but not limited to CD1d, CD1d-fusion proteins, CD1d dimers or larger polymers of CD1d either unloaded or loaded with antigens, CD1d-chimeric antigen receptors (CD1d-CAR), or any other of the five known CD1 isomers existing in humans (CD1a, CD1b, CD1c, CD1e). The methods of the disclosure can also be combined with other treatments such as midostaurin, enasidenib, or a combination thereof.

Therapeutic methods of the disclosure can also be combined with additional immunotherapies and therapies. For example, when used for treating tumors, the compositions of the disclosure can be used in combination with conventional therapies, such as, e.g., surgery, radiotherapy, chemotherapy or combinations thereof, depending on type of the tumor, patient condition, other health issues, and a variety of factors. In certain aspects, other therapeutic agents useful for combination tumor therapy with the inhibitors of the disclosure include anti-angiogenic agents. Many anti-angiogenic agents have been identified and are known in the art, including, e.g., TNP-470, platelet factor 4, thrombospondin-1, tissue inhibitors of metalloproteases (TIMP1 and TIMP2), prolactin (16-Kd fragment), angiostatin (38-Kd fragment of plasminogen), endostatin, bFGF soluble receptor, transforming growth factor beta, interferon alpha, soluble KDR and FLT-1 receptors, placental proliferin-related protein, as well as those listed by Carmeliet and Jain (2000). In one embodiment, the modified host cells of the disclosure can be used in combination with a VEGF antagonist or a VEGF receptor antagonist such as anti-VEGF antibodies, VEGF variants, soluble VEGF receptor fragments, aptamers capable of blocking VEGF or VEGFR, neutralizing anti-VEGFR antibodies, inhibitors of VEGFR tyrosine kinases and any combinations thereof (e.g., anti-hVEGF antibody A4.6.1, bevacizumab or ranibizumab).

Non-limiting examples of chemotherapeutic compounds which can be used in combination treatments of the present disclosure include, for example, aminoglutethimide, amsacrine, anastrozole, asparaginase, azacitidine, bcg, bicalutamide, bleomycin, buserelin, busulfan, campothecin, capecitabine, carboplatin, carmustine, chlorambucil, cisplatin, cladribine, clodronate, colchicine, cyclophosphamide, cyproterone, cytarabine, dacarbazine, dactinomycin, daunorubicin, decitabine, dienestrol, diethylstilbestrol, docetaxel, doxorubicin, epirubicin, estradiol, estramnustine, etoposide, exemestane, filgrastim, fludarabine, fludrocortisone, fluorouracil, fluoxymesterone, flutamide, gemcitabine, genistein, goserelin, hydroxyurea, idarubicin, ifosfamide, imatinib, interferon, irinotecan, ironotecan, letrozole, leucovorin, leuprolide, levamisole, lomustine, mechlorethamine, medroxyprogesterone, megestrol, melphalan, mercaptopurine, mesna, methotrexate, mitomycin, mitotane, mitoxantrone, nilutamide, nocodazole, octreotide, oxaliplatin, paclitaxel, pamidronate, pentostatin, plicamycin, porfimer, procarbazine, raltitrexed, rituximab, streptozocin, suramin, tamoxifen, temozolomide, teniposide, testosterone, thioguanine, thiotepa, titanocene dichloride, topotecan, trastuzumab, tretinoin, vinblastine, vincristine, vindesine, and vinorelbine.

These chemotherapeutic compounds may be categorized by their mechanism of action into, for example, following groups: anti-metabolites/anti-tumor agents, such as pyrimidine analogs (5-fluorouracil, floxuridine, capecitabine, gemcitabine and cytarabine) and purine analogs, folate antagonists and related inhibitors (mercaptopurine, thioguanine, pentostatin and 2-chlorodeoxyadenosine (cladribine)); antiproliferative/antimitotic agents including natural products such as vinca alkaloids (vinblastine, vincristine, and vinorelbine), microtubule disruptors such as taxane (paclitaxel, docetaxel), vincristin, vinblastin, nocodazole, epothilones and navelbine, epidipodophyllotoxins (etoposide, teniposide), DNA damaging agents (actinomycin, amsacrine, anthracyclines, bleomycin, busulfan, camptothecin, carboplatin, chlorambucil, cisplatin, cyclophosphamide, cytoxan, dactinomycin, daunorubicin, doxorubicin, epirubicin, hexamethyhnelamineoxaliplatin, iphosphamide, melphalan, merchlorehtamine, mitomycin, mitoxantrone, nitrosourea, plicamycin, procarbazine, taxol, taxotere, teniposide, triethylenethiophosphoramide and etoposide (VP16)); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes-dacarbazinine (DTIC); antiproliferative/antimitotic antimetabolites such as folic acid analogs (methotrexate); platinum coordination complexes (cisplatin, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory agents; antisecretory agents (breveldin); immunosuppressives (cyclosporine, tacrolimus (FK-506), sirolimus (rapamycin), azathioprine, mycophenolate mofetil); anti-angiogenic compounds (e.g., TNP-470, genistein, bevacizumab) and growth factor inhibitors (e.g., fibroblast growth factor (FGF) inhibitors); angiotensin receptor blocker; nitric oxide donors; anti-sense oligonucleotides; antibodies (trastuzumab); cell cycle inhibitors and differentiation inducers (tretinoin); mTOR inhibitors, topoisomerase inhibitors (doxorubicin (adriamycin), amsacrine, camptothecin, daunorubicin, dactinomycin, eniposide, epirubicin, etoposide, idarubicin and mitoxantrone, topotecan, irinotecan), corticosteroids (cortisone, dexamethasone, hydrocortisone, methylpednisolone, prednisone, and prenisolone); growth factor signal transduction kinase inhibitors; mitochondrial dysfunction inducers and caspase activators; and chromatin disruptors.

In various embodiments of the methods described herein, the subject is a mammal. In some embodiments, the subject is a human. The subject may be a juvenile or an adult, of any age or sex.

EXAMPLES

The following examples are provided to further describe some of the embodiments disclosed herein. The examples are intended to illustrate the disclosed embodiments. It should be understood, however, that the application is not limited to the exemplary embodiments illustrated below.

Example 1. Developing arCARs with Novel VHH Tags

Novel VHHs having specificity to a non-human protein are identified using a phage display technique or by immunization. Candidate VHHs are selected for production and quality control analysis. Candidate VHHs are further tested for specificity and cross-reactivity. Lead VHHs are used for producing anti-VHHs.

Anti-VHHs having specificity to the lead tag VHHs are identified using a phage display technique or generated by immunization in llamas or other camelids. Several commercially available phage campaigns may be employed including Tungsten, VHH and SuperHuman, and scFv. Candidate anti-VHHs are selected that bind to CDRs or other non-framework region of the tag VHHs.

Soluble tagged VHHs are expressed and produced in CHO cells. Soluble tagged VHHs are purified via Protein A chromatography. The anti-VHHs are incorporated as an extracellular tag-binding domain in a CAR construct. T cells are transduced with the lentiviral construct to express the CAR containing the anti-VHH domain. The anti-VHH is also tested for specificity and cross-reactivity.

In vitro assays are established to evaluate T cell activation through soluble, tagged VHH and anti-tag CAR by assessing cytokine production and cytotoxicity, respectively. Lead arCAR constructs are selected for further analysis.

Example 2. Developing arCARs with Pre-Existing VHH Tags

Pre-existing VHHs that bind non-human proteins are selected. Non-limiting examples of VHHs that can be used in constructing the arCARs of the present disclosure include VHHs that target RSV F-protein, *Listeria* Internalin, Cobra Phospholipase A2, Ebola, nucleoprotein, HSV Glycoprotein D, Lacotococcal phage RBP, *Geobacillus stearothermophilus*, Ricin (e.g., V5E4), and chicken egg white lysozyme. The VHHs may also be engineered to eliminate binding by scrambling CDRs. Candidate VHHs are selected for production and quality control analysis. Selected VHHs are used for producing anti-VHHs.

Anti-VHHs having specificity to the lead tag VHHs are identified using phage display technique or by immunization in Llama. Several commercially available phage campaigns may be employed including Tungsten, VHH and SuperHuman, and scFv. Candidate anti-VHHs are selected that bind to CDRs or other non-framework region of the tag VHHs.

Soluble tagged VHHs are expressed and produced in CHO cells. Soluble tagged VHHs are purified via Protein A chromatography. The anti-VHHs are incorporated as an extracellular tag-binding domain in a lentiviral CAR construct. T cells are transduced with the lentiviral construct to express the CAR containing the anti-VHH domain. The anti-VHH is also tested for specificity and cross-reactivity.

In vitro assays are established to evaluate T cell activation through soluble, tagged VHH and anti-tag CAR by assessing cytokine production and cytotoxicity, respectively. Lead arCAR constructs are selected for further analysis.

Example 3. arCARs with BCMA/Anti-BCMA VHH

To test the arCAR concept, several approaches are used as listed below.

Figures 3A, 3B:
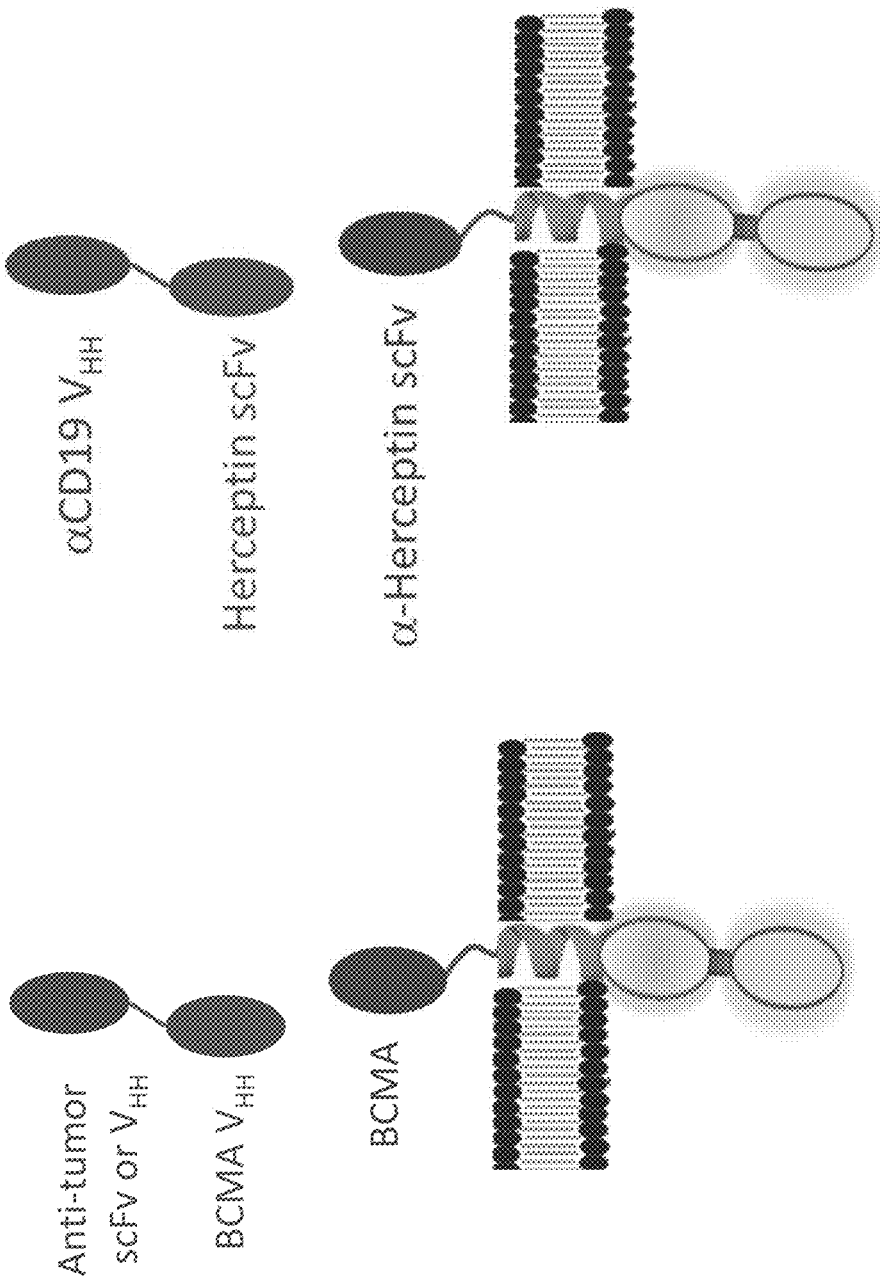
FIG. 3A depicts a schematic representation of another exemplary arCAR of the present disclosure.
FIG. 3B depicts a schematic representation of another exemplary arCAR of the present disclosure.

To test the initial concept of the protein: protein interaction in the arCAR platform, an anti-BCMA antibody is fused to a tumor targeting domain antibody. BCMA is fused to the transmembrane domain of the CAR. The exemplary arCAR incorporating the BCMA/anti-BCMA antibody is shown in FIG. 3A.

In another set of experiments, an scFv is developed which is derived from the Herceptin mAb sequence. The sequence identified for an anti-Herceptin idiotype mAb is converted to an scFv format. These known sequences are engineered into the arCAR platform to demonstrate the concept. Herceptin scFv is fused to the CAR and the Herceptin anti-ID scFv is fused to a soluble tumor targeting domain antibody (e.g., anti-CD19 scFv or VHH). The exemplary arCAR incorporating the Herceptin/Herceptin scFvs is shown in FIG. 3B. This arCAR is tested for cytotoxicity potential in vitro.

Several antibodies with specificity for non-human proteins have been identified in the literature. Such examples include H6dyx, hP3-3, hAnti-Z, hHSV GD, hLP RBP, hVHH4, hSbsB, and hV5E4. These are constructed in an scFv or VHH format for characterization. Candidates are selected based on biophysical properties. An anti-ID cam-

Example 4. arCARs with Herceptin/Anti-Herceptin scFvs

Figure 4A:
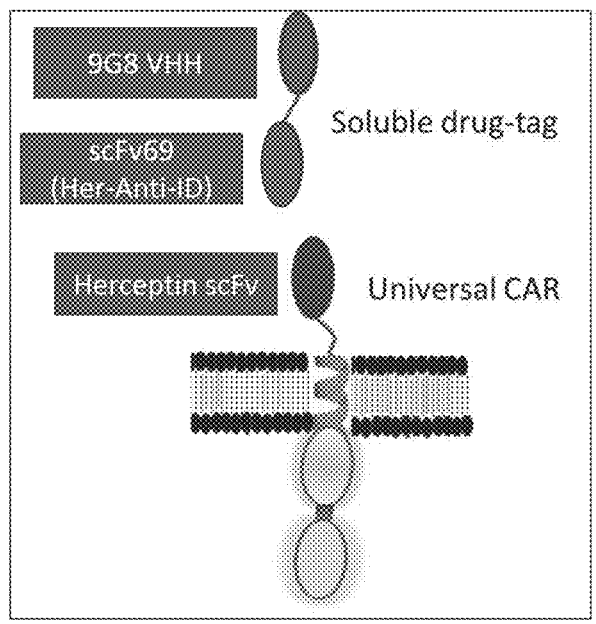
FIG. 4A depicts a schematic representation of another exemplary arCAR of the present disclosure. Herceptin scFv is fused to the CAR and a Herceptin anti-ID scFv is fused to an EGFR-targeting VHH (9G8).
Figure 4B:
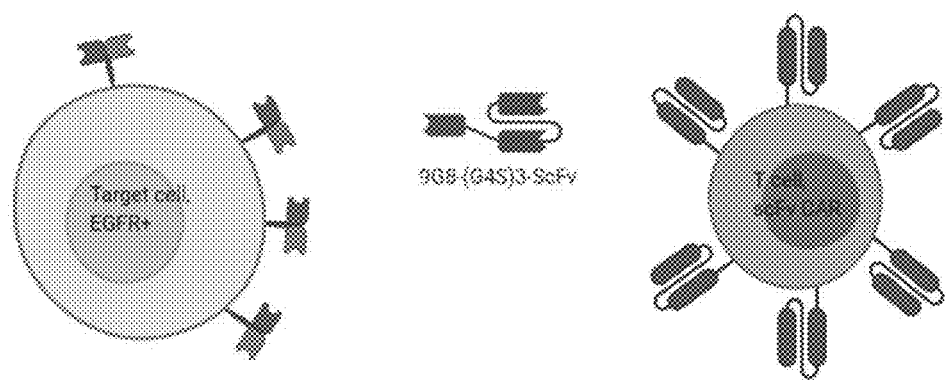
FIG. 4B shows that a T cell expressing the Herceptin scFv CAR, coupled with the 9G8-scFv69 fusion protein, is capable of targeting an EGFR+ cell.

In a Proof-of-Concept study, an scFv was developed which is derived from Herceptin (Trastuzumab) mAb. Another scFv (scFv69) was developed from an anti-Herceptin idiotype mAb. These sequences were assembled into different CAR expression constructs (Table 5), each of which was then packaged into a lentiviral vector and expressed via viral transduction in either Jurkat cells or primary T-cells. CAR expression was detected by flow cytometry and binding to EGFR soluble protein. The CAR expressing cells were used in combination with CHO-cells over-expressing EGFR or cell lines that have native cell surface expression of EGFR to demonstrate EGFR-specific cytotoxicity. FIG. 4A shows an exemplary arCAR where Herceptin scFv is fused to the CAR and the Herceptin anti-ID scFv is fused to an EGFR-targeting VHH (9G8). FIG. 4B shows that a T cell expressing the Herceptin scFv CAR, coupled with the 9G8-scFv69 fusion protein, is capable of targeting an EGFR+ cell.

Figure 5:
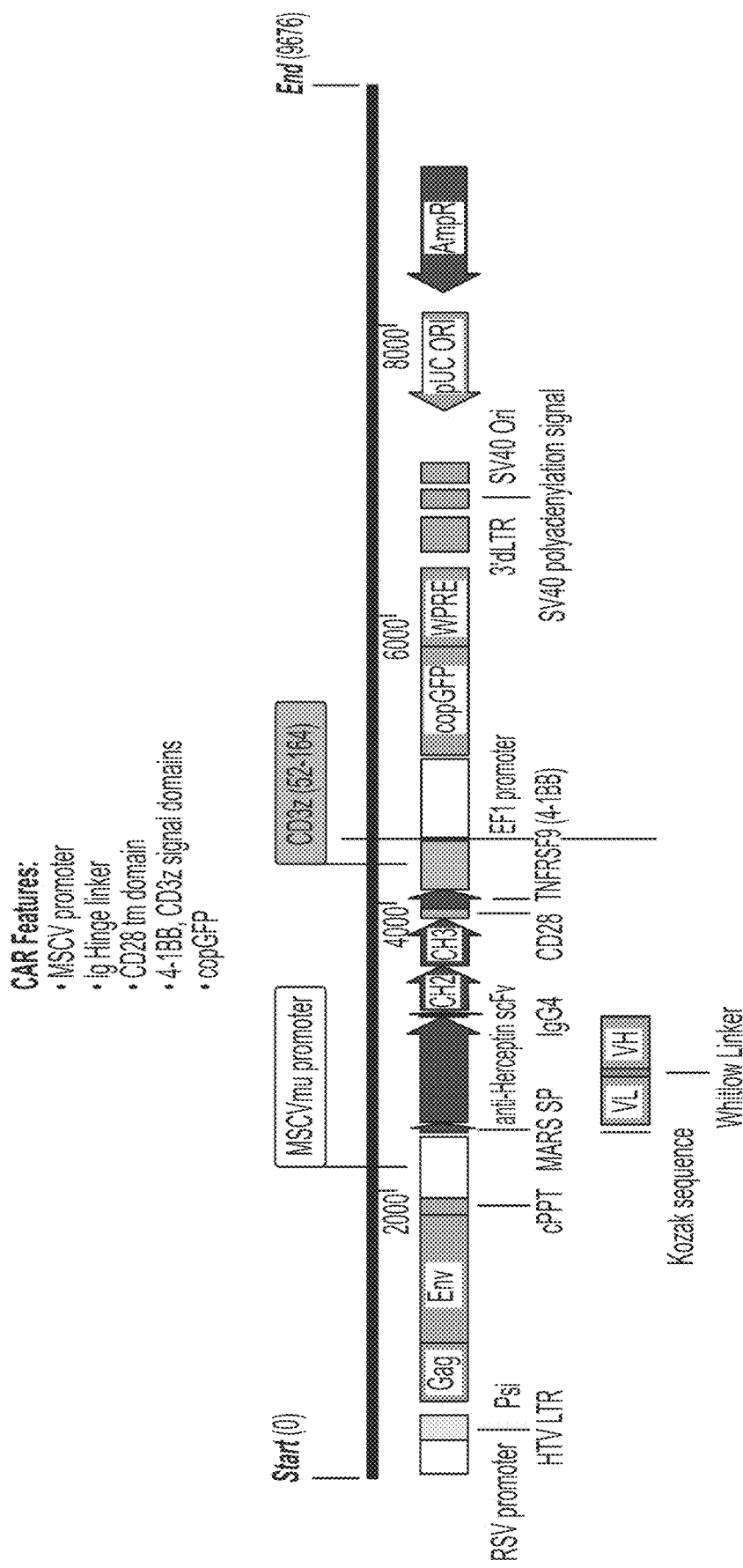
FIG. 5 depicts a vector map of the lentiviral vector used to deliver a CAR construct of the present disclosure.

Table 5 presents the CAR expression constructs generated which comprise either the Herceptin scFv or the anti-Herceptin idiotype scFv69 as the extracellular tag-binding domain. FIG. 5 shows a vector map of the lentiviral vector used to deliver the CAR constructs. Table 6 presents the Herceptin scFv and scFv69 (Herceptin anti-ID).

Jurkat cells were transduced with a lentiviral vector carrying a CAR construct described in Table 5 to evaluate CAR expression and CD69 activation. To measure CD69 regulation as a readout for activation, the CAR expressing Jurkat cells were co-cultured with EGFR positive cells for 24 and 48 hours. After the co-culture, the cells were stained for CD69 levels using an anti-Human CD69-BV421 antibody and measured on an Intellicyte flow cytometer. The CAR constructs were also expressed in T cells to evaluate cytotoxicity. To perform this assay, T-cells were isolated using the Pan T cell Isolation Kit (Miltenyi Cat #130-096-535) according to the manufacturer's directions. Cells were resuspended in RPMI, 10% FBS with 30 units/ml IL2 and activated overnight with Dynabeads™ Human T-Activator CD3/CD28 (ThermoFisher, Cat #11132D). The next day, the T-cells were transduced with Lentivirus plasmids containing the CAR expression cassette using TransDux™ MAX Lentivirus Transduction Reagent (SBI, Cat #LV860A-1) (FIGS. 12A-12K). The T-cells were expanded for seven days and on the seventh day, the cytotox assay was set up. Target cells labeled with Recon cell trace violet were co-cultured with the CAR positive T-cells at various ratios for 24 or 48 hours. After 48 hours, the viability of the cells were checked on the Intellicyte Flow Cytometer.

TABLE 5

CAR expression constructs

| CAR Format | Antibody | PLASMID |
| --- | --- | --- |
| Long Hinge, CD28 tm 4-1BB, CD3z | Herceptin | p518 |
| Long Hinge, CD28 tm 4-1BB, CD3z | scFv69 | p517 |
| Med Hinge, CD28 tm 4-1BB, CD3z | Herceptin | p511 |
| Med Hinge, CD28 tm 4-1BB, CD3z | scFv69 | p516 |
| Long Hinge, CD28 tm 4-1BB, CD3z | Herceptin | p514 |
| Long Hinge, CD28 tm 4-1BB, CD3z | scFv69 | p515 |
| Short Hinge, CD28 tm 4-1BB, CD3z | scFv69 9G8 | p510 |

TABLE 6

Herceptin, scFv69, and 9G8 CAR associated sequences

| CAR regoins | Sequence | SEQ ID NO |
| --- | --- | --- |
| Herceptin scFv (nucleotide sequence) | GACATCCAGATGACTCAGTCACCATCAAGCCTGAGTGCA TCCGTGGGCGATCGAGTGACAATAACATGTAGAGCGAGC CAGGATGTAAATACGGCAGTAGCGTGGTACCAACAGAAA CCCGGCAAGGCTCCTAAGCTGTTAATCTACAGCGCCAGC TTCCTTTATAGTGGAGTGCCTTCAAGGTTCTCAGGATCT AGGTCCGGTACTGACTTCACGCTGACAATCTCGAGCCTA CAACCCGAGGACTTCGCCACTTATTACTGCCAGCAGCAT TACACTACTCCTCCCACATTCGGACAGGGAACCAAAGTC GAGATCAAAGGATCAACCTCTGGATCTGGCAAGCCCGGG AGCGGGGAAGGCTCTACTAAGGGTGAGGTGCAACTAGTG GAGAGTGGCGGAGGGCTCGTCCAGCCAGGAGGTTCCCTG AGGCTGAGTTGCGCTGCAAGCGGATTCAATATCAAGGAC ACGTACATACACTGGGTGCGCCAGGCCCCCGGAAAGGGA CTGGAGTGGGTCGCCCGAATCTATCCTACTAATGGCTAC ACCAGGTATGCTGATTCAGTGAAAGGAAGGTTTACAATC TCTGCCGATACTTCAAAGAATACAGCTTATCTACAGATG AATTCACTTAGAGCCGAGGATACAGCCGTGTATTATTGC TCCCGATGGGGAGGAGATGGGTTCTACGCTATGGACTAC TGGGGTCAAGGAACCCTGGTGACCGTTAGTTCA | 69 |
| Herceptin scFv (amino acid sequence) | DIQMTQSPSSLSASVGDRVTITCRASQDVNTAVAWYQQK PGKAPKLLIYSASFLYSGVPSRFSGSRSGTDFTLTISSL QPEDFATYYCQQHYTTPPTFGQGTKVEIKGSTSGSGKPG SGEGSTKGEVQLVESGGGLVQPGGSLRLSCAASGFNIKD TYIHWVRQAPGKGLEWVARIYPTNGYTRYADSVKGRFTI SADTSKNTAYLQMNSLRAEDTAVYYCSRWGGDGFYAMDY WGQGTLVTVSS | 70 |

TABLE 6-continued

Herceptin, scFv69, and 9G8 CAR associated sequences

| CAR regoins | Sequence | SEQ ID NO |
|---|---|---|
| Herceptin scFv VL | DIQMTQSPSSLSASVGDRVTITCRASQDVNTAVAWYQQK PGKAPKLLIYSASFLYSGVPSRFSGSRSGTDFTLTISSL QPEDFATYYCQQHYTTPPTFGQGTKVEIK | 71 |
| Herceptin scFv VH | EVQLVESGGGLVQPGGSLRLSCAASGFNIKDTYIHWVRQ APGKGLEWVARIYPTNGYTRYADSVKGRFTISADTSKNT AYLQMNSLRAEDTAVYYCSRWGGDGFYAMDYWGQGTLVT VSS | 72 |
| Herceptin scFv Linker | GSTSGSGKPGSGEGSTKG | 3 |
| scFv69 (Herceptin anti-ID) (nucleic acid) | TCTTCTGAGCTGACTCAGGACCCTGCTGTGTCTGTGGCC TTGGGACAGACAGTCAGGATCACATGCCAAGGAGACAGC CTCAGAAGCTATTATGCAAGCTGGTACCAGCAGAAGCCA GGACAGGCCCCTGTACTTGTCATCTATGGTAAAAACAAC CGGCCCTCAGGGATCCCAGACCGATTCTCTGGCTCCAGC TCAGGAAACACAGCTTCCTTGACCATCACTGGGGCTCAG GCGGAAGATGAGGCTGACTATTACTGTAACAGCAGTGAA CCAACCCCACCAAGAGTGGTCTTCGGCGGCGGAACAAAA CTGACAGTGCTGGGCTCTACAAGCGGCAGCGGCAAACCT GGATCTGGCGAGGGATCTACCAAGGGCGAGGTGCAACTA TTGGAAAGTGGTGGCGGGCTGGTCCAACCGGGCGGGTCC TTGAGGCTGTCCTGTGCAGCCAGCGGGTTTACTTTTTCT TCCTACGCCATGTCTTGGGTACGACAGGCTCCCGGAAAA GGGCTCGAGTGGGTGAGTGCAATCTCCGGGAGTGGGGGC TCTACCTACTACGCCGATTCTGTCAAGGGGTAGGTTCACT ATCTCCAGGGATAATTCAAAGAATACTTTATACCTGCAG ATGAATTCACTGCGAGCGGAAGATACAGCAGTGTACTAT TGTGCCAAGAACGTGCACATCCAGCCCTTTGATTACTGG GGCCAGGGCACCAGCGTGACCGTGTCTAGC | 73 |
| scFv69 (Herceptin anti-ID) (amino acid sequence) | SSELTQDPAVSVALGQTVRITCQGDSLRSYYASWYQQKP GQAPVLVIYGKNNRPSGIPDRFSGSSSGNTASLTITGAQ AEDEADYYCNSSEPTPPRVVFGGGTKLTVLGSTSGSGKP GSGEGSTKGEVQLLESGGGLVQPGGSLRLSCAASGFTFS SYAMSWVRQAPGKGLEWVSAISGSGGSTYYADSVKGRFT ISRDNSKNTLYLQMNSLRAEDTAVYYCAKNVHIQPFDYW GQGTSVTVSS | 74 |
| scFv69 VL | SSELTQDPAVSVALGQTVRITCQGDSLRSYYASWYQQKP GQAPVLVIYGKNNRPSGIPDRFSGSSSGNTASLTITGAQ AEDEADYYCNSSEPTPPRVVFGGGTKLTVL | 75 |
| scFv69 VH | EVQLLESGGGLVQPGGSLRLSCAASGFTFSSYAMSWVRQ APGKGLEWVSAISGSGGSTYYADSVKGRFTISRDNSKNT LYLQMNSLRAEDTAVYYCAKNVHIQPFDYWGQGTSVTVS S | 76 |
| scFv69 Linker | GSTSGSGKPGSGEGSTKG | 3 |
| 9G8 VHH (anti-EGFR) (nucleotide sequence) | GAAGTGCAGCTTGTGGAGAGTGGCGGTGGTTTAGTTCAA CCAGGGGGCAGCCTGCGCTTGAGTTGTGCCGCATCGGGT CGTACCTTTTCTAGCTACGCAATGGGGTGGTTTCGTCAA GCTCCTGGGAAGGAACGTGAGTTTGTGGTCGCCATTAAT TGGTCATCAGGGAGTACATACTACGCTGATTCCGTCAAA GGGCGCTTTACAATCTCACGCGATAACAGCAAGAATACC CTTTATTTACAAATGAATAGTCTGCGTGCAGAAGATACG GCTGTGTATTACTGCGCTGCGGGGTACCAAATCAACTCT GGGAATTACAACTTTAAGGACTACGAGTATGATTATTGG GGCCAGGGCACTCAGGTTACAGTCTCGAGC | 77 |
| 9G8 VHH (anti-EGFR) (amino acid sequence) | EVQLVESGGGLVQAGGSLRLSCAASGRTFSSYAMGWFRQ APGKEREFVVAINWSSGSTYYADSVKGRFTISRDNAKNT MYLQMNSLKPEDTAVYYCAAGYQINSGNYNFKDYEYDYW GQGTQVTVSS | 78 |
| T2A sequence (nucleotide sequence) | GGATCCGGCGCCACAAACTTCAGCCTGCTGAAACAGGCC GGCGACGTGGAGGAAAACCCAGGCCCA | 79 |
| T2A sequence (amino acid sequence) | GSGATNFSLLKQAGDVEENPGP | 80 |

TABLE 6-continued

Herceptin, scFv69, and 9G8 CAR associated sequences

| CAR regoins | Sequence | SEQ ID NO |
|---|---|---|
| GFP (for expression detection) (nucleotide sequence) | GTGTCCAAGGGCGAAGAACTGTTCACCGGCGTGGTGCCC ATTCTGGTGGAACTGGACGGGGATGTGAACGGCCACAAG TTCAGCGTTAGAGGCGAAGGCGAAGGGGATGCCACAAAC GGCAAGCTGACCCTGAAGTTCATCTGCACCACCGGAAAG CTGCCCGTGCCTTGGCCTACACTGGTCACCACACTGACA TACGGCGTGCAGTGCTTCAGCAGATACCCCGACCATATG AAGCAGCACGACTTCTTCAAGAGCGCCATGCCTGAGGGC TACGTGCAAGAGAGAACCATCACCTTCAAGGACGACGGC ACCTACAAGACCAGAGCCGAAGTGAAGTTCGAGGGCGAC ACCCTGGTCAACCGGATCGAGCTGAAGGGCATCGACTTC AAAGAGGACGGCAACATCCTGGGCCACAAACTTGAGTAC AACTTCAACAGCCACAACGTGTAtATCACCGCCGACAAG CAGAAGAACGGCATCAAGGCCAACTTCAAGATCCGGCAC AACGTGGAAGATGGCAGCGTGCAGCTGGCCGATCACTAC CAGCAGAACACACCCATCGGAGATGGCCCTGTGCTGCTG CCCGATAACCACTACCTGAGCACCCAGAGCAAGCTGAGC AAGGACCCCAACGAGAAGCGGGACCACATGGTGCTGCTG GAATTTGTGACAGCCGCCGGAATCACCCACGGCATGGAT GAGCTGTACAAG | 81 |
| 8GFP (for expression detection) (amino acid sequence) | VSKGEELFTGVVPILVELDGDVNGHKFSVRGEGEGDATN GKLTLKFICTTGKLPVPWPTLVTTLTYGVQCFSRYPDHM KQHDFFKSAMPEGYVQERTITFKDDGTYKTRAEVKFEGD TLVNRIELKGIDFKEDGNILGHKLEYNFNSHNVYITADK QKNGIKANFKIRHNVEDGSVQLADHYQQNTPIGDGPVLL PDNHYLSTQSKLSKDPNEKRDHMVLLEFVTAAGITHGMD ELYK | 82 |

Figure 6A:
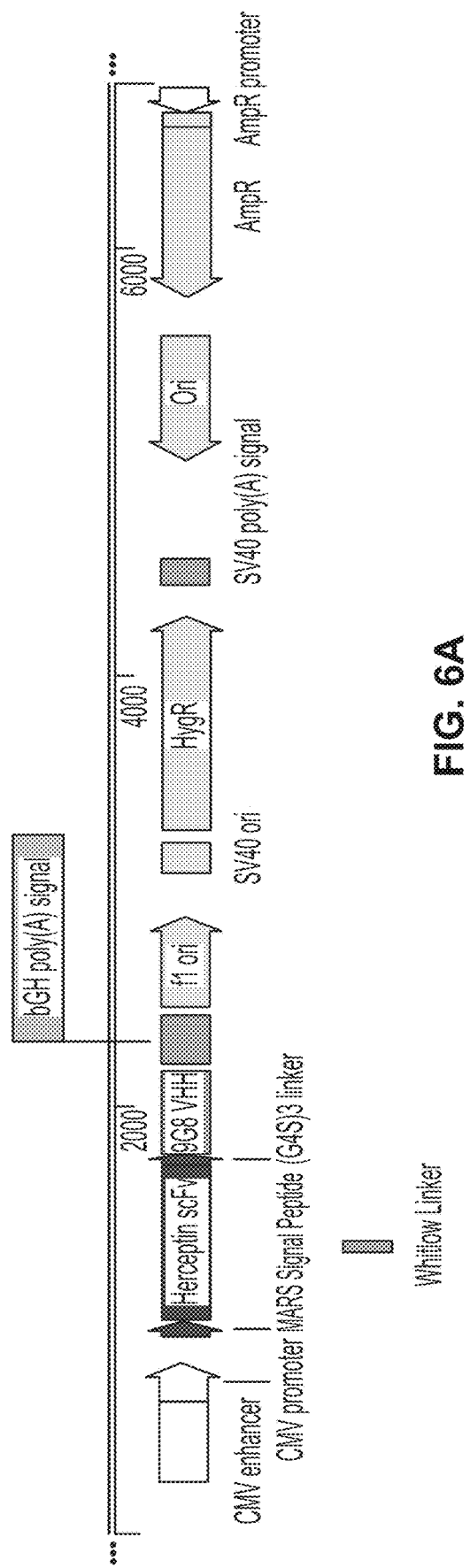
FIG. 6A depicts a vector map of the plasmid used to express a bridge construct of the present disclosure.

Four fusion protein (or bridge protein) constructs were assembled (Table 7) comprising the 9G8 VHH (Table 6) fused with either the Herceptin scFv or the anti-Herceptin idiotype scFv69 via a (G4S)$_3$ linker (SEQ ID NO: 25). FIG. 6A shows a vector map of the plasmid used for cloning the bridge constructs described in Table 7.

Figure 6B:
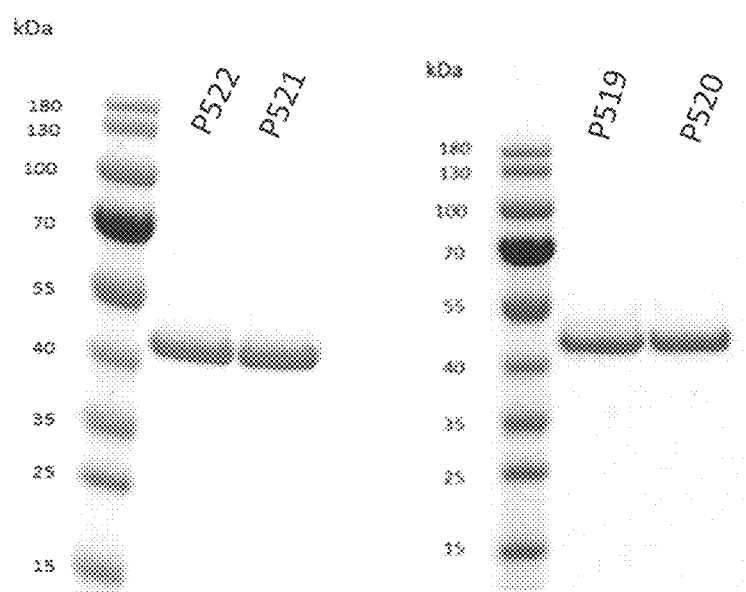
FIG. 6B shows a gel electrophoresis image demonstrating the purity of the bridge proteins.

EXPi-293 cells were transfected with a plasmid carrying a bridge construct described in Table 6 for protein expression using Expifectamine according to manufacturer's directions. Soluble bridge proteins were purified. Clarified supernatant was loaded over 1 ml HiTrap Mab Select SuRe column at 1 ml/min. The column was washed with 20 column volumes of PBS to remove unbound protein. The column was eluted with 10 cV of 0.1 M NaAcetate pH 3.5 and the sample was neutralized with 2.5 M Tris pH 6.5. The protein samples were polished by SEC to remove high molecular weight species. FIG. 6B shows a gel electrophoresis image demonstrating the purity of the bridge proteins purified from each construct.

TABLE 7

Bridge protein constructs

| Bridge Format | PLASMID |
|---|---|
| 9G8-Herceptin | p522 |
| Herceptin-9G8 | p521 |
| 9G8-scFv69 | p519 |
| scFv69-9G8 | p520 |

Figure 7A:
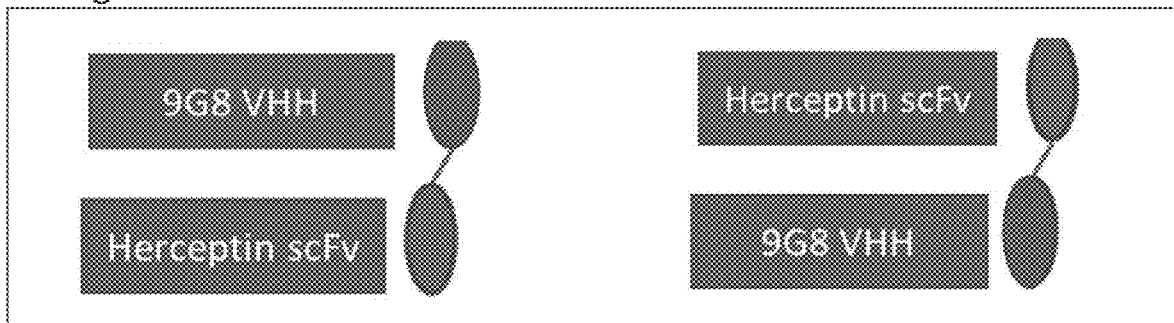
FIG. 7A depicts a schematic representation of the scFv69-CAR and two variants of the bridge protein: 9G8 Herceptin scFv and Herceptin scFv 9G8.
Figure 7A:
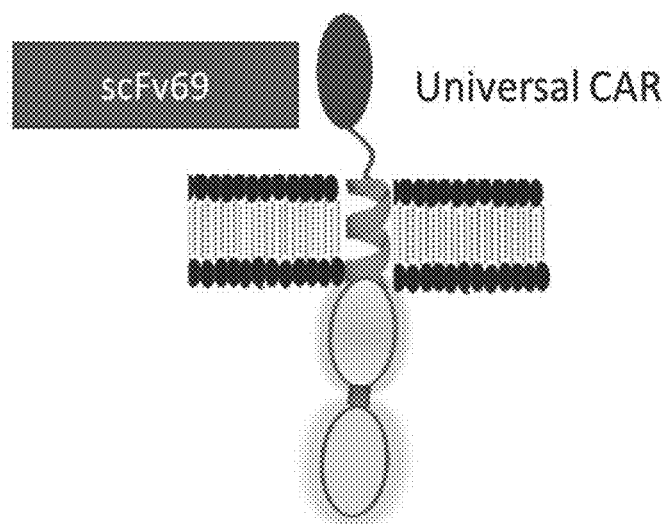
Figure 7B:
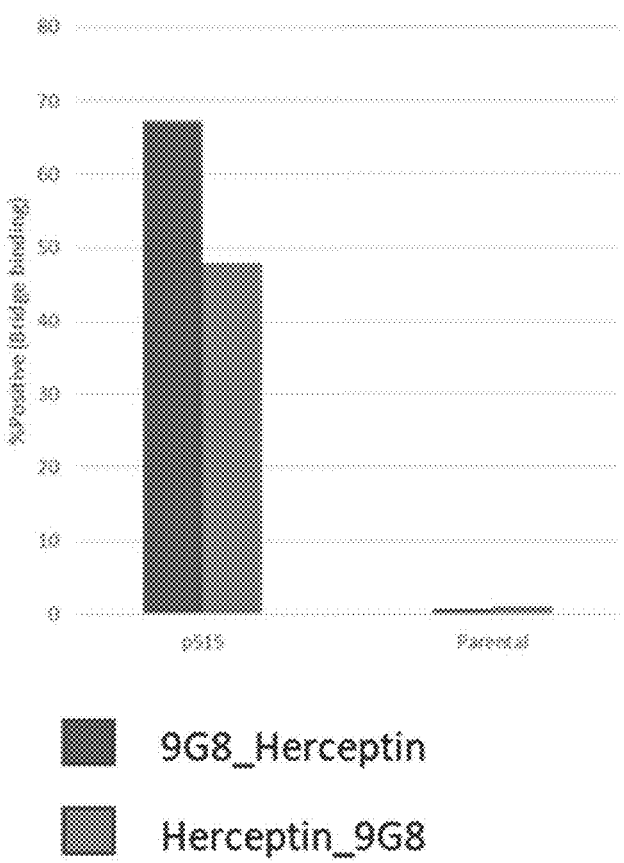
FIG. 7B demonstrates binding of the scFv69-CAR to the bridge proteins. The samples in the graph appear in the following order: 9G8_Herceptin, Herceptin_9G8.

Binding assays for bridge protein binding to CAR transduced Jurkat cells were carried out to detect binding between Jurkat cells transduced with scFv69-CAR and two variants of the bridge protein: 9G8_Herceptin scFv and Herceptin scFv 9G8, as shown in FIG. 7A. Bridge protein binding was detected on the Intellicyte via after incubating the cell staining assay was performed as follows. The CAR transduced Jurkat cells were incubated for 30 minutes with bridge protein. Following the incubation, the cells were washed and then incubated for 30 minutes with Biotinylated EGFR. After a wash step, PE-labeled Streptavidin was incubated with the cells. The bridge protein binding, CAR transduced Jurkat cells were determined by flow cytometry to be 65% positive for 9G8_Herceptin scFv and 45% positive for Herceptin scFv 9G8 (FIG. 7B). Bridge protein binding was also detected in the opposite orientation: Herceptin CAR with scFv69_9G8 bridge and Herceptin CAR with 9G8_scFv69 bridge (data not shown).

Figure 8A:
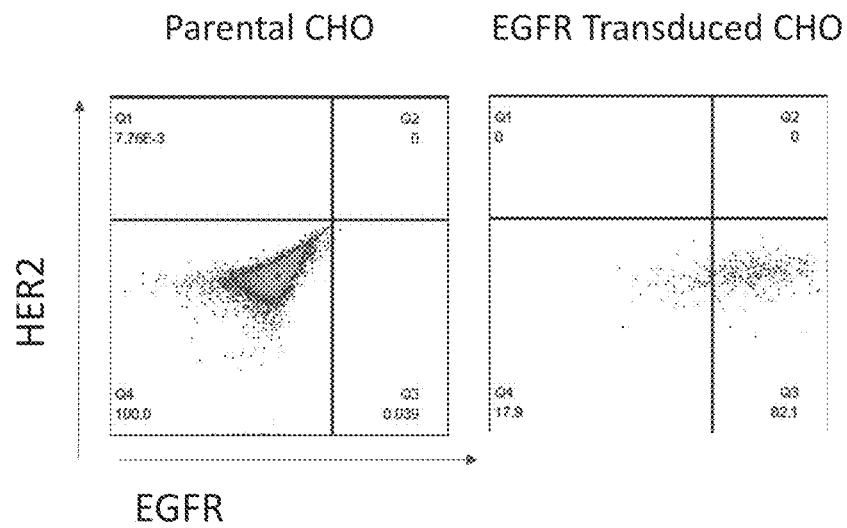
FIG. 8A demonstrates expression of EGFR on the EGFR transduced CHO cells.
Figure 8B:
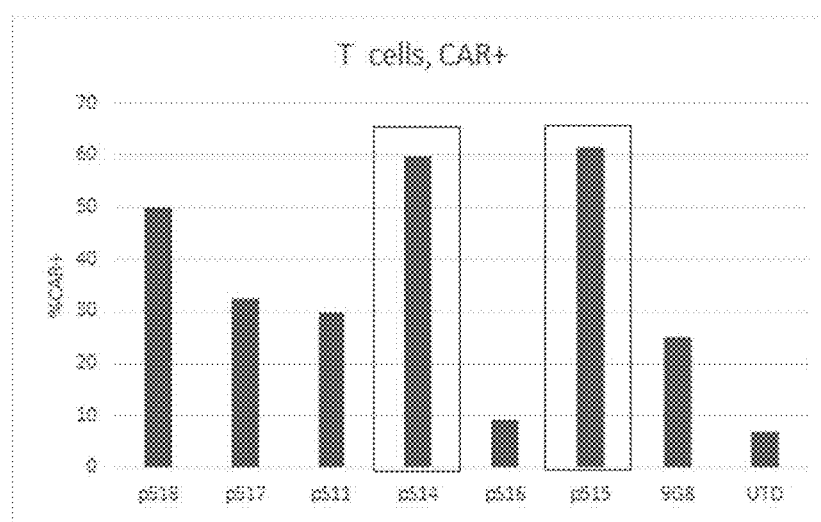
FIG. 8B demonstrates CAR expression in T cells.

Cytotoxicity activity was evaluated between target cells and CAR expressing T cells. As assessed by flow cytometry, expression of EGFR was detected in EGFR transduced CHO cells (FIG. 8A). CAR expression was also evaluated in T cells. Highest expression was observed in CARs with the Long Ig-Hinge format for both HER-CAR (p514) and scFv69-CAR (p515) (FIG. 8B).

To set up the cytotoxicity activity assay, target cells (EGFR transduced CHO and parental CHO) were plated at 10,000 cells/well, labeled with CellTrace™ Violet (CTV). CAR T cells were plated at 100,000 cells/well, for approximate CAR+ effector to target cell ratio (E:T) of ~5:1. CAR-T cells were co-cultured with CHO-EGFR+ cells for 48 hours. The controls used in the assay are shown in Table 8. 10, 1, 0.1, and 0 nM bridge proteins 9G8-Herceptin (p522) and 9G8-scFv69 (p519) were used.

TABLE 8

Cytotoxicity Activity Assay Controls

| Control | Testing |
|---|---|
| 9G8-CAR T | Positive control, target-specific CAR-mediated killing |
| Untransfected T cell | Negative control, non-specific T cell-mediated killing |
| No T cell | Negative control, baseline cell death |
| Herceptin CAR and Herceptin Bridge | Negative control, specificity of CAR-Bridge-killing mechanism |
| scFv69 CAR and scFv69 bridge | Negative control, specificity of CAR-Bridge-killing mechanism |

Figure 9A:
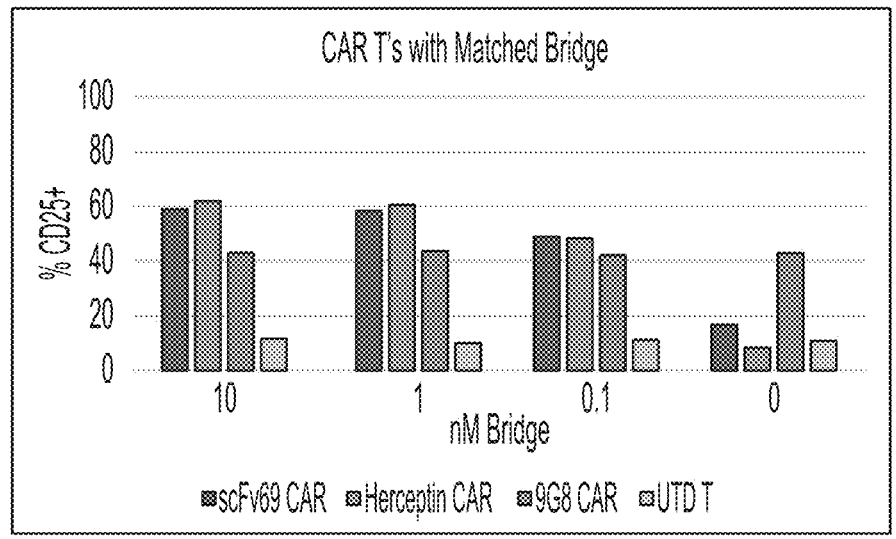
FIGS. 9A-9B show that universal CAR-T cells demonstrated CD25 activation when paired with the correct bridge protein (FIG. 9A) but not when paired with a mis-matched bridge protein (FIG. 9B). The samples in the graphs appear in the order as specified in the legend.
Figure 9B:
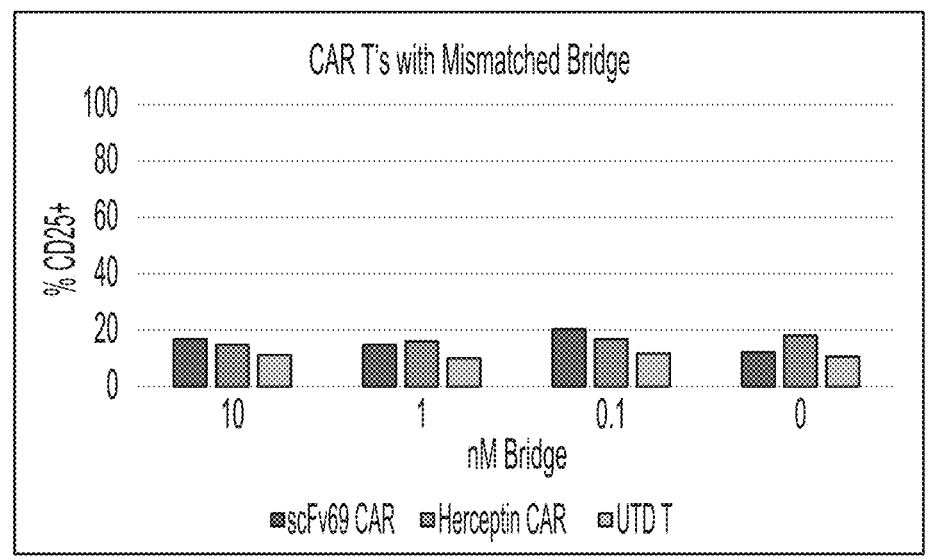
Figure 10A:
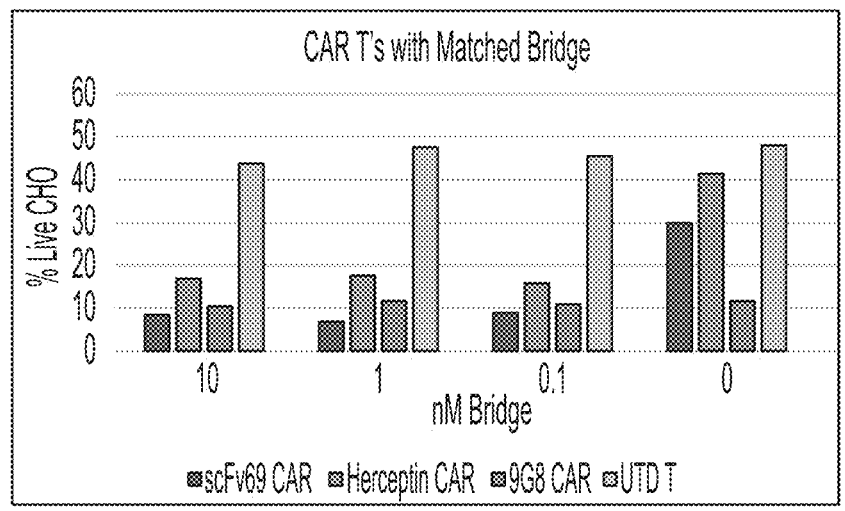
FIGS. 10A, 10B show that universal CAR-T cells demonstrated cytotoxic activity when paired with the correct bridge protein (FIG. 10A) but not when paired with a mis-matched bridge protein (FIG. 10B). The samples in the graphs appear in the order as specified in the legend.
Figure 10B:
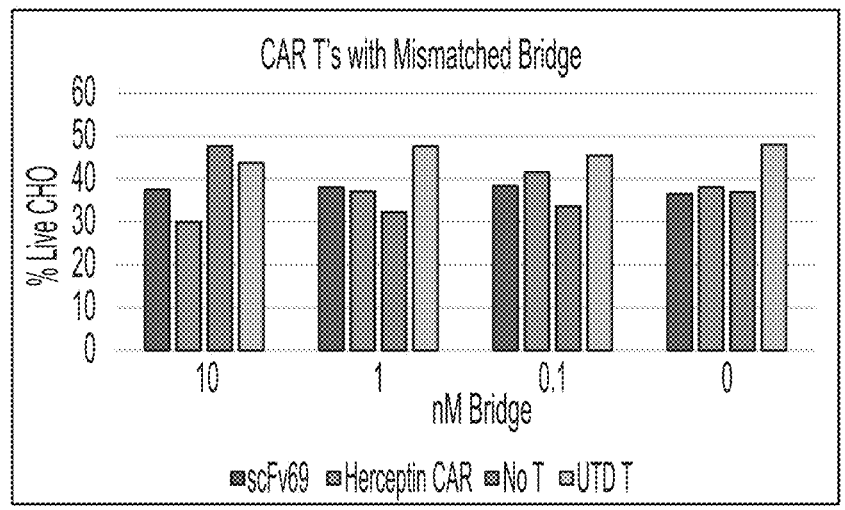

Universal CAR-T cells demonstrated CD25 activation when paired with the correct bridge protein but not when paired with a mis-matched bridge protein (FIGS. 9A, 9B). Further, universal CAR-T cells demonstrated cytotoxic activity when paired with the correct bridge protein but not when paired with a mis-matched bridge protein (FIGS. 10A, 10B).

Example 5. Identification of VHH for Universal CAR Platform

VHH binders were selected as potential targets for discovery of anti-idiotypes to form a specific and unique binding pair which may serve as the "tag" and "anti-tag", interchangeably. A list of VHHs were identified which are known to bind to non-human proteins. Additional VHHs that bind to Hen Egg Lysozyme (HEL) were also obtained. These VHHs and the generated plasmids are provided in Table 9 and sequences are provided in Table 10 (underlined sequences denote CDR locations).

TABLE 9

Candidate VHHs

| Non-human protein target | Plasmid | Corresponding Candidate VVH Polypeptide |
|---|---|---|
| RSV F Protein | p243 | SEQ ID NO.: 94 |
| *Listeria* Internalin | p279 | SEQ ID NO.: 84 |
| Cobra Phospholipase A2 | p247 | SEQ ID NO.: 86 |
| Ebola Nucleoprotein | p246 | SEQ ID NO.: 88 |
| HSV Glycoprotein D | p249 | SEQ ID NO.: 90 |
| Lacotococcal phage RBP | p251 | SEQ ID NO.: 92 |
| *Geobacillus stearothermophilus* | p250 | SEQ ID NO.: 96 |
| Ricin (V5E4) | p252 | SEQ ID NO.: 98 |
| LYSO_CW_P01_B10 | p245 | SEQ ID NO.: 100 |
| LYSO_CW_P01_B11 | p242 | SEQ ID NO.: 102 |
| LYSO_CW_P01_D04 | p244 | SEQ ID NO.: 104 |
| LYSO_CW_P01_F11 | p248 | SEQ ID NO.: 106 |
| LYSO_CW_P01_F09 | p278 | SEQ ID NO.: 108 |
| LYSO_CW_P01_C04 | p253 | SEQ ID NO.: 110 |

TABLE 10

Candidate VHH sequences

| CAR regions | Sequence | SEQ ID NO |
|---|---|---|
| Listeria: internalin 6dyx (nucleotide sequence) | CAGGTGAAGTTGGAAGAGTCTGGTGGTGGCCTCGTCCAGGC TGGGGGGAGTCTTCGCCTTAGTTGCGCAGCTTCAGGTCGGA CATACAGCACTTACGCGATGGGGTGGTTTCGCCAGACTCCG GGGAAGGAGAGAGAATTGGTGGCAGCAATAAATTGGTCAGG GGGCAACACGCACTATGCAGACTCTGTAAAAGGCCGGTTCA CGATCAGTAGAGATAACGCCAAGAGCACCGTCTACCTCCAG ATGAATTCCCTGAAACCTGAGGACACAGCAGTTTATTACTG TGCCGCTCCGAAAGGCCACACAGGGGATCATTACTGGGGAC CCGGCACCCAAGTGACTGTGAGCTCG | 83 |
| Listeria: internalin 6dyx (amino acid sequence) | QVKLEESGGGLVQAGGSLRLSCAASGRTYSTYAMGWFRQTP GKERELVAAINWSGGNTHYADSVKGRFTISRDNAKSTVYLQ MNSLKPEDTAVYYCAAPKGHTGDHYWGPGTQVTVSS | 84 |
| Naja kaouthia (cobra): Phospholipase A2 P3-3 (nucleotide sequence) | CAGGTGCAACTCGTTGAAAGTGGAGGCGGTAGCGTTCAGGC AGGTGGAAGCCTCAGGCTGTCCTGTGCGGCCAGTAGAGACA CGTATGATTCACACTGTATGGGTGGTTCCGGCAAGCGCCC GGAAAAGAGAGGGAACAGGTGGCGGCACATAACGGTGGCCG AAACACATATTACGCAGATAGCGTTAAAGGACGATTTACAA TATCTCAGGACAATGCTAAGAATACGATGTATCTCCAAATG AATAGCCTTAAACCTGAAGATACAGCCATTTACTACTGCGC CGCGGACATGTCCGCGAGAAGGGTCGCAAACACAGGATGCA GATACAATTATTGGGGCCAAGGCACTTTGGTAACTGTGAGC TCG | 85 |
| Naja kaouthia (cobra): Phospholipase A2 P3-3 (amino acid sequence) | QVQLVESGGGSVQAGGSLRLSCAASRDTYDSHCMGWFRQAP GKEREQVAAHNGGRNTYYADSVKGRFTISQDNAKNTMYLQM NSLKPEDTAIYYCAADMSARRVANTGCRYNYWGQGTLVTVS S | 86 |
| Ebola: nucleoprotein Anti-Z C (nucleotide sequence) | CAGGTGCAACTTCAACAAAGCGGCGGGGGATCCGTAACGCC AGGTGGATCACTGCGGCTTTCTTGTGCTGCTTCCGGATCCA TTTCAGACTTTGCTGCTATGGCATGGTATCGGCAGGCCCCT GGCAAAGAAAGGGATTGGGTTTTTGGAACCATATTCTCAGC AGGTGCTTTGTTGTACGCAGAACCAGTTAAAGGTCGGTTTA CCATATCAAGGGATAACGCTAAGAATACTGTATATCTTCAA ATGAACAGTTTGAAACCAGAGGATACTGCCGTATACTATTG TCGCCTCTATGCTAAGGCAATTTATTGGGGTCAGGGCACAC AGGTAACGGTGAGCTCG | 87 |
| Ebola: nucleoprotein Anti-Z C (amino acid sequence) | KVQLQQSGGGSVTPGGSLRLSCAASGSISDFAAMAWYRQAP GKERDWVFGTIFSAGALLYAEPVKGRFTISRDNAKNTVYLQ MNSLKPEDTAVYYCRLYAKAIYWGQGTQVTVSS | 88 |

TABLE 10-continued

Candidate VHH sequences

| CAR regions | Sequence | SEQ ID NO |
|---|---|---|
| Herpes simplex virus: Glycoprotein D (nucleotide sequence) | CAGGTGCAACTTCAGGCTAGTGGAGGGGGACTGGTGCAAGC TGGCGGGTCTTTGCGACTGTCCTGTGCAGCCTCAGGCCGAG CTACAGGCAATTATCCCATGGGATGGTTCCGCCAGGCCCCT GGGAAAAGAACGCGAGTTCGTTGCAGCCATCAGTCGGGACGG CGACAGTACATACTACCGGGATAGTGTTAAAGGCCGATTTA CCATATCCCGAGACAATACGAAAAATACGGCATATCTTCAG ATGAACAGTCTTAAGCCGGAGGACACAGCCGTCTACTATTG TGCAGCTGACCGGCTGACAGCATATCGATACAATCCAGGGC AGATTGACTATTGGGGACAGGGTACACAAGTTACGGTGAGC TCG | 89 |
| Herpes simplex virus: Glycoprotein D (amino acid sequence) | EVQLQASGGGLVQAGGSLRLSCAASGRATGNYPMGWFRQAP GKEREFVAAISRDGDSTYYRDSVKGRFTISRDNTKNTAYLQ MNSLKPEDTAVYYCAADRLTAYRYNPGQIDYWGQTQVTVS S | 90 |
| Lactococcal phage: RBP (nucleotide sequence) | CAGGTGCAACTGGTCGAAAGTGGTGGGGGGCTCGTTCAAGC CGGTGGCAGTTTGCGCTTGTCATGCGCCGCTAGTGAAAGTA CCTTCTCTAACTACGCGATGGGATGGTTCAGGCAAGCACCA GGCCCTGAAAGGGAATTTGTGGCTACGATTTCTCAAACAGG GTCCCACACCTACTACCGCAATTCTGTGAAGGGACGCTTCA CGATTAGTCGGGATAACGCCAAGAACACAGTGTACCTTCAA ATGAACAATATGAAGCCTGAAGACACGGCCGTGTATTATTG TGCAGCCGGAGACAACTATTACTATACCAGAACTTATGAGT ACGACTACTGGGGCCAGGGTACTCAGGTCACTGTGAGCTCG | 91 |
| Lactococcal phage: RBP (amino acid sequence) | QVQLVESGGGLVQAGGSLRLSCAASESTFSNYAMGWFRQAP GPEREFVATISQTGSHTYYRNSVKGRFTISRDNAKNTVYLQ MNNMKPEDTAVYYCAAGDNYYYTRTYEYDYWGQGTQVTVSS | 92 |
| RSV: F-protein (nucleotide sequence) | CAGGTGCAGTTGGTCGAGTCAGGTGGAGGGTCAGTGCAGCC AGGGGGGTCCCTTCGACTTAGTTGTGCAGCCAGTGGTTTTA CACTGGATTACTATTACATTGGGTGGTTTCGACAGGCCCCC GGGAAGGAACGCGAGGGTGTTTCTTGTATTTCCAGCTCACA TGGCTCAACCTATTATGCTGACTCAGTAAAAGGTCGGTTTA CGATAAGCCGGGATAATGCAAAGAATACCGTGTATCTTCAA ATGAATAGCCTTAAACCAGAAGATACCGCTGTGTACTATTG TGCCACTATACGCTCTAGCTCATGGGGGGGCTGTGTCCACT ACGGGATGGATTATTGGGGAAGGGCACGCAAGTCACGGTG AGCTCG | 93 |
| RSV: F-protein (amino acid sequence) | QVQLVESGGGSVQPGGSLRLSCAASGFTLDYYYIGWFRQAP GKEREGVSCISSSHGSTYYADSVKGRFTISRDNAKNTVYLQ MNSLKPEDTAVYYCATIRSSSWGGCVHYGMDYWGKGTQVTV SS | 94 |
| Geobacillus stearothermophilus: SbsB (nucleotide sequence) | CAGGTGCAGTTGCAAGAAAGTGGAGGGGGATTGGTGCAGGC AGGTGGATCTTTGAGGCTGTCCTGTGCAGCCTCTGGTCGCA CTAGCTCTGCGTACGCTATGGGTTGGTTTCGACAGGCCCCT GGGAAGAACGCGAGTTCGTTGCCGGCATTTCAAGCAAAGG CGGTAGCACGTATTATGGTGCCAGCATGAAAGGACGCTTTA CGATATCACGGGATAACGCGAAAAATACGGTCTACTTGCAG ATGAACGGTCTGGCCCCAGAAGACACGGCAGTGTACTACTG CGCTGCGAGCGACAAGTATAATTTCGACACCAGCCATGCGG GATACGGCTATTGGGGCCAAGGGACCCAGGTTACAGTGAGC TCG | 95 |
| Geobacillus stearothermophilus: SbsB (amino acid sequence) | QVQLQESGGGLVQAGGSLRLSCAASGRTSSAYAMGWFRQAP GKEREFVAGISSKGGSTYYGASMKGRFTISRDNAKNTVYLQ MNGLAPEDTAVYYCAASDKYNFDTSHAGYGYWGQGTQVTVS S | 96 |
| Ricin (V5E4) (amino acid sequence) | CAGGTGCAACTCGTGGAGACGGGTGGAGGACTTGTGCAAGC GGGCGGAAGCCTTAGGTTGAGCTGTGCTGCGTCTGGATTTA CATTTAGTAGCTATGCAATGGGCTGGTTTCGCCAGGCGCCG GGGAAGGAACGCGACTTCGTTGCGGGTATCTCACTTAGCGG CGCCGGGACGTACTATGTAAAAGGAAGGTTCACCATTTCAC GCGATAACGCTAAAAACACTGTCTATTTGCAGATGAACAGC CTCAAACCAGAGGATACTGCAGTATATTACTGTAAGGCCAC AGGAGAAAGGGGTATGGAGATCAGGGATATCTTGAAGTCT GGGGGAGAGGGACGCTGGTTACCGTGAGCTCG | 97 |

TABLE 10-continued

Candidate VHH sequences

| CAR regions | Sequence | SEQ ID NO |
|---|---|---|
| Ricin (V5E4) (amino acid sequence) | QVQLVETGGGLVQAGGSLRLSCAASGFTFSSYAMGWFRQAP GKERDFVAGISLSGAGTYYVKGRFTISRDNAKNTVYLQMNS LKPEDTAVYYCKATGERGYGDQGYLEVWGRGTLVTVSS | 98 |
| Lyso CW P01 B10 (nucleotide sequence) | CAGGTGCAACTTGTGGAGAGCGGGGGTGGTCTCGTCCAGGC TGGTGGCTCACTTCGCCTCTCCTGCGCGGCTAGCGGCGGGA TATTCTCAGGTGGAAGAATGGGCTGGTTCAGACAAGCTCCA GGTAAAGAGAGAGAGTTCGTAGCGGCGGTAATCACTCGCGG GGGGTCTACTTATTATGCGGACTCTGTGAAGGGTAGATTTA CAATTTCACGGGACAACGCAAAGAATACTGTGTACCTTCAA ATGAACTCACTTAAACCTGAGGACACGGCGGTTTATTACTG CGCTGCAAGCGAGGTAACCTATGACGAGGGACATTACATCG GAACCAAATCCACTTACGACACTTGGGGACAGGGCACGCAG GTAACTGTGAGCTCG | 99 |
| Lyso CW P01 B10 (amino acid sequence) | QVQLVESGGGLVQAGGSLRLSCAASGGIFSGGRMGWFRQAP GKEREFVAAVITRGGSTYYADSVKGRFTISRDNAKNTVYLQ MNSLKPEDTAVYYCAASEVTYDEGHYIGTKSTYDTWGQGTQ VTVSS | 100 |
| Lyso CW P01 B11 (nucleotide sequence) | CAGGTGCAGCTCGTAGAGTCCGGGGGAGGTCTGGTGCAAGC TGGAGGTTCCTTGCGATTGTCATGTGCGGCAAGCGGAGGAA TTTTTTCTGGAGGACGAATGGGGTGGTTCCGACAGGCACCG GGAAAAGAGAGGGAGTTCGTAGCTGCCGTGATTACAAGGGG TGGTAGCACATACTATGCAGATAGCGTAAAGGGTAGGTTTA CGATATCCAGGGATAACGCAAAGAACACGGTCTACCTGCAG ATGAACTCCCTTAAACCAGAAGATACTGCCGTTTATTATTG CGCCGCATCAGAGGTAACTTACGATGAAGGTCGATACATTG GGACGAAGAGCACCTATGACACATGGGGGCAGGGTACTCAA GTGACCGTGAGCTCG | 101 |
| Lyso CW P01 B11 (amino acid sequence) | QVQLVESGGGLVQAGGSLRLSCAASGGIFSGGRMGWFRQAP GKEREFVAAVITRGGSTYYADSVKGRFTISRDNAKNTVYLQ MNSLKPEDTAVYYCAASEVTYDEGRYIGTKSTYDTWGQGTQ VTVSS | 102 |
| Lyso CW P01 D04 (nucleotide sequence) | CAGGTGCAACTGGTGGAATCCGGGGGTGGACTGGTACAAGC CGGAGGGAGTTTGAGACTCTCTTGCGCTGCCTCCGGTAGAA TTTTTTTCAATATACGCACCATAGGATGGTTTCGACAAGCG CCTGGAAAGGAAAGAGAGTTTGTAGCGGCCACTATCACAAC GGCGGGTATTACGACATATGATGATAGCGTTAAAGGACGGT TCACGATAAGCCGCGACAATGCCAAGAACACAGTGTACCTC CAAATGAATAGCCTTAAGCCCGAGGATACAGCCGTTTACTA TTGTTACGTCCGAGTTGGTCGCGGTGACTACTGGGGTCAAG GTACTCAGGTGACTGTAAGCTCG | 103 |
| Lyso CW P01 D04 (amino acid sequence) | QVQLVESGGGLVQAGGSLRLSCAASGRIFSIYDTIGWFRQA PGKEREFVAATITTAGITTYDDSVKGRFTISRDNAKNTVYL QMNSLKPEDTAVYYCYVRVGRGDYWGQGTQVTVSS | 104 |
| Lyso CW P01 F11 (nucleotide sequence) | CAGGTGCAACTGGTTGAATCTGGTGGTGGGCTGGTCCAAGC GGGAGGCAGTCTTCGACTTTCCTGCGCAGCCTCAGGGAGTA TATTCAGCTTTTACGACGTAGGTTGGTTCCGCCAAGCGCCC GGTAAAGAACGAGAGTTCGTCGCTGCCAGTATAACGAAGGG AGGCGGGACGTACTACGTAGATTCAGTAAAAGGGAGATTTA CCATAAGTAGGGACAATGCAAAGAACACGGTCTACCTCCAG ATGAATAGCCTTAAACCAGAAGATACGGCAGTCTATTACTG CGCCCTGGCAACCCCCCACGGATATGACTTTTGGGGCCAAG GTACGCAAGTCACGGTGAGCTCG | 105 |
| Lyso CW P01 F11 (amino acid sequence) | QVQLVESGGGLVQAGGSLRLSCAASGSIFSFYDVGWFRQAP GKEREFVAASITKGGGTYYVDSVKGRFTISRDNAKNTVYLQ MNSLKPEDTAVYYCALATPHGYDFWGQGTQVTVSS | 106 |
| Lyso CW P01 F09 (nucleotide sequence) | CAGGTGCAGCTCGTTGAAAGCGGGGGTGGCTTGGTCCAAGC GGGAGGTTCCCTGAGACTGTCCTGCGCTGCGTCAGGATCAA TAATCACGATTTATGTAGTCGGATGGTTCCGACAAGCCCCA GGTAAAGAGCGGGAATTTGTGGCCTCCGACATAGGCTCTGG TGGGTCAACTTATTACAGTGACTCCGTAAAAGGTCGGTTCA CAATCTCAAGGGATAACGCAAAGAATACAGTCTACTTGCAA ATGAATTCATTGAAGCCTGAGGATACAGCAGTGTACTACTG CGTTACTGGAGATCCCTCTACTCCGTATTCATACTGGGGTC AAGGCACACAGGTTACAGTGAGCTCG | 107 |

TABLE 10-continued

Candidate VHH sequences

| CAR regions | Sequence | SEQ ID NO |
|---|---|---|
| Lyso CW P01 F09 (amino acid sequence) | QVQLVESGGGLVQAGGSLRLSCAASGSIITIYVVGWFRQAP GKEREFVASDIGSGGSTYYSDSVKGRFTISRDNAKNTVYLQ MNSLKPEDTAVYYCVTGDPSTPYSYWGQGTQVTVSS | 108 |
| Lyso CW P01 C04 (nucleotide sequence) | CAGGTGCAACTGGTCGAGAGTGGTGGTGGACTGGTTCAAGC TGGGGGCAGCCTGAGATTGTCCTGCGCCGCATCTGGCTCCT CCTTCTCAATTTACGACGTGGGCTGGTTCCGCCAAGCACCT GGAAAGGAAAGAGAGTTTGTTGCTGCGACAATTGAGACTGG GGGACACACGTCTTACGCCGACTCAGTGAAAGGTAGATTTA CAATCTCAAGGGATAACGCTAAAAACACCGTTTATCTGCAA ATGAACTCCCTGAAACCGGAGGATACAGCTGTGTACTATTG TTATGCGAAGATTGTCTACGACCAGGGCCCGAGCTACTACT ATTGGGGCCAGGGGACACAGGTTACCGTGAGCTCG | 109 |
| Lyso CW P01 C04 (amino acid sequence) | QVQLVESGGGLVQAGGSLRLSCAASGSSFSIYDVGWFRQAP GKEREFVAATIETGGHTSYADSVKGRFTISRDNAKNTVYLQ MNSLKPEDTAVYYCYAKIVYDQGPSYYWGQGTQVTVSS | 110 |

Figure 11A:
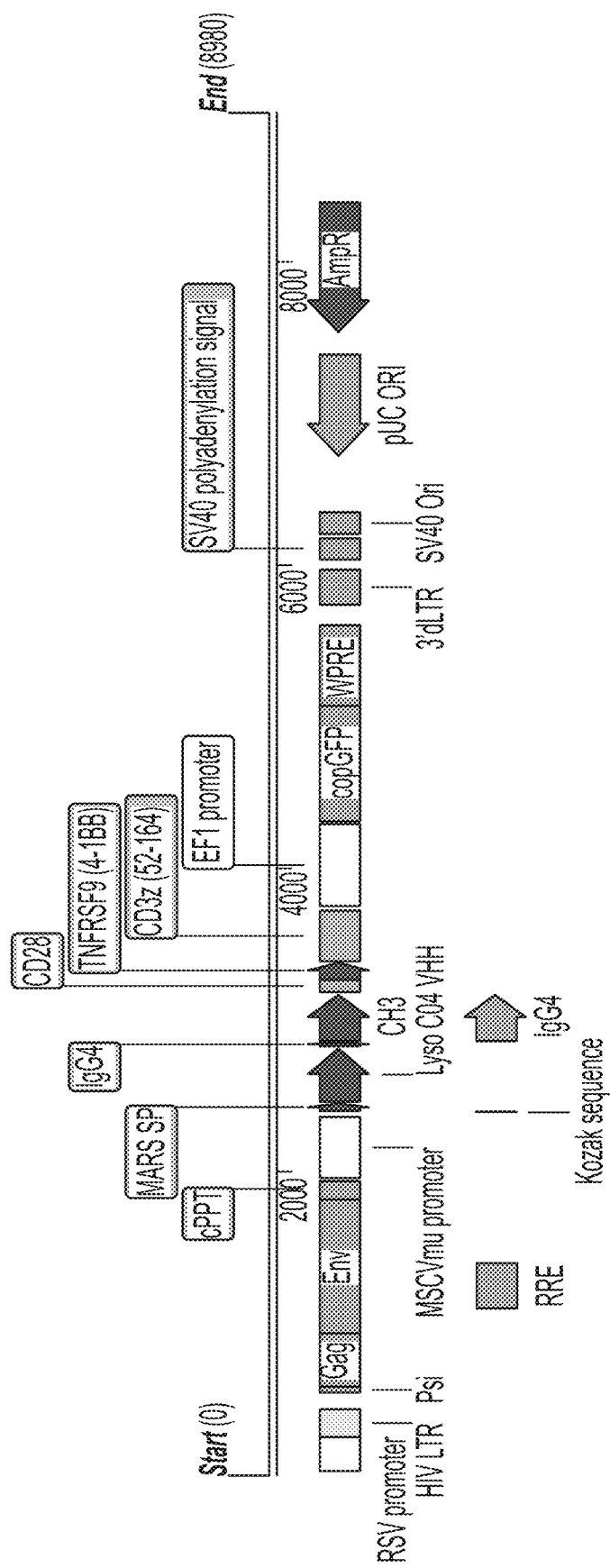
FIG. 11A depicts a vector map of the lentiviral vector used to deliver a VHH CAR of the present disclosure.
Figure 11B:
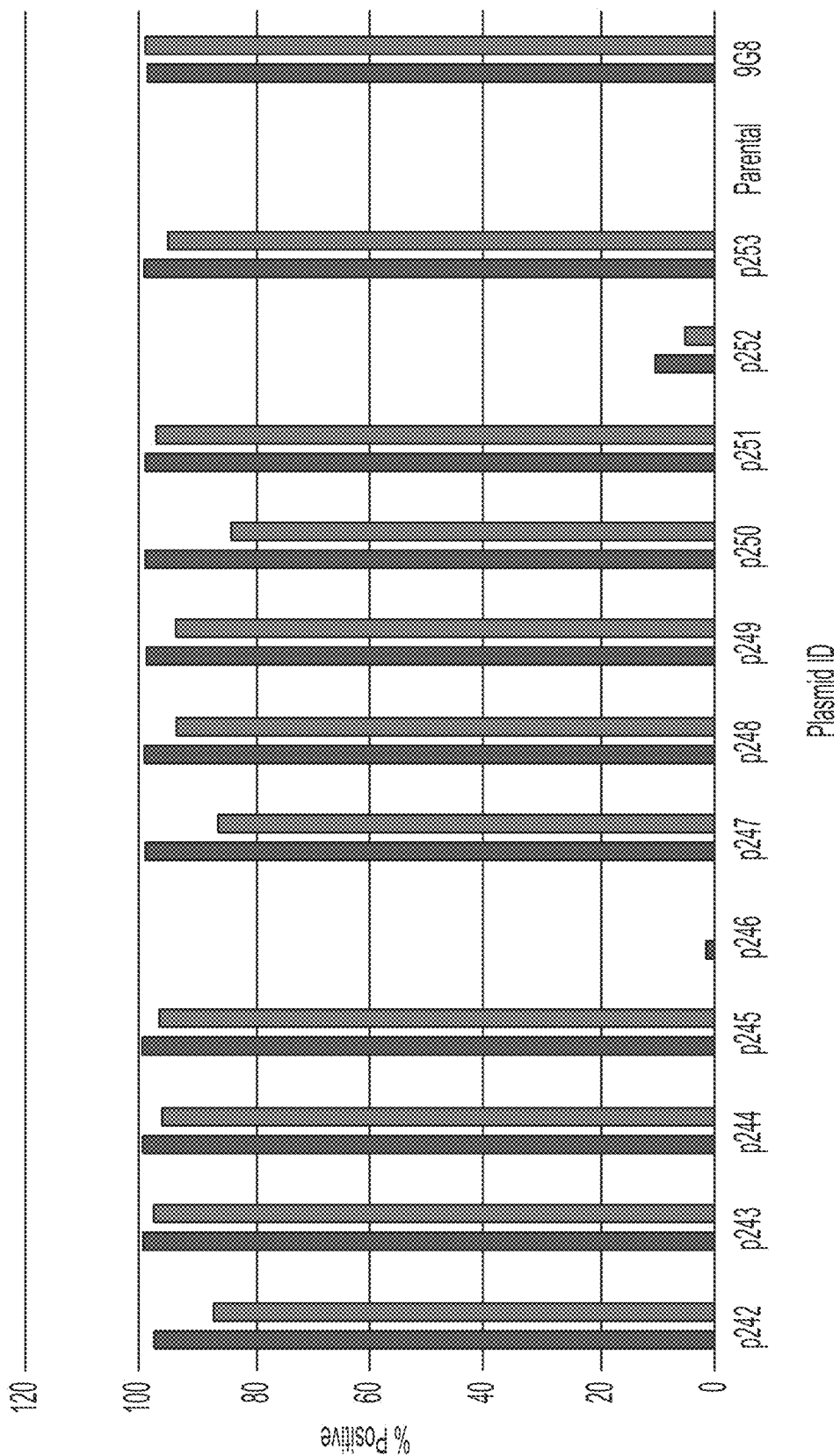
FIG. 11B shows expression for VHH CAR on Jurkat cells.
Figure 11C:
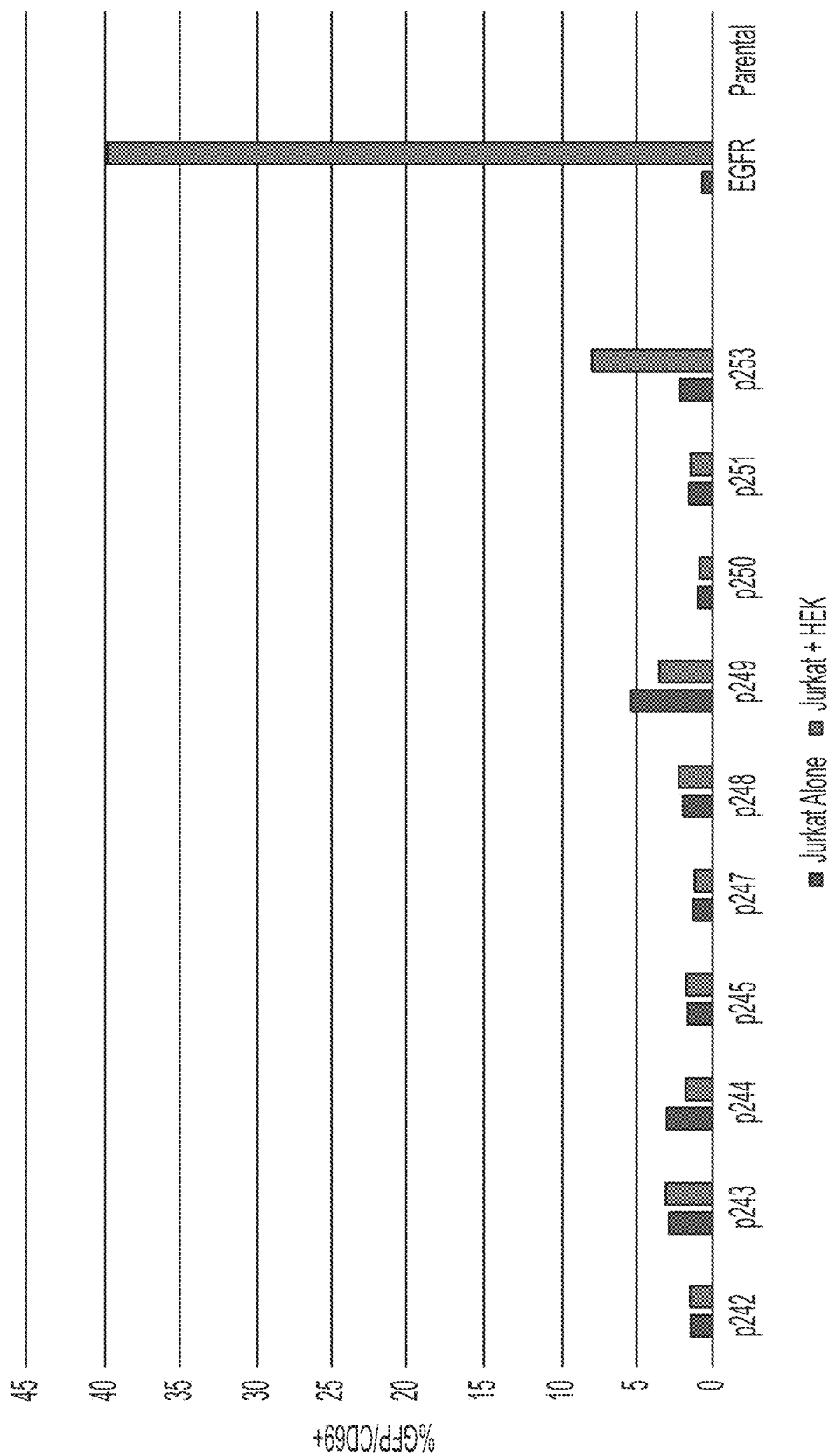
FIG. 11C shows lack of tonic signaling on the surface of Jurkat cells transduced VHH CAR.
Figure 11D:
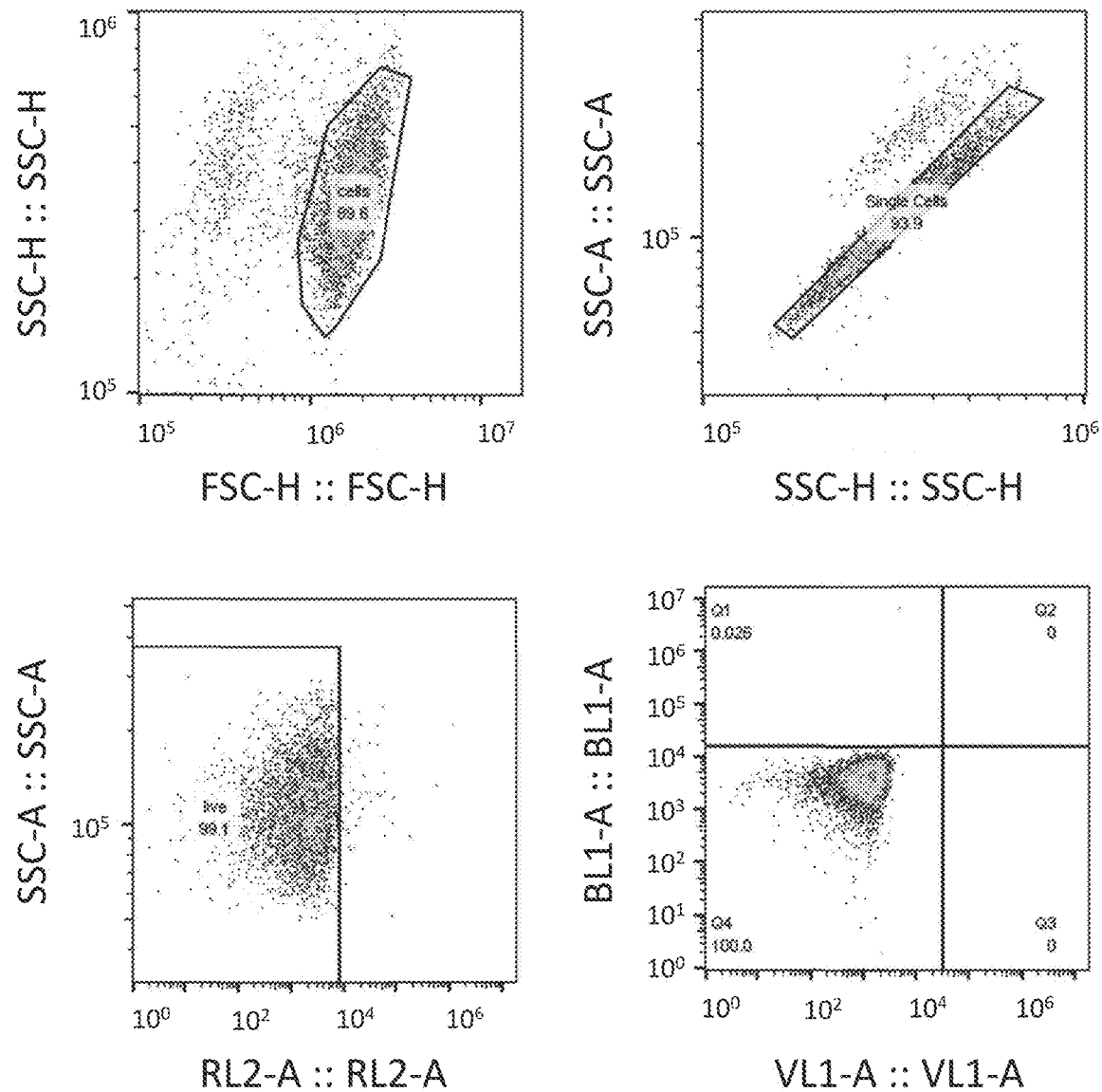
FIG. 11D shows the FACs gating strategy used for CD69 detection in FIG. 11C.

Lentiviral CAR expression constructs comprising a VHH described in Table 9 were assembled. FIG. 11A shows a vector map of the lentiviral vector used to deliver the VHH CARs. The lentiviral vectors were then used to transduce Jurkat cells. Robust CAR expression was observed for 10/14 VHH CAR on Jurkat cells (FIG. 11B). All candidate VHH expressed at very high levels in Jurkat cells as a CAR. To determine if there was any tonic signaling or nonspecific activation of these VHH when present on a CAR, transduced Jurkat cells were incubated with human embryonic kidney cells (HEK) overnight and assessed the next day for the T cell activation marker CD69. Low or no non-specific activation on Jurkat cells was observed for all VHH CAR constructs (FIGS. 11C, 11D) indicating that there was little or no signaling through the CAR without target-driven activation. Three anti-lysozyme VHH CARs bind to chicken lysozyme and are not cross-reactive to human (FIG. 11E), demonstrating specificity for the chicken protein.

Based on these data, the LYSO_CW_P01_B11 (B11) and LYSO_CW_P01_D04 (D04) VHHs were selected for further consideration owing to their high expression as CARs, low to no tonic signaling and nonspecific activity, and ideal biophysical characteristics (indicated by their strong expression as soluble proteins). These VHHs had good expression either in the CAR or in the bridge protein.

FIG. 11F shows alignment of the amino acid sequences of VHHs targeting *Geobacillus stearothermophilus*, LYSO_CW_P01_B11 and LYSO_CW_P01_D04. A consensus sequence was generated based on the aligned sequences.

Figure 11E:
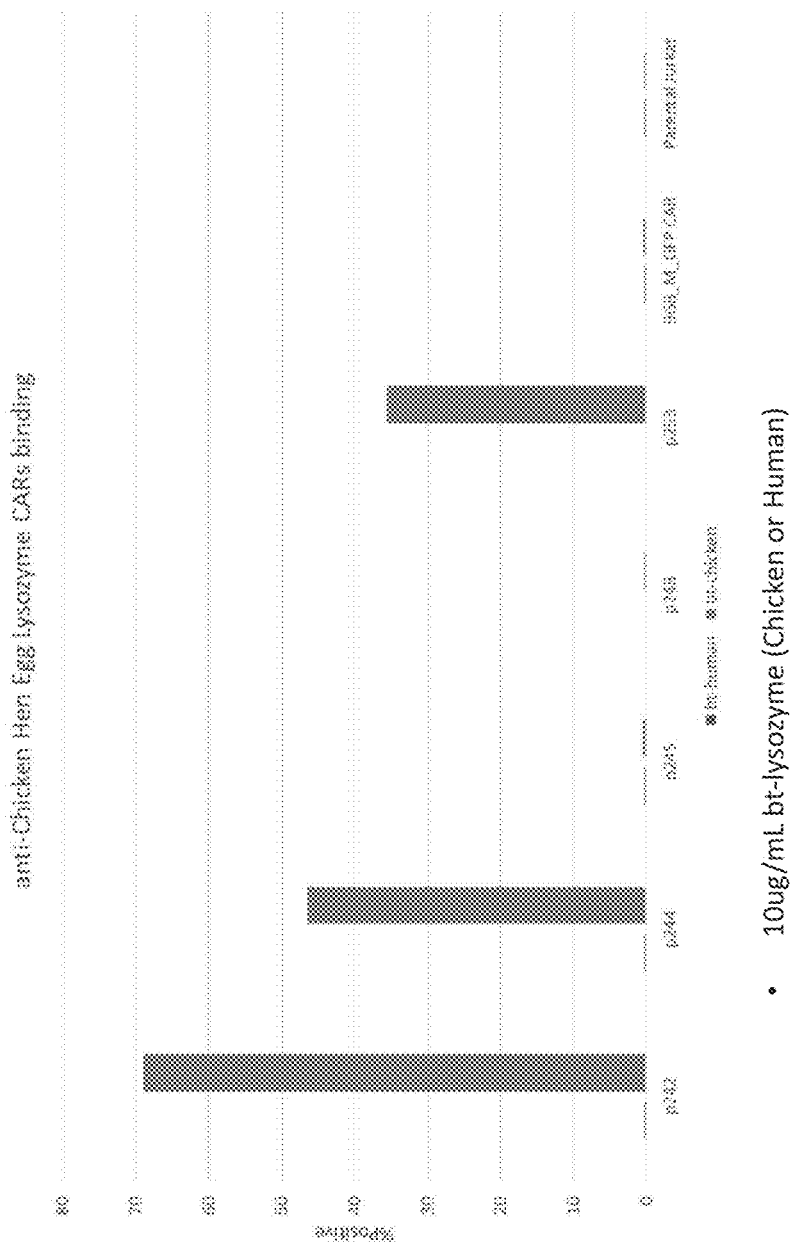
FIG. 11E shows binding of anti-Chicken Hen Egg Lysozyme-VHH CARS to lysozyme from chicken or human.
Figures 1, 12A:
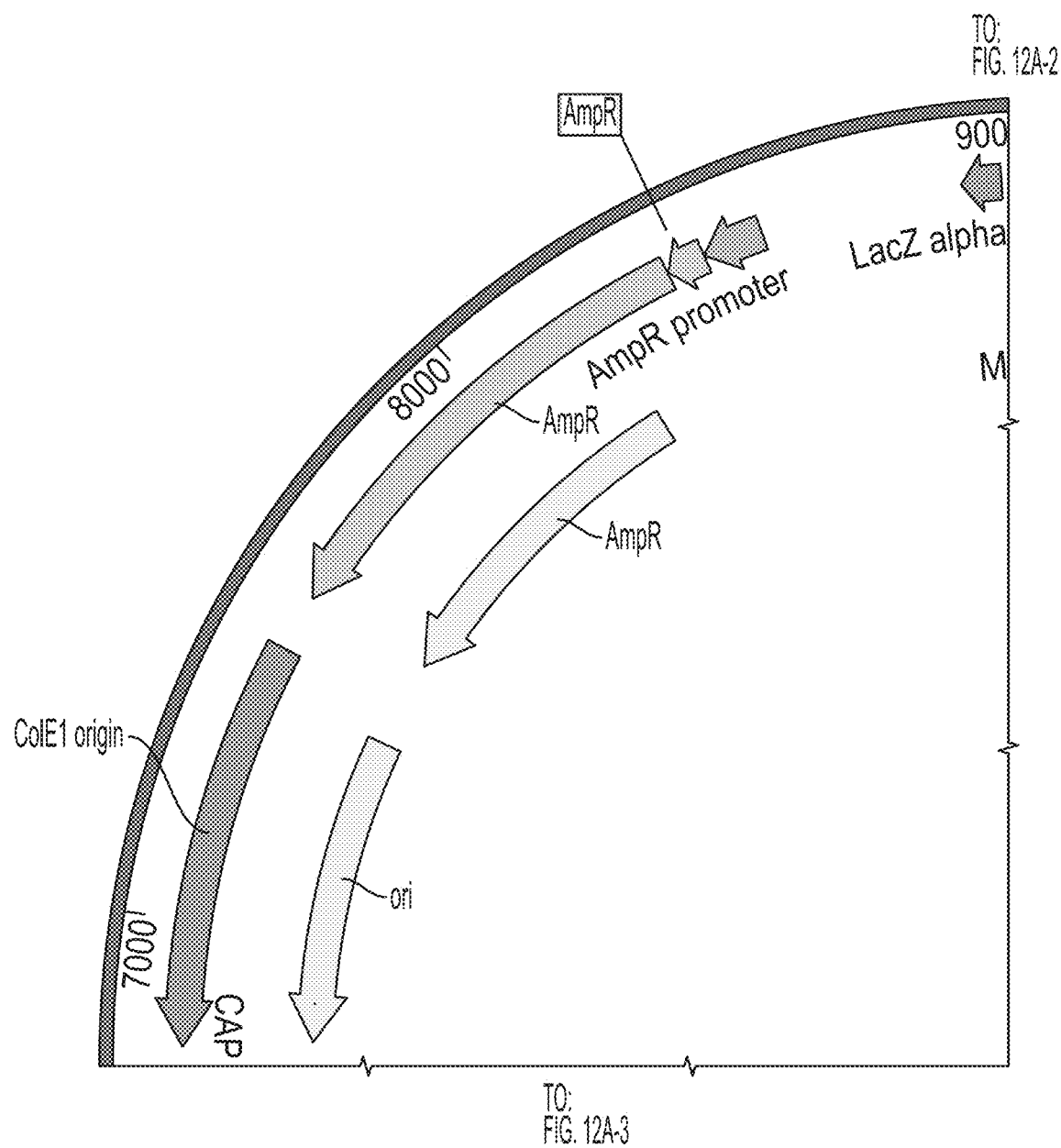
FIGS. 12A-12K shows plasmid maps p510, p511, p514, p515, p516, p517, p518, p519, p520, p521, and p522 for the arCAR proof-of-concept studies.
Figures 2, 12A:
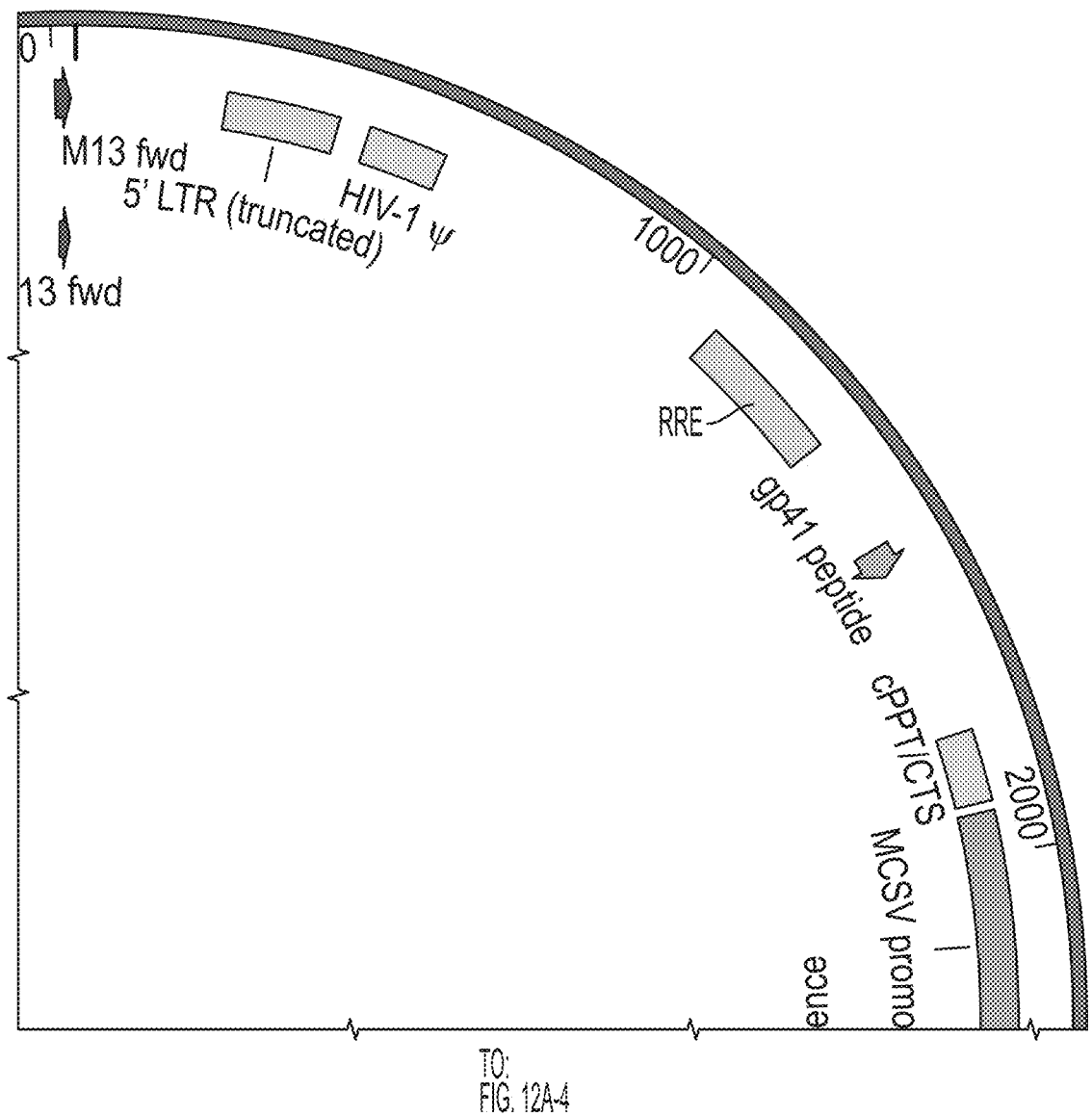
Figures 3, 12A:
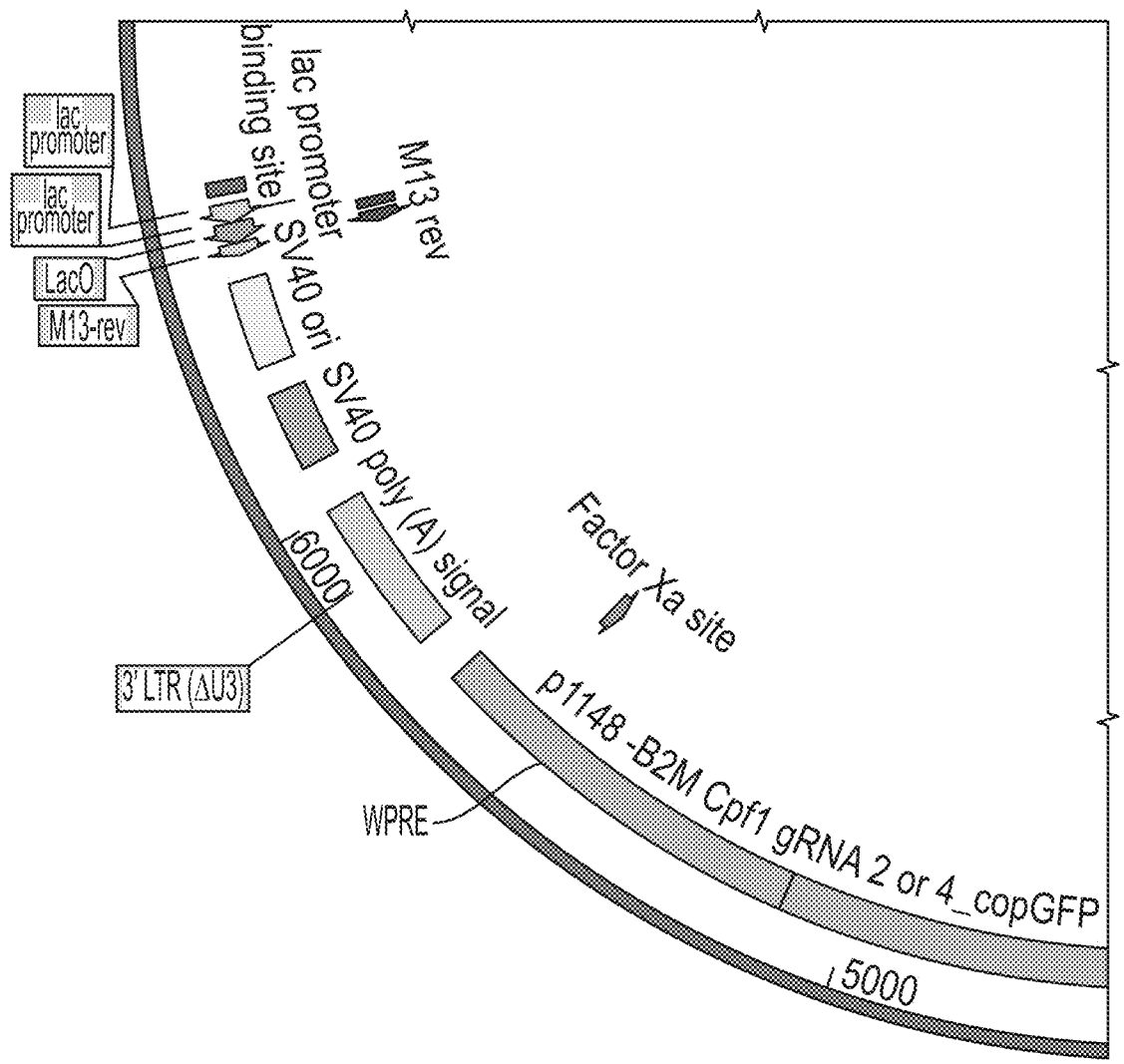
Figures 4, 12A:
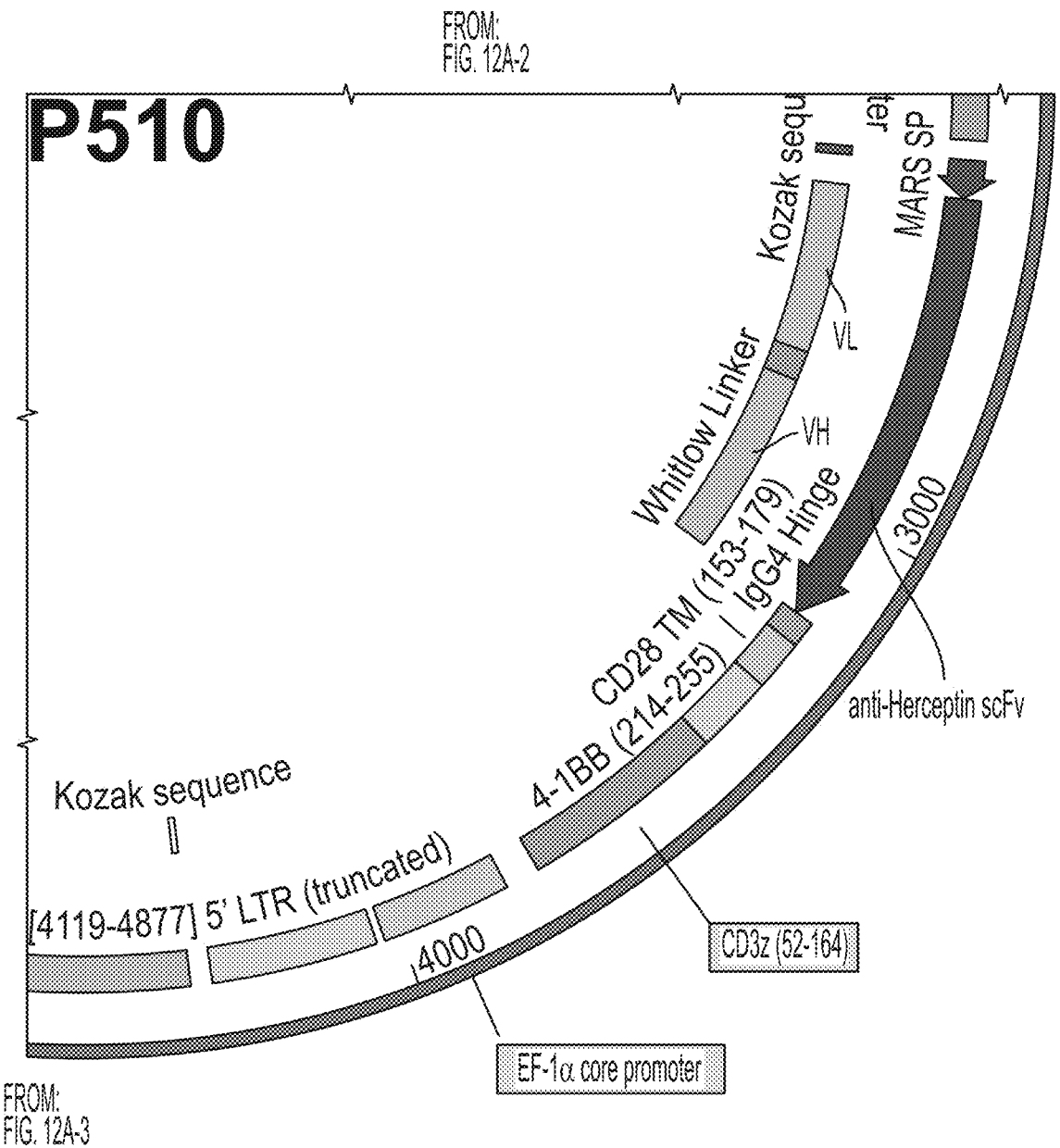
Figures 1, 12B:
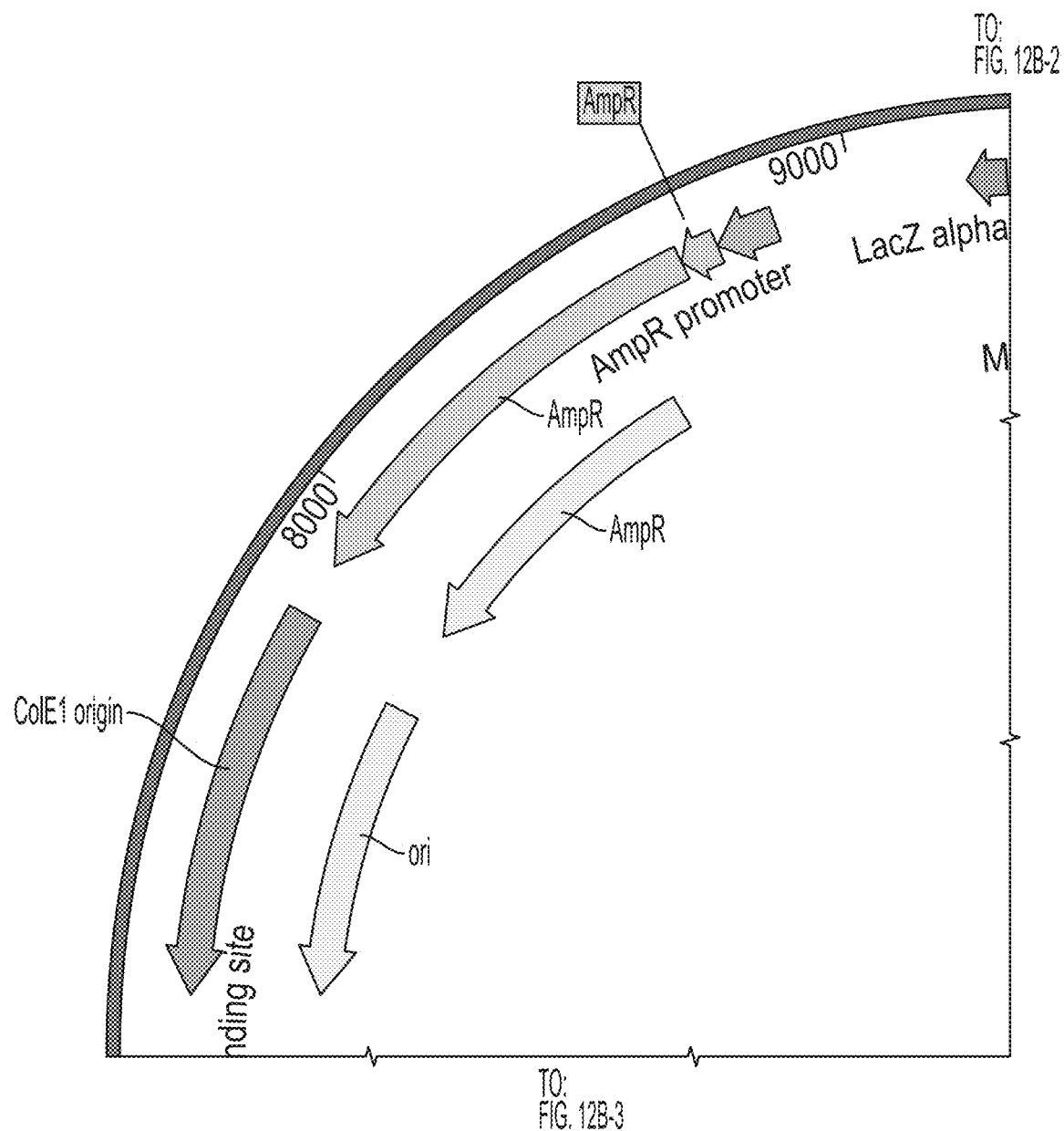
Figures 2, 12B:
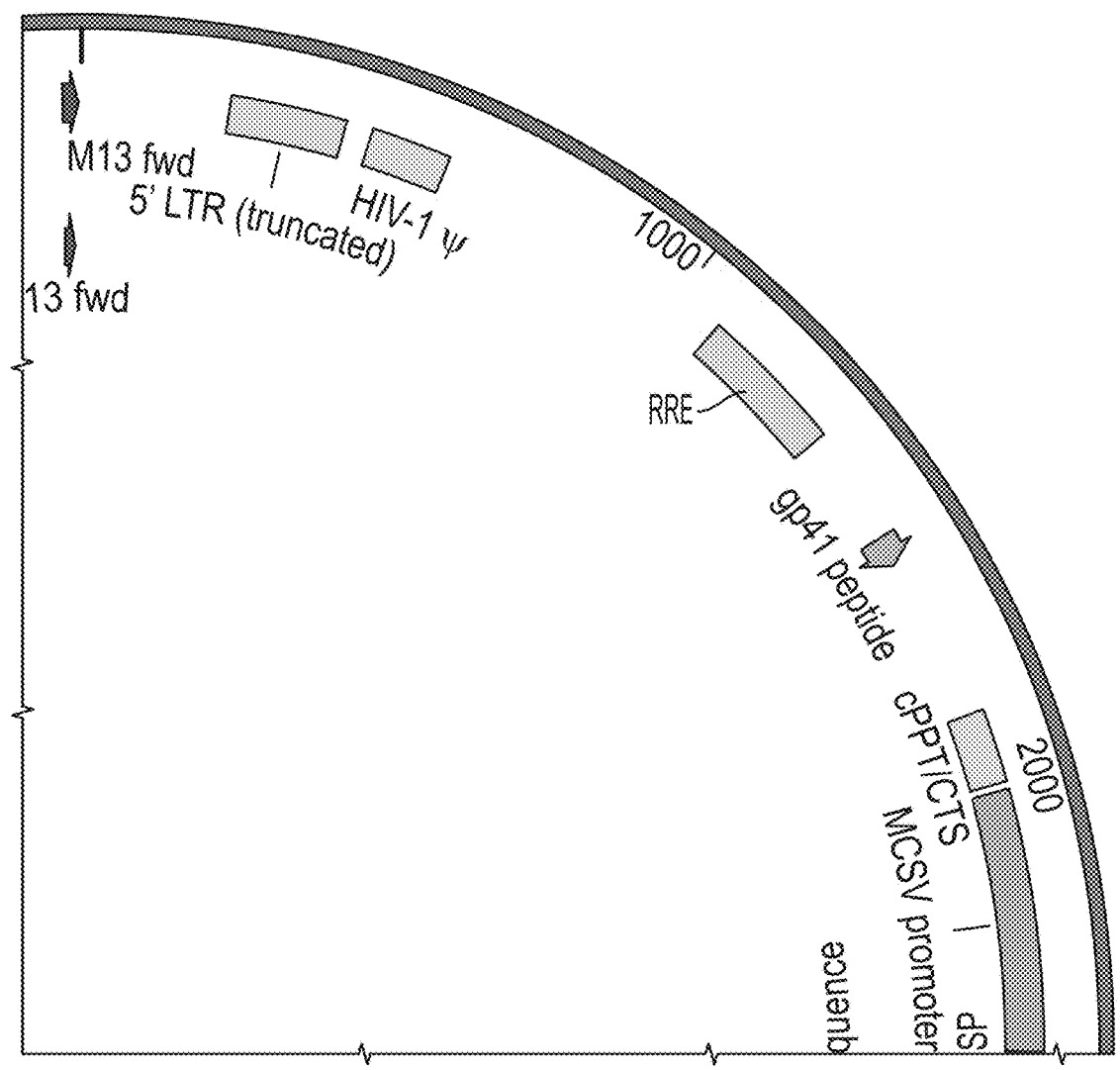
Figures 3, 12B:
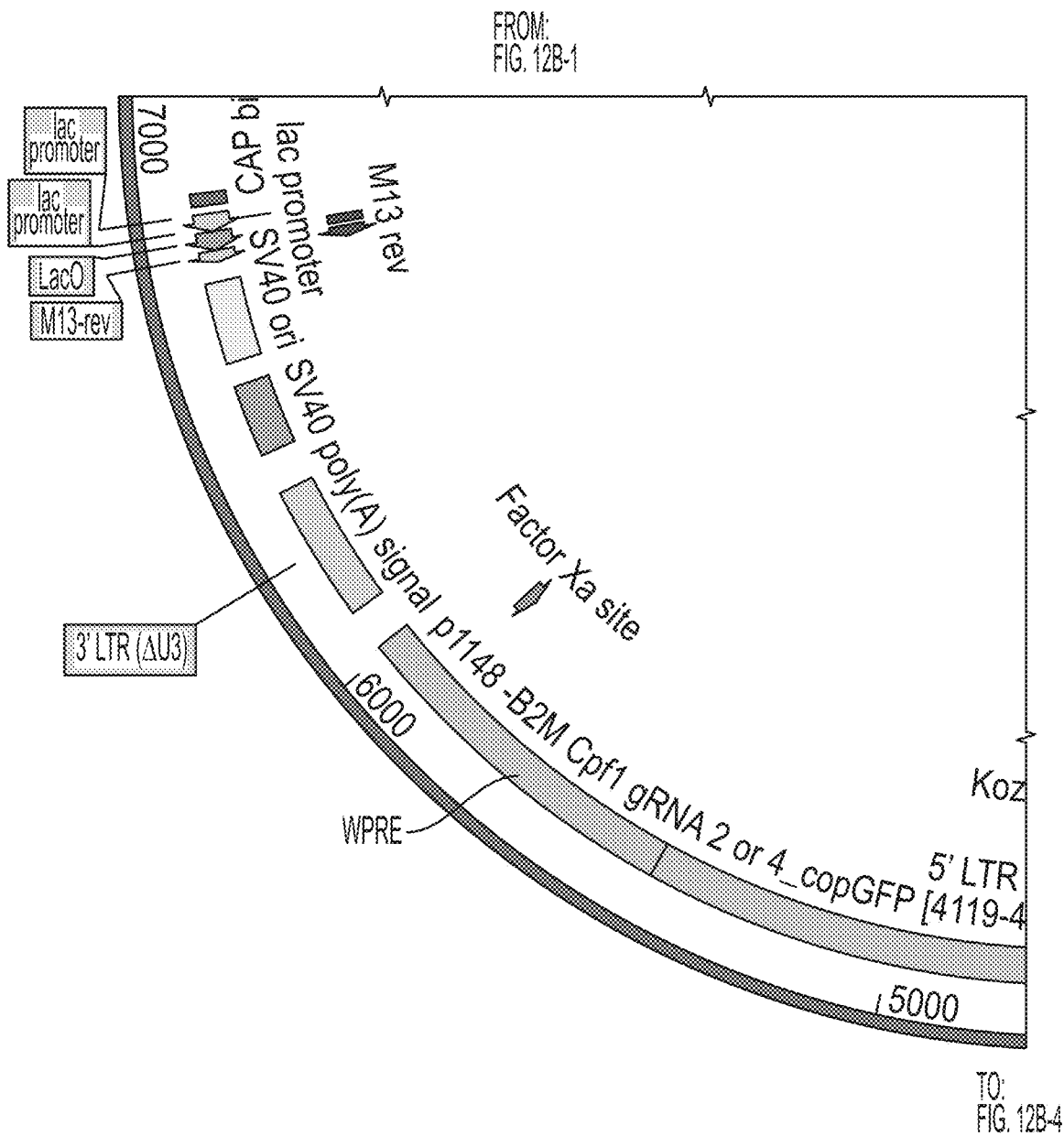
Figures 4, 12B:
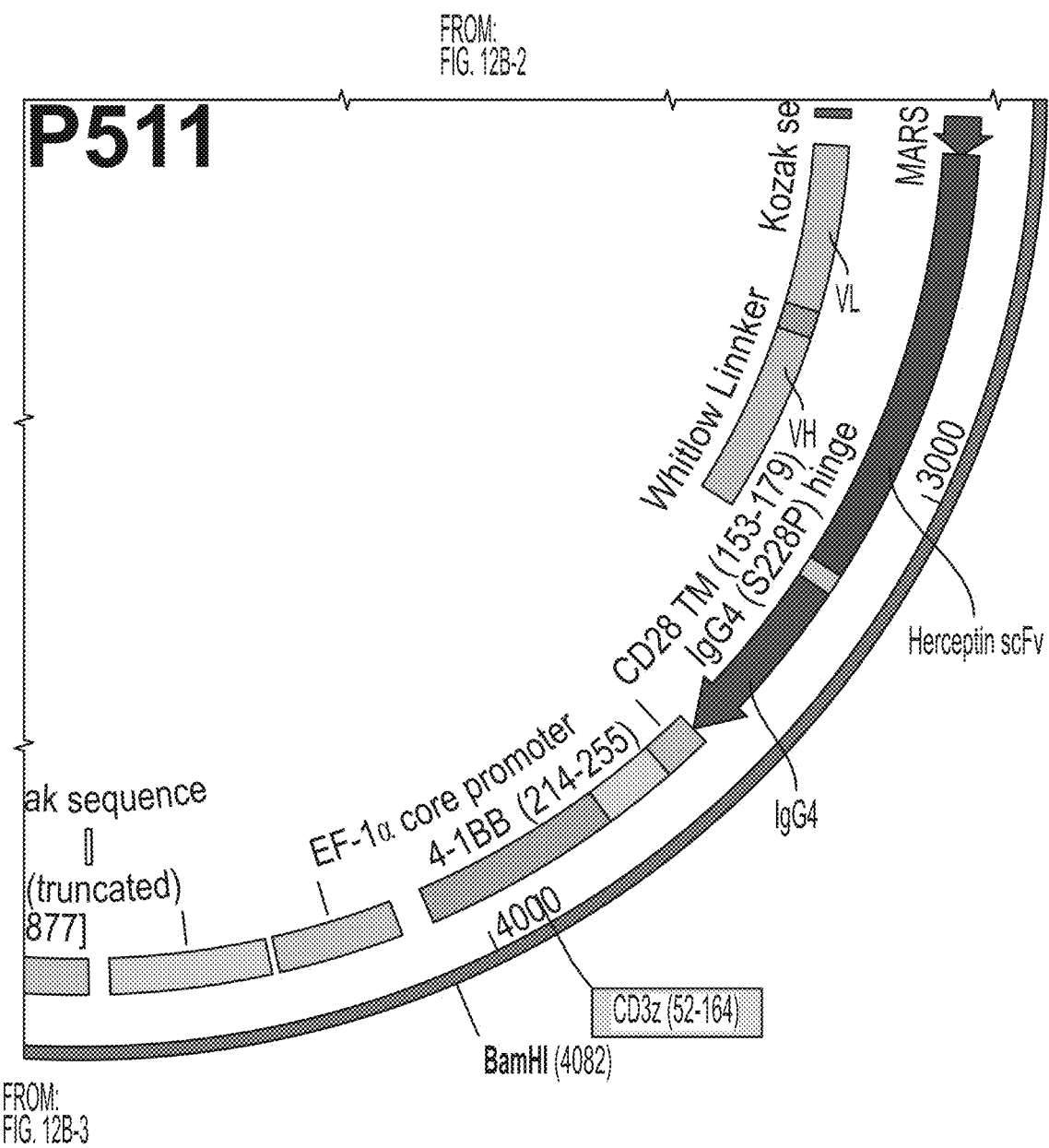
Figures 1, 12C:
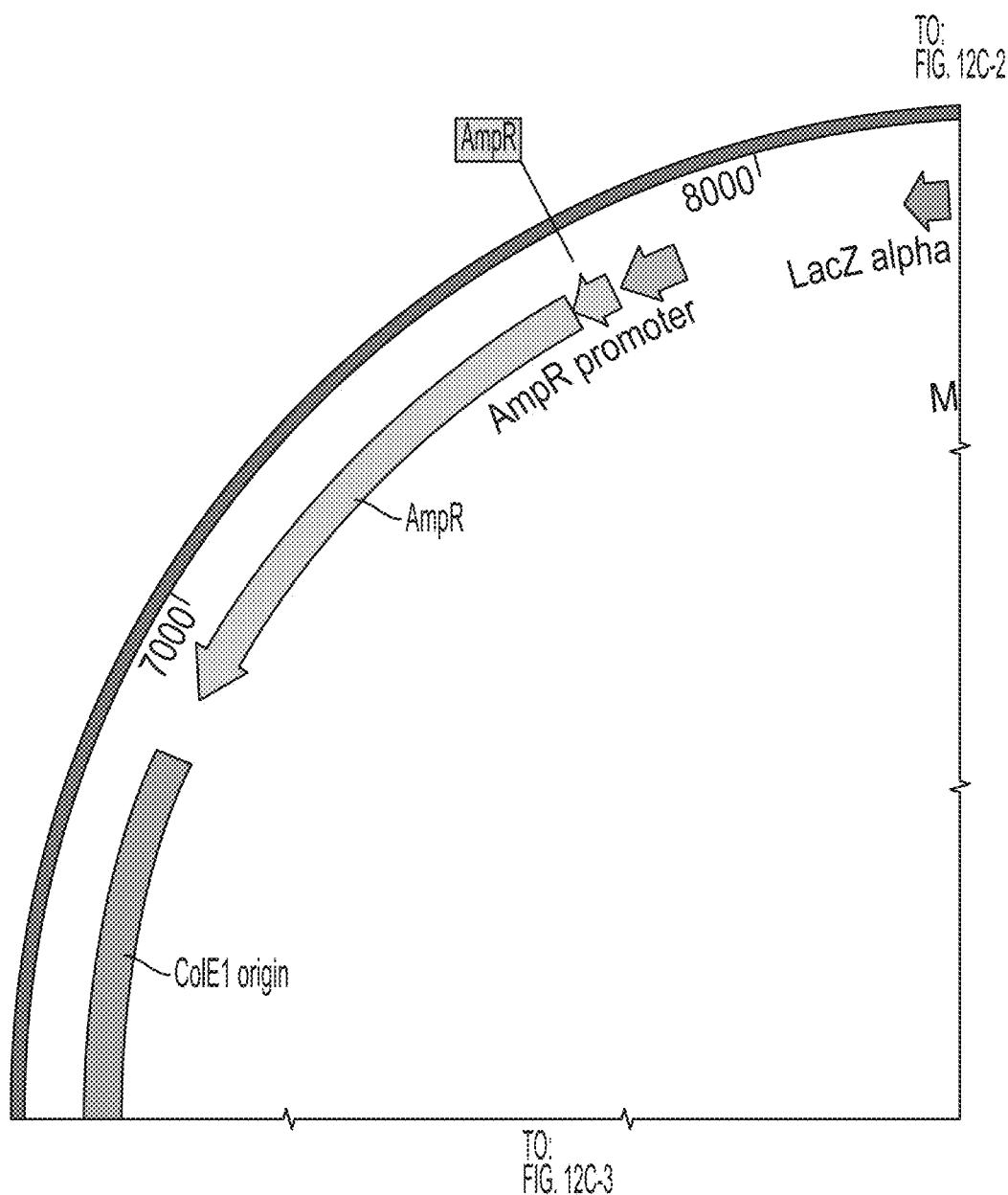
Figures 2, 12C:
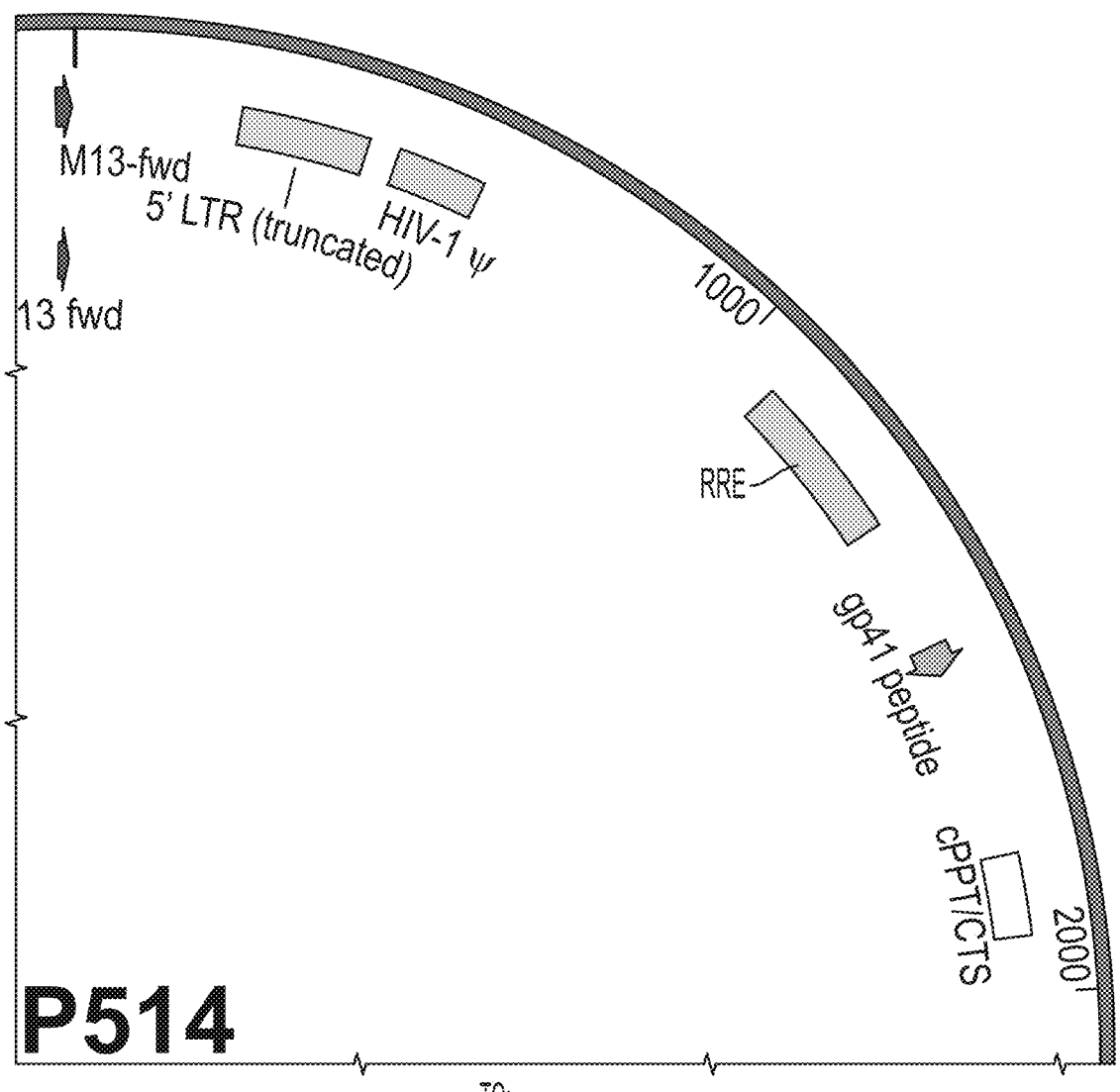
Figures 3, 12C:
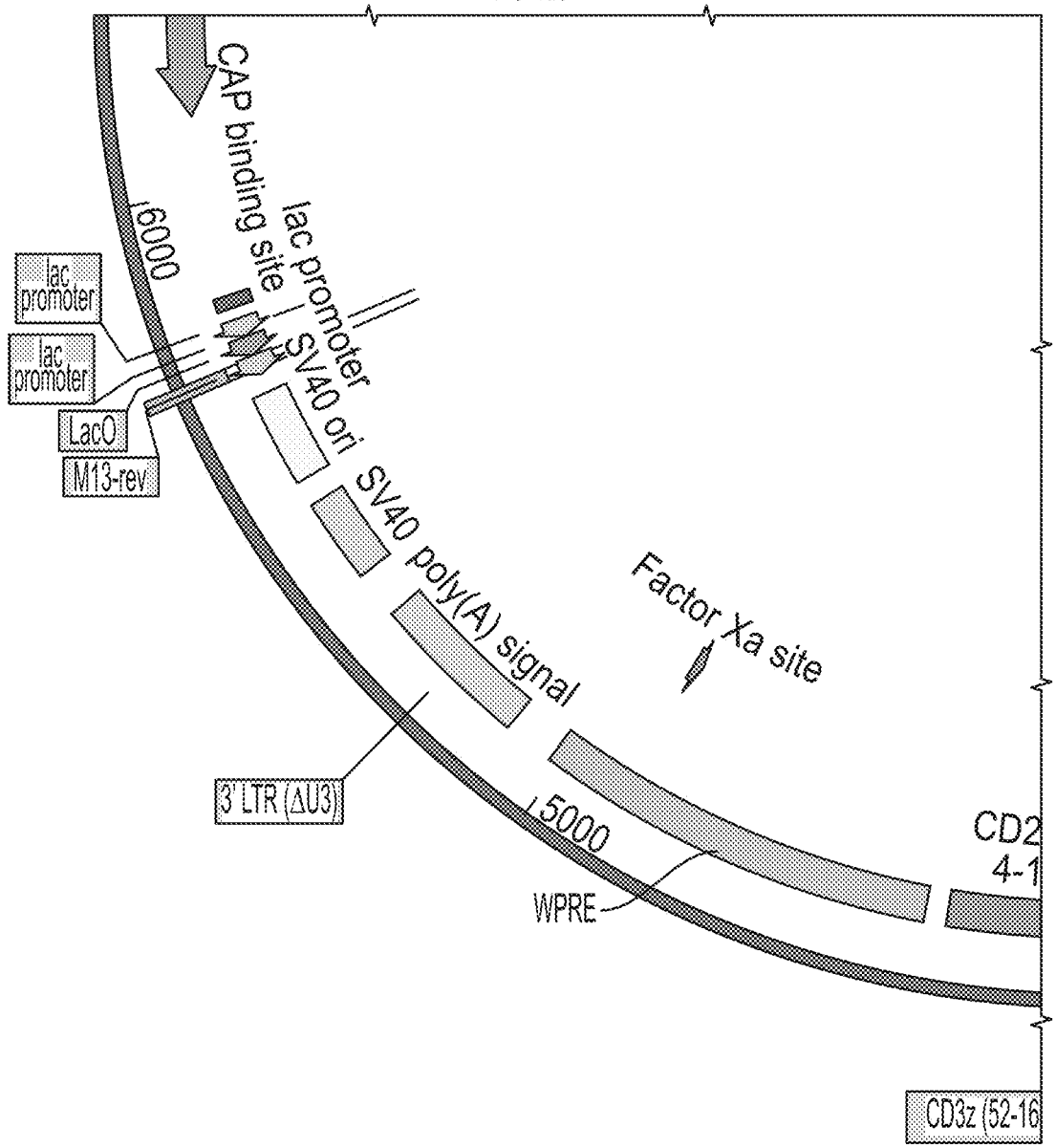
Figures 4, 12C:
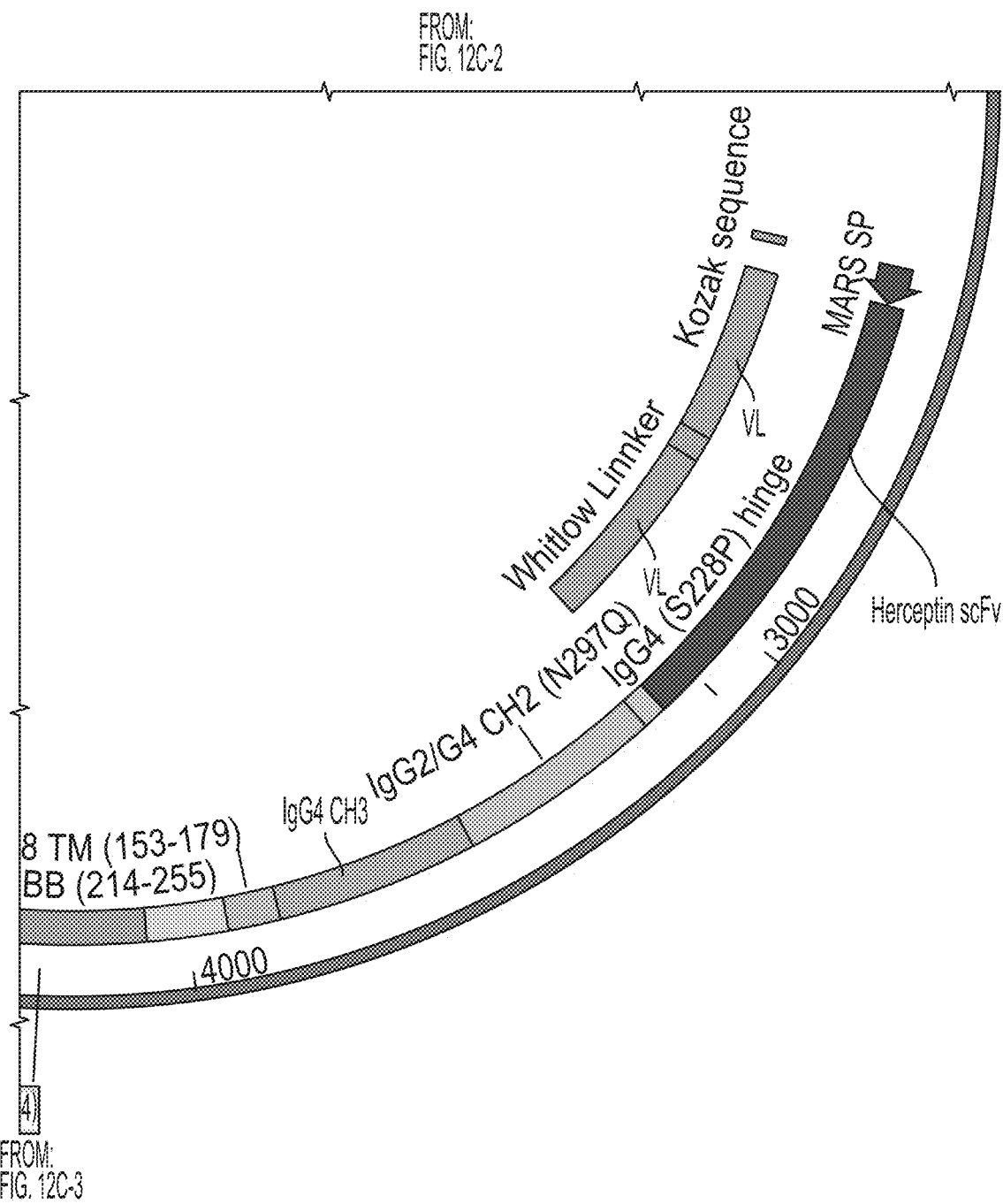
Figures 1, 12D:
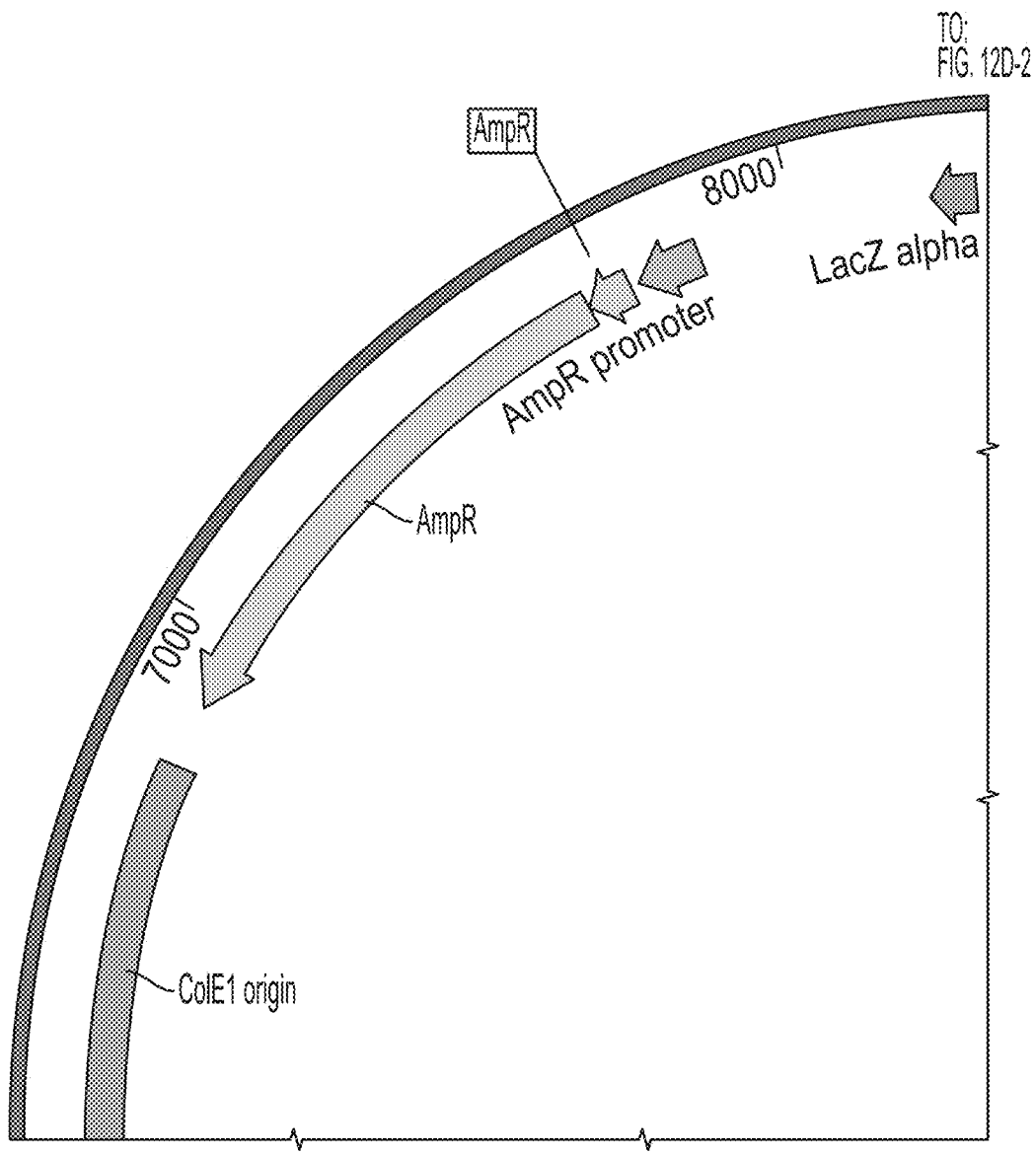
Figures 2, 12D:
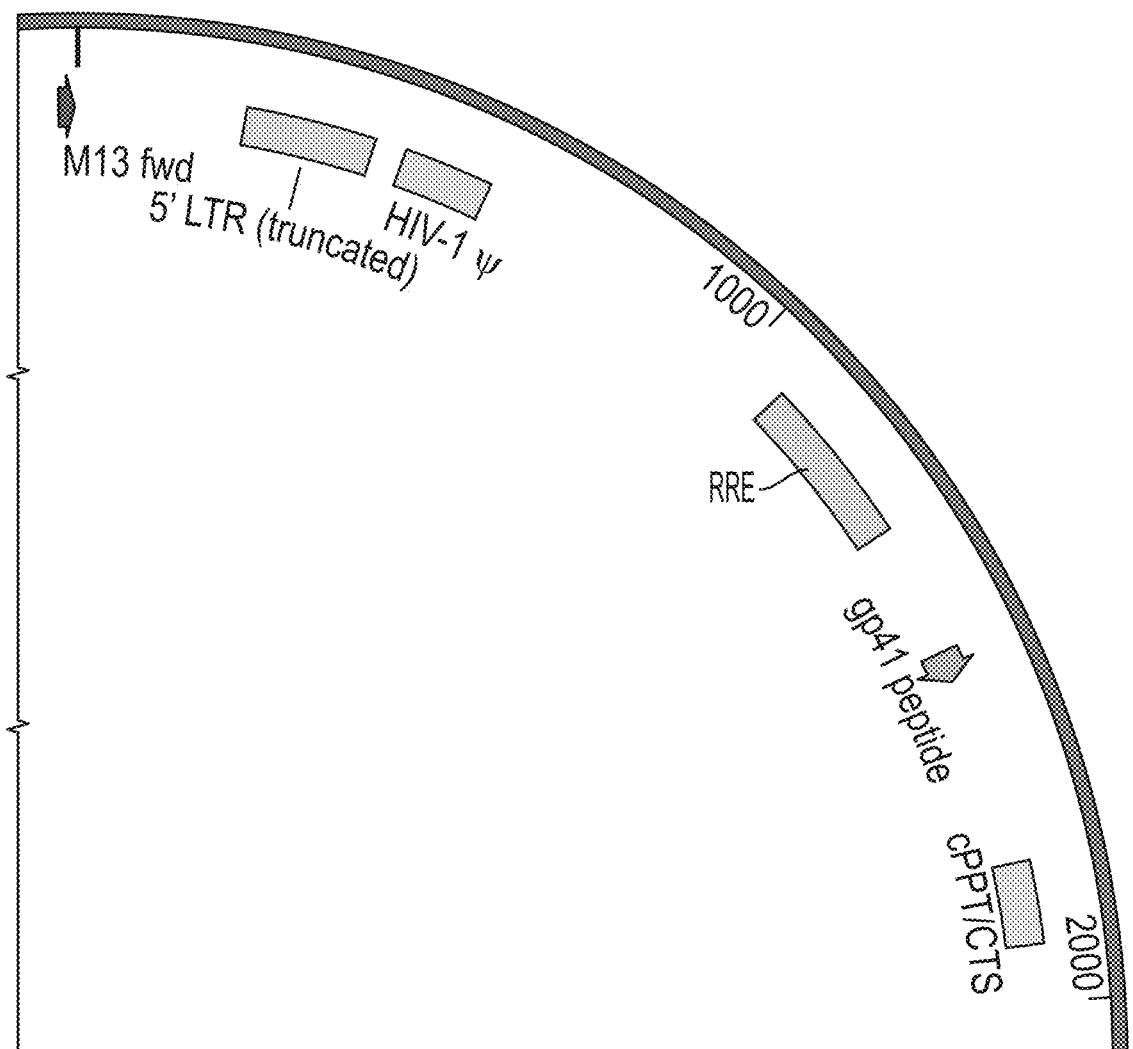
Figures 3, 12D:
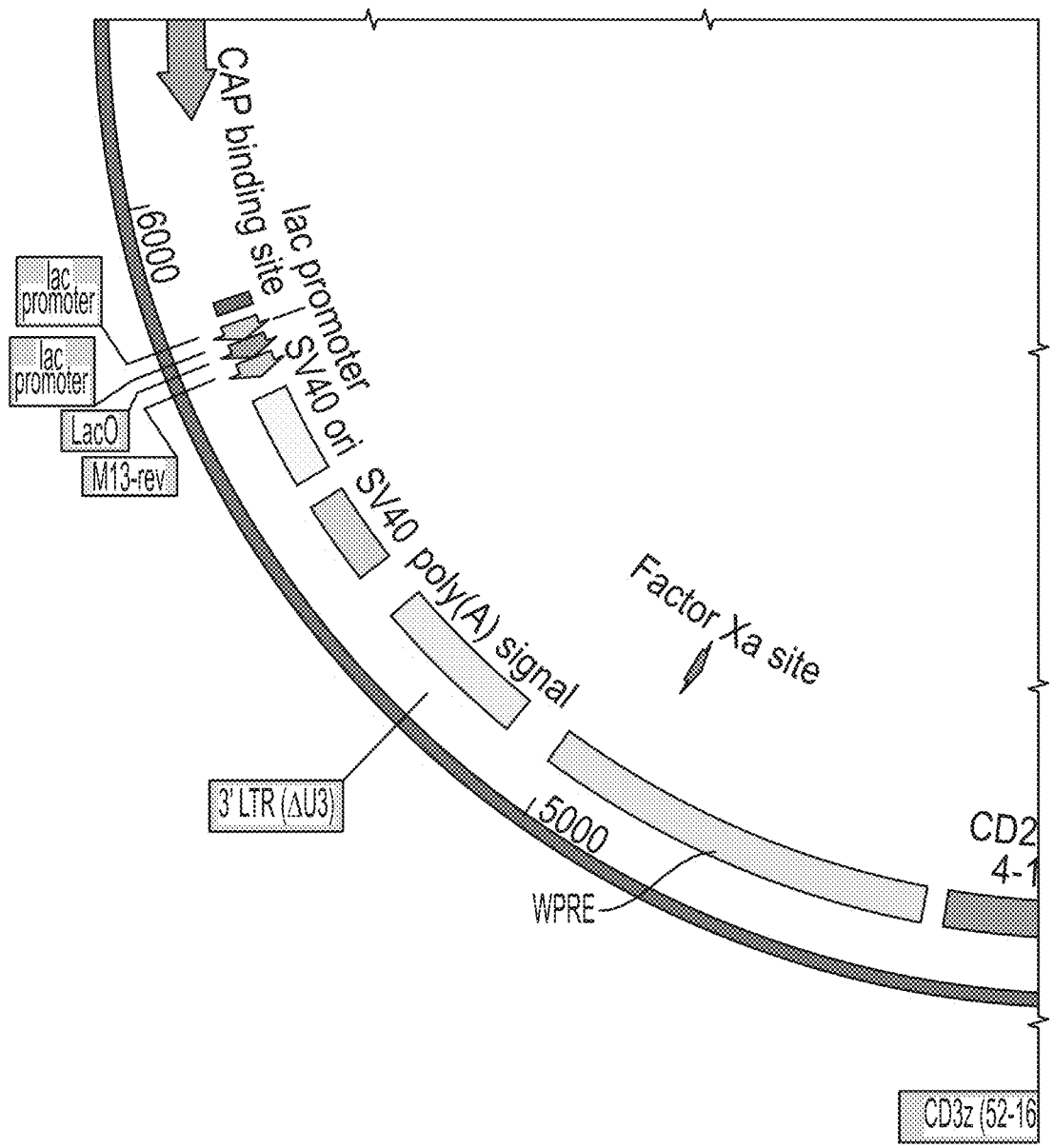
Figures 4, 12D:
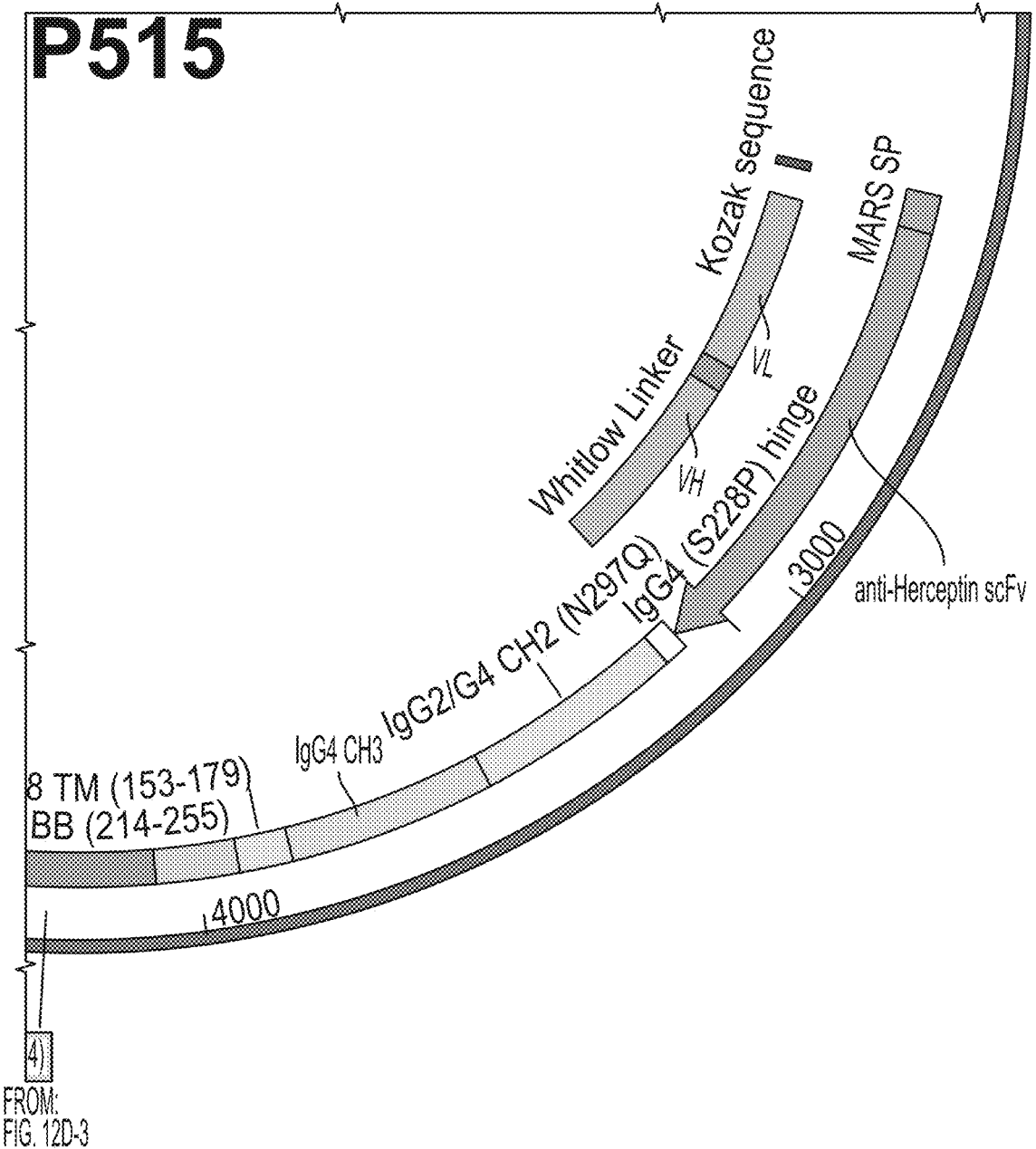
Figures 1, 12E:
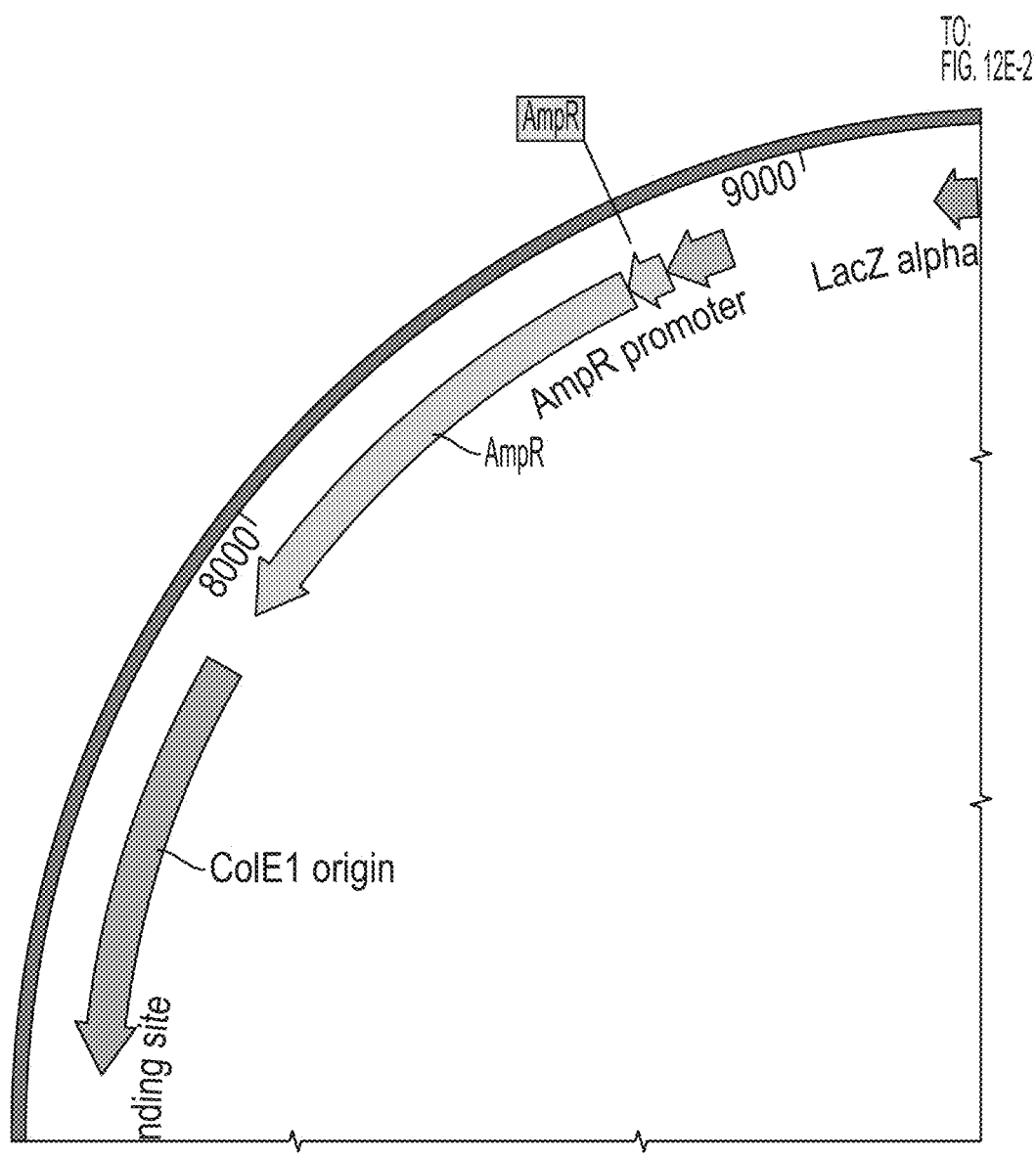
Figures 2, 12E:
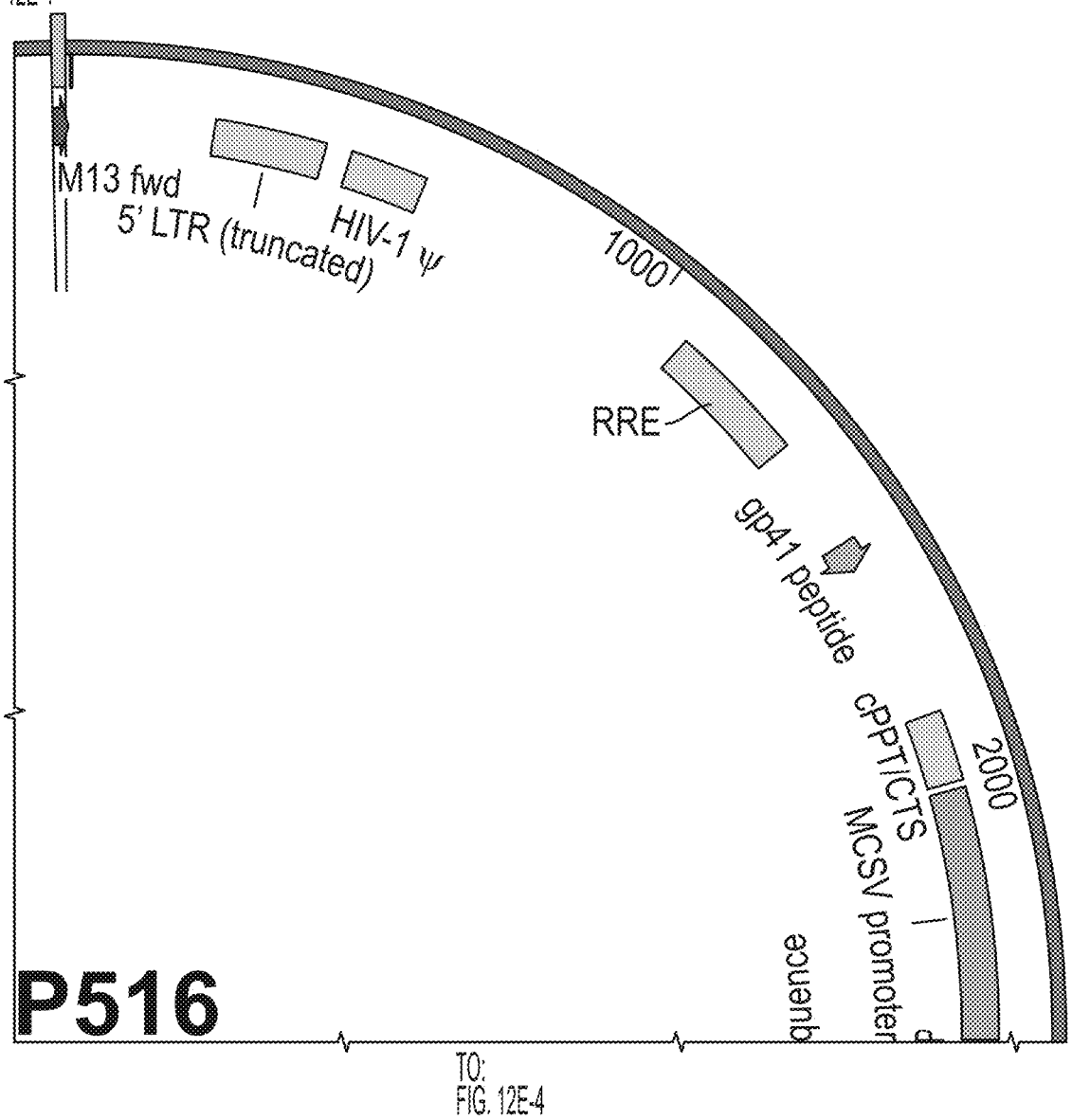
Figures 3, 12E:
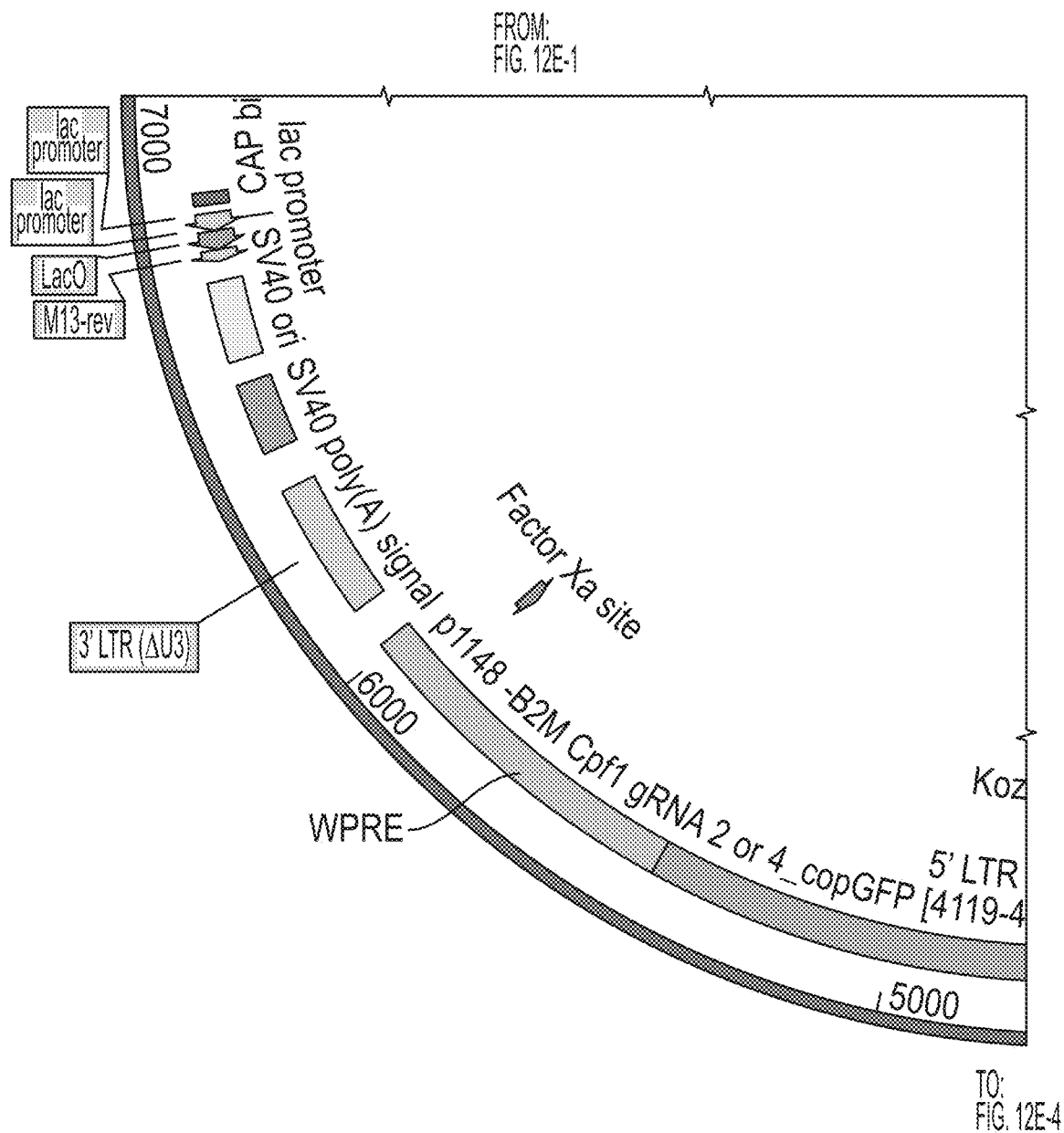
Figures 4, 12E:
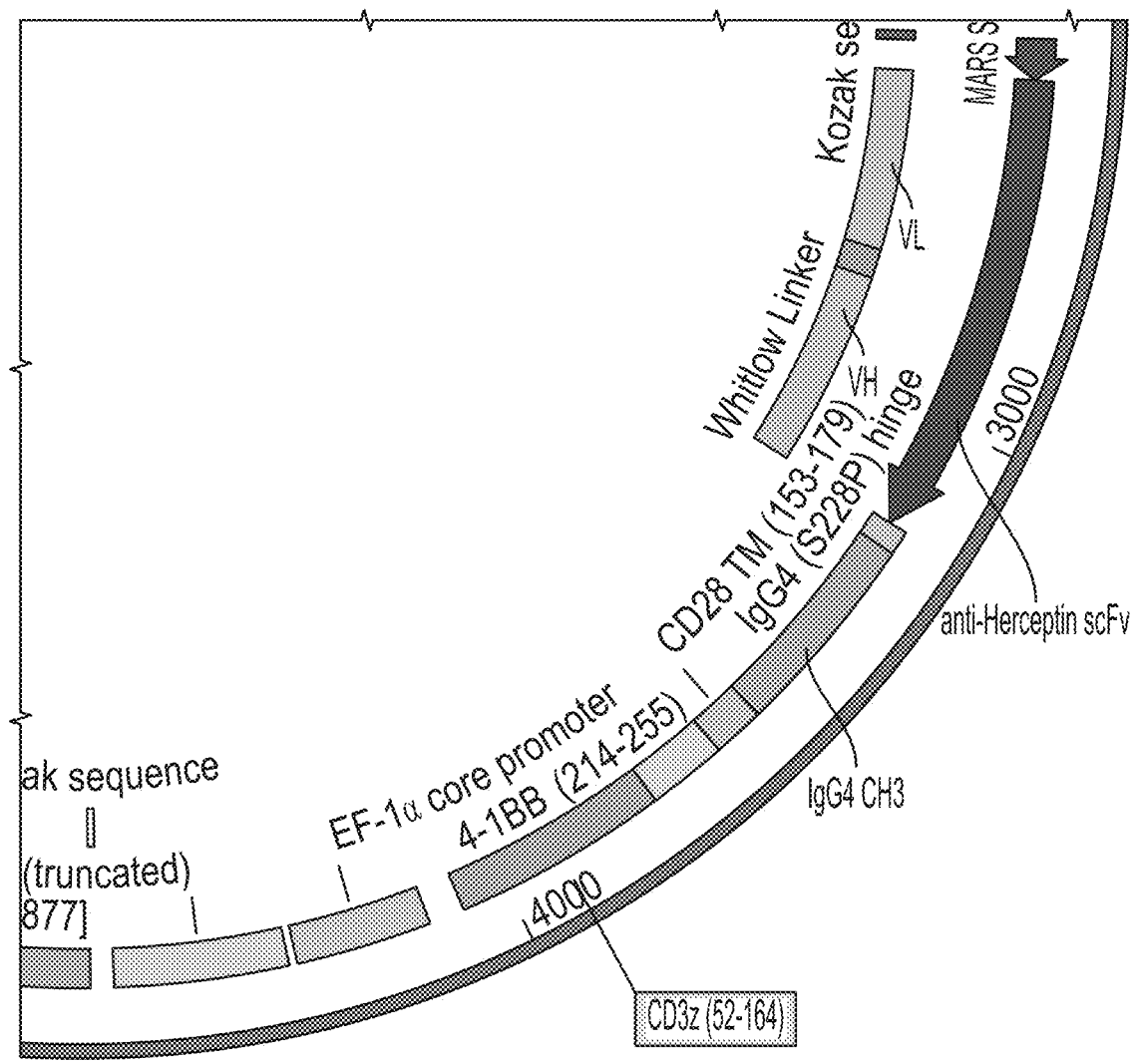
Figure 12F:
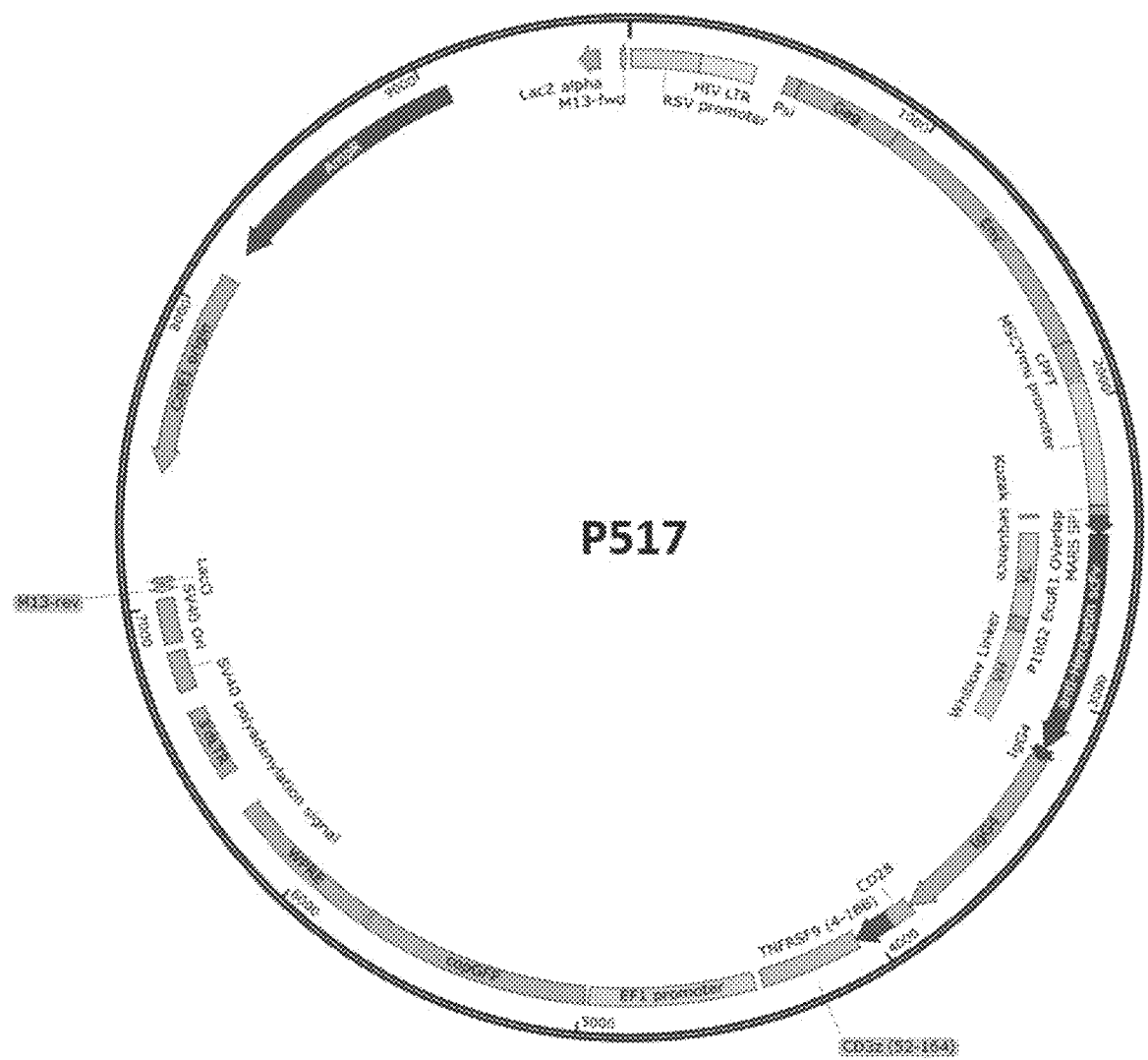
Figure 12G:
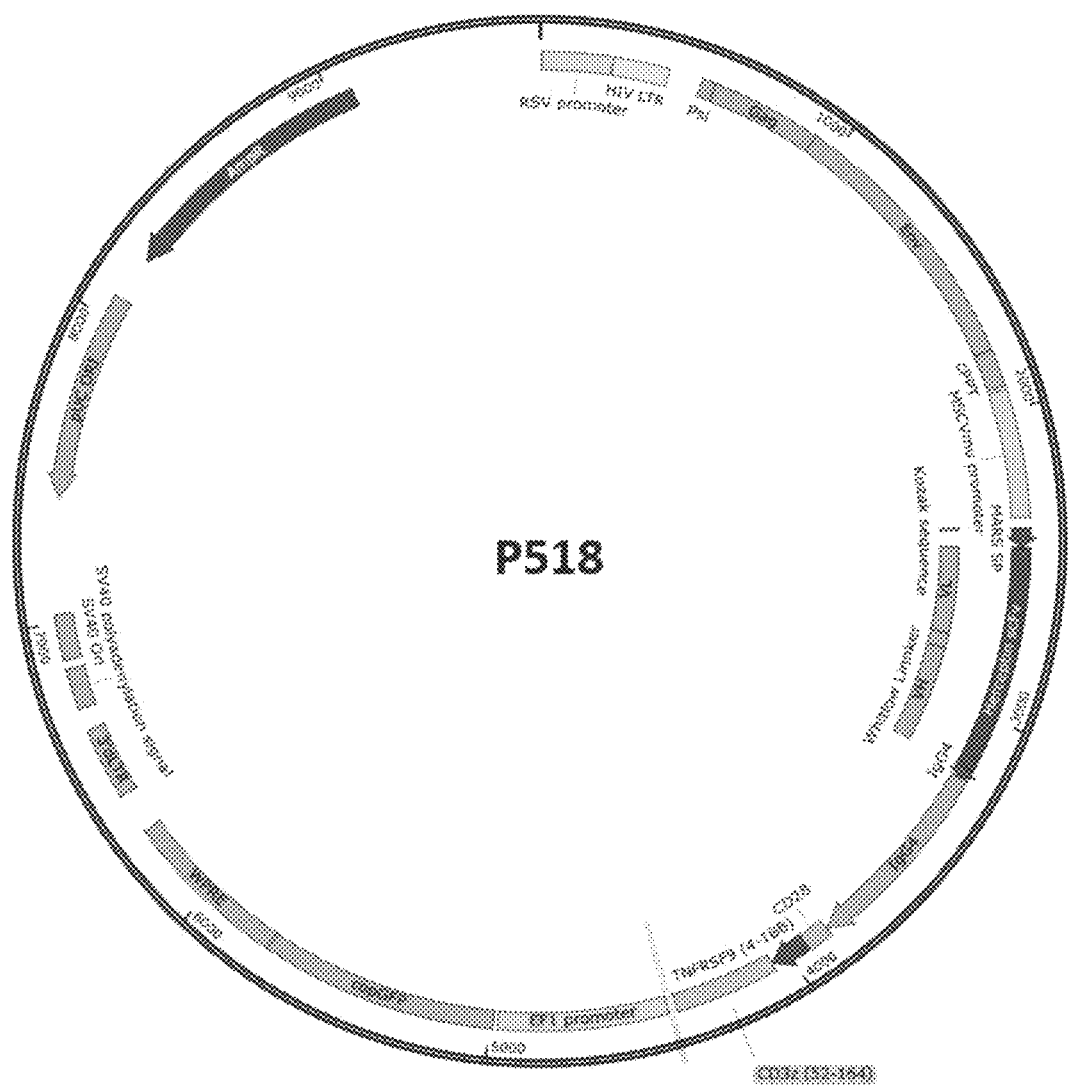
Figure 12H:
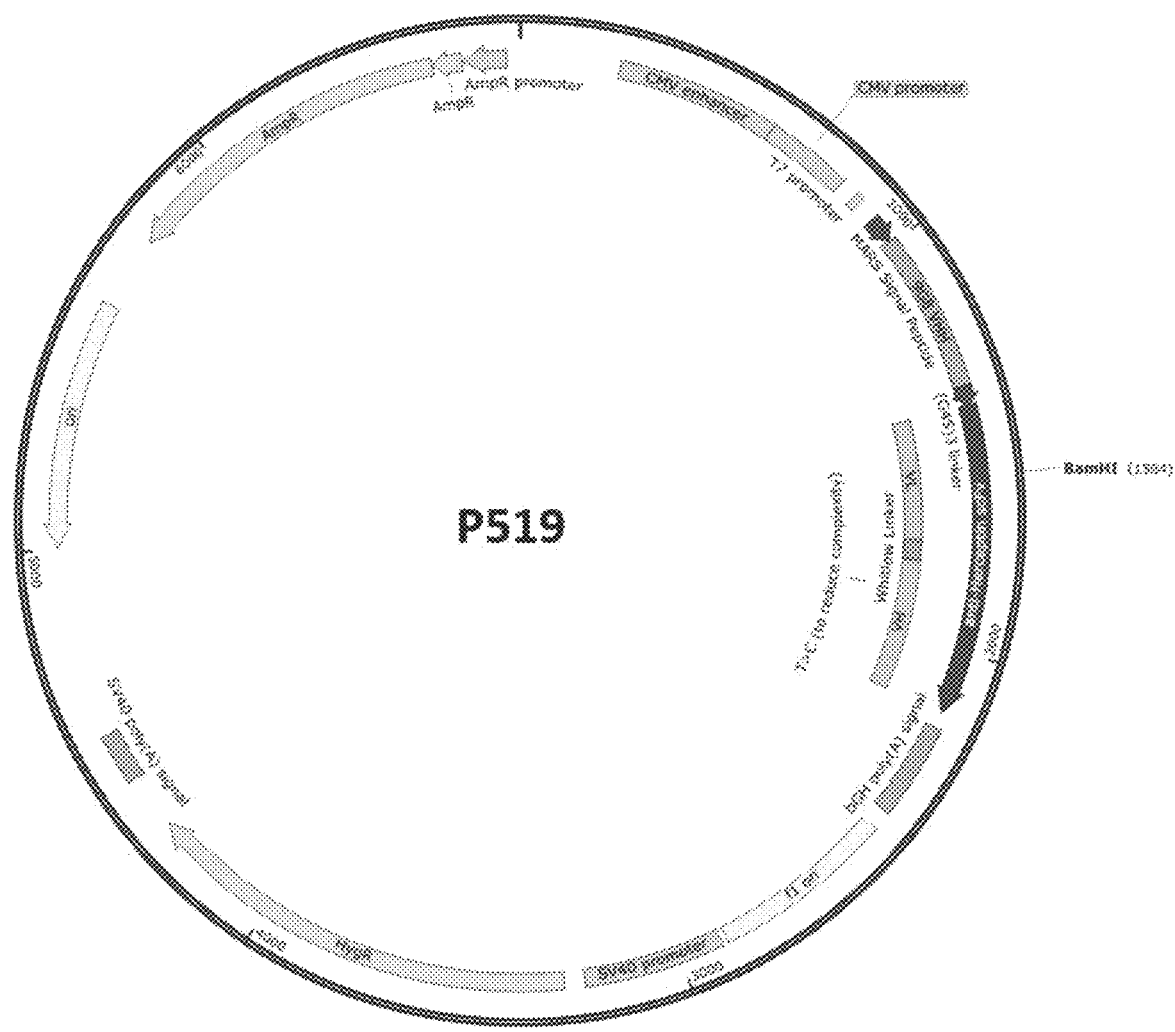
Figure 12I:
Figure 12J:
Figure 12K:

As a final characterization of the specificity of these VHH, CAR Jurkat cells transduced with B11 and D04 VHH were tested, as well as the other anti-HEL VHH of the panel of candidates, for binding to biotinylated chicken and human lysozyme, to ensure there was no binding to human lysozyme protein. Both the B11 (p242) and D04 (p244) VHH show binding to chicken lysozyme with no cross-reactivity to human lysozyme protein (FIG. 11E).

Example 6. Humanization of the B11 and D04 VHH

The B11 and D04 proteins were derived from the camelid VHH phage display library at Distributed Bio (San Francisco, Calif.). To limit the possibility of immunogenicity of these VHH, they were humanized in the framework regions of the VHH. From this Example onward, references to B11 and D04 are to the humanized VHH.

TABLE 11

Purification data for B11 and D04

| DNA ID | Protein ID | VHH | Construct Format | Conc. (mg/mL) | Vol (uL) | Yield (ug) | % Monomer |
|---|---|---|---|---|---|---|---|
| P1184 | PROT951 | LYSO_CW_P01_B11 | VHH_IgG1.Fc | 1.53 | 200 | 306.7 | 98.50 |
| P1186 | PROT949 | LYSO_CW_P01_D04 | VHH_IgG1.Fc | 1.94 | 200 | 387.1 | >99 |

TABLE 12

Humanized versions of the originally camelid VHH B11 and D04

| VHH | CAR Vector Number | Amino Acid Sequence | SEQ ID NO |
|---|---|---|---|
| hyLYSO_CW_P01_B11 | P1649 | EVQLLESGGGLVQPGGSLRLSCAASGGIFSGGRMGWFRQAPGKERE FVAAVITRGGSTYYADSVKGRFTISRDNSKNTLYLQMNSLRAEDTA VYYCAASEVTYDEGRYIGTKSTYDTWGQGTQVTVSS | 111 |
| hyLYSO_CW_P01_D04 | P1650 | EVQLLESGGGLVQPGGSLRLSCAASGRIFSIYDTIGWFRQAPGKER EFVAATITTAGITTYDDSVKGRFTISRDNSKNTLYLQMNSLRAEDT AVYYCYVRVGRGDYWGQGTQVTVSS | 112 |

The humanized B11 and D04 went through similar characterization steps as the camelid versions to ensure that humanization of the framework regions did not compromise their biophysical characteristics, ability to express as CARs, or their properties when present on a CAR.

TABLE 13

Purification data for humanized B11 and D04

| DNA ID | PROT ID | VHH | Conc. (mg/mL) | Volume (mL) | Yield (mg) | % Monomer | Endotoxin units/mL |
|---|---|---|---|---|---|---|---|
| P1376 | PROT1045 | huLysoB11 | 4.21 | 2.85 | 12.0 | >99 | <1 |
| P1377 | PROT1046 | huLysoD04 | 3.17 | 4.20 | 13.3 | >99 | <1 |

Figure 13:
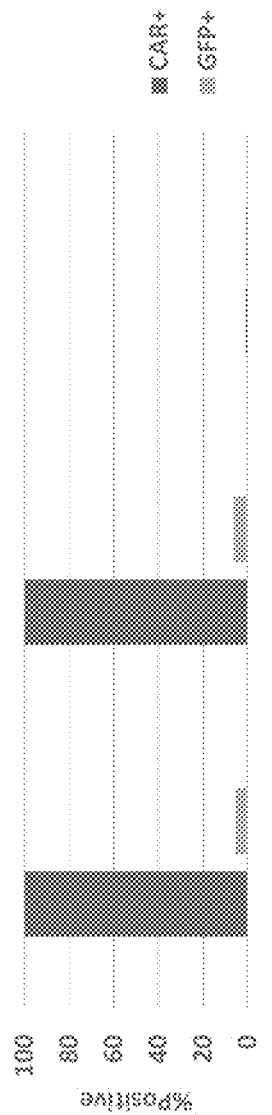
FIG. 13 shows CAR and GFP expression of Nurkat cells (Nur77 reporter line of Jurkat cells) transduced with lentivirus (LV) containing the humanized B11 (p1649) and D04 (p1648) CARs. Also shown are results for untransduced (UTD) Nurkats. CAR expression was measured by the polyclonal anti-camelid VHH cocktail from Genscript (e.g., sufficient homology between the humanized and camelid versions of VHH for robust detection).

As before, each VHH CAR was transduced into Jurkat cells. Additionally, each VHH CAR was transduced into Nurkat cells, the Nur77 reporter line of Jurkat cells (Nurkat). This cell line contains a GFP reporter that is responsive to Nur77, a transcription factor that is activated by CD3z stimulation and serves as a reporter for CAR activation. Thus, activation via a CAR in Nurkat cells causes the cells to express GFP. FIG. 13 shows CAR and GFP expression of Nurkat cells transduced with lentivirus containing the humanized B11 (p1649) and D04 (p1648) CARs. UTD cells are untransduced Nurkat cells. CAR Expression was measured using the polyclonal anti-camelid VHH cocktail (Genscript). These results indicated that the expression of the B11 and D04 VHH as CARs was not impacted by the humanization of their sequences. Additionally, the lack of GFP expression in these CAR Nurkats show that there is very little tonic signaling mediated by the humanized versions of the CARs.

Figure 14:
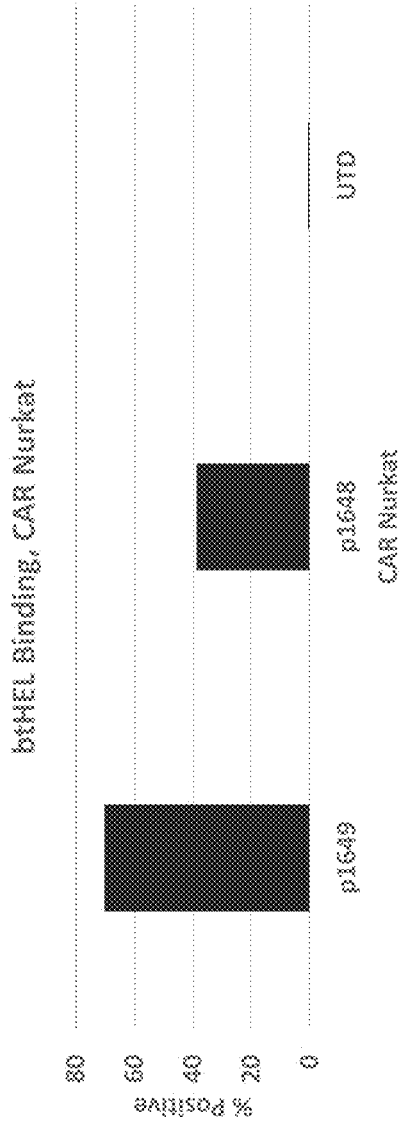
FIG. 14 shows B11 (p1649) and D04 (p1648) CAR Nurkat cells stained with biotinylated HEL detected with streptavidin-APC via flow cytometry. UTD are untransduced Nurkat cells used as a negative control.

To ensure that there was no change in the binding characteristics of each VHH as a result of humanization, we tested whether these humanized VHH CARs could still bind HEL FIG. 14 shows the results of an assay in which B11 (p1649) and D04 (p1648) CAR Nurkats were stained with biotinylated HEL and detected with streptavidin-APC via flow cytometry. UTD are untransduced Nurkats as a negative control. Both B11 and D04 retained their ability to bind HEL after humanization.

Example 7. Phage Display Panning for Anti-Idiotype VHH Against B11 and D04

Humanized B11 and D04 VHH were used in phage library panning to identify specific, anti-ID VHH against each specifically. The synthetic VHH phage library consisted of four sub-libraries that are differentiated primarily by the length of their CDR3 sequence, with library 1 (CNTY1) having the shortest CDR length, and libraries 3 and 4 (CNTY3 and CNTY4) having the longest CDR lengths.

Figure 15:
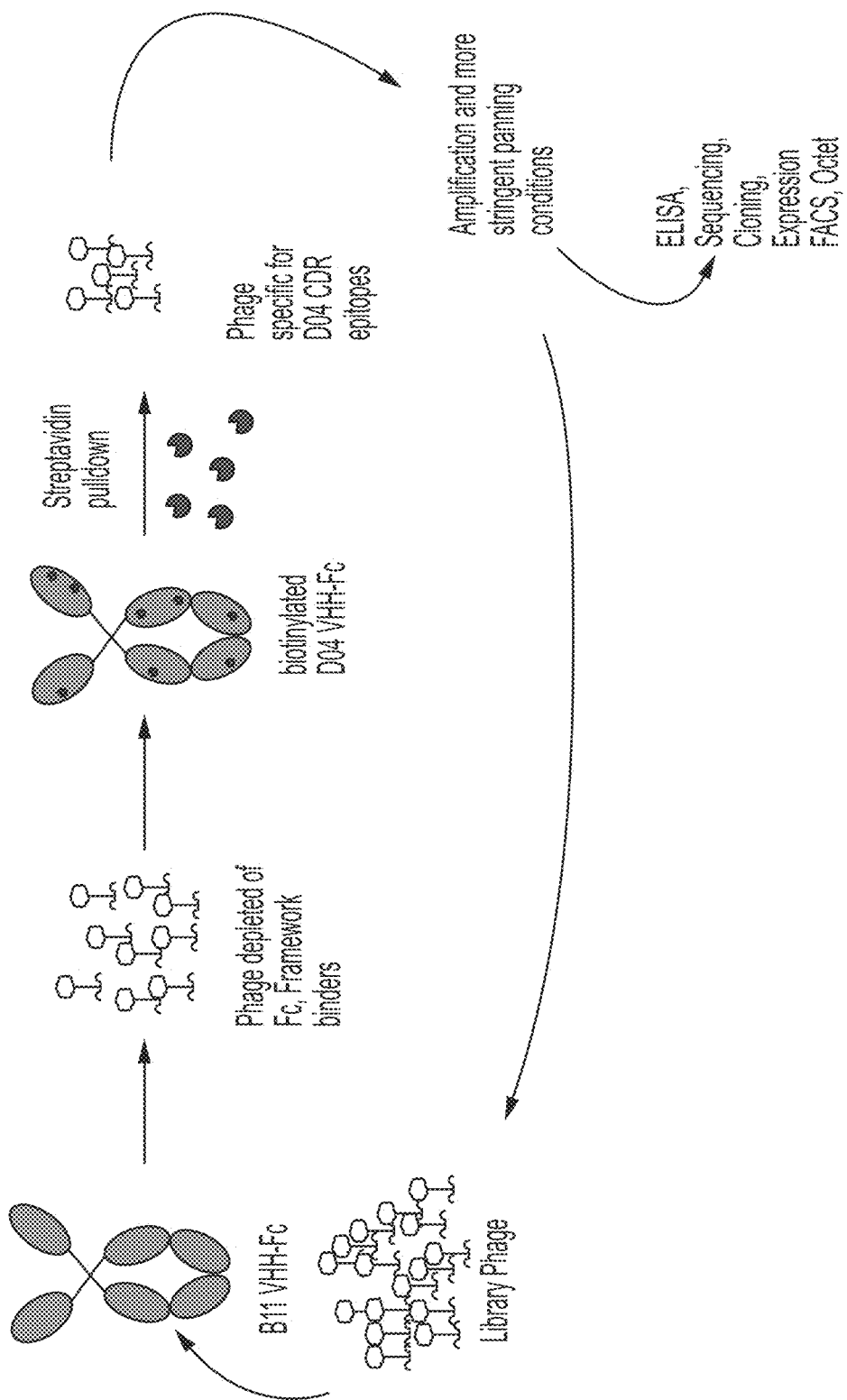
FIG. 15 shows an overview of the phage display panning schema. The schema for anti-idiotype discovery against D04 is shown as an example. Likewise, for anti-idiotype discovery against B11, the two VHH would swap places in the diagram.

One panning schema used is shown in FIG. 15. In this method, the anti-idiotype VHH were discovered against D04 by first depleting the library against the B11-Fc protein. This was done to remove any phage that bind the framework regions of the VHH and the Fc portion of the protein. This depleted phage output was then panned on biotinylated D04-Fc protein. The biotinylated D04, with any phage binders could be isolated via streptavidin. The output phage were amplified in bacteria and used in further rounds of the panning with increasingly stringent panning conditions. Alternatively, the VHH displayed by the phage could be tested by ELISA for binding to D04 or B11 protein, sequenced, and cloned into expression vectors for more rigorous testing. This phage library panning approach was used to identify VHH binders to both D04 and B11.

Figure 16A:
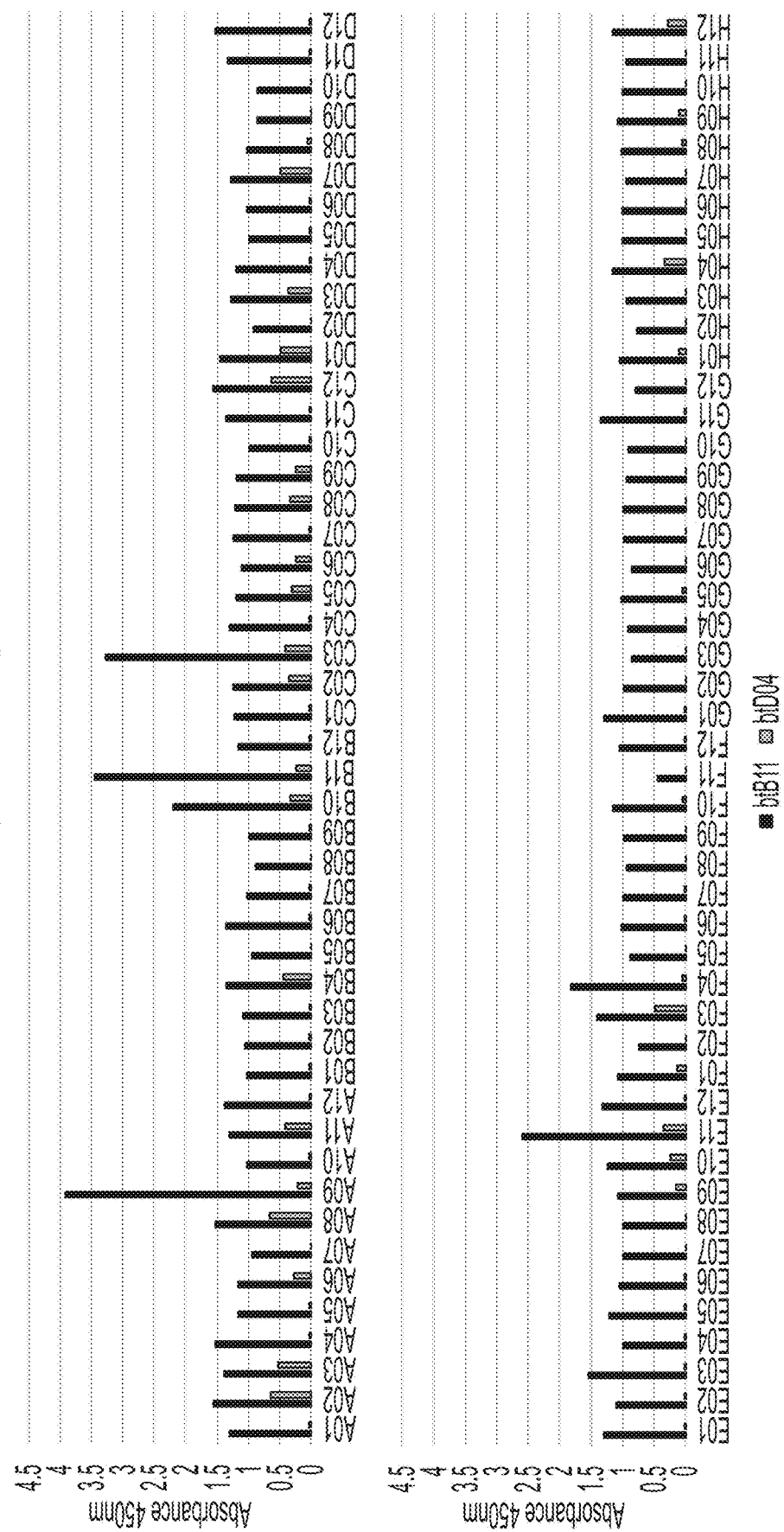
Figure 16D:
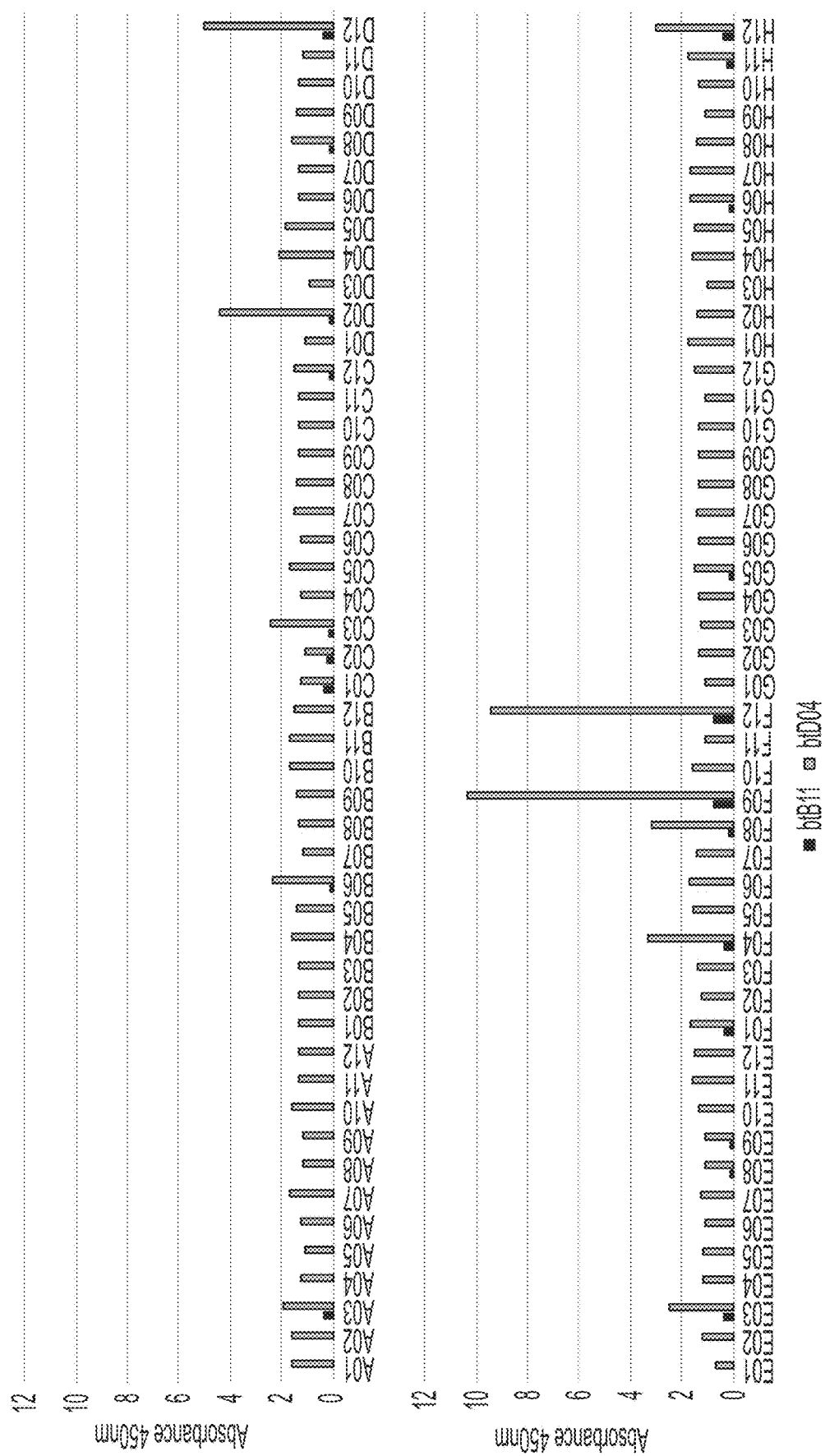

This panning schema was iterated 4 times with progressively decreasing target antigen concentration to select for high affinity binders (200 nM for the first and second rounds, 50 nM for the third round, and 10 nM for the fourth round). The output phage of the final round of panning was used to transform bacteria to single colonies, which were screened as periplasmic extract (PPE) in an ELISA against both the target VHH and off target VHH (FIG. 16).

PPE samples that showed specific responses to their target protein and little response to the off target proteins were selected for additional characterization. 6 unique B11 binders and 18 unique D04 binders were identified. These unique sequences were cloned into Fc-fusion expression vectors for further testing. The sequences for these proteins and identifiers are shown in Table 14.

TABLE 14

Anti-idiotypes expressed as IgG1-Fc fusions

| Fc Fusion Prot ID | Anti-ID VHH | Amino Acid Sequence of anti-Idiotype VHH | SEQ ID NO |
|---|---|---|---|
| Anti-idiotypes that arose from panning that targeted D04 ||||
| AMD67 | huD04_CNTY2_F09 | EVQLLESGGGLVQPGGSLRLSCAASGRTFSSGAMGWYRQAPGKERELVSAISNRGSTVYADSVKGRFTISRDNSKNTLYLQMNSLRAEDTAVYYCAADRNPSSAGAGVAAYRLIARFNYWGQGTQVTVSS | 113 |
| AMD68 | huD04_CNTY2_F08 | EVQLLESGGGLVQPGGSLRLSCAASGFTLSSYAMGWYRQAPGKEREGVSSISYAGVTNYADSVKGRFTISRDNSKNTLYLQMNSLRAEDTAVYYCAAALGTGYYAYRRLWSYRIGSQAYDYWGQGTQVTVSS | 114 |
| AMD69 | huD04_CNTY2_E03 | EVQLLESGGGLVQPGGSLRLSCAASGLTYTGYAMGWYRQAPGKERELVSAISSRSSIYYADSVKGRFTISRDNSKNTLYLQMNSLRAEDTAVYYCAAGRPVALGSWRRTATWSAGLGAEYAYWGQGTQVTVSS | 115 |
| AMD70 | huD04_CNTY2_F04 | EVQLLESGGGLVQPGGSLRLSCAASGRTFSSYGMGWYRQAPGKERELVSAISNRGSTYYADSVKGRFTISRDNSKNTLYLQMNSLRAEDTAVYYCAASPARVGVSGHSSSRRSYYGYSYDYWGQGTQVTVSS | 116 |
| ABD72 | huD04_CNTY2_H12 | EVQLLESGGGLVQPGGSLRLSCAASGSIFSSDVMGWYRQAPGKERELVSAISSGGSTRYADSVKGRFTISRDNSKNTLYLQMNSLRAEDTAVYYCAATMGKSTNRRNYGTWRYGAYAYWGQGTQVTVSS | 117 |
| AMD74 | huD04_CNTY2_F12 | EVQLLESGGGLVQPGGSLRLSCAASGFTFSSNAMGWYRQAPGKEREFVSSISSGRSTTYADSVKGRFTISRDNSKNTLYLQMNSLRAEDTAVYYCAAHGTKYKWTRARLRSARQKQLETYRYWGQGTQVTVSS | 118 |
| AMD77 | huD04_CNTY1_A11 | EVQLLESGGGLVQPGGSLRLSCAASGFTSSNYVMGWYRQAPGKEREFVSAIGSGGSTYYADSVKGRFTISRDNSKNTLYLQMNSLRAEDTAVYYCAAEIYTSGARDYWGQGTQVTVSS | 119 |
| AMD78 | huD04_CNTY2_C03 | EVQLLESGGGLVQPGGSLRLSCAASGLTFSRYAMGWYRQAPGKERELVSAISSRRSTYYADSVKGRFTISRDNSKNTLYLQMNSLRAEDTAVYYCAADYRLTSLERARYASASITYDYWGQGTQVTVSS | 120 |
| AMD79 | huD04_CNTY2_B06 | EVQLLESGGGLVQPGGSLRLSCAASGFTFNRYSMGWYRQAPGKERELVSAISSGGSGYYADSVKGRFTISRDNSKNTLYLQMNSLRAEDTAVYYCAIQDYSRIWEYIALDRRRSYYGMDYWGQGTQVTVSS | 121 |
| AMD80 | huD04_CNTY2_D02 | EVQLLESGGGLVQPGGSLRLSCAASGFTFRSYAMGWYRQAPGKEREGVSVISSGGTPSYADSVKGRFTISRDNSKNTLYLQMNSLRAEDTAVYYCDAIMGLVEADYVSTGTYEYTAYAYWGQGTQVTVSS | 122 |
| AMD81 | huD04_CNTY2_D04 | EVQLLESGGGLVQPGGSLRLSCAASGLTFSGVCMGWFRQAPGKEREGVSAIYSSGSTYYADSVKGRFTISRDNSKNTLYLQMNSLRAEDTAVYYCAADRIPDLGEPCIGTTNLARTYNYWGQGTQVTVSS | 123 |
| AMD82 | huD04_CNTY1_B12 | EVQLLESGGGLVQPGGSLRLSCAASGRTSSNYVMGWYRQAPGKEREGVSAITSGGSTYYADSVKGRFTISRDNSKNTLYLQMNSLRAEDTAVYYCAANLYSRTGAYDYWGQGTQVTVSS | 124 |
| AMD84 | huD04_CNTY2_D05 | EVQLLESGGGLVQPGGSLRLSCAASGYIYSSYSMGWYRQAPAKNASLSAITSSGETYYADSVKGRFTISRDNSKNTLYLQMNSLRAEDTAVYYCAADALDAPIAGDRYYRGSGAGYAYWGQGTQVTVSS | 125 |
| AMD85 | huD04_CNTY2_D12 | EVQLLESGGGLVQPGGSLRLSCAASGSAFSSNAMGWYRQAPGKERELVSAISSGGSTNYADSVKGRFTISRDNSKNTLYLQMNSLRAEDTAVYYCAARNPLTYTALVSNAPSGDYYLFEYRLWGQGTQVTVSS | 126 |
| AMD86 | huD04_CNTY1_D12 | EVQLLESGGGLVQPGGSLRLSCAASGFTSSNYVMGWYRQAPGKEREGVSAISSSGRTYYADSVKGRFTISRDNSKNTLYLQMNSLRAEDTAVYYCAAAYYSGYGETDYWGQGTQVTVSS | 127 |
| AMD87 | huD04_CNTY1_D11 | EVQLLESGGGLVQPGGSLRLSCAASGSTFSYYMGWYRQAPGKERELVSAISSGGSIYYADSVKGRFTISRDNSKNTLYLQMNSLRAEDTAVYYCARRTYYGDEADYWGQGTQVTVSS | 128 |
| AMD88 | huD04_CNTY1_D10 | EVQLLESGGGLVQPGGSLRLSCAASGRTSSNYVIGWYRQAPGKEREFVSAIGGGSTYYADSVKGRFTISRDNSKNTLYLQMNSLRAEDTAVYYCATRIYTARGAGDYWGQGTQVTVSSS | 129 |
| Anti-idiotypes that arose from panning that targeted B11 ||||
| AMD71 | huB11_CNTY3+4_A02 | EVQLLESGGGLVQPGGSLRLSCAASGRTYTGSAMGWYRQAPGKERELVSAISTGGETYYADSVKGRFTISRDNSKNTLYLQMNSLRAEDTAVYYCAAGYVGLPYTYRPATSRRGTYTWGQGTQVTVSS | 130 |
| AMD73 | huB11_CNTY3+4_A01 | EVQLLESGGGLVQPGGSLRLSCAASGFTFSSYSIGWYRAPGGKERELVSVISSGGSTYYADSVKGRFTISRDNSKNTLYLQMNSLRAEDTAVYYCAASDWSYSWITYTGTWRLYEYWGQGTQVTVSS | 131 |
| AMD75 | huB11_CNTY1_E11 | EVQLLESGGGLVQPGGSLRLSCAASGFAFSDYVMGWYRQAPGKEREFVSAIRSTTSTYYADSVKGRFTISRDNSKNTLYLQMNSLRAEDTAVYYCAADVWSGYEYDWGQGTQVTVSS | 132 |
| AMD76 | huB11_CNTY1_B11 | EVQLLESGGGLVQPGGSLRLSCAASGLAFSSYAMGWYRQAPGKEREFVSVISGTGETLYADSVKGRFTISRDNSKNTLYLQMNSLRAEDTAVYYCAADVWSGYEYDWGQGTQVTVSS | 133 |

Example 8. Specificity and Affinity Testing of Anti-Idiotype VHH

To determine the specificity and binding of anti-idiotypes, the Fc fusion proteins were tested via FACS against Nurkat cells expressing either B11 or D04 VHH CARs.

Figure 17A:
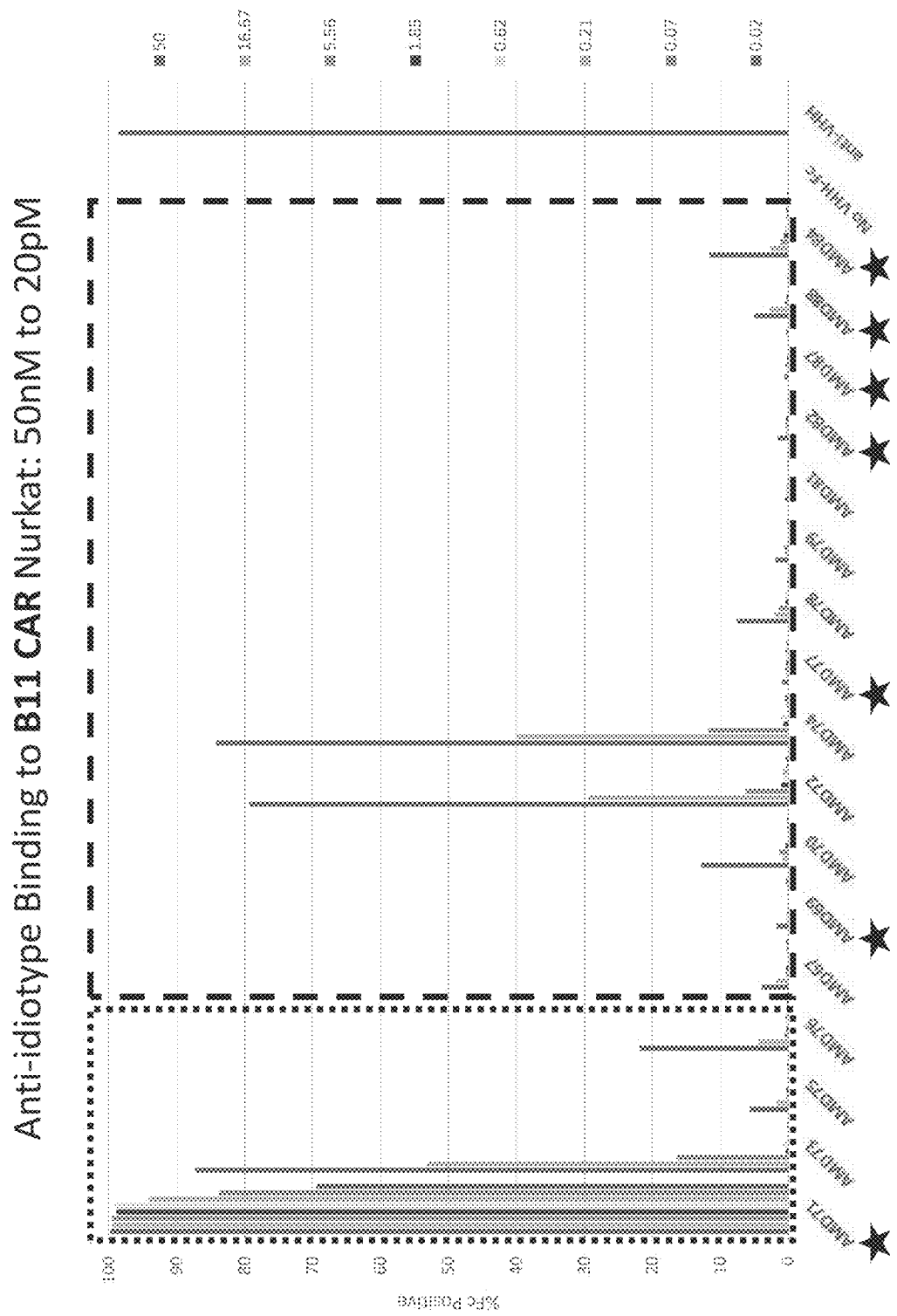
FIGS. 17A-17B show FACS binding of anti-Idiotype VHH-Fc fusion constructs to (FIG. 17A) B11 and (FIG. 17B) D04 CAR-expressing Nurkat cells without an IgG-based linker. The dashed outline identifies select proteins from Table 15 that were observed in ELISA to bind D04. The dotted outline identifies select proteins from Table 16 that were observed in ELISA to bind B11. Each protein was tested on both cell lines in a 3-fold dilution series from 50 nM down to 0.02 pM (as shown in the legend). Fc-fusion protein was detected via anti-Fc APC, and the percentage of cells that were positive for this detection method are shown. Proteins that showed specific binding down the dilution series to their target cell line are starred below the protein ID. Controls include (i) no VHH-Fc added and (ii) the anti-VHH cocktail detection reagent (far right). The samples shown in the graphs for each protein appear in the order as specified in the legend.
Figure 17B:
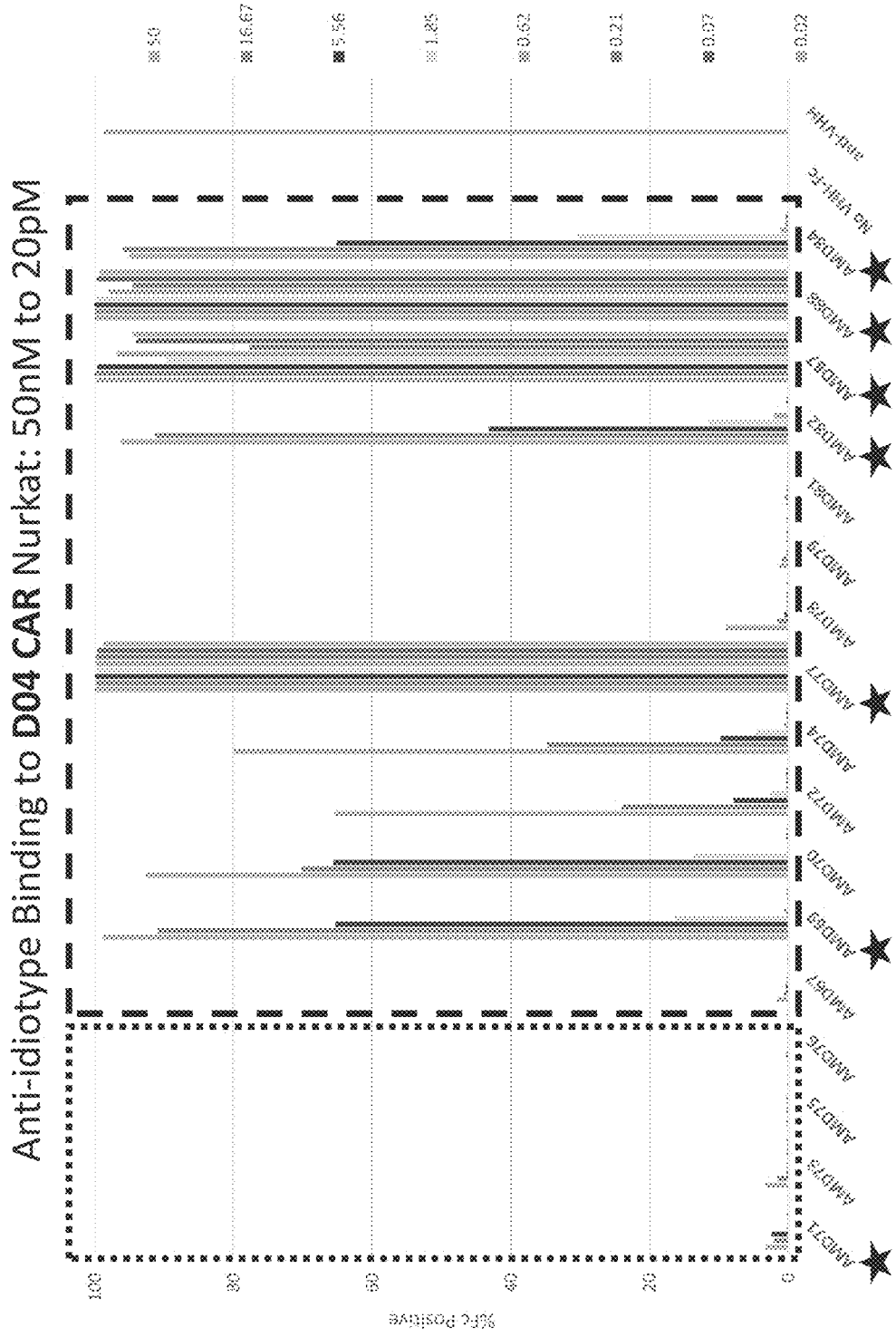

As shown in FIGS. 17A-17B, several of the anti-idiotypes showed robust and specific binding to the VHH on the CAR in a range of concentrations with negligible binding to the off-target CAR (e.g., AMD 71 (to B11) and AMD 69, AMD 77, AMD 82, AMD 84 AMD 87, and AMD 88 (to D04)). Also noted were a few binders that showed nonspecific binding, indicated by binding to both cell lines (AMD 72 and AMD 74). Of these, AMD 71, AMD 77, AMD 82, AMD 84, AMD 87, and AMD 88 were chosen for further specificity testing. Biotinylated anti-Idiotype VHH-Fc fusion proteins were arrayed against a variety of other VHH CAR-Nurkat, and any binding to those cell lines via FACS was subsequently detected.

Figure 18:
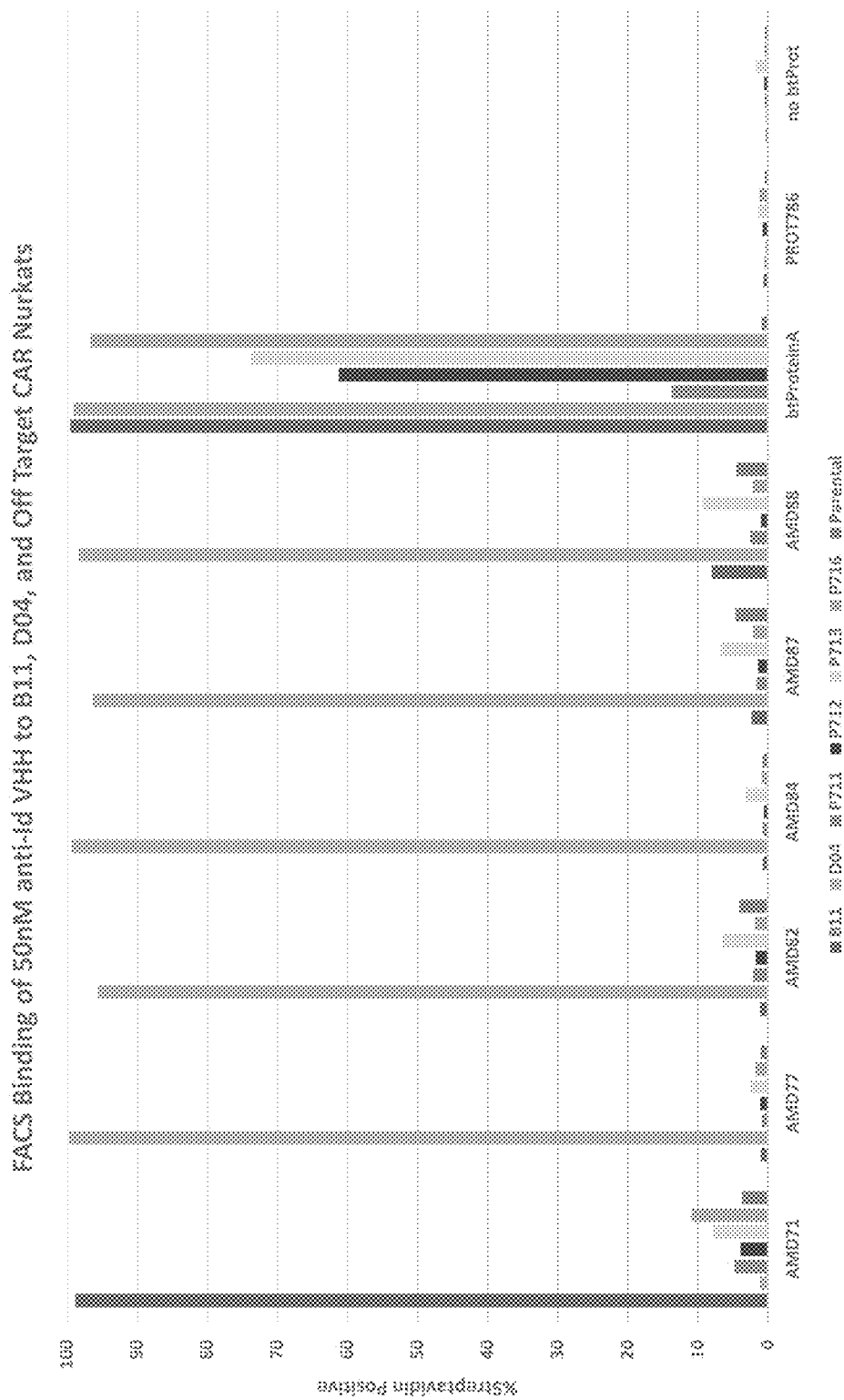
FIG. 18 shows binding of the lead anti-idiotype biotinylated VHH-Fc to target and off target CAR Nurkat cells detected via FACS with streptavidin-APC. The cells lines that were tested include B11, D04, P711, P712, P713, P716, and parental cells. B11 and D04 cells are CAR Nurkats expressing B11 and D04 VHH CARs, respectively. P711, P712, P713, P716 cells are off-target CAR Nurkats. Parental cells are untransduced, non-CAR-expressing Nurkats. Controls include biotinylated Protein A (which nonspecifically binds most VHH), PROT786 (an unrelated biotinylated VHH-Fc protein), and no biotinylated protein added. The samples shown in the graphs for each protein appear in the order as specified in the legend.

FIG. 18 shows binding of the lead anti-idiotype biotinylated VHH-Fc to target and off target CAR Nurkat cells detected via FACS with streptavidin-APC. The cells lines that were tested include B11, D04, P711, P712, P713, P716, and parental cells. B11 and D04 cells are CAR Nurkat cells expressing B11 and D04 VHH CARs, respectively. P711, 712, 713, 716 cells are off-target CAR Nurkat cells. Parental cells are untransduced, non-CAR-expressing Nurkat cells. Controls include biotinylated Protein A, which nonspecifically binds most VHH, PROT786, an unrelated biotinylated VHH-Fc protein, and no biotinylated protein added. The lead VHH demonstrated negligible binding to off-target VHH CARS and Parental Nurkat while still having robust binding to the target VHH.

Figure 19A:
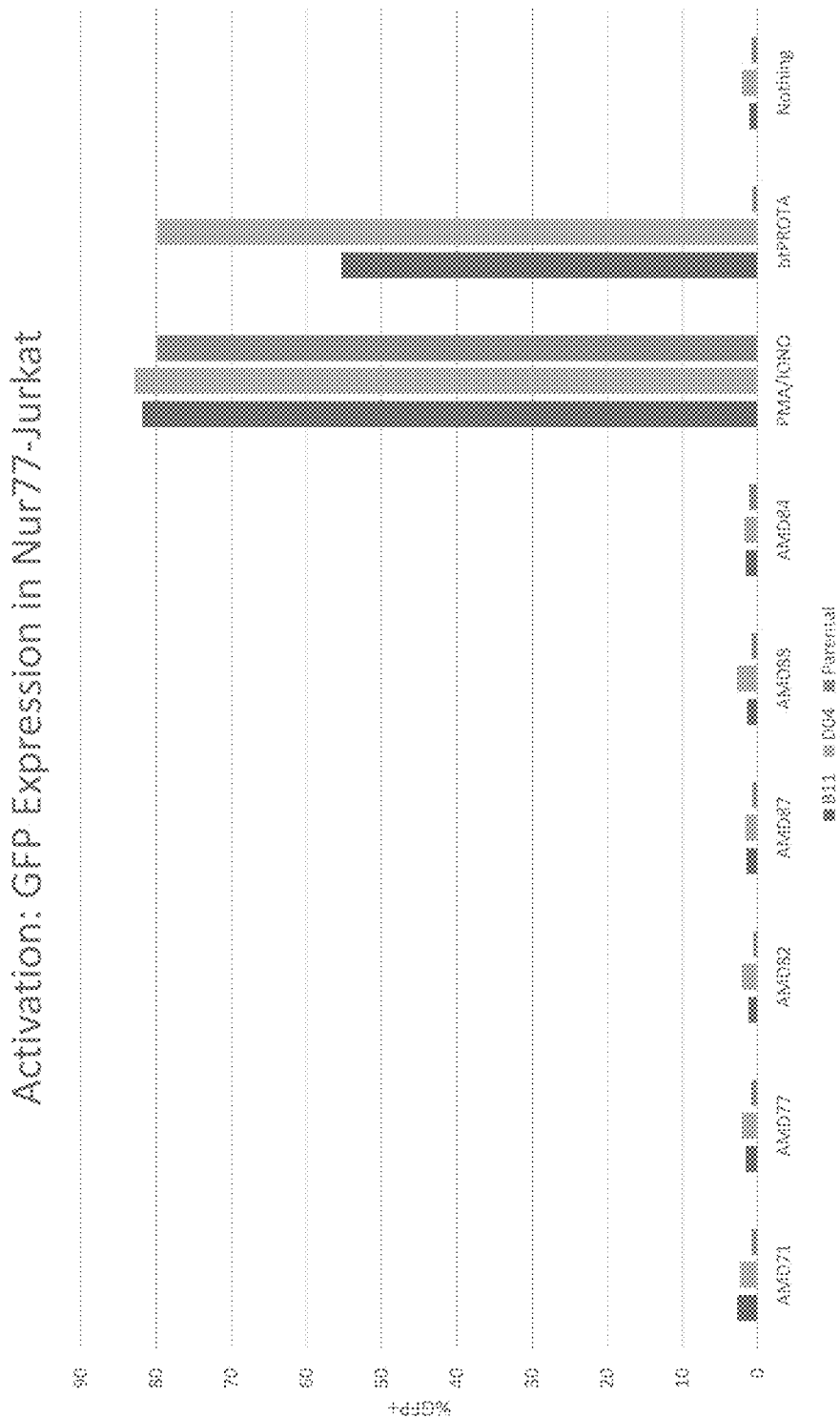
FIGS. 19A-19B show results of an overnight stimulation assay with Nurkat cells incubated with 10 nM anti-idiotype VHH Fc-fusion via FACS.
Figure 19B:
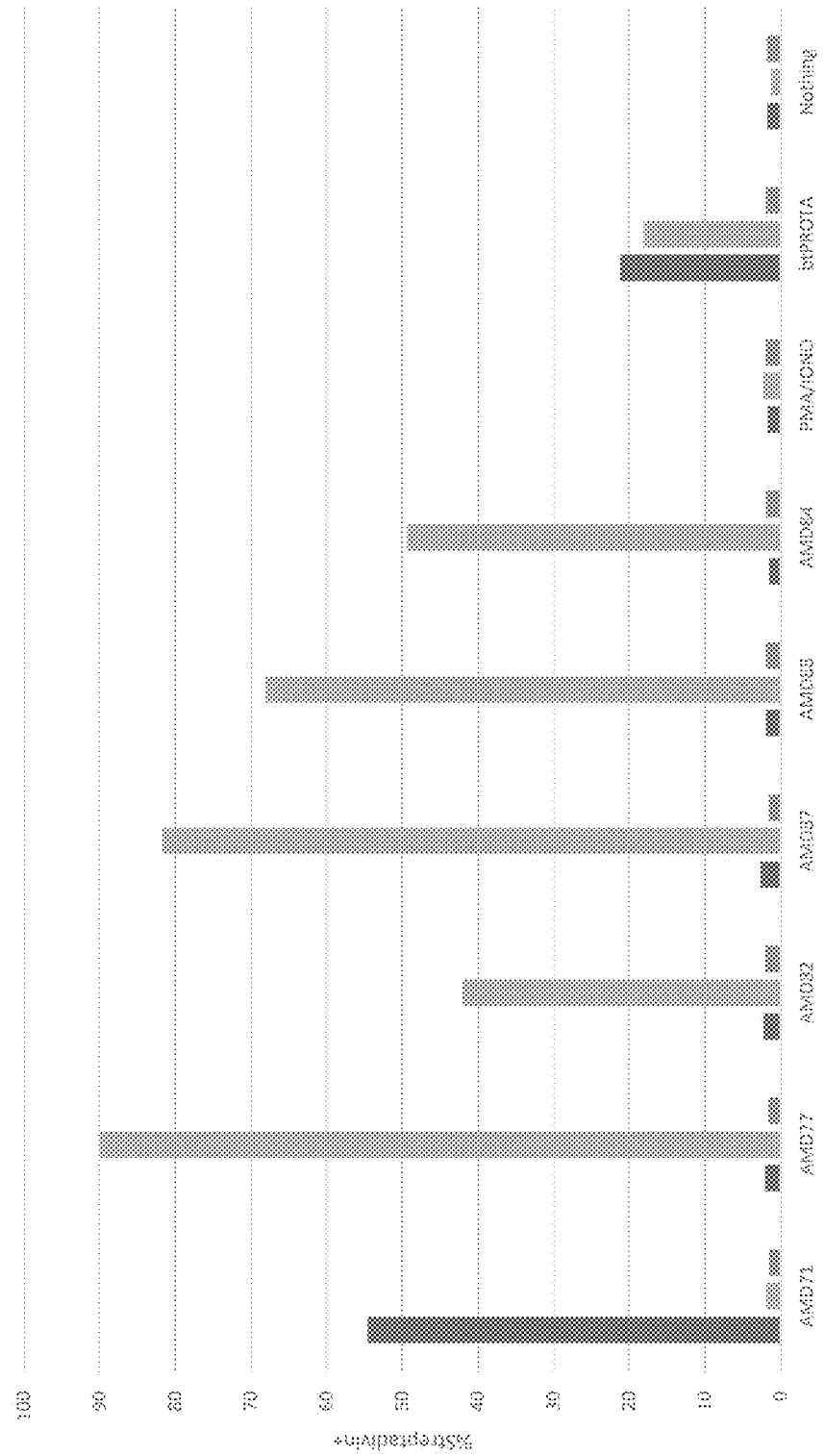

In some instances, the specific binding event that forms the basis of the "tag" and "anti-tag" interaction of the universal CAR is an important aspect to the safety profile of the platform. In addition, the binding event of the lysozyme VHH and an anti-idiotype alone should not be sufficient to cause CAR-induced activation. To determine whether the binding of B11 or D04 to their soluble anti-idiotype(s) causes CAR-induced activation absent the fusion of a tumor-antigen-targeting VHH to the soluble protein, an overnight stimulation assay in which the lead soluble anti-Idiotype Fc-fusion proteins were incubated with their target and off target CAR Nurkats as well as parental Nurkat. FIGS. 19A-19B show results of an overnight stimulation assay with Nurkat cells incubated with 10 nM anti-idiotype VHH Fc-fusion via FACS. FIG. 19A shows GFP expression of B11 and D04 CAR Nurkat cells, as well as parental Nurkat cells after overnight coculture with anti-idiotype Fc-fusion proteins. FIG. 19B shows detection of biotinylated protein via streptavidin-APC after the overnight incubation. Controls include PMA/Ionomycin (a TCR-crosslinker that results in robust Nurkat cell activation), biotinylated protein A, and a sample with no protein added. None of the anti-idiotype leads caused observable activation in the Nurkats as measured by GFP expression, compared to PMA/ionomycin induction. The anti-idiotypes were also still detectable after the overnight incubation, indicating that, if the anti-idiotypes did trigger CAR activation, the concentration of antigen used in the assay was sufficient to cause activation over the time course of the experiment that would have been observable.

Affinity measurements were obtained by Octet for the anti-ID binders to both the B11-his tagged VHH and D04-his tagged VHH.

TABLE 15

Octet results of anti-idiotype VHH Fc-fusion proteins tested against B11 his-tagged proteins

| Sample ID | KD (M) | kon(1/Ms) | kdis(1/s) | Response |
|---|---|---|---|---|
| AMD71 | <1.0E−12 | 2.16E+03 | <1.0E−07 | 0.0062 |
| AMD77 | 2.08E−09 | 6.96E+05 | 1.45E−03 | 0.497 |
| AMD82 | 1.25E−07 | 6.97E+05 | 8.68E−02 | 0.1718 |
| AMD87 | 3.69E−06 | 1.76E+04 | 6.49E−02 | 0.1306 |
| AMD88 | 7.23E−08 | 5.88E+05 | 4.25E−02 | 0.2893 |
| AMD84 | 1.85E−07 | 7.90E+05 | 1.47E−01 | 0.0991 |
| PROT253 | NA | NA | NA | −0.05 |

Shown are affinity values (KD), on rates (kon), off rates (kdis), and response for anti-idiotype VHH fc-fusion proteins against B11-his protein

TABLE 16

Octet results of anti-idiotype VHH Fc-fusion proteins tested against D04 his-tagged proteins

| Sample ID | KD (M) | kon(1/Ms) | kdis(1/s) | Response |
|---|---|---|---|---|
| AMD71 | 5.15E−07 | 2.73E+05 | 1.40E−01 | 0.0566 |
| AMD77 | 7.96E−08 | 3.54E+03* | 2.82E−04 | 0.1785 |
| AMD82 | NA | NA | NA | −0.0225 |
| AMD87 | NA | NA | NA | −0.0301 |
| AMD88 | NA | NA | NA | −0.0183 |
| AMD84 | NA | NA | NA | −0.0341 |
| PROT253 | NA | NA | NA | −0.0648 |

Shown are affinity values (KD), on rates (kon), off rates (kdis), and response for anti-idiotype VHH fc-fusion proteins against B11-his protein.

The anti-idiotype proteins demonstrated a range of affinities from 2 nM (AMD77 to D04) to 3.7 μM (AMD87 to D04). To verify the specificity of the two highest affinity binders, AMD77 (2 nM) and AMD88 (72 nM) via Octet, we tested each protein for binding against itself, its target VHH, off-target VHH, total human IgG from sera, and Fc-γ fragment.

TABLE 17

Octet specificity analysis of anti-idiotypes AMD77 and AMD88

| Sample ID | Analyte | Response |
|---|---|---|
| AMD77 | LysoD04.His | 0.3374 |
| AMD77 | AMD77 | 0.0493 |
| AMD77 | AMD88 | 0.2773 |
| AMD77 | IgG | −0.0155 |
| AMD77 | Fc | −0.009 |
| AMD77 | PROT939 | −0.0053 |
| AMD77 | LysoD04.Fc | 2.6741 |
| AMD88 | LysoD04.His | 0.0923 |
| AMD88 | AMD77 | 0.0229 |
| AMD88 | AMD88 | 0.1492 |
| AMD88 | IgG | −0.0338 |
| AMD88 | Fc | −0.0261 |
| AMD88 | PROT939 | −0.024 |
| AMD88 | LysoD04.Fc | 2.1784 |

Each sample (either AMD77 or AMD88) was tested against the analytes D04-his, AMD77, AMD88, IgG from sera, Fc-γ fragment, PROT939 (an off target VHH-fc soluble), and D04-fc. Response values are shown in Table 17. AMD77 and AMD88 both showed minimal responses to human IgG, Fc, and the off target VHH-fc PROT939, while maintaining strong responses to D04-his and D04-Fc. AMD88 did show a response to itself and to AMD77. AMD77 did not associate with itself.

Example 9. Bridge Protein Designs

Bridge proteins contain the VHH arCAR binder and a tumor targeting VHH, specifically in this example anti-CD70 and anti-EGFR. These were constructed with and without an Fc domain that would function in vivo as a half-life extender. To achieve the specificity of the universal CAR, bridge proteins were designed that incorporated selected anti-idiotypes to D04 partnered with the D04 CAR or D04 on the soluble bridge protein partnered with an anti-ID to D04 as the CAR.

TABLE 18

Bridge Proteins without Fc: VHH1-linker-VHH2

| Protein ID | VHH1 | VHH2 | Linker | Tumor Target |
|---|---|---|---|---|
| AMD1 | CD70W_DB02_D08 | huLysoB11 | (G4S)3 | CD70 |
| AMD2 | CD70W_DB02_D08 | huLysoB11 | WHITLOW | CD70 |
| AMD3 | CD70W_DB02_G07 | huLysoB11 | (G4S)3 | CD70 |
| AMD4 | CD70W_DB02_G07 | huLysoB11 | WHITLOW | CD70 |
| AMD5 | CD70W_DB02_G08 | huLysoB11 | (G4S)3 | CD70 |
| AMD6 | CD70W_DB02_G08 | huLysoB11 | WHITLOW | CD70 |
| AMD7 | CD70W_DB02_G09 | huLysoB11 | (G4S)3 | CD70 |
| AMD8 | CD70W_DB02_G09 | huLysoB11 | WHITLOW | CD70 |
| AMD9 | CD70W_DB02_E01 | huLysoB11 | (G4S)3 | CD70 |
| AMD10 | CD70W_DB02_E01 | huLysoB11 | WHITLOW | CD70 |
| AMD11 | CD70W_DB02_E06 | huLysoB11 | (G4S)3 | CD70 |
| AMD12 | CD70W_DB02_E06 | huLysoB11 | WHITLOW | CD70 |
| AMD13 | CD70W_DB02_D08 | huLysoB11 | (G4S)3 | CD70 |
| AMD14 | CD70W_DB02_D08 | huLysoB11 | WHITLOW | CD70 |
| AMD15 | CD70W_DB02_G07 | huLysoB11 | (G4S)3 | CD70 |
| AMD16 | CD70W_DB02_G07 | huLysoB11 | WHITLOW | CD70 |
| AMD17 | CD70W_DB02_G08 | huLysoB11 | (G4S)3 | CD70 |
| AMD18 | CD70W_DB02_G08 | huLysoB11 | WHITLOW | CD70 |
| AMD19 | CD70W_DB02_G09 | huLysoB11 | (G4S)3 | CD70 |
| AMD20 | CD70W_DB02_G09 | huLysoB11 | WHITLOW | CD70 |
| AMD21 | CD70W_DB02_E01 | huLysoB11 | (G4S)3 | CD70 |
| AMD22 | CD70W_DB02_E01 | huLysoB11 | WHITLOW | CD70 |
| AMD23 | CD70W_DB02_E06 | huLysoB11 | (G4S)3 | CD70 |
| AMD24 | CD70W_DB02_E06 | huLysoB11 | WHITLOW | CD70 |
| AMD25 | CD70W_DB02_D08 | huLysoD04 | (G4S)3 | CD70 |
| AMD26 | CD70W_DB02_D08 | huLysoD04 | WHITLOW | CD70 |
| AMD27 | CD70W_DB02_G07 | huLysoD04 | (G4S)3 | CD70 |
| AMD28 | CD70W_DB02_G07 | huLysoD04 | WHITLOW | CD70 |
| AMD29 | CD70W_DB02_G08 | huLysoD04 | (G4S)3 | CD70 |
| AMD30 | CD70W_DB02_G08 | huLysoD04 | WHITLOW | CD70 |
| AMD31 | CD70W_DB02_G09 | huLysoD04 | (G4S)3 | CD70 |
| AMD32 | CD70W_DB02_G09 | huLysoD04 | WHITLOW | CD70 |
| AMD33 | CD70W_DB02_E01 | huLysoD04 | (G4S)3 | CD70 |
| AMD34 | CD70W_DB02_E01 | huLysoD04 | WHITLOW | CD70 |
| AMD35 | CD70W_DB02_E06 | huLysoD04 | (G4S)3 | CD70 |
| AMD36 | CD70W_DB02_E06 | huLysoD04 | WHITLOW | CD70 |
| AMD37 | CD70W_DB02_D08 | huLysoD04 | (G4S)3 | CD70 |
| AMD38 | CD70W_DB02_D08 | huLysoD04 | WHITLOW | CD70 |
| AMD39 | CD70W_DB02_G07 | huLysoD04 | (G4S)3 | CD70 |
| AMD40 | CD70W_DB02_G07 | huLysoD04 | WHITLOW | CD70 |
| AMD41 | CD70W_DB02_G08 | huLysoD04 | (G4S)3 | CD70 |
| AMD42 | CD70W_DB02_G08 | huLysoD04 | WHITLOW | CD70 |
| AMD43 | CD70W_DB02_G09 | huLysoD04 | (G4S)3 | CD70 |
| AMD44 | CD70W_DB02_G09 | huLysoD04 | WHITLOW | CD70 |
| AMD45 | CD70W_DB02_E01 | huLysoD04 | (G4S)3 | CD70 |
| AMD46 | CD70W_DB02_E01 | huLysoD04 | WHITLOW | CD70 |
| AMD47 | CD70W_DB02_E06 | huLysoD04 | (G4S)3 | CD70 |
| AMD48 | CD70W_DB02_E06 | huLysoD04 | WHITLOW | CD70 |

TABLE 19

Bridge proteins with VHH1-whitlow-VHH2-IgG1 Fc constructs

| Protein ID | VHH1 | VHH2 | Tumor Target |
|---|---|---|---|
| AMD99 | huD04_CNTY1_A11 | CD70W_DB02_G08 | CD70 |
| AMD100 | huD04_CNTY1_B12 | CD70W_DB02_G08 | CD70 |
| AMD101 | huD04_CNTY1_D10 | CD70W_DB02_G08 | CD70 |
| AMD102 | CD70W_DB02_G08 | huD04_CNTY1_A11 | CD70 |
| AMD103 | CD70W_DB02_G08 | huD04_CNTY1_B12 | CD70 |
| AMD104 | CD70W_DB02_G08 | huD04_CNTY1_D10 | CD70 |
| AMD105 | huLysoD04 | CD70W_DB02_G08 | CD70 |
| AMD106 | CD70W_DB02_G08 | huLysoD04 | CD70 |
| AMD107 | huD04_CNTY1_A11 | 9G8 | EGFR |
| AMD108 | huD04_CNTY1_B12 | 9G8 | EGFR |
| AMD109 | huD04_CNTY1_D10 | 9G8 | EGFR |
| AMD110 | 9G8 | huD04_CNTY1_A11 | EGFR |
| AMD111 | 9G8 | huD04_CNTY1_B12 | EGFR |
| AMD112 | 9G8 | huD04_CNTY1_D10 | EGFR |
| AMD113 | huLysoD04 | 9G8 | EGFR |
| AMD114 | 9G8 | huLysoD04 | EGFR |

TABLE 20

Bridge proteins with VHH-IgG1 Fc-(G4S)1-VHH constructs

| Protein ID | VHH1 | VHH2 | Tumor Target |
|---|---|---|---|
| AMD115 | huD04_CNTY1_A11 | CD70W_DB02_G08 | CD70 |
| AMD116 | huD04_CNTY1_B12 | CD70W_DB02_G08 | CD70 |
| AMD117 | huD04_CNTY1_D10 | CD70W_DB02_G08 | CD70 |
| AMD118 | CD70W_DB02_G08 | huD04_CNTY1_A11 | CD70 |
| AMD119 | CD70W_DB02_G08 | huD04_CNTY1_B12 | CD70 |
| AMD120 | CD70W_DB02_G08 | huD04_CNTY1_D10 | CD70 |
| AMD121 | huLysoD04 | CD70W_DB02_G08 | CD70 |
| AMD122 | CD70W_DB02_G08 | huLysoD04 | CD70 |
| AMD123 | huD04_CNTY1_A11 | 9G8 | EGFR |
| AMD124 | huD04_CNTY1_B12 | 9G8 | EGFR |
| AMD125 | huD04_CNTY1_D10 | 9G8 | EGFR |
| AMD126 | 9G8 | huD04_CNTY1_A11 | EGFR |
| AMD127 | 9G8 | huD04_CNTY1_B12 | EGFR |
| AMD128 | 9G8 | huD04_CNTY1_D10 | EGFR |
| AMD129 | huLysoD04 | 9G8 | EGFR |
| AMD130 | 9G8 | huLysoD04 | EGFR |

Example 10. T Cell Cytotoxicity with D04 CAR and huD04_CNTY1_D10 Bridge

To determine if the universal platform could mediate cytotoxicity by T cells, we created bridge proteins that consisted of the VHH from the AMD88 protein, (huD04_CNTY1_D10) linked in tandem by a Whitlow linker to the EGFR targeting VHH 9G8, fused to an IgG1 Fc fragment (Table 19). Each bridge protein was tested in a T cell cytotoxicity assay with primary T cells expressing the D04 CAR.

TABLE 21

Protein concentration and percent monomer for AMD109 and AMD112 bridge proteins

| DNA ID | Concentration (mg/mL) | % Monomer |
|---|---|---|
| AMD109 | 0.35 | 97.40 |
| AMD112 | 0.46 | 97.34 |

Figure 20A:
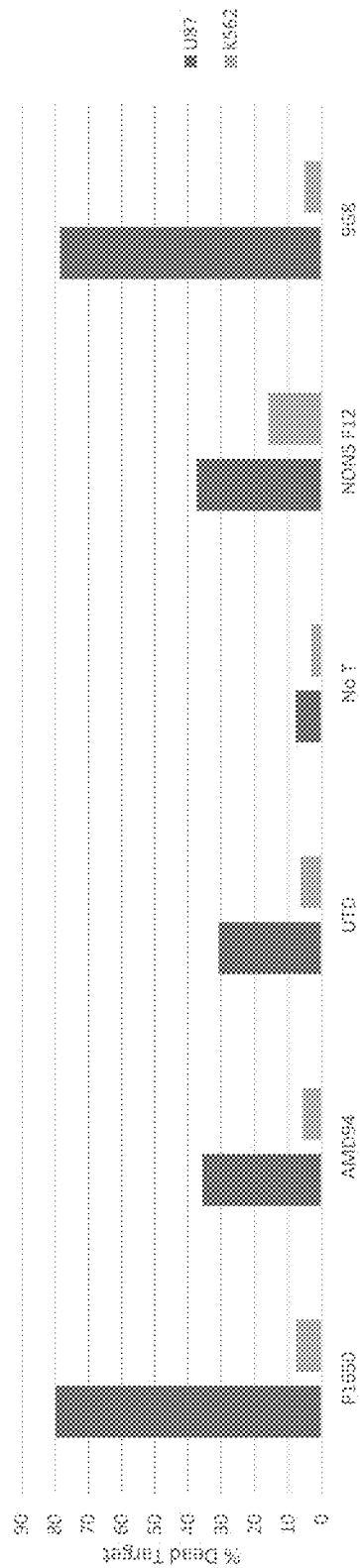
FIGS. 20A-20B show results of identical T cell killing assays in which either bridge protein (FIG. 20A) AMD109 or (FIG. 20B) AMD112 was added at 5 nM. Percent dead targets are shown for either U87 target cells, or K562 target cells.
Figure 20B:
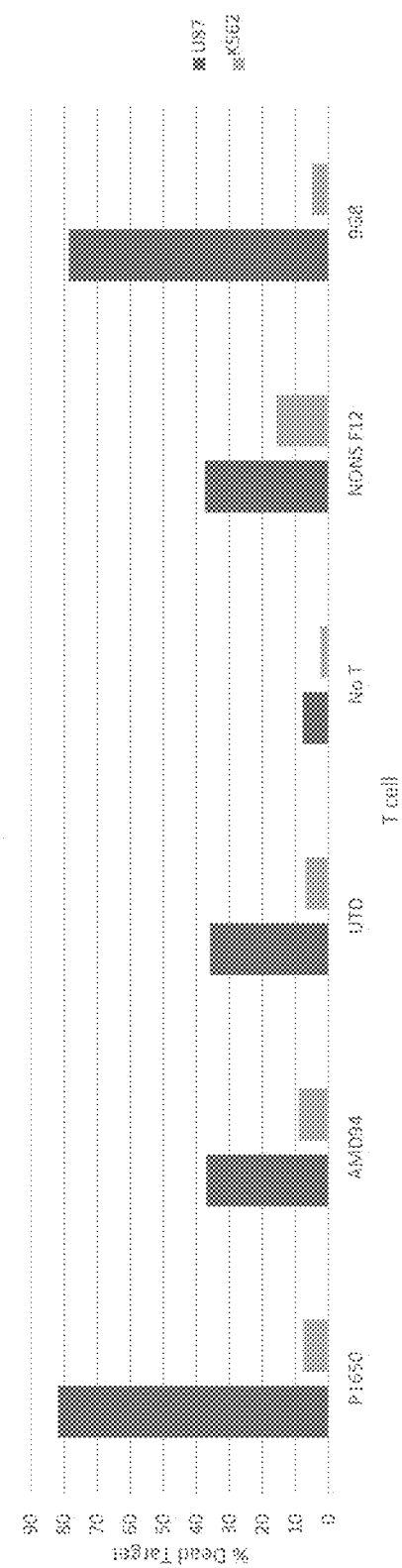

The killing assay was performed by coculturing CAR T cells, with EGFR positive cells labeled with CellTrace Violet at an effector to target ratio of 1:2, adjusted for the percent CAR positivity of the T cells, for 48 hours. 5 nM of the bridge, either AMD109 (FIG. 20A) or AMD112 (FIG. 20B).

As shown in FIGS. 20A-20B, when the bridge and CAR are 'matched' (e.g., an anti-idiotype VHH is present on the bridge protein while its target VHH is present on the CAR) robust cytotoxicity of EGFR positive cells is observed as in the case of P1650 CAR expressing T cells, which have D04 on their CAR (huD04_CNTY1_D10, an anti-idiotype to D04 on the soluble bridge protein). This cytotoxic activity is comparable to the 9G8 CAR. When the CAR and bridge are mismatched, as with the CAR AMD94 or the NONS F12 CAR, no cytotoxicity is observed.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

All patents, applications, publications, test methods, literature, and other materials cited herein are hereby incorporated by reference in their entirety as if physically present in this specification.

What is claimed is:

1. A universal chimeric antigen receptor system having an adaptable receptor specificity component (arCAR), comprising
   (i) an immune effector cell having a chimeric antigen receptor comprising a first polypeptide comprising:
      (a) an extracellular tag-binding domain,
      (b) a transmembrane domain, and
      (c) at least one intracellular signaling domain; and
   (ii) a second soluble polypeptide comprising:
      (a) an antigen-binding domain that binds to at least one antigen on a target cell, and
      (b) a tag that is recognized by the extracellular tag-binding domain;
   wherein:
      the tag comprises the polypeptide sequence of SEQ ID NO: 112, and the extracellular tag-binding domain comprises the polypeptide sequence of SEQ ID NO: 129; or
      the tag comprises the polypeptide sequence of SEQ ID NO: 129, and the extracellular tag-binding domain comprises the polypeptide sequence of SEQ ID NO: 112.

2. The arCAR system of claim 1, wherein the antigen-binding domain of the second polypeptide comprises an antibody, or antigen-binding fragment thereof, or an alternative scaffold.

3. The arCAR system of claim 1, wherein the antigen-binding domain binds to at least one tumor antigen or autoimmune antigen.

4. The arCAR system of claim 3, wherein the at least one tumor antigen is associated with glioblastoma, ovarian cancer, cervical cancer, head and neck cancer, liver cancer, prostate cancer, pancreatic cancer, renal cell carcinoma, bladder cancer, or hematologic malignancy.

5. The arCAR system of claim 1, wherein the immune effector cell is derived from an induced pluripotent stem cell (iPSC).

6. The arCAR system of claim 5, wherein the immune effector cell is a T cell or NK cell derived from an induced pluripotent stem cell (iPSC).

7. A method of treating a disease in a subject in need thereof, comprising administering to the subject a therapeutically effective amount of:
   (i) an immune effector cell comprising a chimeric antigen receptor comprising the first polypeptide of the arCAR system of claim 1, and
   (ii) the second polypeptide of the arCAR system of claim 1, a polynucleotide encoding the second polypeptide of the arCAR system of claim 1, or a host cell comprising the second soluble polypeptide of the arCAR system of claim 1.

8. The method of claim 7, wherein the immune effector cell is a T cell, a Natural Killer (NK) cell, a cytotoxic T lymphocyte (CTL), a regulatory T cell or a tumor-infiltrating lymphocyte (TIL), a dendritic cell, or a macrophage.

9. The method of claim 7, wherein the immune effector cell is derived from an iPSC.

10. The method of claim 7, wherein the immune effector cell constitutively expresses the first polypeptide.

11. The method of claim 7, wherein the disease is a cancer or autoimmune disease.

12. The method of claim 11, wherein the cancer is glioblastoma, ovarian cancer, cervical cancer, head and neck cancer, liver cancer, prostate cancer, pancreatic cancer, renal cell carcinoma, bladder cancer, or hematologic malignancy.

13. The method of claim 7, wherein the immune effector cell is an allogeneic cell.

\* \* \* \* \*